US007655235B2

(12) United States Patent
Ertl

(10) Patent No.: US 7,655,235 B2
(45) Date of Patent: Feb. 2, 2010

(54) VACCINE

(75) Inventor: Peter Franz Ertl, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 16 days.

(21) Appl. No.: 10/533,734

(22) PCT Filed: Nov. 3, 2003

(86) PCT No.: PCT/EP03/12402

§ 371 (c)(1),
(2), (4) Date: May 19, 2006

(87) PCT Pub. No.: WO2004/041852

PCT Pub. Date: May 21, 2004

(65) Prior Publication Data

US 2007/0042977 A1     Feb. 22, 2007

(30) Foreign Application Priority Data

Nov. 5, 2002    (GB) ................................ 0225788.9

(51) Int. Cl.
*A61K 39/00* (2006.01)
(52) U.S. Cl. .................................................. 424/184.1
(58) Field of Classification Search ........................ None
See application file for complete search history.

(56) References Cited

U.S. PATENT DOCUMENTS

| 2003/0108562 A1 | 6/2003 | Hanke et al. |
| 2003/0190308 A1 | 10/2003 | Braun et al. |
| 2004/0073008 A1 | 4/2004 | Inglesias et al. |

FOREIGN PATENT DOCUMENTS

| CA | 2 430 702 | | 9/2002 |
| EP | 0 577 894 | | 1/1994 |
| EP | 1015596 | | 8/2006 |
| WO | WO 98/41536 | * | 9/1998 |
| WO | WO 9841536 | | 9/1998 |
| WO | 99/016884 | | 4/1999 |
| WO | WO 01/27291 | | 4/2001 |
| WO | 02/0220080 | | 3/2002 |
| WO | WO 02/32943 | * | 4/2002 |
| WO | WO 02/36792 | * | 5/2002 |
| WO | 02/099101 | | 12/2002 |
| WO | WO 03/025003 | | 3/2003 |
| WO | 04/041851 | | 5/2004 |
| WO | WO 2004/041852 | | 5/2004 |

OTHER PUBLICATIONS

Farina, S., et al., Replication-defective vector based on a chimpanzee adenovirus, Journal of Virology, 75(3):11603-11613, 2001.*
Roy, S. et al., Characterization of a family of chimpanzee adenoviruses and development of molecular clones for gene transfer vectors, Human Gene Therapy, 15:519-530, 2004.*
Fynan, E. et al., DNA vaccines: protective immunizations by parenteral, mucosal, and gene-gun inoculations, Proc. Natl. Acad. Sci. USA, 90: 11478-82, 1993.*
Botarelli et al., N-Glycosylation of HIV-gp120 May Constrain Recognition by T Lymphocytes, Journal of Immunology, 1991, 147(9):3128-3132.*
Jiang et al., Construction of engineering yeast strain expressing gap-gp120 chimeric gene of HIV-1 and optimization of the expression condition, Chinese Journal of Microbiology and Immunology, 2002, 22(5):482-484. (Abstract Only).*
Li et al., Glycosylation Is Necessary for the Correct Folding of Human Immunodeficiency Virus gp120 in CD4 Binding, Journal of Virology, 1993, 67(1):584-588.*
Fenouillet et al., *Virology*, vol. 218 pp. 224-231 (1996).
Kayman et al., *Journal of Virology*, The American Society for Microbiology, vol. 6(1) pp. 400-410 (1994).
Andre, et al., *Journal of Virology*, 72(2):1497-1503 (1998).
Benko, et al., *Journal of Virology*, 64(6):2505-2518 (1990).
Buck, et al, *Journal of Virology*, 75(1):181-191 (2001).
Doe, *Eur. J. Immunol*, 24:2369-75, (1994).
Hone, et al, *Dev. Biol. Stand.*, 82:159-62, (1994).
Inglesias, et al., *J. Biochem. Mol Bio & Biophys*, 5:109-122, (2000).
Kong, et al., *Journal of Virology*, 77:12764-12772 (2003).
Kotsopoulou, et al., *Journal of Virology*, 74(10):4839-4852 (2000).
Liu, et al., *Virology*, 274(2):374-382 (2000).
Mooij, et al, *Journal of Virology*, 78(7):333-42 (2004).
Mooji, et al., *Vaccine*, 20:304-321 (2001).
Moore, et al., *Vaccine*, 17:2517-2527 (1999).
Salfeld, et al., *Embo. Journal*, 9(3):965-970 (1990).
Vazquez-Blomquist, et al., *Vaccine*, 22:145-155 (2003).
Woodberry, et al., *Journal of Virology*, 73(7):5320-5325 (1999).
Asjo et al., Phase 1 trial of a therapeutic HIV type 1 vaccine, Vacc-4x, in HIV type 1-infected individuals with or without antiretroviral therapy, AIDS Res Hum Retroviruses 18(18):1357-1365 (Dec 2002).
Azad et al., Large-scale production and characterization of recombinant HIV-1 Nef, J. General Virology, 75:651-655 (1994).
Berzofsky, Progress toward an artivicial vaccine for HIV: identification of helper and cytotoxic T-cell epitopes and methods of immunization, Biotechnol. Ther. 2(1-2): 123-135 (1991).

(Continued)

*Primary Examiner*—Gary B Nickol
*Assistant Examiner*—Nicole Kinsey White
(74) *Attorney, Agent, or Firm*—Gwynedd Warren; Virginia Gail Campen; GlaxoSmithKline Corporate Intellectual Property-US

(57) ABSTRACT

The invention relates to polynucleotides for DNA vaccination which polynucleotides encode an HIV envelope protein or fragment or immunogenic derivative, which is non-glycosylated when expressed in a mammalian target cell, operably linked to a heterologous promoter. Preferably the HIV envelope molecule, such as gp120 or gp140 or gp160, lacks a functional secretion signal. It may be fused to additional HIV proteins such as Nef, Gag, RT or Tat.

31 Claims, 53 Drawing Sheets

OTHER PUBLICATIONS

Betts et al., Optimal antigens for HIV vaccines based on CD8 + T response, protein length, and sequence variability, DNA Cell Biology 21(9):665-670 (Sep. 2002).

Cosma et al., Therapeutic vaccination with MVA-HIV-1 nef elicits Nef-specific T-helper cell responses in chronically HIV-1 infected individuals, Vaccine 22(1), 21-29 (Dec 2003).

Deml et al, Multiple effects of codon usage optimization on expression and immunogenicity of DNA candidate vaccines encoding the human immunodeficiency virus type 1 Gag protein, J. Virology 75(22);10991-11001 (2001).

Estaquier et al., Comprehensive delineation of antigenic and immunogenic properties of peptides derived from the nef HIV-1 regulatory protein, Vaccine 11(11):1083-1092 (1993).

Gahery-Segard et al., Long term specific immune responses induced in humans by a human immunodeficiency virus type 1 lipopeptide vaccine: characterization of CD8+T cell epitopes recognized, J. Virol. 77(20):11220-11231 (Oct. 2003).

Gahery-Segard et al., Multiepitopic B- and T-cell responses induced in humans by a human immunodeficiency virus type 1 lipopeptide vaccine, J. Virol. 74(4):1694-1703 (Feb. 2000).

Hinkula et al., Recognition of prominent viral epitopes induced by immunization with HIV-1 regulatory genes, J. Virology, 71(7), 5528-5539 (1997).

Johnson and Walker, Cytotoxic T lymphocytes in human immunodeficiency virus infection: responses to structural protein, Curr Top Microbiol Immunol 189:35-63 (1994).

Kmieciak et al., Enhancement of cellular and humoral immune responses to human immunodeficiency virus type 1 Gag and Pol by G/P-92 fusion protein expressing highly immunogenic Gag P1 7/p24 and Pol p51 antigens, J Human Virology 4(6):306-316 (2001).

Letvin et al., Progress in the development of Nan HIV-1 Vaccine, Science 280:1875 (1998).

Pialoux et al., Lipopeptides induce cell-mediated anti-HIV immune responses in seronegative volunteers, AIDS 15(10):1239-1249 (Jul. 2001).

Robert Guroff, HIV Regulatory and accessory proteins, new targets for vaccine development, DNA and Cell Biology, 21(9): 597-598 (Sep 2002).

Zur Megede et al., Increased expression and immunogenicity of sequence modified HIV-1 gag gene, J. Virology 74:2628 (2000).

* cited by examiner

Figure 2

Map of pgp120c:

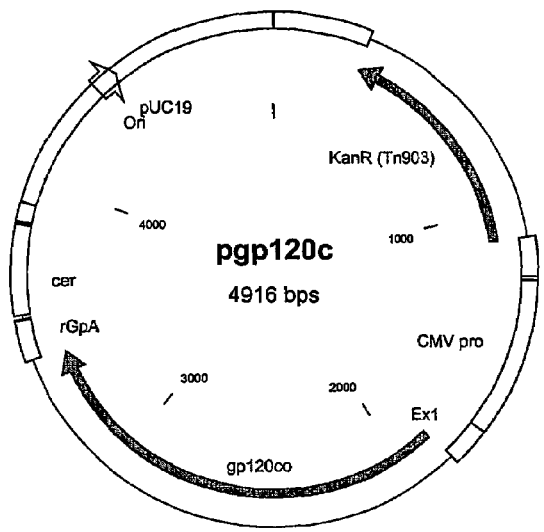

The amino acid sequence of the W61D gp120 is below. The signal sequence is underlined and bold, up to the predicted cleavage site between amino acids 29 and 30. This is the sequence removed in dsgp120 (pRix12 etc).

MKVKETRKNYQHLWRWGTMLLGMLMICSAAEQLWVTVYYGVPVWKEATTTLFCASDAKAYDTEVHNVWATH
ACVPTDPNPQEVVLGNVTEYFNMWKNNMVDQMHEDIISLWDQSLKPCVKLTPLCVTLDCDDVNTTNSTTTT
SNGWTGEIRKGEIKNCSFNITTSIRDKVQKEYALFYNLDVVPIDDDNATTKNKTTRNFRLIHCNSSVMTQA
CPKVSFEPIPIHYCAPAGFAILKCNNKTFDGKGLCTNVSTVQCTHGIRPVVSTQLLLNGSLAEEEVVIRSD
NFMDNTKTIIVQLNESVAINCTRPNNNTRKGIHIGPGRAFYAARKIIGDIRQAHCNLSRAQWNNTLKQIVI
KLREHFGNKTIKFNQSSGGDPEIVRHSFNCGGEFFYCDTTQLFNSTWNGTEGNNTEGNSTITLPCRIKQII
NMWQEVGKAMYAPPIGGQIRCSSNITGLLLTRDGGTEGNGTENETEIFRPGGGDMRDNWRSELYKYKVVKV
EPLGVAPTRAKRRVVQR       [SEQ ID NO: 49]

The codon optimised DNA sequence for the W61D gp120 gene is:

ATGAAGGTCAAGGAGACCAGAAAGAACTACCAGCATCTGTGGCGCTGGGGCACCATGCTCCTGGGAATGCT
GATGATCTGCTCCGCCGCCGAGCAGCTGTGGGTCACCGTCTACTACGGCGTGCCTGTGTGGAAGGAGGCCA
CGACCACCCTCTTCTGCGCGAGCGACGCCAAGGCCTACGACACGGAAGTGCATAACGTGTGGGCGACGCAT
GCTTGCGTGCCTACGGACCCCAACCCCCAGGAGGTGGTGCTGGGAAACGTGACCGAGTACTTCAACATGTG
GAAGAATAACATGGTGGATCAGATGCACGAGGACATCATCTCTCTGTGGGACCAGTCCCTGAAGCCCTGCG
TGAAGCTGACGCCTCTCTGCGTGACACTGGACTGTGACGACGTCAACACCACCAACAGCACTACCACCACC
AGCAACGGCTGGACCGGAGAGATTCGGAAGGGCGAGATCAAGAACTGCTCCTTCAATATCACGACCTCGAT
CAGAGACAAGGTGCAGAAGGAATACGCGCTGTTTTATAATCTCGATGTGGTCCCCATCGACGACGACAATG
CCACCACCAAGAACAAGACGACGCGTAATTTCAGACTCATTCACTGCAACAGCAGCGTCATGACGCAGGCC
TGCCCCAAGGTGTCCTTCGAACCAATCCCGATCCATTACTGTGCCCCTGCCGGATTCGCGATCCTCAAGTG
TAACAACAAGACCTTCGACGGGAAGGGCCTGTGCACCAACGTCAGCACGGTGCAGTGCACCCATGGCATCC

Figure 2 continued

```
GCCCCGTCGTGAGCACCCAGCTGCTGCTGAACGGGTCCCTGGCTGAGGAGGAGGTGGTGATCCGGTCGGAC
AACTTCATGGACAACACCAAGACAATCATCGTCCAGCTGAACGAGTCTGTGGCGATTAACTGTACCCGGCC
TAACAACAACACCCGTAAGGGCATCCACATCGGGCCTGGACGGGCCTTCTATGCCGCCCGCAAGATCATCG
GCGACATCCGGCAGGCCCATTGCAACCTCTCCCGCGCCCAGTGGAATAACACCCTGAAGCAGATCGTGATC
AAGCTGAGAGAGCACTTTGGAAACAAGACCATCAAGTTCAATCAGAGTTCTGGCGGAGACCCCGAGATCGT
GCGGCACTCCTTCAACTGCGGGGCGAGTTCTTCTACTGCGATACGACACAGCTCTTCAACTCCACCTGGA
ACGGCACCGAGGGCAACAACACAGAGGGAAACTCCACTATCACCCTCCCTTGCCGCATCAAGCAGATCATC
AACATGTGGCAGGAGGTGGGAAAGGCCATGTATGCCCCCCCCATCGGGGCCAGATCCGCTGCTCCTCCAA
CATCACCGGCCTGCTGCTCACCAGAGACGGGGGCACCGAGGGCAACGGCACGGAGAACGAGACGGAGATCT
TCAGGCCCGGCGGCGGCGACATGAGGGATAACTGGCGGAGCGAGCTGTACAAGTACAAGGTGGTGAAGGTG
GAGCCGCTCGGCGTGGCCCCCACCCGGGCCAAGCGCCGCGTCGTGCAGAGATGA [SEQ ID NO: 50]
```

Map of pRix15244:

Figure 4

Plasmid pNTm:

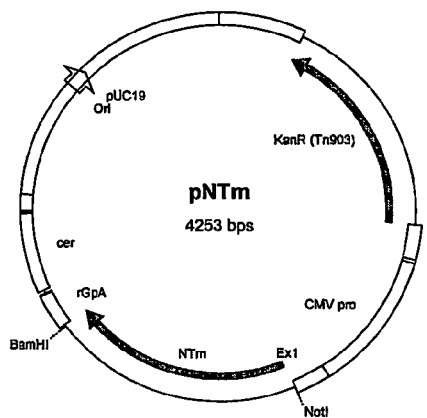

Sequence of insert:

ATGGGTGGCAAGTGGTCAAAAAGTAGTGTGGTTGGATGGCCTACTGTAAGGGAAAGAATGAGACGAGCTGA
GCCAGCAGCAGATGGGGTGGGAGCAGCATCTCGAGACCTGGAAAAACATGGAGCAATCACAAGTAGCAATA
CAGCAGCTACCAATGCTGCTTGTGCCTGGCTAGAAGCACAAGAGGAGGAGGAGGTGGGTTTTCCAGTCACA
CCTCAGGTACCTTTAAGACCAATGACTTACAAGGCAGCTGTAGATCTTAGCCACTTTTTAAAAGAAAAGGG
GGGACTGGAAGGGCTAATTCACTCCCAACGAAGACAAGATATCCTTGATCTGTGGATCTACCACACACAAG
GCTACTTCCCTGATTGGCAGAACTACACACCAGGGCCAGGGGTCAGATATCCACTGACCTTTGGATGGTGC
TACAAGCTAGTACCAGTTGAGCCAGATAAGGTAGAAGAGGCCAATAAAGGAGAGAACACCAGCTTGTTACA
CCCTGTGAGCCTGCATGGAATGGATGACCCTGAGAGAGAAGTGTTAGAGTGGAGGTTTGACAGCCGCCTAG
CATTTCATCACGTGGCCCGAGAGCTGCATCCGGAGTACTTCAAGAACTGCACTAGTGAGCCAGTAGATCCT
AGACTAGAGCCCTGGAAGCATCCAGGAAGTCAGCCTAAAACTGCTTGTACCAATTGCTATTGTAAAAAGTG
TTGCTTTCATTGCCAAGTTTGTTTCATAACAGCTGCCTTAGGCATCTCCTATGGCAGGAAGAAGCGGAGAC
AGCGACGAAGACCTCCTCAAGGCAGTCAGACTCATCAAGTTTCTCTATCAAAGCAACCCACCTCCCAATCC
AAAGGGGAGCCGACAGGCCCGAAGGAATAA [SEQ ID NO: 51]

Amino acid sequence of antigen:

MGGKWSKSSVVGWPTVRERMRRAEPAADGVGAASRDLEKHGAITSSNTAATNAACAWLEAQEE
EEVGFPVTPQVPLRPMTYKAAVDLSHFLKEKGGLEGLIHSQRRQDILDLWIYHTQGYFPDWQNYT
PGPGVRYPLTFGWCYKLVPVEPDKVEEANKGENTSLLHPVSLHGMDDPEREVLEWRFDSRLAFH
HVARELHPEYFKNCTSEPVDPRLEPWKHPGSQPKTACTNCYCKKCCFHCQVCFITAALGISYGRK
KRRQRRRPPQGSQTHQVSLSKQPTSQSKGEPTGPKE [SEQ ID NO: 52]

Figure 5

Plasmid ptrNTm:

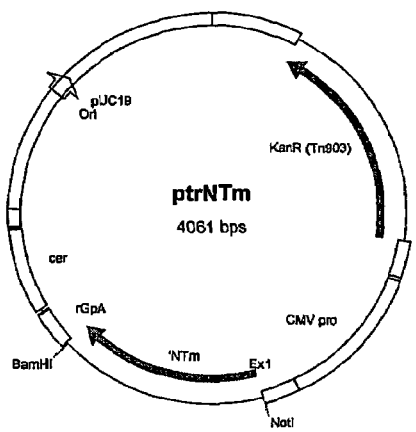

Sequence of insert:

ATGGTGGGTTTTCCAGTCACACCTCAGGTACCTTTAAGACCAATGACTTACAAGGCAGCTGTAGATCTTAG
CCACTTTTTAAAAGAAAAGGGGGGACTGGAAGGGCTAATTCACTCCCAACGAAGACAAGATATCCTTGATC
TGTGGATCTACCACACACAAGGCTACTTCCCTGATTGGCAGAACTACACACCAGGGCCAGGGGTCAGATAT
CCACTGACCTTTGGATGGTGCTACAAGCTAGTACCAGTTGAGCCAGATAAGGTAGAAGAGGCCAATAAAGG
AGAGAACACCAGCTTGTTACACCCTGTGAGCCTGCATGGAATGGATGACCCTGAGAGAGAAGTGTTAGAGT
GGAGGTTTGACAGCCGCCTAGCATTTCATCACGTGGCCCGAGAGCTGCATCCGGAGTACTTCAAGAACTGC
ACTAGTGAGCCAGTAGATCCTAGACTAGAGCCCTGGAAGCATCCAGGAAGTCAGCCTAAAACTGCTTGTAC
CAATTGCTATTGTAAAAAGTGTTGCTTTCATTGCCAAGTTTGTTTCATAACAGCTGCCTTAGGCATCTCCT
ATGGCAGGAAGAAGCGGAGACAGCGACGAAGACCTCCTCAAGGCAGTCAGACTCATCAAGTTTCTCTATCA
AAGCAACCCACCTCCCAATCCAAAGGGGAGCCGACAGGCCCGAAGGAATAA [SEQ ID NO: 53]

Amino acid sequence of antigen:

MVGFPVTPQVPLRPMTYKAAVDLSHFLKEKGGLEGLIHSQRRQDILDLWIYHTQGYFPDWQNYTPGPGVRY
PLTFGWCYKLVPVEPDKVEEANKGENTSLLHPVSLHGMDDPEREVLEWRFDSRLAFHHVARELHPEYFKNC
TSEPVDPRLEPWKHPGSQPKTACTNCYCKKCCFHCQVCFITAALGISYGRKKRRQRRRPPQGSQTHQVSLS
KQPTSQSKGEPTGPKE [SEQ ID NO: 54]

Figure 6

Plasmid pRix12:

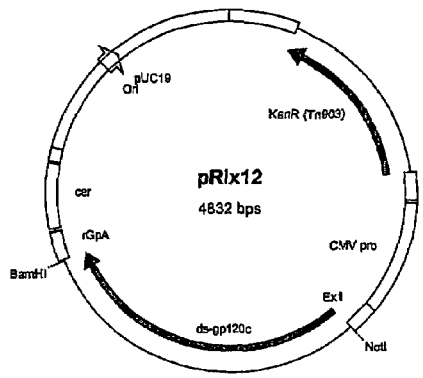

Sequence of insert:

```
ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGATGA [SEQ ID NO: 55]
```

Amino acid sequence of antigen:

```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQR       [SEQ  ID
NO: 56]
```

Figure 7

Plasmid pRix28:

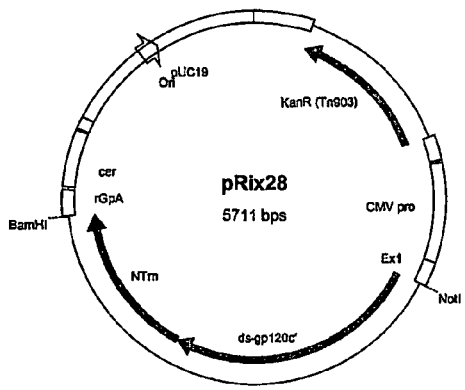

Sequence of insert:

ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCAGGCGGCAGTGCACCCATGGCATCCGCCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGTGGCAAGTGGTCAAAAAGTAGTGTGGTT
GGATGGCCTACTGTAAGGGAAAGAATGAGACGAGCTGAGCCAGCAGCAGATGGGGTGGGAGCAGCATCTCG
AGACCTGGAAAAACATGGAGCAATCACAAGTAGCAATACAGCAGCTACCAATGCTGCTTGTGCCTGGCTAG
AAGCACAAGAGGAGGAGGAGGTGGGTTTTCCAGTCACACCTCAGGTACCTTTAAGACCAATGACTTACAAG
GCAGCTGTAGATCTTAGCCACTTTTTAAAAGAAAAGGGGGGACTGGAAGGGCTAATTCACTCCCAACGAAG
ACAAGATATCCTTGATCTGTGGATCTACCACACACAAGGCTACTTCCCTGATTGGCAGAACTACACACCAG
GGCCAGGGGTCAGATATCCACTGACCTTTGGATGGTGCTACAAGCTAGTACCAGTTGAGCCAGATAAGGTA
GAAGAGGCCAATAAAGGAGAGAACACCAGCTTGTTACACCCTGTGAGCCTGCATGGAATGGATGACCCTGA
GAGAGAAGTGTTAGAGTGGAGGTTTGACAGCCGCCTAGCATTTCATCACGTGGCCCGAGAGCTGCATCCGG
AGTACTTCAAGAACTGCACTAGTGAGCCAGTAGATCCTAGACTAGAGCCCTGGAAGCATCCAGGAAGTCAG

Figure 7 continued

CCTAAAACTGCTTGTACCAATTGCTATTGTAAAAAGTGTTGCTTTCATTGCCAAGTTTGTTTCATAACAGC
TGCCTTAGGCATCTCCTATGGCAGGAAGAAGCGGAGACAGCGACGAAGACCTCCTCAAGGCAGTCAGACTC
ATCAAGTTTCTCTATCAAAGCAACCCACCTCCCAATCCAAAGGGGAGCCGACAGGCCCGAAGGAATAA

[SEQ ID NO: 57]

Amino acid sequence of antigen:

MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGGKWSKSSVV
GWPTVRERMRRAEPAADGVGAASRDLEKHGAITSSNTAATNAACAWLEAQEEEEVGFPVTPQVPLRPMTYK
AAVDLSHFLKEKGGLEGLIHSQRRQDILDLWIYHTQGYFPDWQNYTPGPGVRYPLTFGWCYKLVPVEPDKV
EEANKGENTSLLHPVSLHGMDDPEREVLEWRFDSRLAFHHVARELHPEYFKNCTSEPVDPRLEPWKHPGSQ
PKTACTNCYCKKCCFHCQVCFITAALGISYGRKKRRQRRRPPQGSQTHQVSLSKQPTSQSKGEPTGPKE
[SEQ ID NO: 58]

Figure 8

Plasmid pRix29:

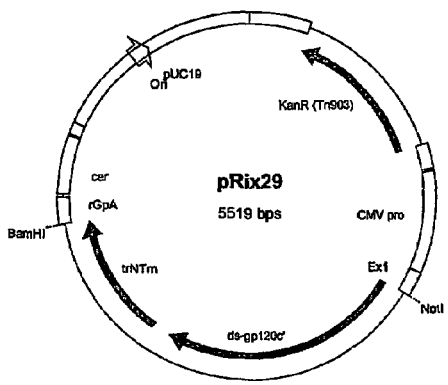

Sequence of insert:

ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGTGGGTTTTCCAGTCACACCTCAGGTACCT
TTAAGACCAATGACTTACAAGGCAGCTGTAGATCTTAGCCACTTTTTAAAAGAAAAGGGGGGACTGGAAGG
GCTAATTCACTCCCAACGAAGACAAGATATCCTTGATCTGTGGATCTACCACACACAAGGCTACTTCCCTG
ATTGGCAGAACTACACACCAGGGCCAGGGGTCAGATATCCACTGACCTTTGGATGGTGCTACAAGCTAGTA
CCAGTTGAGCCAGATAAGGTAGAAGAGGCCAATAAAGGAGAGAACACCAGCTTGTTACACCCTGTGAGCCT
GCATGGAATGGATGACCCTGAGAGAGAAGTGTTAGAGTGGAGGTTTGACAGCCGCCTAGCATTTCATCACG
TGGCCCGAGAGCTGCATCCGGAGTACTTCAAGAACTGCACTAGTGAGCCAGTAGATCCTAGACTAGAGCCC
TGGAAGCATCCAGGAAGTCAGCCTAAAACTGCTTGTACCAATTGCTATTGTAAAAAGTGTTGCTTTCATTG
CCAAGTTTGTTTCATAACAGCTGCCTTAGGCATCTCCTATGGCAGGAAGAAGCGGAGACAGCGACGAAGAC
CTCCTCAAGGCAGTCAGACTCATCAAGTTTCTCTATCAAAGCAACCCACCTCCCAATCCAAAGGGGAGCCG
ACAGGCCCGAAGGAATAA [SEQ ID NO: 59]

Figure 8 continued

Amino acid sequence of antigen:

MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMVGFPVTPQVP
LRPMTYKAAVDLSHFLKEKGGLEGLIHSQRRQDILDLWIYHTQGYFPDWQNYTPGPGVRYPLTFGWCYKLV
PVEPDKVEEANKGENTSLLHPVSLHGMDDPEREVLEWRFDSRLAFHHVARELHPEYFKNCTSEPVDPRLEP
WKHPGSQPKTACTNCYCKKCCFHCQVCFITAALGISYGRKKRRQRRRPPQGSQTHQVSLSKQPTSQSKGEP
TGPKE [SEQ ID NO: 60]

Figure 9

Plasmid pRix31:

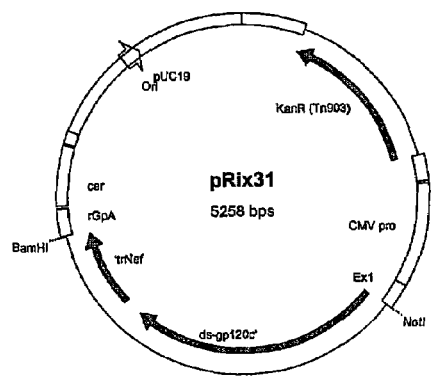

Sequence of insert:

ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGTGGGTTTTCCAGTCACACCTCAGGTACCT
TTAAGACCAATGACTTACAAGGCAGCTGTAGATCTTAGCCACTTTTTAAAAGAAAAGGGGGGACTGGAAGG
GCTAATTCACTCCCAACGAAGACAAGATATCCTTGATCTGTGGATCTACCACACACAAGGCTACTTCCCTG
ATTGGCAGAACTACACACCAGGGCCAGGGGTCAGATATCCACTGACCTTTGGATGGTGCTACAAGCTAGTA
CCAGTTGAGCCAGATAAGGTAGAAGAGGCCAATAAAGGAGAGAACACCAGCTTGTTACACCCTGTGAGCCT
GCATGGAATGGATGACCCTGAGAGAGAAGTGTTAGAGTGGAGGTTTGACAGCCGCCTAGCATTTCATCACG
TGGCCCGAGAGCTGCATCCGGAGTACTTCAAGAACTGCTAA [SEQ ID NO: 61]

Amino acid sequence of antigen:

Figure 9 continued

```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMVGFPVTPQVP
LRPMTYKAAVDLSHFLKEKGGLEGLIHSQRRQDILDLWIYHTQGYFPDWQNYTPGPGVRYPLTFGWCYKLV
PVEPDKVEEANKGENTSLLHPVSLHGMDDPEREVLEWRFDSRLAFHHVARELHPEYFKNC
[SEQ ID NO: 62]
```

Figure 10

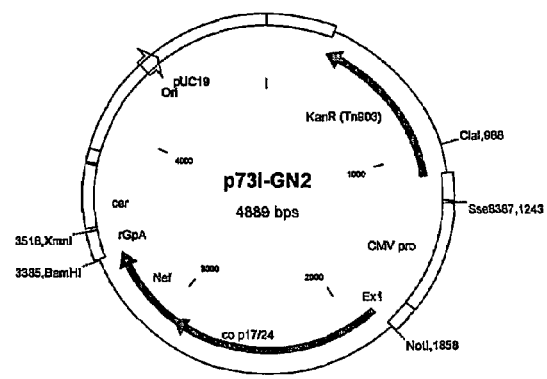

Sequence of insert:

TGGGTGCCCGAGCTTCGGTACTGTCTGGTGGAGAGCTGGACAGATGGGAGAAAATTAGGCTGCGCCCGGGA
GGCAAAAAGAAATACAAGCTCAAGCATATCGTGTGGGCCTCGAGGGAGCTTGAACGGTTTGCCGTGAACCC
AGGCCTGCTGGAAACATCTGAGGGATGTCGCCAGATCCTGGGCAATTGCAGCCATCCCTCCAGACCGGGA
GTGAAGAGCTGAGGTCCTTGTATAACACAGTGGCTACCCTCTACTGCGTACACCAGAGGATCGAGATTAAG
GATACCAAGGAGGCCTTGGACAAAATTGAGGAGGAGCAAAACAAGAGCAAGAAGAAGGCCCAGCAGGCAGC
TGCTGACACTGGGCATAGCAACCAGGTATCACAGAACTATCCTATTGTCCAAAACATTCAGGGCCAGATGG
TTCATCAGGCCATCAGCCCCGGACGCTCAATGCCTGGGTGAAGGTTGTCGAAGAGAAGGCCTTTTCTCCT
GAGGTTATCCCCATGTTCTCCGCTTTGAGTGAGGGGCCACTCCTCAGGACCTCAATACAATGCTTAATAC
CGTGGGCGGCCATCAGGCCGCCATGCAAATGTTGAAGGAGACTATCAACGAGGAGGCAGCCGAGTGGGACA
GAGTGCATCCCGTCCACGCTGGCCCAATCGCGCCCGGACAGATGCGGGAGCCTCGCGGCTCTGACATTGCC
GGCACCACCTCTACACTGCAAGAGCAAATCGGATGGATGACCAACAATCCTCCCATCCCAGTTGGAGAAAT
CTATAAACGGTGGATCATTCTCGGTCTCAATAAAATTGTTAGAATGTACTCTCCGACATCCATCCTTGACA
TTAGACAGGGACCCAAAGAGCCTTTTAGGGATTACGTCGACCGGTTTTATAAGACCCTGCGAGCAGAGCAG
GCCTCTCAGGAGGTCAAAAACTGGATGACGGAGACACTCCTGGTACAGAACGCTAACCCCGACTGCAAAAC
AATCTTGAAGGCACTAGGCCCGGCTGCCACCCTGGAAGAGATGATGACCGCCTGTCAGGGAGTAGGCGGAC
CCGGACACAAAGCCAGAGTGTTG*ATGGTGGGTTTTCCAGTCACACCTCAGGTACCTTTAAGACCAATGAC
TTACAAGGCAGCTGTAGATCTTAGCCACTTTTTAAAAGAAAAGGGGGACTGGAAGGGCTAATTCACTCCC
AAAGAAGACAAGATATCCTTGATCTGTGGATCTACCACACACAAGGCTACTTCCCTGATTGGCAGAACTAC
ACACCAGGGCCAGGGGTCAGATATCCACTGACCTTTGGATGGTGCTACAAGCTAGTACCAGTTGAGCCAGA
TAAGGTAGAAGAGGCCAATAAAGGAGAGAACACCAGCTTGTTACACCCTGTGAGCCTGCATGGGATGGATG
ACCCGGAGAGAGAAGTGTTAGAGTGGAGGTTTGACAGCCGCCTAGCATTTCATCACGTGGCCCGAGAGCTG
CATCCGGAGTACTTCAAGAACTGCTGA [SEQ ID NO: 63]

Figure 11

Plasmid pRix33:

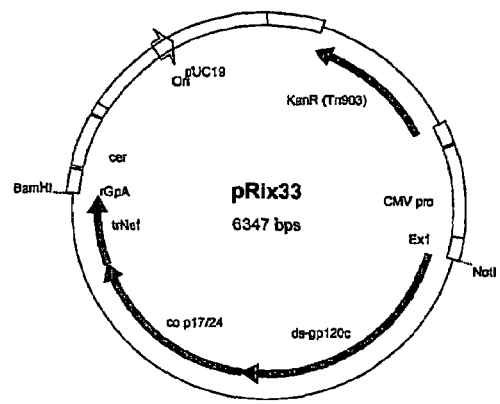

Sequence of insert:

ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGTGCCCGAGCTTCGGTACTGTCTGGTGGA
GAGCTGGACAGATGGGAGAAAATTAGGCTGCGCCCGGGAGGCAAAAAGAAATACAAGCTCAAGCATATCGT
GTGGGCCTCGAGGGAGCTTGAACGGTTTGCCGTGAACCCAGGCCTGCTGGAAACATCTGAGGGATGTCGCC
AGATCCTGGGGCAATTGCAGCCATCCCTCCAGACCGGGAGTGAAGAGCTGAGGTCCTTGTATAACACAGTG
GCTACCCTCTACTGCGTACACCAGAGGATCGAGATTAAGGATACCAAGGAGGCCTTGGACAAAATTGAGGA
GGAGCAAAACAAGAGCAAGAAGAAGGCCCAGCAGGCAGCTGCTGACACTGGGCATAGCAACCAGGTATCAC
AGAACTATCCTATTGTCCAAAACATTCAGGGCCAGATGGTTCATCAGGCCATCAGCCCCCGGACGCTCAAT
GCCTGGGTGAAGGTTGTCGAAGAGAAGGCCTTTTCTCCTGAGGTTATCCCCATGTTCTCCGCTTTGAGTGA
GGGGGCCACTCCTCAGGACCTCAATACAATGCTTAATACCGTGGGCGGCCATCAGGCCGCCATGCAAATGT
TGAAGGAGACTATCAACGAGGAGGCAGCCGAGTGGGACAGAGTGCATCCCGTCCACGCTGGCCCAATCGCG
CCCGGACAGATGCGGGAGCCTCGCGGCTCTGACATTGCCGGCACCACCTCTACACTGCAAGAGCAAATCGG

Figure 11 continued

```
ATGGATGACCAACAATCCTCCCATCCCAGTTGGAGAAATCTATAAACGGTGGATCATTCTCGGTCTCAATA
AAATTGTTAGAATGTACTCTCCGACATCCATCCTTGACATTAGACAGGGACCCAAAGAGCCTTTTAGGGAT
TACGTCGACCGGTTTTATAAGACCCTGCGAGCAGAGCAGGCCTCTCAGGAGGTCAAAAACTGGATGACGGA
GACACTCCTGGTACAGAACGCTAACCCCGACTGCAAAACAATCTTGAAGGCACTAGGCCCGGCTGCCACCC
TGGAAGAGATGATGACCGCCTGTCAGGGAGTAGGCGGACCCGGACACAAAGCCAGAGTGTTGATGGTGGGT
TTTCCAGTCACACCTCAGGTACCTTTAAGACCAATGACTTACAAGGCAGCTGTAGATCTTAGCCACTTTTT
AAAAGAAAAGGGGGGACTGGAAGGGCTAATTCACTCCCAACGAAGACAAGATATCCTTGATCTGTGGATCT
ACCACACACAAGGCTACTTCCCTGATTGGCAGAACTACACACCAGGGCCAGGGGTCAGATATCCACTGACC
TTTGGATGGTGCTACAAGCTAGTACCAGTTGAGCCAGATAAGGTAGAAGAGGCCAATAAAGGAGAGAACAC
CAGCTTGTTACACCCTGTGAGCCTGCATGGAATGGATGACCCTGAGAGAGAAGTGTTAGAGTGGAGGTTTG
ACAGCCGCCTAGCATTTCATCACGTGGCCCGAGAGCTGCATCCGGAGTACTTCAAGAACTGCTAA
```
[SEQ ID NO: 64]

Amino acid sequence of antigen:

```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGARASVLSGG
ELDRWEKIRLRPGGKKKYKLKHIVWASRELERFAVNPGLLETSEGCRQILGQLQPSLQTGSEELRSLYNTV
ATLYCVHQRIEIKDTKEALDKIEEEQNKSKKKAQQAAADTGHSNQVSQNYPIVQNIQGQMVHQAISPRTLN
AWVKVVEEKAFSPEVIPMFSALSEGATPQDLNTMLNTVGGHQAAMQMLKETINEEAAEWDRVHPVHAGPIA
PGQMREPRGSDIAGTTSTLQEQIGWMTNNPPIPVGEIYKRWIILGLNKIVRMYSPTSILDIRQGPKEPFRD
YVDRFYKTLRAEQASQEVKNWMTETLLVQNANPDCKTILKALGPAATLEEMMTACQGVGGPGHKARVLMVG
FPVTPQVPLRPMTYKAAVDLSHFLKEKGGLEGLIHSQRRQDILDLWIYHTQGYFPDWQNYTPGPGVRYPLT
FGWCYKLVPVEPDKVEEANKGENTSLLHPVSLHGMDDPEREVLEWRFDSRLAFHHVARELHPEYFKNC
```

[SEQ ID NO: 65]

Figure 12

Plasmid pRix35:

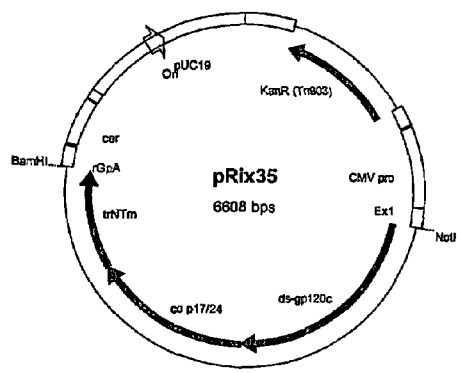

Sequence of insert

ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGTGCCCGAGCTTCGGTACTGTCTGGTGGA
GAGCTGGACAGATGGGAGAAAATTAGGCTGCGCCCGGGAGGCAAAAAGAAATACAAGCTCAAGCATATCGT
GTGGGCCTCGAGGGAGCTTGAACGGTTTGCCGTGAACCCAGGCCTGCTGGAAACATCTGAGGGATGTCGCC
AGATCCTGGGCAATTGCAGCCATCCCTCCAGACCGGGAGTGAAGACTGAGGTCCTTGTATAACACAGTG
GCTACCCTCTACTGCGTACACCAGAGGATCGAGATTAAGGATACCAAGGAGGCCTTGGACAAAATTGAGGA
GGAGCAAAACAAGAGCAAGAAGAAGGCCCAGCAGGCAGCTGCTGACACTGGGCATAGCAACCAGGTATCAC
AGAACTATCCTATTGTCCAAAACATTCAGGGCCAGATGGTTCATCAGGCCATCAGCCCCGGACGCTCAAT
GCCTGGGTGAAGGTTGTCGAAGAGAAGGCCTTTTTCTCCTGAGGTTATCCCCATGTTCTCCGCTTTGAGTGA
GGGGGCCACTCCTCAGGACCTCAATACAATGCTTAATACCGTGGGCGGCCATCAGGCCGCCATGCAAATGT
TGAAGGAGACTATCAACGAGGAGGCAGCCGAGTGGGACAGAGTGCATCCCGTCCACGCTGGCCCAATCGCG
CCCGGACAGATGCGGGAGCCTCGCGGCTCTGACATTGCCGGCACCACCTCTACACTGCAAGAGCAAATCGG

Figure 12 continued

ATGGATGACCAACAATCCTCCCATCCCAGTTGGAGAAATCTATAAACGGTGGATCATTCTCGGTCTCAATA
AAATTGTTAGAATGTACTCTCCGACATCCATCCTTGACATTAGACAGGGACCCAAAGAGCCTTTTAGGGAT
TACGTCGACCGGTTTTATAAGACCCTGCGAGCAGAGCAGGCCTCTCAGGAGGTCAAAAACTGGATGACGGA
GACACTCCTGGTACAGAACGCTAACCCCGACTGCAAAACAATCTTGAAGGCACTAGGCCCGGCTGCCACCC
TGGAAGAGATGATGACCGCCTGTCAGGGAGTAGGCGGACCCGGACACAAAGCCAGAGTGTTGATGGTGGGT
TTTCCAGTCACACCTCAGGTACCTTTAAGACCAATGACTTACAAGGCAGCTGTAGATCTTAGCCACTTTTT
AAAAGAAAAGGGGGGACTGGAAGGGCTAATTCACTCCCAACGAAGACAAGATATCCTTGATCTGTGGATCT
ACCACACACAAGGCTACTTCCCTGATTGGCAGAACTACACACCAGGGCCAGGGGTCAGATATCCACTGACC
TTTGGATGGTGCTACAAGCTAGTACCAGTTGAGCCAGATAAGGTAGAAGAGGCCAATAAAGGAGAGAACAC
CAGCTTGTTACACCCTGTGAGCCTGCATGGAATGGATGACCCTGAGAGAGAAGTGTTAGAGTGGAGGTTTG
ACAGCCGCCTAGCATTTCATCACGTGGCCCGAGAGCTGCATCCGGAGTACTTCAAGAACTGCACTAGTGAG
CCAGTAGATCCTAGACTAGAGCCCTGGAAGCATCCAGGAAGTCAGCCTAAAACTGCTTGTACCAATTGCTA
TTGTAAAAAGTGTTGCTTTCATTGCCAAGTTTGTTTCATAACAGCTGCCTTAGGCATCTCCTATGGCAGGA
AGAAGCGGAGACAGCGACGAAGACCTCCTCAAGGCAGTCAGACTCATCAAGTTTCTCTATCAAAGCAACCC
ACCTCCCAATCCAAAGGGGAGCCGACAGGCCCGAAGGAATAA [SEQ ID NO: 66]

Amino acid sequence of antigen:

MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGARASVLSGG
ELDRWEKIRLRPGGKKKYKLKHIVWASRELERFAVNPGLLETSEGCRQILGQLQPSLQTGSEELRSLYNTV
ATLYCVHQRIEIKDTKEALDKIEEEQNKSKKKAQQAAADTGHSNQVSQNYPIVQNIQGQMVHQAISPRTLN
AWVKVVEEKAFSPEVIPMFSALSEGATPQDLNTMLNTVGGHQAAMQMLKETINEEAAEWDRVHPVHAGPIA
PGQMREPRGSDIAGTTSTLQEQIGWMTNNPPIPVGEIYKRWIILGLNKIVRMYSPTSILDIRQGPKEPFRD
YVDRFYKTLRAEQASQEVKNWMTETLLVQNANPDCKTILKALGPAATLEEMMTACQGVGGPGHKARVLMVG
FPVTPQVPLRPMTYKAAVDLSHFLKEKGGLEGLIHSQRRQDILDLWIYHTQGYFPDWQNYTPGPGVRYPLT
FGWCYKLVPVEPDKVEEANKGENTSLLHPVSLHGMDDPEREVLEWRFDSRLAFHHVARELHPEYFKNCTSE
PVDPRLEPWKHPGSQPKTACTNCYCKKCCFHCQVCFITAALGISYGRKKRRQRRRPPQGSQTHQVSLSKQP
TSQSKGEPTGPKE [SEQ ID NO: 67]

Figure 13

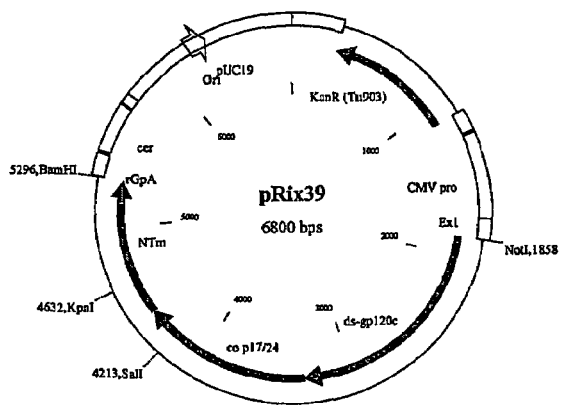

Sequence of insert:

ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGTGCCCGAGCTTCGGTACTGTCTGGTGGA
GAGCTGGACAGATGGGAGAAAATTAGGCTGCGCCCGGGAGGCAAAAAGAAATACAAGCTCAAGCATATCGT
GTGGGCCTCGAGGGAGCTTGAACGGTTTGCCGTGAACCCAGGCCTGCTGGAAACATCTGAGGGATGTCGCC
AGATCCTGGGGCAATTGCAGCCATCCCTCCAGACCGGGAGTGAAGAGCTGAGGTCCTTGTATAACACAGTG
GCTACCCTCTACTGCGTACACCAGAGGATCGAGATTAAGGATACCAAGGAGGCCTTGGACAAAATTGAGGA
GGAGCAAAACAAGAGCAAGAAGAAGGCCCAGCAGGCAGCTGCTGACACTGGGCATAGCAACCAGGTATCAC
AGAACTATCCTATTGTCCAAAACATTCAGGGCCAGATGGTTCATCAGGCCATCAGCCCCGGACGCTCAAT
GCCTGGGTGAAGGTTGTCGAAGAGAAGGCCTTTTCTCCTGAGGTTATCCCCATGTTCTCCGCTTTGAGTGA
GGGGGCCACTCCTCAGGACCTCAATACAATGCTTAATACCGTGGGCGGCCATCAGGCCGCCATGCAAATGT
TGAAGGAGACTATCAACGAGGAGGCAGCCGAGTGGGACAGAGTGCATCCCGTCCACGCTGGCCCAATCGCG
CCCGGACAGATGCGGGAGCCTCGCGGCTCTGACATTGCCGGCACCACCTCTACACTGCAAGAGCAAATCGG
ATGGATGACCAACAATCCTCCCATCCCAGTTGGAGAAATCTATAAACGGTGGATCATTCTCGGTCTCAATA
AAATTGTTAGAATGTACTCTCCGACATCCATCCTTGACATTAGACAGGGACCCAAAGAGCCTTTTAGGGAT

Figure 13 continued

```
TACGTCGACCGGTTTTATAAGACCCTGCGAGCAGAGCAGGCCTCTCAGGAGGTCAAAAACTGGATGACGGA
GACACTCCTGGTACAGAACGCTAACCCCGACTGCAAAACAATCTTGAAGGCACTAGGCCCGGCTGCCACCC
TGGAAGAGATGATGACCGCCTGTCAGGGAGTAGGCGGACCCGGACACAAAGCCAGAGTGTTGATGGGTGGC
AAGTGGTCAAAAAGTAGTGTGGTTGGATGGCCTACTGTAAGGGAAAGAATGAGACGAGCTGAGCCAGCAGC
AGATGGGGTGGGAGCAGCATCTCGAGACCTGGAAACACACAGTAGCAATACAGCAGCTA
CCAATGCTGCTTGTGCCTGGCTAGAAGCACAAGAGGAGGAGGAGGTGGGTTTTCCAGTCACACCTCAGGTA
CCTTTAAGACCAATGACTTACAAGGCAGCTGTAGATCTTAGCCACTTTTTAAAAGAAAAGGGGGGACTGGA
AGGGCTAATTCACTCCCAACGAAGACAAGATATCCTTGATCTGTGGATCTACCACACACAAGGCTACTTCC
CTGATTGGCAGAACTACACACCAGGGCCAGGGGTCAGATATCCACTGACCTTTGGATGGTGCTACAAGCTA
GTACCAGTTGAGCCAGATAAGGTAGAAGAGGCCAATAAAGGAGAGAACACCAGCTTGTTACACCCTGTGAG
CCTGCATGGAATGGATGACCCTGAGAGAGAAGTGTTAGAGTGGAGGTTTGACAGCCGCCTAGCATTTCATC
ACGTGGCCCGAGAGCTGCATCCGGAGTACTTCAAGAACTGCACTAGTGAGCCAGTAGATCCTAGACTAGAG
CCCTGGAAGCATCCAGGAAGTCAGCCTAAAACTGCTTGTACCAATTGCTATTGTAAAAAGTGTTGCTTTCA
TTGCCAAGTTTGTTTCATAACAGCTGCCTTAGGCATCTCCTATGGCAGGAAGAAGCGGAGACAGCGACGAA
GACCTCCTCAAGGCAGTCAGACTCATCAAGTTTCTCTATCAAAGCAACCCACCTCCCAATCCAAAGGGGAG
CCGACAGGCCCGAAGGAATAA [SEQ ID NO: 68]
```

Amino acid sequence of antigen:

```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGARASVLSGG
ELDRWEKIRLRPGGKKKYKLKHIVWASRELERFAVNPGLLETSEGCRQILGQLQPSLQTGSEELRSLYNTV
ATLYCVHQRIEIKDTKEALDKIEEEQNKSKKKAQQAAADTGHSNQVSQNYPIVQNIQGQMVHQAISPRTLN
AWVKVVEEKAFSPEVIPMFSALSEGATPQDLNTMLNTVGGHQAAMQMLKETINEEAAEWDRVHPVHAGPIA
PGQMREPRGSDIAGTTSTLQEQIGWMTNNPPIPVGEIYKRWIILGLNKIVRMYSPTSILDIRQGPKEPFRD
YVDRFYKTLRAEQASQEVKNWMTETLLVQNANPDCKTILKALGPAATLEEMMTACQGVGGPGHKARVLMGG
KWSKSSVVGWPTVRERMRRAEPAADGVGAASRDLEKHGAITSSNTAATNAACAWLEAQEEEEVGFPVTPQV
PLRPMTYKAAVDLSHFLKEKGGLEGLIHSQRRQDILDLWIYHTQGYFPDWQNYTPGPGVRYPLTFGWCYKL
VPVEPDKVEEANKGENTSLLHPVSLHGMDDPEREVLEWRFDSRLAFHHVARELHPEYFKNCTSEPVDPRLE
PWKHPGSQPKTACTNCYCKKCCFHCQVCFITAALGISYGRKKRRQRRRPPQGSQTHQVSLSKQPTSQSKGE
PTGPKE [SEQ ID NO: 69]
```

Figure 14 pRix40

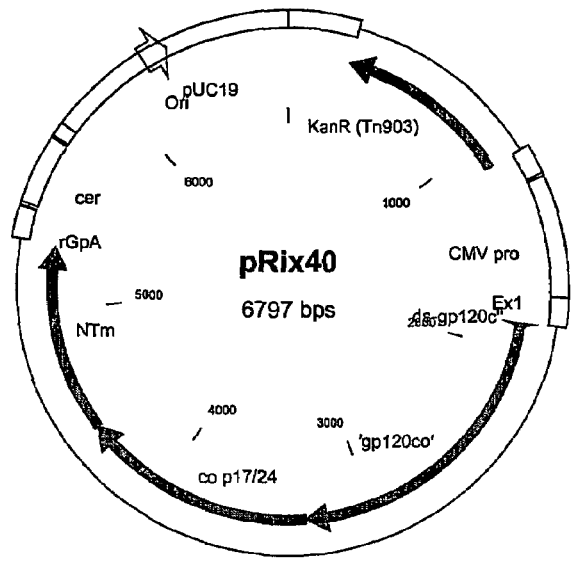

DNA sequence of insert
ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGTGCCCGAGCTTCGGTACTGTCTGGTGGA
GAGCTGGACAGATGGGAGAAAATTAGGCTGCGCCCGGGAGGCAAAAAGAAATACAAGCTCAAGCATATCGT
GTGGGCCTCGAGGGAGCTTGAACGGTTTGCCGTGAACCCAGGCCTGCTGGAAACATCTGAGGGATGTCGCC
AGATCCTGGGGCAATTGCAGCCATCCCTCCAGACCGGGAGTGAAGAGCTGAGGTCCTTGTATAACACAGTG
GCTACCCTCTACTGCGTACACCAGAGGATCGAGATTAAGGATACCAAGGAGGCCTTGGACAAAATTGAGGA
GGAGCAAAACAAGAGCAAGAAGAAGGCCCAGCAGGCAGCTGCTGACACTGGGCATAGCAACCAGGTATCAC
AGAACTATCCTATTGTCCAAAACATTCAGGGCCAGATGGTTCATCAGGCCATCAGCCCCGGACGCTCAAT
GCCTGGGTGAAGGTTGTCGAAGAGAAGGCCTTTTCTCCTGAGGTTATCCCCATGTTCTCCGCTTTGAGTGA
GGGGGCCACTCCTCAGGACCTCAATACAATGCTTAATACCGTGGGCGGCCATCAGGCCGCCATGCAAATGT
TGAAGGAGACTATCAACGAGGAGGCAGCCGAGTGGGACAGAGTGCATCCCGTCCACGCTGGCCCAATCGCG

Figure 14 continued

```
CCCGGACAGATGCGGGAGCCTCGCGGCTCTGACATTGCCGGCACCACCTCTACACTGCAAGAGCAAATCGG
ATGGATGACCAACAATCCTCCCATCCCAGTTGGAGAAATCTATAAACGGTGGATCATTCTCGGTCTCAATA
AAATTGTTAGAATGTACTCTCCGACATCCATCCTTGACATTAGACAGGGACCCAAAGAGCCTTTTAGGGAT
TACGTCGACCGGTTTTATAAGACCCTGCGAGCAGAGCAGGCCTCTCAGGAGGTCAAAAACTGGATGACGGA
GACACTCCTGGTACAGAACGCTAACCCCGACTGCAAAACAATCTTGAAGGCACTAGGCCCGGCTGCCACCC
TGGAAGAGATGATGACCGCCTGTCAGGGAGTAGGCGGACCCGGACACAAAGCCAGAGTGTTGATGGGCAAG
TGGTCAAAAAGTAGTGTGGTTGGATGGCCTACTGTAAGGGAAAGAATGAGACGAGCTGAGCCAGCAGCAGA
TGGGGTGGGAGCAGCATCTCGAGACCTGGAAAAACATGGAGCAATCACAAGTAGCAATACAGCAGCTACCA
ATGCTGCTTGTGCCTGGCTAGAAGCACAAGAGGAGGAGGAGGTGGGTTTTCCAGTCACACCTCAGGTACCT
TTAAGACCAATGACTTACAAGGCAGCTGTAGATCTTAGCCACTTTTTAAAAGAAAAGGGGGGACTGGAAGG
GCTAATTCACTCCCAACGAAGACAAGATATCCTTGATCTGTGGATCTACCACACACAAGGCTACTTCCCTG
ATTGGCAGAACTACACACCAGGGCCAGGGGTCAGATATCCACTGACCTTTGGATGGTGCTACAAGCTAGTA
CCAGTTGAGCCAGATAAGGTAGAAGAGGCCAATAAAGGAGAGAACACCAGCTTGTTACACCCTGTGAGCCT
GCATGGAATGGATGACCCTGAGAGAGAAGTGTTAGAGTGGAGGTTTGACAGCCGCCTAGCATTTCATCACG
TGGCCCGAGAGCTGCATCCGGAGTACTTCAAGAACTGCACTAGTGAGCCAGTAGATCCTAGACTAGAGCCC
TGGAAGCATCCAGGAAGTCAGCCTAAAACTGCTTGTACCAATTGCTATTGTAAAAAGTGTTGCTTTCATTG
CCAAGTTTGTTTCATAACAGCTGCCTTAGGCATCTCCTATGGCAGGAAGAAGCGGAGACAGCGACGAAGAC
CTCCTCAAGGCAGTCAGACTCATCAAGTTTCTCTATCAAAGCAACCCACCTCCCAATCCAAAGGGGAGCCG
ACAGGCCCGAAGGAATAA      [SEQ ID NO: 70]
```

Aminoacid sequence of insert

```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGARASVLSGG
ELDRWEKIRLRPGGKKKYKLKHIVWASRELERFAVNPGLLETSEGCRQILGQLQPSLQTGSEELRSLYNTV
ATLYCVHQRIEIKDTKEALDKIEEEQNKSKKKAQQAAADTGHSNQVSQNYPIVQNIQGQMVHQAISPRTLN
AWVKVVEEKAFSPEVIPMFSALSEGATPQDLNTMLNTVGGHQAAMQMLKETINEEAAEWDRVHPVHAGPIA
PGQMREPRGSDIAGTTSTLQEQIGWMTNNPPIPVGEIYKRWIILGLNKIVRMYSPTSILDIRQGPKEPFRD
YVDRFYKTLRAEQASQEVKNWMTETLLVQNANPDCKTILKALGPAATLEEMMTACQGVGGPGHKARVLMGK
WSKSSVVGWPTVRERMRRAEPAADGVGAASRDLEKHGAITSSNTAATNAACAWLEAQEEEEVGFPVTPQVP
LRPMTYKAAVDLSHFLKEKGGLEGLIHSQRRQDILDLWIYHTQGYFPDWQNYTPGPGVRYPLTFGWCYKLV
PVEPDKVEEANKGENTSLLHPVSLHGMDDPEREVLEWRFDSRLAFHHVARELHPEYFKNCTSEPVDPRLEP
WKHPGSQPKTACTNCYCKKCCFHCQVCFITAALGISYGRKKRRQRRRPPQGSQTHQVSLSKQPTSQSKGEP
TGPKE   [SEQ ID NO: 71]
```

Figure 15 pRix41

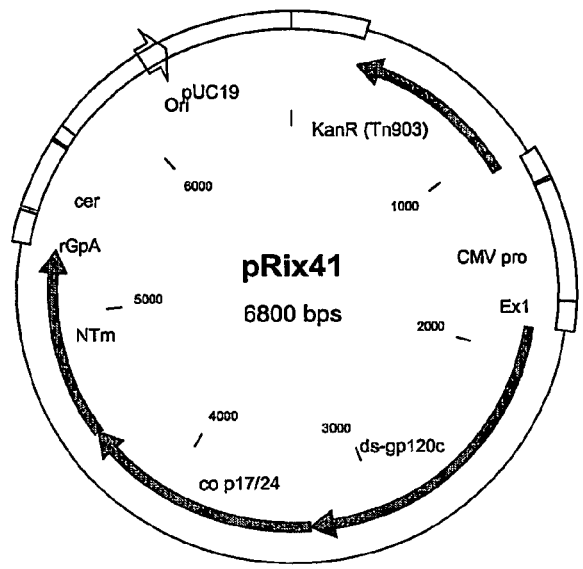

DNA sequence of insert
ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGTGCCCGAGCTTCGGTACTGTCTGGTGGA
GAGCTGGACAGATGGGAGAAAATTAGGCTGCGCCCGGGAGGCAAAAAGAAATACAAGCTCAAGCATATCGT
GTGGGCCTCGAGGGAGCTTGAACGGTTTGCCGTGAACCCAGGCCTGCTGGAAACATCTGAGGGATGTCGCC
AGATCCTGGGGCAATTGCAGCCATCCCTCCAGACCGGGAGTGAAGAGCTGAGGTCCTTGTATAACACAGTG
GCTACCCTCTACTGCGTACACCAGAGGATCGAGATTAAGGATACCAAGGAGGCCTTGGACAAAATTGAGGA
GGAGCAAAACAAGAGCAAGAAGAAGGCCCAGCAGGCAGCTGCTGACACTGGGCATAGCAACCAGGTATCAC
AGAACTATCCTATTGTCCAAAACATTCAGGGCCAGATGGTTCATCAGGCCATCAGCCCCCGGACGCTCAAT
GCCTGGGTGAAGGTTGTCGAAGAGAAGGCCTTTTCTCCTGAGGTTATCCCCATGTTCTCCGCTTTGAGTGA
GGGGGCCACTCCTCAGGACCTCAATACAATGCTTAATACCGTGGGCGGCCATCAGGCCGCCATGCAAATGT

Figure 15 continued

```
TGAAGGAGACTATCAACGAGGAGGCAGCCGAGTGGGACAGAGTGCATCCCGTCCACGCTGGCCCAATCGCG
CCCGGACAGATGCGGGAGCCTCGCGGCTCTGACATTGCCGGCACCACCTCTACACTGCAAGAGCAAATCGG
ATGGATGACCAACAATCCTCCCATCCCAGTTGGAGAAATCTATAAACGGTGGATCATTCTCGGTCTCAATA
AAATTGTTAGAATGTACTCTCCGACATCCATCCTTGACATTAGACAGGGACCCAAAGAGCCTTTTAGGGAT
TACGTCGACCGGTTTTATAAGACCCTGCGAGCAGAGCAGGCCTCTCAGGAGGTCAAAAACTGGATGACGGA
GACACTCCTGGTACAGAACGCTAACCCCGACTGCAAAACAATCTTGAAGGCACTAGGCCCGGCTGCCACCC
TGGAAGAGATGATGACCGCCTGTCAGGGAGTAGGCGGACCCGGACACAAAGCCAGAGTGTTGATGGGTGGC
AAGTGGTCAAAAAGTAGTGTGGTTGGATGGCCTACTGTAAGGGAAAGAATGAGACGAGCTGAGCCAGCAGC
AGATGGGGTGGGAGCAGCATCTCGAGACCTGGAAAAACATGGAGCAATCACAAGTAGCAATACAGCAGCTA
CCAATGCTGCTTGTGCCTGGCTAGAAGCACAAGAGGAGGAGGAGGTGGGTTTTCCAGTCACACCTCAGGTA
CCTTTAAGACCAATGACTTACAAGGCAGCTGTAGATCTTAGCCACTTTTTAAAAGAAAAGGGGGGACTGGA
AGGGCTAATTCACTCCCAACGAAGACAAGATATCCTTGATCTGTGGATCTACCACACACAAGGCTACTTCC
CTGATTGGCAGAACTACACACCAGGGCCAGGGGTCAGATATCCACTGACCTTTGGATGGTGCTACAAGCTA
GTACCAGTTGAGCCAGATAAGGTAGAAGAGGCCAATAAAGGAGAGAACACCAGCGCCTTACACCCTGTGAG
CCTGCATGGAATGGATGACCCTGAGAGAGAAGTGTTAGAGTGGAGGTTTGACAGCCGCCTAGCATTTCATC
ACGTGGCCCGAGAGCTGCATCCGGAGTACTTCAAGAACTGCACTAGTGAGCCAGTAGATCCTAGACTAGAG
CCCTGGAAGCATCCAGGAAGTCAGCCTAAAACTGCTTGTACCAATTGCTATTGTAAAAAGTGTTGCTTTCA
TTGCCAAGTTTGTTTCATAACAGCTGCCTTAGGCATCTCCTATGGCAGGAAGAAGCGGAGACAGCGACGAA
GACCTCCTCAAGGCAGTCAGACTCATCAAGTTTCTCTATCAAAGCAACCCACCTCCCAATCCAAAGGGGAG
CCGACAGGCCCGAAGGAATAA   [SEQ ID NO: 72]
```

Aminoacid sequence of insert
```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGARASVLSGG
ELDRWEKIRLRPGGKKKYKLKHIVWASRELERFAVNPGLLETSEGCRQILGQLQPSLQTGSEELRSLYNTV
ATLYCVHQRIEIKDTKEALDKIEEEQNKSKKKAQQAAADTGHSNQVSQNYPIVQNIQGQMVHQAISPRTLN
AWVKVVEEKAFSPEVIPMFSALSEGATPQDLNTMLNTVGGHQAAMQMLKETINEEAAEWDRVHPVHAGPIA
PGQMREPRGSDIAGTTSTLQEQIGWMTNNPPIPVGEIYKRWIILGLNKIVRMYSPTSILDIRQGPKEPFRD
YVDRFYKTLRAEQASQEVKNWMTETLLVQNANPDCKTILKALGPAATLEEMMTACQGVGGPGHKARVLMGG
KWSKSSVVGWPTVRERMRRAEPAADGVGAASRDLEKHGAITSSNTAATNAACAWLEAQEEEEVGFPVTPQV
PLRPMTYKAAVDLSHFLKEKGGLEGLIHSQRRQDILDLWIYHTQGYFPDWQNYTPGPGVRYPLTFGWCYKL
VPVEPDKVEEANKGENTSALHPVSLHGMDDPEREVLEWRFDSRLAFHHVARELHPEYFKNCTSEPVDPRLE
PWKHPGSQPKTACTNCYCKKCCFHCQVCFITAALGISYGRKKRRQRRRPPQGSQTHQVSLSKQPTSQSKGE
PTGPKE  [SEQ ID NO: 73]
```

Figure 16 pRix42

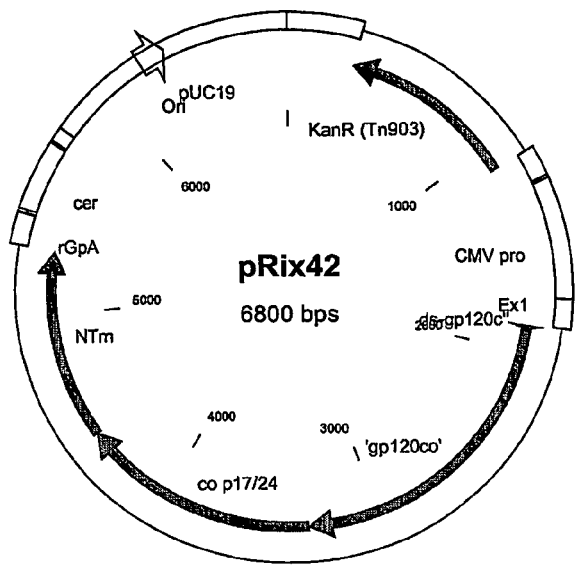

DNA sequence of insert
ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGTGCCCGAGCTTCGGTACTGTCTGGTGGA
GAGCTGGACAGATGGGAGAAAATTAGGCTGCGCCCGGGAGGCAAAAAGAAATACAAGCTCAAGCATATCGT
GTGGGCCTCGAGGGAGCTTGAACGGTTTGCCGTGAACCCAGGCCTGCTGGAAACATCTGAGGGATGTCGCC
AGATCCTGGGGCAATTGCAGCCATCCCTCCAGACCGGGAGTGAAGAGCTGAGGTCCTTGTATAACACAGTG
GCTACCCTCTACTGCGTACACCAGAGGATCGAGATTAAGGATACCAAGGAGGCCTTGGACAAAATTGAGGA
GGAGCAAAACAAGAGCAAGAAGAAGGCCCAGCAGGCAGCTGCTGACACTGGGCATAGCAACCAGGTATCAC
AGAACTATCCTATTGTCCAAAACATTCAGGGCCAGATGGTTCATCAGGCCATCAGCCCCCGGACGCTCAAT
GCCTGGGTGAAGGTTGTCGAAGAGAAGGCCTTTTCTCCTGAGGTTATCCCCATGTTCTCCGCTTTGAGTGA
GGGGGCCACTCCTCAGGACCTCAATACAATGCTTAATACCGTGGGCGGCCATCAGGCCGCCATGCAAATGT

Figure 16 continued

```
TGAAGGAGACTATCAACGAGGAGGCAGCCGAGTGGGACAGAGTGCATCCCGTCCACGCTGGCCCAATCGCG
CCCGGACAGATGCGGGAGCCTCGCGGCTCTGACATTGCCGGCACCACCTCTACACTGCAAGAGCAAATCGG
ATGGATGACCAACAATCCTCCCATCCCAGTTGGAGAAATCTATAAACGGTGGATCATTCTCGGTCTCAATA
AAATTGTTAGAATGTACTCTCCGACATCCATCCTTGACATTAGACAGGGACCCAAAGAGCCTTTTAGGGAT
TACGTCGACCGGTTTTATAAGACCCTGCGAGCAGAGCAGGCCTCTCAGGAGGTCAAAAACTGGATGACGGA
GACACTCCTGGTACAGAACGCTAACCCCGACTGCAAAACAATCTTGAAGGCACTAGGCCCGGCTGCCACCC
TGGAAGAGATGATGACCGCCTGTCAGGGAGTAGGCGGACCCGGACACAAAGCCAGAGTGTTGATGGGTGGC
AAGTGGTCAAAAAGTAGTGTGGTTGGATGGCCTACTGTAAGGGAAAGAATGAGACGAGCTGAGCCAGCAGC
AGATGGGGTGGGAGCAGCATCTCGAGACCTGGAAAAACATGGAGCAATCACAAGTAGCAATACAGCAGCTA
CCAATGCTGCTTGTGCCTGGCTAGAAGCACAAGAGGAGGAGGAGGTGGGTTTTCCAGTCACACCTCAGGTA
CCTTTAAGACCAATGACTTACAAGGCAGCTGTAGATCTTAGCCACTTTTTAAAAGAAAAGGGGGGACTGGA
AGGGCTAATTCACTCCCAACGAAGACAAGATATCCTTGATCTGTGGATCTACCACACACAAGGCTACTTCC
CTGATTGGCAGAACTACACACCAGGGCCAGGGGTCAGATATCCACTGACCTTTGGATGGTGCTACAAGCTA
GTACCAGTTGAGCCAGATAAGGTAGAAGAGGCAATAAAGGAGAGAACACCAGCTTGGCACACCCTGTGAG
CCTGCATGGAATGGATGACCCTGAGAGAGAAGTGTTAGAGTGGAGGTTTGACAGCCGCCTAGCATTTCATC
ACGTGGCCCGAGAGCTGCATCCGGAGTACTTCAAGAACTGCACTAGTGAGCCAGTAGATCCTAGACTAGAG
CCCTGGAAGCATCCAGGAAGTCAGCCTAAAACTGCTTGTACCAATTGCTATTGTAAAAAGTGTTGCTTTCA
TTGCCAAGTTTGTTTCATAACAGCTGCCTTAGGCATCTCCTATGGCAGGAAGAAGCGGAGACAGCGACGAA
GACCTCCTCAAGGCAGTCAGACTCATCAAGTTTCTCTATCAAAGCAACCCACCTCCCAATCCAAAGGGGAG
CCGACAGGCCCGAAGGAATAA  [SEQ ID NO: 74]
```

Aminoacid sequence of insert
```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGARASVLSGG
ELDRWEKIRLRPGGKKKYKLKHIVWASRELERFAVNPGLLETSEGCRQILGQLQPSLQTGSEELRSLYNTV
ATLYCVHQRIEIKDTKEALDKIEEEQNKSKKKAQQAAADTGHSNQVSQNYPIVQNIQGQMVHQAISPRTLN
AWVKVVEEKAFSPEVIPMFSALSEGATPQDLNTMLNTVGGHQAMQMLKETINEEAAEWDRVHPVHAGPIA
PGQMREPRGSDIAGTTSTLQEQIGWMTNNPPIPVGEIYKRWIILGLNKIVRMYSPTSILDIRQGPKEPFRD
YVDRFYKTLRAEQASQEVKNWMTETLLVQNANPDCKTILKALGPAATLEEMMTACQGVGGPGHKARVLMGG
KWSKSSVVGWPTVRERMRRAEPAADGVGAASRDLEKHGAITSSNTAATNAACAWLEAQEEEEVGFPVTPQV
PLRPMTYKAAVDLSHFLKEKGGLEGLIHSQRRQDILDLWIYHTQGYFPDWQNYTPGPGVRYPLTFGWCYKL
VPVEPDKVEEANKGENTSLAHPVSLHGMDDPEREVLEWRFDSRLAFHHVARELHPEYFKNCTSEPVDPRLE
PWKHPGSQPKTACTNCYCKKCCFHCQVCFITAALGISYGRKKRRQRRRPPQGSQTHQVSLSKQPTSQSKGE
PTGPKE  [SEQ ID NO: 75]
```

Figure 17 pRix43

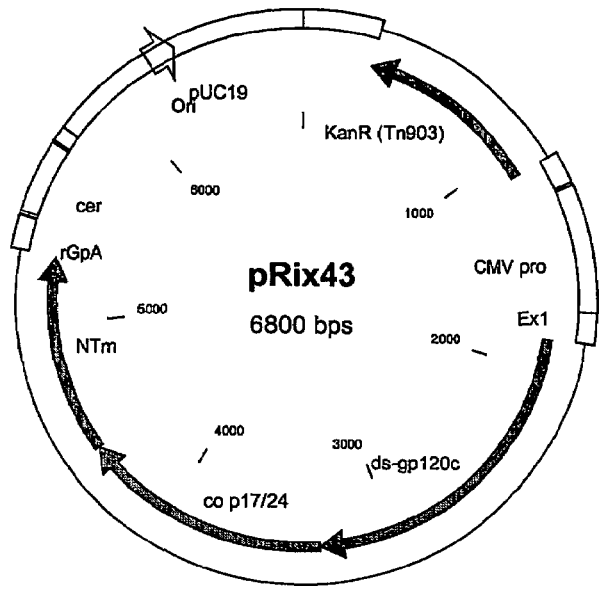

DNA sequence of insert
ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGTGCCCGAGCTTCGGTACTGTCTGGTGGA
GAGCTGGACAGATGGGAGAAAATTAGGCTGCGCCCGGGAGGCAAAAAGAAATACAAGCTCAAGCATATCGT
GTGGGCCTCGAGGGAGCTTGAACGGTTTGCCGTGAACCCAGGCCTGCTGGAAACATCTGAGGGATGTCGCC
AGATCCTGGGGCAATTGCAGCCATCCCTCCAGACCGGGAGTGAAGAGCTGAGGTCCTTGTATAACACAGTG
GCTACCCTCTACTGCGTACACCAGAGGATCGAGATTAAGGATACCAAGGAGGCCTTGGACAAAATTGAGGA
GGAGCAAAACAAGAGCAAGAAGAAGGCCCAGCAGGCAGCTGCTGACACTGGGCATAGCAACCAGGTATCAC
AGAACTATCCTATTGTCCAAAACATTCAGGGCCAGATGGTTCATCAGGCCATCAGCCCCCGGACGCTCAAT
GCCTGGGTGAAGGTTGTCGAAGAGAAGGCCTTTTCTCCTGAGGTTATCCCCATGTTCTCCGCTTTGAGTGA
GGGGGCCACTCCTCAGGACCTCAATACAATGCTTAATACCGTGGGCGGCCATCAGGCCGCCATGCAAATGT

Figure 17 continued

```
TGAAGGAGACTATCAACGAGGAGGCAGCCGAGTGGGACAGAGTGCATCCCGTCCACGCTGGCCCAATCGCG
CCCGGACAGATGCGGGAGCCTCGCGGCTCTGACATTGCCGGCACCACCTCTACACTGCAAGAGCAAATCGG
ATGGATGACCAACAATCCTCCCATCCCAGTTGGAGAAATCTATAAACGGTGGATCATTCTCGGTCTCAATA
AAATTGTTAGAATGTACTCTCCGACATCCATCCTTGACATTAGACAGGGACCCAAAGAGCCTTTTAGGGAT
TACGTCGACCGGTTTTATAAGACCCTGCGAGCAGAGCAGGCCTCTCAGGAGGTCAAAAACTGGATGACGGA
GACACTCCTGGTACAGAACGCTAACCCCGACTGCAAAACAATCTTGAAGGCACTAGGCCCGGCTGCCACCC
TGGAAGAGATGATGACCGCCTGTCAGGGAGTAGGCGGACCCGGACACAAAGCCAGAGTGTTGATGGGTGGC
AAGTGGTCAAAAAGTAGTGTGGTTGGATGGCCTACTGTAAGGGAAAGAATGAGACGAGCTGAGCCAGCAGC
AGATGGGGTGGGAGCAGCATCTCGAGACCTGGAAAAACATGGAGCAATCACAAGTAGCAATACAGCAGCTA
CCAATGCTGCTTGTGCCTGGCTAGAAGCACAAGAGGAGGAGGAGGTGGGTTTTCCAGTCACACCTCAGGTA
CCTTTAAGACCAATGACTTACAAGGCAGCTGTAGATCTTAGCCACTTTTTAAAAGAAAAGGGGGACTGGA
AGGGCTAATTCACTCCCAACGAAGACAAGATATCCTTGATCTGTGGATCTACCACACACAAGGCTACTTCC
CTGATTGGCAGAACTACACACCAGGGCCAGGGGTCAGATATCCACTGACCTTTGGATGGTGCTACAAGCTA
GTACCAGTTGAGCCAGATAAGGTAGAAGAGGCCAATAAAGGAGAGAACACCAGCGCCGCACACCCTGTGAG
CCTGCATGGAATGGATGACCCTGAGAGAGAAGTGTTAGAGTGGAGGTTTGACAGCCGCCTAGCATTTCATC
ACGTGGCCCGAGAGCTGCATCCGGAGTACTTCAAGAACTGCACTAGTGAGCCAGTAGATCCTAGACTAGAG
CCCTGGAAGCATCCAGGAAGTCAGCCTAAAACTGCTTGTACCAATTGCTATTGTAAAAAGTGTTGCTTTCA
TTGCCAAGTTTGTTTCATAACAGCTGCCTTAGGCATCTCCTATGGCAGGAAGAAGCGGAGACAGCGACGAA
GACCTCCTCAAGGCAGTCAGACTCATCAAGTTTCTCTATCAAAGCAACCCACCTCCCAATCCAAAGGGGAG
CCGACAGGCCCGAAGGAATAA   [SEQ ID NO: 76]
```

Aminoacid sequence of insert

```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGARASVLSGG
ELDRWEKIRLRPGGKKKYKLKHIVWASRELERFAVNPGLLETSEGCRQILGQLQPSLQTGSEELRSLYNTV
ATLYCVHQRIEIKDTKEALDKIEEEQNKSKKKAQQAAADTGHSNQVSQNYPIVQNIQGQMVHQAISPRTLN
AWVKVVEEKAFSPEVIPMFSALSEGATPQDLNTMLNTVGGHQAAMQMLKETINEEAAEWDRVHPVHAGPIA
PGQMREPRGSDIAGTTSTLQEQIGWMTNNPPIPVGEIYKRWIILGLNKIVRMYSPTSILDIRQGPKEPFRD
YVDRFYKTLRAEQASQEVKNWMTETLLVQNANPDCKTILKALGPAATLEEMMTACQGVGGPGHKARVLMGG
KWSKSSVVGWPTVRERMRRAEPAADGVGAASRDLEKHGAITSSNTAATNAACAWLEAQEEEEVGFPVTPQV
PLRPMTYKAAVDLSHFLKEKGGLEGLIHSQRRQDILDLWIYHTQGYFPDWQNYTPGPGVRYPLTFGWCYKL
VPVEPDKVEEANKGENTSAAHPVSLHGMDDPEREVLEWRFDSRLAFHHVARELHPEYFKNCTSEPVDPRLE
PWKHPGSQPKTACTNCYCKKCCFHCQVCFITAALGISYGRKKRRQRRRPPQGSQTHQVSLSKQPTSQSKGE
PTGPKE [SEQ ID NO: 77]
```

Figure 18 pRix44

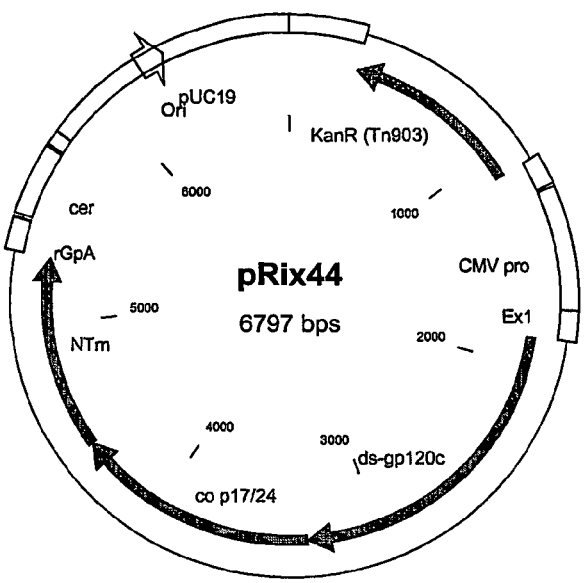

DNA sequence of insert
ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGTGCCCGAGCTTCGGTACTGTCTGGTGGA
GAGCTGGACAGATGGGAGAAAATTAGGCTGCGCCCGGGAGGCAAAAAGAAATACAAGCTCAAGCATATCGT
GTGGGCCTCGAGGGAGCTTGAACGGTTTGCCGTGAACCCAGGCCTGCTGGAAACATCTGAGGGATGTCGCC
AGATCCTGGGGCAATTGCAGCCATCCCTCCAGACCGGGAGTGAAGAGCTGAGGTCCTTGTATAACACAGTG
GCTACCCTCTACTGCGTACACCAGAGGATCGAGATTAAGGATACCAAGGAGGCCTTGGACAAAATTGAGGA
GGAGCAAAACAAGAGCAAGAAGAAGGCCCAGCAGGCAGCTGCTGACACTGGGCATAGCAACCAGGTATCAC
AGAACTATCCTATTGTCCAAAACATTCAGGGCCAGATGGTTCATCAGGCCATCAGCCCCCGGACGCTCAAT
GCCTGGGTGAAGGTTGTCGAAGAGAAGGCCTTTTCTCCTGAGGTTATCCCCATGTTCTCCGCTTTGAGTGA
GGGGGCCACTCCTCAGGACCTCAATACAATGCTTAATACCGTGGGCGGCCATCAGGCCGCCATGCAAATGT

Figure 18 continued

```
TGAAGGAGACTATCAACGAGGAGGCAGCCGAGTGGGACAGAGTGCATCCCGTCCACGCTGGCCCAATCGCG
CCCGGACAGATGCGGGAGCCTCGCGGCTCTGACATTGCCGGCACCACCTCTACACTGCAAGAGCAAATCGG
ATGGATGACCAACAATCCTCCCATCCCAGTTGGAGAAATCTATAAACGGTGGATCATTCTCGGTCTCAATA
AAATTGTTAGAATGTACTCTCCGACATCCATCCTTGACATTAGACAGGGACCCAAAGAGCCTTTTAGGGAT
TACGTCGACCGGTTTTATAAGACCCTGCGAGCAGAGCAGGCCTCTCAGGAGGTCAAAAACTGGATGACGGA
GACACTCCTGGTACAGAACGCTAACCCCGACTGCAAAACAATCTTGAAGGCACTAGGCCCGGCTGCCACCC
TGGAAGAGATGATGACCGCCTGTCAGGGAGTAGGCGGACCCGGACACAAAGCCAGAGTGTTGATGGGCAAG
TGGTCAAAAAGTAGTGTGGTTGGATGGCCTACTGTAAGGGAAAGAATGAGACGAGCTGAGCCAGCAGCAGA
TGGGGTGGGAGCAGCATCTCGAGACCTGGAAAAACATGGAGCAATCACAAGTAGCAATACAGCAGCTACCA
ATGCTGCTTGTGCCTGGCTAGAAGCACAAGAGGAGGAGGAGGTGGGTTTTCCAGTCACACCTCAGGTACCT
TTAAGACCAATGACTTACAAGGCAGCTGTAGATCTTAGCCACTTTTTAAAAGAAAAGGGGGGACTGGAAGG
GCTAATTCACTCCCAACGAAGACAAGATATCCTTGATCTGTGGATCTACCACACACAAGGCTACTTCCCTG
ATTGGCAGAACTACACACCAGGGCCAGGGGTCAGATATCCACTGACCTTTGGATGGTGCTACAAGCTAGTA
CCAGTTGAGCCAGATAAGGTAGAAGAGGCCAATAAAGGAGAGAACACCAGCGCCGCACACCCTGTGAGCCT
GCATGGAATGGATGACCCTGAGAGAGAAGTGTTAGAGTGGAGGTTTGACAGCCGCCTAGCATTTCATCACG
TGGCCCGAGAGCTGCATCCGGAGTACTTCAAGAACTGCACTAGTGAGCCAGTAGATCCTAGACTAGAGCCC
TGGAAGCATCCAGGAAGTCAGCCTAAAACTGCTTGTACCAATTGCTATTGTAAAAAGTGTTGCTTTCATTG
CCAAGTTTGTTTCATAACAGCTGCCTTAGGCATCTCCTATGGCAGGAAGAAGCGGAGACAGCGACGAAGAC
CTCCTCAAGGCAGTCAGACTCATCAAGTTTCTCTATCAAAGCAACCCACCTCCCAATCCAAAGGGGAGCCG
ACAGGCCCGAAGGAATAA    [SEQ ID NO: 78]
```

Aminoacid sequence of insert

```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGARASVLSGG
ELDRWEKIRLRPGGKKKYKLKHIVWASRELERFAVNPGLLETSEGCRQILGQLQPSLQTGSEELRSLYNTV
ATLYCVHQRIEIKDTKEALDKIEEEQNKSKKKAQQAAADTGHSNQVSQNYPIVQNIQGQMVHQAISPRTLN
AWVKVVEEKAFSPEVIPMFSALSEGATPQDLNTMLNTVGGHQAAMQMLKETINEEAAEWDRVHPVHAGPIA
PGQMREPRGSDIAGTTSTLQEQIGWMTNNPPIPVGEIYKRWIILGLNKIVRMYSPTSILDIRQGPKEPFRD
YVDRFYKTLRAEQASQEVKNWMTETLLVQNANPDCKTILKALGPAATLEEMMTACQGVGGPGHKARVLMGK
WSKSSVVGWPTVRERMRRAEPAADGVGAASRDLEKHGAITSSNTAATNAACAWLEAQEEEEVGFPVTPQVP
LRPMTYKAAVDLSHFLKEKGGLEGLIHSQRRQDILDLWIYHTQGYFPDWQNYTPGPGVRYPLTFGWCYKLV
PVEPDKVEEANKGENTSAAHPVSLHGMDDPEREVLEWRFDSRLAFHHVARELHPEYFKNCTSEPVDPRLEP
WKHPGSQPKTACTNCYCKKCCFHCQVCFITAALGISYGRKKRRQRRPPQGSQTHQVSLSKQPTSQSKGEP
TGPKE   [SEQ ID NO: 79]
```

Figure 19 pRix46

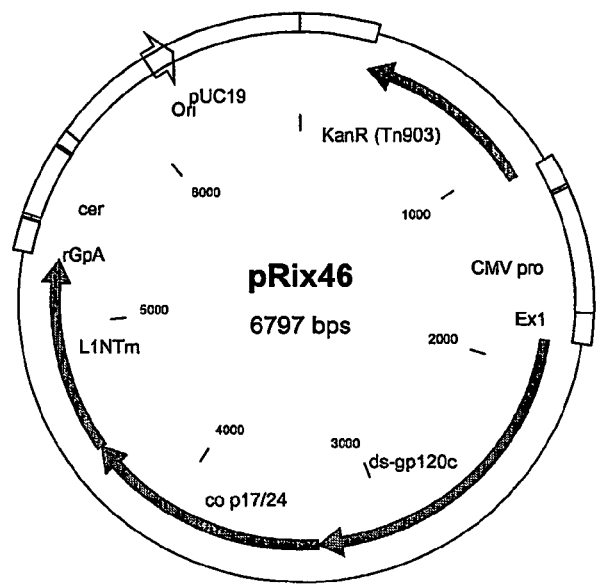

DNA sequence of insert
ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGTGCCCGAGCTTCGGTACTGTCTGGTGGA
GAGCTGGACAGATGGGAGAAAATTAGGCTGCGCCCGGGAGGCAAAAAGAAATACAAGCTCAAGCATATCGT
GTGGGCCTCGAGGGAGCTTGAACGGTTTGCCGTGAACCCAGGCCTGCTGGAAACATCTGAGGGATGTCGCC
AGATCCTGGGGCAATTGCAGCCATCCCTCCAGACCGGGAGTGAAGAGCTGAGGTCCTTGTATAACACAGTG
GCTACCCTCTACTGCGTACACCAGAGGATCGAGATTAAGGATACCAAGGAGGCCTTGGACAAAATTGAGGA
GGAGCAAAACAAGAGCAAGAAGAAGGCCCAGCAGGCAGCTGCTGACACTGGGCATAGCAACCAGGTATCAC
AGAACTATCCTATTGTCCAAAACATTCAGGGCCAGATGGTTCATCAGGCCATCAGCCCCCGGACGCTCAAT
GCCTGGGTGAAGGTTGTCGAAGAGAAGGCCTTTTCTCCTGAGGTTATCCCCATGTTCTCCGCTTTGAGTGA
GGGGGCCACTCCTCAGGACCTCAATACAATGCTTAATACCGTGGGCGGCCATCAGGCCGCCATGCAAATGT

Figure 19 continued

```
TGAAGGAGACTATCAACGAGGAGGCAGCCGAGTGGGACAGAGTGCATCCCGTCCACGCTGGCCCAATCGCG
CCCGGACAGATGCGGGAGCCTCGCGGCTCTGACATTGCCGGCACCACCTCTACACTGCAAGAGCAAATCGG
ATGGATGACCAACAATCCTCCCATCCCAGTTGGAGAAATCTATAAACGGTGGATCATTCTCGGTCTCAATA
AAATTGTTAGAATGTACTCTCCGACATCCATCCTTGACATTAGACAGGGACCCAAAGAGCCTTTTAGGGAT
TACGTCGACCGGTTTTATAAGACCCTGCGAGCAGAGCAGGCCTCTCAGGAGGTCAAAAACTGGATGACGGA
GACACTCCTGGTACAGAACGCTAACCCCGACTGCAAAACAATCTTGAAGGCACTAGGCCCGGCTGCCACCC
TGGAAGAGATGATGACCGCCTGTCAGGGAGTAGGCGGACCCGGACACAAAGCCAGAGTGTTGATGGGCAAG
TGGTCAAAAAGTAGTGTGGTTGGATGGCCTACTGTAAGGGAAAGAATGAGACGAGCTGAGCCAGCAGCAGA
TGGGGTGGGAGCAGCATCTCGAGACCTGGAAAAACATGGAGCAATCACAAGTAGCAATACAGCAGCTACCA
ATGCTGCTTGTGCCTGGCTAGAAGCACAAGAGGAGGAGGAGGTGGGTTTTCCAGTCACACCTCAGGTACCT
TTAAGACCAATGACTTACAAGGCAGCTGTAGATCTTAGCCACTTTTTAAAAGAAAAGGGGGGACTGGAAGG
GCTAATTCACTCCCAACGAAGACAAGATATCCTTGATCTGTGGATCTACCACACACAAGGCTACTTCCCTG
ATTGGCAGAACTACACACCAGGGCCAGGGGTCAGATATCCACTGACCTTTGGATGGTGCTACAAGCTAGTA
CCAGTTGAGCCAGATAAGGTAGAAGAGGCCAATAAAGGAGAGAACACCAGCGCCTTACACCCTGTGAGCCT
GCATGGAATGGATGACCCTGAGAGAGAAGTGTTAGAGTGGAGGTTTGACAGCCGCCTAGCATTTCATCACG
TGGCCCGAGAGCTGCATCCGGAGTACTTCAAGAACTGCACTAGTGAGCCAGTAGATCCTAGACTAGAGCCC
TGGAAGCATCCAGGAAGTCAGCCTAAAACTGCTTGTACCAATTGCTATTGTAAAAAGTGTTGCTTTCATTG
CCAAGTTTGTTTCATAACAGCTGCCTTAGGCATCTCCTATGGCAGGAAGAAGCGGAGACAGCGACGAAGAC
CTCCTCAAGGCAGTCAGACTCATCAAGTTTCTCTATCAAAGCAACCCACCTCCCAATCCAAAGGGGAGCCG
ACAGGCCCGAAGGAATAA   [SEQ ID NO: 80]
```

Aminoacid sequence of insert
```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGARASVLSGG
ELDRWEKIRLRPGGKKKYKLKHIVWASRELERFAVNPGLLETSEGCRQILGQLQPSLQTGSEELRSLYNTV
ATLYCVHQRIEIKDTKEALDKIEEEQNKSKKKAQQAAADTGHSNQVSQNYPIVQNIQGQMVHQAISPRTLN
AWVKVVEEKAFSPEVIPMFSALSEGATPQDLNTMLNTVGGHQAAMQMLKETINEEAAEWDRVHPVHAGPIA
PGQMREPRGSDIAGTTSTLQEQIGWMTNNPPIPVGEIYKRWIILGLNKIVRMYSPTSILDIRQGPKEPFRD
YVDRFYKTLRAEQASQEVKNWMTETLLVQNANPDCKTILKALGPAATLEEMMTACQGVGGPGHKARVLMGK
WSKSSVVGWPTVRERMRRAEPAADGVGAASRDLEKHGAITSSNTAATNAACAWLEAQEEEEVGFPVTPQVP
LRPMTYKAAVDLSHFLKEKGGLEGLIHSQRRQDILDLWIYHTQGYFPDWQNYTPGPGVRYPLTFGWCYKLV
PVEPDKVEEANKGENTSALHPVSLHGMDDPEREVLEWRFDSRLAFHHVARELHPEYFKNCTSEPVDPRLEP
WKHPGSQPKTACTNCYCKKCCFHCQVCFITAALGISYGRKKRRQRRRPPQGSQTHQVSLSKQPTSQSKGEP
TGPKE [SEQ ID NO: 81]
```

Figure 20 pRix47

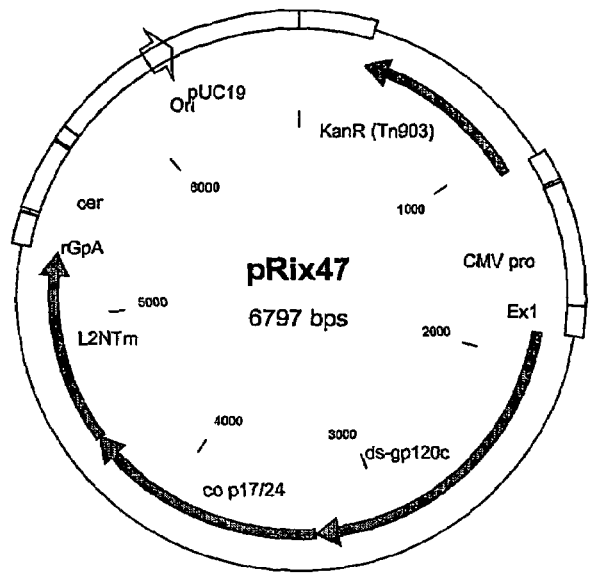

DNA sequence of insert
ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGTGCCCGAGCTTCGGTACTGTCTGGTGGA
GAGCTGGACAGATGGGAGAAAATTAGGCTGCGCCCGGGAGGCAAAAAGAAATACAAGCTCAAGCATATCGT
GTGGGCCTCGAGGGAGCTTGAACGGTTTGCCGTGAACCCAGGCCTGCTGGAAACATCTGAGGGATGTCGCC
AGATCCTGGGGCAATTGCAGCCATCCCTCCAGACCGGGAGTGAAGAGCTGAGGTCCTTGTATAACACAGTG
GCTACCCTCTACTGCGTACACCAGAGGATCGAGATTAAGGATACCAAGGAGGCCTTGGACAAAATTGAGGA
GGAGCAAAACAAGAGCAAGAAGAAGGCCCAGCAGGCAGCTGCTGACACTGGGCATAGCAACCAGGTATCAC
AGAACTATCCTATTGTCCAAAACATTCAGGGCCAGATGGTTCATCAGGCCATCAGCCCCGGACGCTCAAT
GCCTGGGTGAAGGTTGTCGAAGAGAAGGCCTTTTCTCCTGAGGTTATCCCCATGTTCTCCGCTTTGAGTGA
GGGGGCCACTCCTCAGGACCTCAATACAATGCTTAATACCGTGGGCGGCCATCAGGCCGCCATGCAAATGT

Figure 20 continued

```
TGAAGGAGACTATCAACGAGGAGGCAGCCGAGTGGGACAGAGTGCATCCCGTCCACGCTGGCCCAATCGCG
CCCGGACAGATGCGGGAGCCTCGCGGCTCTGACATTGCCGGCACCACCTCTACACTGCAAGAGCAAATCGG
ATGGATGACCAACAATCCTCCCATCCCAGTTGGAGAAATCTATAAACGGTGGATCATTCTCGGTCTCAATA
AAATTGTTAGAATGTACTCTCCGACATCCATCCTTGACATTAGACAGGGACCCAAAGAGCCTTTTAGGGAT
TACGTCGACCGGTTTTATAAGACCCTGCGAGCAGAGCAGGCCTCTCAGGAGGTCAAAAACTGGATGACGGA
GACACTCCTGGTACAGAACGCTAACCCCGACTGCAAAACAATCTTGAAGGCACTAGGCCCGGCTGCCACCC
TGGAAGAGATGATGACCGCCTGTCAGGGAGTAGGCGGACCCGGACACAAAGCCAGAGTGTTGATGGGCAAG
TGGTCAAAAAGTAGTGTGGTTGGATGGCCTACTGTAAGGGAAAGAATGAGACGAGCTGAGCCAGCAGCAGA
TGGGGTGGGAGCAGCATCTCGAGACCTGGAAAAACATGGAGCAATCACAAGTAGCAATACAGCAGCTACCA
ATGCTGCTTGTGCCTGGCTAGAAGCACAAGAGGAGGAGGAGGTGGGTTTTCCAGTCACACCTCAGGTACCT
TTAAGACCAATGACTTACAAGGCAGCTGTAGATCTTAGCCACTTTTTAAAAGAAAAGGGGGACTGGAAGG
GCTAATTCACTCCCAACGAAGACAAGATATCCTTGATCTGTGGATCTACCACACACAAGGCTACTTCCCTG
ATTGGCAGAACTACACACCAGGGCCAGGGGTCAGATATCCACTGACCTTTGGATGGTGCTACAAGCTAGTA
CCAGTTGAGCCAGATAAGGTAGAAGAGGCCAATAAAGGAGAGAACACCAGCTTGGCACACCCTGTGAGCCT
GCATGGAATGGATGACCCTGAGAGAGAAGTGTTAGAGTGGAGGTTTGACAGCCGCCTAGCATTTCATCACG
TGGCCCGAGAGCTGCATCCGGAGTACTTCAAGAACTGCACTAGTGAGCCAGTAGATCCTAGACTAGAGCCC
TGGAAGCATCCAGGAAGTCAGCCTAAAACTGCTTGTACCAATTGCTATTGTAAAAAGTGTTGCTTTCATTG
CCAAGTTTGTTTCATAACAGCTGCCTTAGGCATCTCCTATGGCAGGAAGAAGCGGAGACAGCGACGAAGAC
CTCCTCAAGGCAGTCAGACTCATCAAGTTTCTCTATCAAAGCAACCCACCTCCCAATCCAAAGGGGAGCCG
ACAGGCCCGAAGGAATAA [SEQ ID NO: 82]
```

Aminoacid sequence of insert
```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGARASVLSGG
ELDRWEKIRLRPGGKKKYKLKHIVWASRELERFAVNPGLLETSEGCRQILGQLQPSLQTGSEELRSLYNTV
ATLYCVHQRIEIKDTKEALDKIEEEQNKSKKKAQQAAADTGHSNQVSQNYPIVQNIQGQMVHQAISPRTLN
AWVKVVEEKAFSPEVIPMFSALSEGATPQDLNTMLNTVGGHQAAMQMLKETINEEAAEWDRVHPVHAGPIA
PGQMREPRGSDIAGTTSTLQEQIGWMTNNPPIPVGEIYKRWIILGLNKIVRMYSPTSILDIRQGPKEPFRD
YVDRFYKTLRAEQASQEVKNWMTETLLVQNANPDCKTILKALGPAATLEEMMTACQGVGGPGHKARVLMGK
WSKSSVVGWPTVRERMRRAEPAADGVGAASRDLEKHGAITSSNTAATNAACAWLEAQEEEEVGFPVTPQVP
LRPMTYKAAVDLSHFLKEKGGLEGLIHSQRRQDILDLWIYHTQGYFPDWQNYTPGPGVRYPLTFGWCYKLV
PVEPDKVEEANKGENTSLAHPVSLHGMDDPEREVLEWRFDSRLAFHHVARELHPEYFKNCTSEPVDPRLEP
WKHPGSQPKTACTNCYCKKCCFHCQVCFITAALGISYGRKKRRQRRRPPQGSQTHQVSLSKQPTSQSKGEP
TGPKE [SEQ ID NO: 83]
```

Figure 21 pRix58

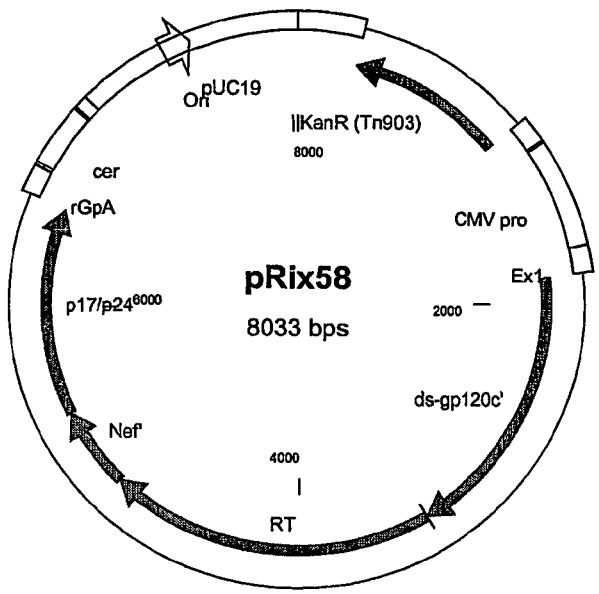

DNA sequence of insert
ATGGCCGAGCAGCTGTGGGTCACCGTCTACTACGGCGTGCCTGTGTGGAAGGAGGCCACGACCACCCTCTT
CTGCGCGAGCGACGCCAAGGCCTACGACACGGAAGTGCATAACGTGTGGGCGACGCATGCTTGCGTGCCTA
CGGACCCCAACCCCCAGGAGGTGGTGCTGGGAAACGTGACCGAGTACTTCAACATGTGGAAGAATAACATG
GTGGATCAGATGCACGAGGACATCATCTCTCTGTGGGACCAGTCCCTGAAGCCCTGCGTGAAGCTGACGCC
TCTCTGCGTGACACTGGACTGTGACGACGTCAACACCACCAACAGCACTACCACCACCAGCAACGGCTGGA
CCGGAGAGATTCGGAAGGGCGAGATCAAGAACTGCTCCTTCAATATCACGACCTCGATCAGAGACAAGGTG
CAGAAGGAATACGCGCTGTTTTATAATCTCGATGTGGTCCCCATCGACGACGACAATGCCACCACCAAGAA
CAAGACGACGCGTAATTTCAGACTCATTCACTGCAACAGCAGCGTCATGACGCAGGCCTGCCCCAAGGTGT
CCTTCGAACCAATCCCGATCCATTACTGTGCCCCTGCCGGATTCGCGATCCTCAAGTGTAACAACAAGACC
TTCGACGGGAAGGGCCTGTGCACCAACGTCAGCACGGTGCAGTGCACCCATGGCATCCGCCCCGTCGTGAG
CACCCAGCTGCTGCTGAACGGGTCCCTGGCTGAGGAGGAGGTGGTGATCCGGTCGGACAACTTCATGGACA
ACACCAAGACAATCATCGTCCAGCTGAACGAGTCTGTGGCGATTAACTGTACCCGGCCTAACAACAACACC
CGTAAGGGCATCCACATCGGGCCTGGACGGGCCTTCTATGCCGCCCGCAAGATCATCGGCGACATCCGGCA
GGCCCATTGCAACCTCTCCCGCGCCCAGTGGAATAACACCCTGAAGCAGATCGTGATCAAGCTGAGAGAGC
ACTTTGGAAACAAGACCATCAAGTTCAATCAGAGTTCTGGCGGAGACCCCGAGATCGTGCGGCACTCCTTC
AACTGCGGGGGCGAGTTCTTCTACTGCGATACGACACAGCTCTTCAACTCCACCTGGAACGGCACCGAGGG
CAACAACACAGAGGGAAACTCCACTATCACCCTCCCTTGCCGCATCAAGCAGATCATCAACATGTGGCAGG
AGGTGGGAAAGGCCATGTATGCCCCCCCCATCGGGGCCAGATCCGCTGCTCCTCCAACATCACCGGCCTG
CTGCTCACCAGAGACGGGGGCACCGAGGGCAACGGCACGGAGAACGAGACGGAGATCTTCAGGCCCGGCGG
CGGCGACATGAGGGATAACTGGCGGAGCGAGCTGTACAAGTACAAGGTGGTGAAGGTGGAGCCGCTCGGCG
TGGCCCCCACCCGGGCCAAGCGCCGCGTCGTGCAGAGAATGGGCCCCATCAGTCCCATCGAGACCGTGCCG
GTGAAGCTGAAACCCGGGATGGACGGCCCCAAGGTCAAGCAGTGGCCACTCACCGAGGAGAAGATCAAGGC
CCTGGTGGAGATCTGCACCGAGATGGAGAAAGAGGGCAAGATCAGCAAGATCGGGCCTGAGAACCCATACA
ACACCCCCGTGTTTGCCATCAAGAAGAAGGACAGCACCAAGTGGCGCAAGCTGGTGGATTTCCGGGAGCTG
AATAAGCGGACCCAGGATTTCTGGGAGGTCCAGCTGGGCATCCCCATCCGGCCGGCCTGAAGAAGAAGAA
GAGCGTGACCGTGCTGGACGTGGGCGACGCTTACTTCAGCGTCCCTCTGGACGAGGACTTTAGAAAGTACA
CCGCCTTTACCATCCCATCTATCAACAACGAGACCCCTGGCATCAGATATCAGTACAACGTCCTCCCCCAG
GGCTGGAAGGGCTCTCCCGCCATTTTCCAGAGCTCCATGACCAAGATCCTGGAGCCGTTTCGGAAGCAGAA
CCCCGATATCGTCATCTACCAGTACATGGACGACCTGTACGTGGGCTCTGACCTGGAAATCGGGCAGCATC

Figure 21 continued

```
GCACGAAGATTGAGGAGCTGAGGCAGCATCTGCTGAGATGGGGCCTGACCACTCCGGACAAGAAGCATCAG
AAGGAGCCGCCATTCCTGAAGATGGGCTACGAGCTCCATCCCGACAAGTGGACCGTGCAGCCTATCGTCCT
CCCCGAGAAGGACAGCTGGACCGTGAACGACATCCAGAAGCTGGTGGGCAAGCTCAACTGGGCTAGCCAGA
TCTATCCCGGGATCAAGGTGCGCCAGCTCTGCAAGCTGCTGCGCGGCACCAAGGCCCTGACCGAGGTGATT
CCCCTCACGGAGGAAGCCGAGCTCGAGCTGGCTGAGAACCGGGAGATCCTGAAGGAGCCCGTGCACGGCGT
GTACTATGACCCCTCCAAGGACCTGATCGCCGAAATCCAGAAGCAGGGCCAGGGGCAGTGGACATACCAGA
TTTACCAGGAGCCTTTCAAGAACCTCAAGACCGGCAAGTACGCCCGCATGAGGGGCGCCCACACCAACGAT
GTCAAGCAGCTGACCGAGGCCGTCCAGAAGATCACGACCGAGTCCATCGTGATCTGGGGGAAGACACCCAA
GTTCAAGCTGCCTATCCAGAAGGAGACCTGGGAGACGTGGTGGACCGAATATTGGCAGGCCACCTGGATTC
CCGAGTGGGAGTTCGTGAATACACCTCCTCTGGTGAAGCTGTGGTACCAGCTCGAGAAGGAGCCCATCGTG
GGCGCGGAGACATTCTACGTGGACGGCGCGGCCAACCGCGAAACAAAGCTCGGGAAGGCCGGGTACGTCAC
CAACCGGGGCCGCCAGAAGGTCGTCACCCTGACCGACACCACCAACCAGAAGACGGAGCTGCAGGCCATCT
ATCTCGCTCTCCAGGACTCCGGCCTGGAGGTGAACATCGTGACGGACAGCCAGTACGCGCTGGGCATTATT
CAGGCCCAGCCGGACCAGTCCGAGAGCGAACTGGTGAACCAGATTATCGAGCAGCTGATCAAGAAAGAGAA
GGTCTACCTCGCCTGGGTCCCGGCCCATAAGGGCATTGGCGGCAACGAGCAGGTCGACAAGCTGGTGAGTG
CGGGGATTAGAAAGGTGCTGATGGTGGGTTTTCCAGTCACACCTCAGGTACCTTTAAGACCAATGACTTAC
AAGGCAGCTGTAGATCTTAGCCACTTTTTAAAAGAAAAGGGGGGACTGGAAGGGCTAATTCACTCCCAAAG
AAGACAAGATATCCTTGATCTGTGGATCTACCACACACAAGGCTACTTCCCTGATTGGCAGAACTACACAC
CAGGGCCAGGGGTCAGATATCCACTGACCTTTGGATGGTGCTACAAGCTAGTACCAGTTGAGCCAGATAAG
GTAGAAGAGGCCAATAAAGGAGAGAACACCAGCTTGTTACACCCTGTGAGCCTGCATGGGATGGATGACCC
GGAGAGAGAAGTGTTAGAGTGGAGGTTTGACAGCCGCCTAGCATTTCATCGTGGCCCGAGAGCTGCATC
CGGAGTACTTCAAGAACTGCATGGGTGCCCGAGCTTCGGTACTGTCTGGTGGAGAGCTGGACAGATGGGAG
AAAATTAGGCTGCGCCCGGGAGGCAAAAAGAAATACAAGCTCAAGCATATCGTGTGGGCCTCGAGGGAGCT
TGAACGGTTTGCCGTGAACCCAGGCCTGCTGGAAACATCTGAGGGATGTCGCCAGATCCTGGGGCAATTGC
AGCCATCCCTCCAGACCGGGAGTGAAGAGCTGAGGTCCTTGTATAACACAGTGGCTACCCTCTACTGCGTA
CACCAGAGGATCGAGATTAAGGATACCAAGGAGGCCTTGGACAAAATTGAGGAGGAGCAAAACAAGAGCAA
GAAGAAGGCCCAGCAGGCAGCTGCTGACACTGGGCATAGCAACCAGGTATCACAGAACTATCCTATTGTCC
AAAACATTCAGGGCCAGATGGTTCATCAGGCCATCAGCCCCCGGACGCTCAATGCCTGGGTGAAGGTTGTC
GAAGAGAAGGCCTTTTCTCCTGAGGTTATCCCCATGTTCTCCGCTTTGAGTGAGGGGGCCACTCCTCAGGA
CCTCAATACAATGCTTAATACCGTGGGCGGCCATCAGGCCGCCATGCAAATGTTGAAGGAGACTATCAACG
AGGAGGCAGCCGAGTGGGACAGAGTGCATCCCGTCCACGCTGGCCCAATCGCGCCCGGACAGATGCGGGAG
CCTCGCGGCTCTGACATTGCCGGCACCACCTCTACACTGCAAGAGCAAATCGGATGGATGACCAACAATCC
TCCCATCCCAGTTGGAGAAATCTATAAACGGTGGATCATCCTGGGCCTGAACAAGATCGTGCGCATGTACT
CTCCGACATCCATCCTTGACATTAGACAGGGACCCAAAGAGCCTTTTAGGGATTACGTCGACCGGTTTTAT
AAGACCCTGCGAGCAGAGCAGGCCTCTCAGGAGGTCAAAAACTGGATGACGGAGACACTCCTGGTACAGAA
CGCTAACCCCGACTGCAAAACAATCTTGAAGGCACTAGGCCCGGCTGCCACCCTGGAAGAGATGATGACCG
CCTGTCAGGGAGTAGGCGGACCCGGACACAAAGCCAGAGTGTTGTAA    [SEQ ID NO: 84]
```

Aminoacid sequence of insert

```
MAEQLWVTVYYGVPVWKEATTTLFCASDAKAYDTEVHNVWATHACVPTDPNPQEVVLGNVTEYFNMWKNNM
VDQMHEDIISLWDQSLKPCVKLTPLCVTLDCDDVNTTNSTTTTSNGWTGEIRKGEIKNCSFNITTSIRDKV
QKEYALFYNLDVVPIDDDNATTKNKTTRNFRLIHCNSSVMTQACPKVSFEPIPIHYCAPAGFAILKCNNKT
FDGKGLCTNVSTVQCTHGIRPVVSTQLLLNGSLAEEEVVIRSDNFMDNTKTIIVQLNESVAINCTRPNNNT
RKGIHIGPGRAFYAARKIIGDIRQAHCNLSRAQWNNTLKQIVIKLREHFGNKTIKFNQSSGGDPEIVRHSF
NCGGEFFYCDTTQLFNSTWNGTEGNNTEGNSTITLPCRIKQIINMWQEVGKAMYAPPIGGQIRCSSNITGL
LLTRDGGTEGNGTENETEIFRPGGGDMRDNWRSELYKYKVVKVEPLGVAPTRAKRRVVQRMGPISPIETVP
VKLKPGMDGPKVKQWPLTEEKIKALVEICTEMEKEGKISKIGPENPYNTPVFAIKKKDSTKWRKLVDFREL
NKRTQDFWEVQLGIPHPAGLKKKKSVTVLDVGDAYFSVPLDEDFRKYTAFTIPSINNETPGIRYQYNVLPQ
GWKGSPAIFQSSMTKILEPFRKQNPDIVIYQYMDDLYVGSDLEIGQHRTKIEELRQHLLRWGLTTPDKKHQ
KEPPFLKMGYELHPDKWTVQPIVLPEKDSWTVNDIQKLVGKLNWASQIYPGIKVRQLCKLLRGTKALTEVI
PLTEEAELELAENREILKEPVHGVYYDPSKDLIAEIQKQGQGQWTYQIYQEPFKNLKTGKYARMRGAHTND
VKQLTEAVQKITTESIVIWGKTPKFKLPIQKETWETWWTEYWQATWIPEWEFVNTPPLVKLWYQLEKEPIV
GAETFYVDGAANRETKLGKAGYVTNRGRQKVVTLTDTTNQKTELQAIYLALQDSGLEVNIVTDSQYALGII
```

Figure 21 continued

QAQPDQSESELVNQIIEQLIKKEKVYLAWVPAHKGIGGNEQVDKLVSAGIRKVLMVGFPVTPQVPLRPMTY
KAAVDLSHFLKEKGGLEGLIHSQRRQDILDLWIYHTQGYFPDWQNYTPGPGVRYPLTFGWCYKLVPVEPDK
VEEANKGENTSLLHPVSLHGMDDPEREVLEWRFDSRLAFHHVARELHPEYFKNCMGARASVLSGGELDRWE
KIRLRPGGKKKYKLKHIVWASRELERFAVNPGLLETSEGCRQILGQLQPSLQTGSEELRSLYNTVATLYCV
HQRIEIKDTKEALDKIEEEQNKSKKKAQQAAADTGHSNQVSQNYPIVQNIQGQMVHQAISPRTLNAWVKVV
EEKAFSPEVIPMFSALSEGATPQDLNTMLNTVGGHQAAMQMLKETINEEAAEWDRVHPVHAGPIAPGQMRE
PRGSDIAGTTSTLQEQIGWMTNNPPIPVGEIYKRWIILGLNKIVRMYSPTSILDIRQGPKEPFRDYVDRFY
KTLRAEQASQEVKNWMTETLLVQNANPDCKTILKALGPAATLEEMMTACQGVGGPGHKARVL [SEQ ID
NO: 85]

Figure 22 pRix59

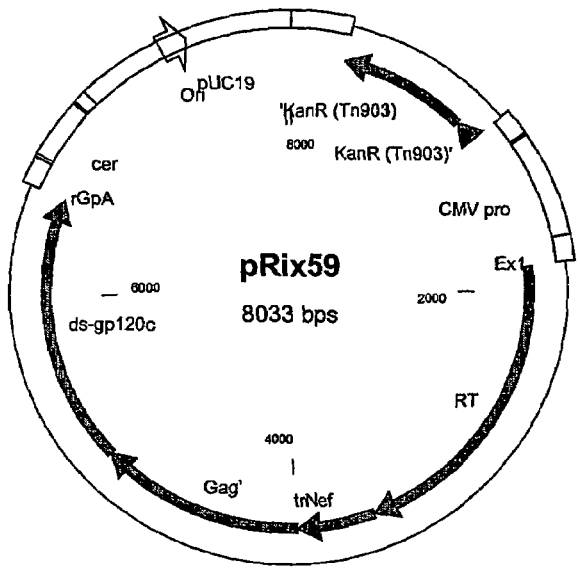

DNA sequence of insert
ATGGGCCCCATCAGTCCCATCGAGACCGTGCCGGTGAAGCTGAAACCCGGGATGGACGGCCCCAAGGTCAA
GCAGTGGCCACTCACCGAGGAGAAGATCAAGGCCCTGGTGGAGATCTGCACCGAGATGGAGAAAGAGGGCA
AGATCAGCAAGATCGGGCCGGAGAACCCATACAACACCCCCGTGTTTGCCATCAAGAAGAAGGACAGCACC
AAGTGGCGCAAGCTGGTGGATTTCCGGGAGCTGAATAAGCGGACCCAGGATTTCTGGGAGGTCCAGCTGGG
CATCCCCCATCCGGCCGGCCTGAAGAAGAAGAAGAGCGTGACCGTGCTGGACGTGGGCGACGCTTACTTCA
GCGTCCCTCTGGACGAGGACTTTAGAAAGTACACCGCCTTTACCATCCCATCTATCAACAACGAGACCCCT
GGCATCAGATATCAGTACAACGTCCTCCCCCAGGGCTGGAAGGGCTCTCCCGCCATTTTCCAGAGCTCCAT
GACCAAGATCCTGGAGCCGTTTCGGAAGCAGAACCCCGATATCGTCATCTACCAGTACATGGACGACCTGT
ACGTGGGCTCTGACCTGGAAATCGGGCAGCATCGCACGAAGATTGAGGAGCTGAGGCAGCATCTGCTGAGA
TGGGGCCTGACCACTCCGGACAAGAAGCATCAGAAGGAGCCGCCATTCCTGAAGATGGGCTACGAGCTCCA
TCCCGACAAGTGGACCGTGCAGCCTATCGTCCTCCCCGAGAAGGACAGCTGGACCGTGAACGACATCCAGA
AGCTGGTGGGCAAGCTCAACTGGGCTAGCCAGATCTATCCCGGGATCAAGGTGCGCCAGCTCTGCAAGCTG
CTGCGCGGCACCAAGGCCCTGACCGAGGTGATTCCCCTCACGGAGGAAGCCGAGCTCGAGCTGGCTGAGAA
CCGGGAGATCCTGAAGGAGCCCGTGCACGGCGTGTACTATGACCCCTCCAAGGACCTGATCGCCGAAATCC
AGAAGCAGGGCCAGGGGCAGTGGACATACCAGATTTACCAGGAGCCTTTCAAGAACCTCAAGACCGGCAAG
TACGCCCGCATGAGGGGCGCCCACACCAACGATGTCAAGCAGCTGACCGAGGCCGTCCAGAAGATCACGAC
CGAGTCCATCGTGATCTGGGGGAAGACACCCAAGTTCAAGCTGCCTATCCAGAAGGAGACCTGGGAGACGT
GGTGGACCGAATATTGGCAGGCCACCTGGATTCCCGAGTGGGAGTTCGTGAATACACCTCCTCTGGTGAAG
CTGTGGTACCAGCTCGAGAAGGAGCCCATCGTGGGCGCGGAGACATTCTACGTGGACGGCGCGGCCAACCG
CGAAACAAAGCTCGGGAAGGCCGGGTACGTCACCAACCGGGGCCGCCAGAAGGTCGTCACCCTGACCGACA
CCACCAACCAGAAGACGGAGCTGCAGGCCATCTATCTCGCTCTCCAGGACTCCGGCCTGGAGGTGAACATC
GTGACGGACAGCCAGTACGCGCTGGGCATTATTCAGGCCCAGCCGGACCAGTCCGAGAGCGAACTGGTGAA
CCAGATTATCGAGCAGCTGATCAAGAAGAGAAGGTCTACCTCGCCTGGGTCCCGGCCCATAAGGGCATTG
GCGGCAACGAGCAGGTCGACAAGCTGGTGAGTGCGGGGATTAGAAAGGTGCTGATGGTGGGTTTTCCAGTC
ACACCTCAGGTACCTTTAAGACCAATGACTTACAAGGCAGCTGTAGATCTTAGCCACTTTTTAAAAGAAAA
GGGGGGACTGGAAGGGCTAATTCACTCCCAAAGAAGACAAGATATCCTTGATCTGTGGATCTACCACACAC
AAGGCTACTTCCCTGATTGGCAGAACTACACACCAGGGCCAGGGGTCAGATATCCACTGACCTTTGGATGG
TGCTACAAGCTAGTACCAGTTGAGCCAGATAAGGTAGAAGAGGCCAATAAAGGAGAGAACACCAGCTTGTT
ACACCCTGTGAGCCTGCATGGGATGGATGACCCGGAGAGAGAAGTGTTAGAGTGGAGGTTTGACAGCCGCC

Figure 22 continued

```
TAGCATTTCATCACGTGGCCCGAGAGCTGCATCCGGAGTACTTCAAGAACTGCATGGGTGCCCGAGCTTCG
GTACTGTCTGGTGGAGAGCTGGACAGATGGGAGAAAATTAGGCTGCGCCCGGGAGGCAAAAAGAAATACAA
GCTCAAGCATATCGTGTGGGCCTCGAGGGAGCTTGAACGGTTTGCCGTGAACCCAGGCCTGCTGGAAACAT
CTGAGGGATGTCGCCAGATCCTGGGCAATTGCAGCCATCCCTCCAGACCGGGAGTGAAGAGCTGAGGTCC
TTGTATAACACAGTGGCTACCCTCTACTGCGTACACCAGAGGATCGAGATTAAGGATACCAAGGAGGCCTT
GGACAAAATTGAGGAGGAGCAAAACAAGAGCAAGAAGAAGGCCCAGCAGGCAGCTGCTGACACTGGGCATA
GCAACCAGGTATCACAGAACTATCCTATTGTCCAAAACATTCAGGGCCAGATGGTTCATCAGGCCATCAGC
CCCCGGACGCTCAATGCCTGGGTGAAGGTTGTCGAAGAGAAGGCCTTTTCTCCTGAGGTTATCCCCATGTT
CTCCGCTTTGAGTGAGGGGGCCACTCCTCAGGACCTCAATACAATGCTTAATACCGTGGGCGGCCATCAGG
CCGCCATGCAAATGTTGAAGGAGACTATCAACGAGGAGGCAGCCGAGTGGGACAGAGTGCATCCCGTCCAC
GCTGGCCCAATCGCGCCCGGACAGATGCGGGAGCCTCGCGGCTCTGACATTGCCGGCACCACCTCTACACT
GCAAGAGCAAATCGGATGGATGACCAACAATCCTCCCATCCCAGTTGGAGAAATCTATAAACGGTGGATCA
TCCTGGGCCTGAACAAGATCGTGCGCATGTACTCTCCGACATCCATCCTTGACATTAGACAGGGACCCAAA
GAGCCTTTTAGGGATTACGTCGACCGGTTTTATAAGACCCTGCGAGCAGAGCAGGCCTCTCAGGAGGTCAA
AAACTGGATGACGGAGACACTCCTGGTACAGAACGCTAACCCCGACTGCAAAACAATCTTGAAGGCACTAG
GCCCGGCTGCCACCCTGGAAGAGATGATGACCGCCTGTCAGGGAGTAGGCGGACCCGGACACAAAGCCAGA
GTGTTGATGGCCGAGCAGCTGTGGGTCACCGTCTACTACGGCGTGCCTGTGTGGAAGGAGGCCACGACCAC
CCTCTTCTGCGCGAGCGACGCCAAGGCCTACGACACGGAAGTGCATAACGTGTGGGCGACGCATGCTTGCG
TGCCTACGGACCCCAACCCCCAGGAGGTGGTGCTGGGAAACGTGACCGAGTACTTCAACATGTGGAAGAAT
AACATGGTGGATCAGATGCACGAGGACATCATCTCTCTGTGGGACCAGTCCCTGAAGCCCTGCGTGAAGCT
GACGCCTCTCTGCGTGACACTGGACTGTGACGACGTCAACACCACCAACAGCACTACCACCACCAGCAACG
GCTGGACCGGAGAGATTCGGAAGGGCGAGATCAAGAACTGCTCCTTCAATATCACGACCTCGATCAGAGAC
AAGGTGCAGAAGGAATACGCGCTGTTTTATAATCTCGATGTGGTCCCCATCGACGACGACAATGCCACCAC
CAAGAACAAGACGACGCGTAATTTCAGACTCATTCACTGCAACAGCAGCGTCATGACGCAGGCCTGCCCCA
AGGTGTCCTTCGAACCAATCCCGATCCATTACTGTGCCCCTGCCGGATTCGCGATCCTCAAGTGTAACAAC
AAGACCTTCGACGGGAAGGGCCTGTGCACCAACGTCAGCACGGTGCAGTGCACCCATGGCATCCGCCCCGT
CGTGAGCACCCAGCTGCTGCTGAACGGGTCCCTGGCTGAGGAGGAGGTGGTGATCCGGTCGGACAACTTCA
TGGACAACACCAAGACAATCATCGTCCAGCTGAACGAGTCTGTGGCGATTAACTGTACCCGGCCTAACAAC
AACACCCGTAAGGGCATCCACATCGGGCCTGGACGGGCCTTCTATGCCGCCCGCAAGATCATCGGCGACAT
CCGGCAGGCCCATTGCAACCTCTCCCGCGCCCAGTGGAATAACACCCTGAAGCAGATCGTGATCAAGCTGA
GAGAGCACTTTGGAAACAAGACCATCAAGTTCAATCAGAGTTCTGGCGGAGACCCCGAGATCGTGCGGCAC
TCCTTCAACTGCGGGGGCGAGTTCTTCTACTGCGATACGACACAGCTCTTCAACTCCACCTGGAACGGCAC
CGAGGGCAACAACACAGAGGGAAACTCCACTATCACCCTCCCTTGCCGCATCAAGCAGATCATCAACATGT
GGCAGGAGGTGGGAAAGGCCATGTATGCCCCCCCCATCGGGGGCCAGATCCGCTGCTCCTCCAACATCACC
GGCCTGCTGCTCACCAGAGACGGGGGCACCGAGGGCAACGGCACGGAGAACGAGACGGAGATCTTCAGGCC
CGGCGGCGGCGACATGAGGGATAACTGGCGGAGCGAGCTGTACAAGTACAAGGTGGTGAAGGTGGAGCCGC
TCGGCGTGGCCCCCACCCGGGCCAAGCGCCGCGTCGTGCAGAGATGA          [SEQ ID NO: 86]
```

Aminoacid sequence of insert
```
MGPISPIETVPVKLKPGMDGPKVKQWPLTEEKIKALVEICTEMEKEGKISKIGPENPYNTPVFAIKKKDST
KWRKLVDFRELNKRTQDFWEVQLGIPHPAGLKKKKSVTVLDVGDAYFSVPLDEDFRKYTAFTIPSINNETP
GIRYQYNVLPQGWKGSPAIFQSSMTKILEPFRKQNPDIVIYQYMDDLYVGSDLEIGQHRTKIEELRQHLLR
WGLTTPDKKHQKEPPFLKMGYELHPDKWTVQPIVLPEKDSWTVNDIQKLVGKLNWASQIYPGIKVRQLCKL
LRGTKALTEVIPLTEEAELELAENREILKEPVHGVYYDPSKDLIAEIQKQGQGQWTYQIYQEPFKNLKTGK
YARMRGAHTNDVKQLTEAVQKITTESIVIWGKTPKFKLPIQKETWETWWTEYWQATWIPEWEFVNTPPLVK
LWYQLEKEPIVGAETFYVDGAANRETKLGKAGYVTNRGRQKVVTLTDTTNQKTELQAIYLALQDSGLEVNI
VTDSQYALGIIQAQPDQSESELVNQIIEQLIKKEKVYLAWVPAHKGIGGNEQVDKLVSAGIRKVLMVGFPV
TPQVPLRPMTYKAAVDLSHFLKEKGGLEGLIHSQRRQDILDLWIYHTQGYFPDWQNYTPGPGVRYPLTFGW
CYKLVPVEPDKVEEANKGENTSLLHPVSLHGMDDPEREVLEWRFDSRLAFHHVARELHPEYFKNCMGARAS
VLSGGELDRWEKIRLRPGGKKKYKLKHIVWASRELERFAVNPGLLETSEGCRQILGQLQPSLQTGSEELRS
LYNTVATLYCVHQRIEIKDTKEALDKIEEEQNKSKKKAQQAAADTGHSNQVSQNYPIVQNIQGQMVHQAIS
PRTLNAWVKVVEEKAFSPEVIPMFSALSEGATPQDLNTMLNTVGGHQAAMQMLKETINEEAAEWDRVHPVH
AGPIAPGQMREPRGSDIAGTTSTLQEQIGWMTNNPPIPVGEIYKRWIILGLNKIVRMYSPTSILDIRQGPK
EPFRDYVDRFYKTLRAEQASQEVKNWMTETLLVQNANPDCKTILKALGPAATLEEMMTACQGVGGPGHKAR
```

Figure 22 continued

```
VLMAEQLWVTVYYGVPVWKEATTTLFCASDAKAYDTEVHNVWATHACVPTDPNPQEVVLGNVTEYFNMWKN
NMVDQMHEDIISLWDQSLKPCVKLTPLCVTLDCDDVNTTNSTTTTSNGWTGEIRKGEIKNCSFNITTSIRD
KVQKEYALFYNLDVVPIDDDNATTKNKTTRNFRLIHCNSSVMTQACPKVSFEPIPIHYCAPAGFAILKCNN
KTFDGKGLCTNVSTVQCTHGIRPVVSTQLLLNGSLAEEEVVIRSDNFMDNTKTIIVQLNESVAINCTRPNN
NTRKGIHIGPGRAFYAARKIIGDIRQAHCNLSRAQWNNTLKQIVIKLREHFGNKTIKFNQSSGGDPEIVRH
SFNCGGEFFYCDTTQLFNSTWNGTEGNNTEGNSTITLPCRIKQIINMWQEVGKAMYAPPIGGQIRCSSNIT
GLLLTRDGGTEGNGTENETEIFRPGGGDMRDNWRSELYKYKVVKVEPLGVAPTRAKRRVVQR  [SEQ  ID
NO: 87]
``` pRix50

DNA and amino acid sequences of inserts:

Identical to pNTm and pRix12 pRix51

DNA and amino acid sequences of inserts:

Identical to p73I-GN2 and pRix12 pRix53

DNA and amino acid sequences of inserts:

Identical to pRix52 and pRix12 pRix54

DNA and amino acid sequences of inserts:

Identical to pT-RNG and pRix12 pRix60

DNA and amino acid sequences of inserts:

Identical to pRix12 and pT-rng

Figure 28 pT-RNG

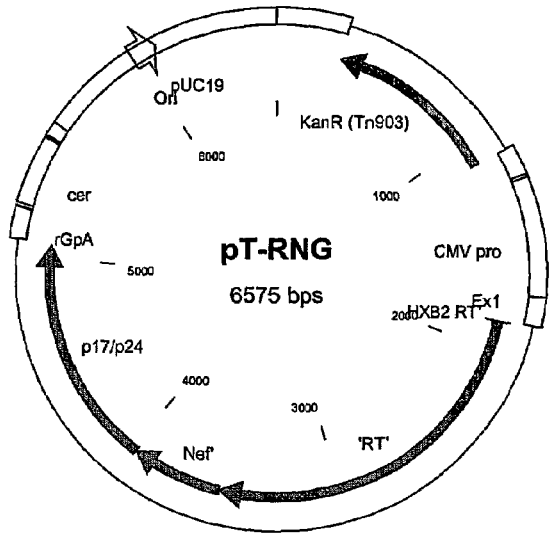

DNA sequence of insert:

ATGGGCCCCATCAGTCCCATCGAGACCGTGCCGGTGAAGCTGAAACCCGGGATGGACGGCCCCAAGGTCAA
GCAGTGGCCACTCACCGAGGAGAAGATCAAGGCCCTGGTGGAGATCTGCACCGAGATGGAGAAAGAGGGCA
AGATCAGCAAGATCGGGCCTGAGAACCCATACAACACCCCCGTGTTTGCCATCAAGAAGAAGGACAGCACC
AAGTGGCGCAAGCTGGTGGATTTCCGGGAGCTGAATAAGCGGACCCAGGATTTCTGGGAGGTCCAGCTGGG
CATCCCCCATCCGGCCGGCCTGAAGAAGAAGAAGAGCGTGACCGTGCTGGACGTGGGCGACGCTTACTTCA
GCGTCCCTCTGGACGAGGACTTTAGAAAGTACACCGCCTTTACCATCCCATCTATCAACAACGAGACCCCT
GGCATCAGATATCAGTACAACGTCCTCCCCCAGGGCTGGAAGGGCTCTCCCGCCATTTTCCAGAGCTCCAT
GACCAAGATCCTGGAGCCGTTTCGGAAGCAGAACCCCGATATCGTCATCTACCAGTACATGGACGACCTGT
ACGTGGGCTCTGACCTGGAAATCGGGCAGCATCGCACGAAGATTGAGGAGCTGAGGCAGCATCTGCTGAGA
TGGGGCCTGACCACTCCGGACAAGAAGCATCAGAAGGAGCCGCCATTCCTGAAGATGGGCTACGAGCTCCA
TCCCGACAAGTGGACCGTGCAGCCTATCGTCCTCCCCGAGAAGGACAGCTGGACCGTGAACGACATCCAGA
AGCTGGTGGGCAAGCTCAACTGGGCTAGCCAGATCTATCCCGGGATCAAGGTGCGCCAGCTCTGCAAGCTG
CTGCGCGGCACCAAGGCCCTGACCGAGGTGATTCCCCTCACGGAGGAAGCCGAGCTCGAGCTGGCTGAGAA
CCGGGAGATCCTGAAGGAGCCCGTGCACGGCGTGTACTATGACCCCTCCAAGGACCTGATCGCCGAAATCC
AGAAGCAGGGCCAGGGGCAGTGGACATACCAGATTTACCAGGAGCCTTTCAAGAACCTCAAGACCGGCAAG
TACGCCCGCATGAGGGGCGCCCACACCAACGATGTCAAGCAGCTGACCGAGGCCGTCCAGAAGATCACGAC
CGAGTCCATCGTGATCTGGGGGAAGACACCCAAGTTCAAGCTGCCTATCCAGAAGGAGACCTGGGAGACGT
GGTGGACCGAATATTGGCAGGCCCACCTGGATTCCCGAGTGGGAGTTCGTGAATACACCTCCTCTGGTGAAG
CTGTGGTACCAGCTCGAGAAGGAGCCCATCGTGGGCGCGGAGACATTCTACGTGGACGGCGCGGCCAACCG
CGAAACAAAGCTCGGGAAGGCCGGGTACGTCACCAACCGGGGCGCCCAGAAGGTCGTCACCCTGACCGACA
CCACCAACCAGAAGACGGAGCTGCAGGCCATCTATCTCGCTCTCCAGGACTCCGGCCTGGAGGTGAACATC
GTGACGGACAGCCAGTACGCGCTGGGCATTATTCAGGCCCAGCCGGACCAGTCCGAGAGCGAACTGGTGAA
CCAGATTATCGAGCAGCTGATCAAGAAAGAGAAGGTCTACCTCGCCTGGGTCCCGGCCCATAAGGGCATTG
GCGGCAACGAGCAGGTCGACAAGCTGGTGAGTGCGGGGATTAGAAAGGTGCTGATGGTGGGTTTTCCAGTC
ACACCTCAGGTACCTTTAAGACCAATGACTTACAAGGCAGCTGTAGATCTTAGCCACTTTTTTAAAAGAAAA
GGGGGGACTGGAAGGGCTAATTCACTCCCAAAGAAGACAAGATATCCTTGATCTGTGGATCTACCACACAC
AAGGCTACTTCCCTGATTGGCAGAACTACACACCAGGGCCAGGGGTCAGATATCCACTGACCTTTGGATGG
TGCTACAAGCTAGTACCAGTTGAGCCAGATAAGGTAGAAGAGGCCAATAAAGGAGAGAACACCAGCTTGTT

Figure 28 continued

```
ACACCCTGTGAGCCTGCATGGGATGGATGACCCGGAGAGAGAAGTGTTAGAGTGGAGGTTTGACAGCCGCC
TAGCATTTCATCACGTGGCCCGAGAGCTGCATCCGGAGTACTTCAAGAACTGCATGGGTGCCCGAGCTTCG
GTACTGTCTGGTGGAGAGCTGGACAGATGGGAGAAAATTAGGCTGCGCCCGGGAGGCAAAAAGAAATACAA
GCTCAAGCATATCGTGTGGGCCTCGAGGGAGCTTGAACGGTTTGCCGTGAACCCAGGCCTGCTGGAAACAT
CTGAGGGATGTCGCCAGATCCTGGGGCAATTGCAGCCATCCCTCCAGACCGGGAGTGAAGAGCTGAGGTCC
TTGTATAACACAGTGGCTACCCTCTACTGCGTACACCAGAGGATCGAGATTAAGGATACCAAGGAGGCCTT
GGACAAAATTGAGGAGGAGCAAAACAAGAGCAAGAAGAAGCCCAGCAGGCAGCTGCTGACACTGGGCATA
GCAACCAGGTATCACAGAACTATCCTATTGTCCAAAACATTCAGGGCCAGATGGTTCATCAGGCCATCAGC
CCCCGGACGCTCAATGCCTGGGTGAAGGTTGTCGAAGAGAAGGCCTTTTCTCCTGAGGTTATCCCCATGTT
CTCCGCTTTGAGTGAGGGGGCCACTCCTCAGGACCTCAATACAATGCTTAATACCGTGGGCGGCCATCAGG
CCGCCATGCAAATGTTGAAGGAGACTATCAACGAGGAGGCAGCCGAGTGGGACAGAGTGCATCCCGTCCAC
GCTGGCCCAATCGCGCCCGGACAGATGCGGGAGCCTCGCGGCTCTGACATTGCCGGCACCACCTCTACACT
GCAAGAGCAAATCGGATGGATGACCAACAATCCTCCCATCCCAGTTGGAGAAATCTATAAACGGTGGATCA
TCCTGGGCCTGAACAAGATCGTGCGCATGTACTCTCCGACATCCATCCTTGACATTAGACAGGGACCCAAA
GAGCCTTTTAGGGATTACGTCGACCGGTTTTATAAGACCCTGCGAGCAGAGCAGGCCTCTCAGGAGGTCAA
AAACTGGATGACGGAGACACTCCTGGTACAGAACGCTAACCCCGACTGCAAAACAATCTTGAAGGCACTAG
GCCCGGCTGCCACCCTGGAAGAGATGATGACCGCCTGTCAGGGAGTAGGCGGACCCGGACACAAAGCCAGA
GTGTTGTAA [SEQ ID NO: 88]
```

Amino acid sequence of insert:

```
MGPISPIETVPVKLKPGMDGPKVKQWPLTEEKIKALVEICTEMEKEGKISKIGPENPYNTPVFAIKKKDST
KWRKLVDFRELNKRTQDFWEVQLGIPHPAGLKKKKSVTVLDVGDAYFSVPLDEDFRKYTAFTIPSINNETP
GIRYQYNVLPQGWKGSPAIFQSSMTKILEPFRKQNPDIVIYQYMDDLYVGSDLEIGQHRTKIEELRQHLLR
WGLTTPDKKHQKEPPFLKMGYELHPDKWTVQPIVLPEKDSWTVNDIQKLVGKLNWASQIYPGIKVRQLCKL
LRGTKALTEVIPLTEEAELELAENREILKEPVHGVYYDPSKDLIAEIQKQGQGQWTYQIYQEPFKNLKTGK
YARMRGAHTNDVKQLTEAVQKITTESIVIWGKTPKFKLPIQKETWETWWTEYWQATWIPEWEFVNTPPLVK
LWYQLEKEPIVGAETFYVDGAANRETKLGKAGYVTNRGRQKVVTLTDTTNQKTELQAIYLALQDSGLEVNI
VTDSQYALGIIQAQPDQSESELVNQIIEQLIKKEKVYLAWVPAHKGIGGNEQVDKLVSAGIRKVLMVGFPV
TPQVPLRPMTYKAAVDLSHFLKEKGGLEGLIHSQRRQDILDLWIYHTQGYFPDWQNYTPGPGVRYPLTFGW
CYKLVPVEPDKVEEANKGENTSLLHPVSLHGMDDPEREVLEWRFDSRLAFHHVARELHPEYFKNCMGARAS
VLSGGELDRWEKIRLRPGGKKKYKLKHIVWASRELERPAVNPGLLETSEGCRQILGQLQPSLQTGSEELRS
LYNTVATLYCVHQRIEIKDTKEALDKIEEEQNKSKKKAQQAAADTGHSNQVSQNYPIVQNIQGQMVHQAIS
PRTLNAWVKVVEEKAFSPEVIPMFSALSEGATPQDLNTMLNTVGGHQAAMQMLKETINEEAAEWDRVHPVH
AGPIAPGQMREPRGSDIAGTTSTLQEQIGWMTNNPPIPVGEIYKRWIILGLNKIVRMYSPTSILDIRQGPK
EPFRDYVDRFYKTLRAEQASQEVKNWMTETLLVQNANPDCKTILKALGPAATLEEMMTACQGVGGPGHKAR
VL [SEQ ID NO: 89]
```

Figure 29
A schematic representation of the constructs and associated expression data is shown below
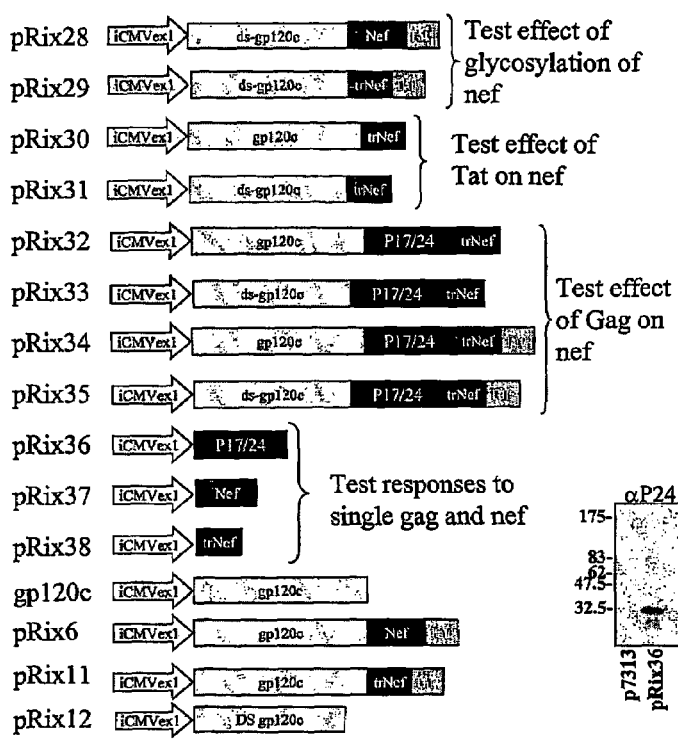
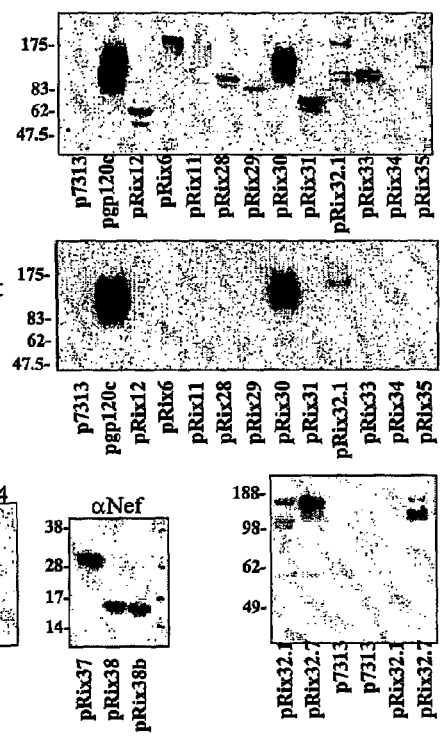

Figure 30
A schematic representation of further constructs and associated expression data:
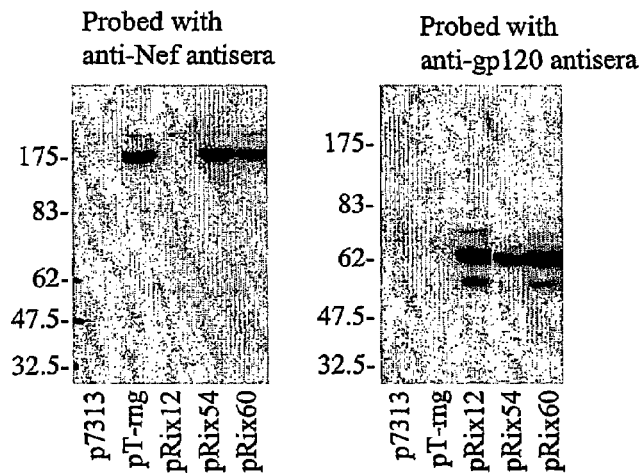
Western blots probed with anti-nef (left) or anti-gp120 (right) antisera showing the expression of RNG and dsgp120 from dual promoter and single vectors.
Plasmid schematics:
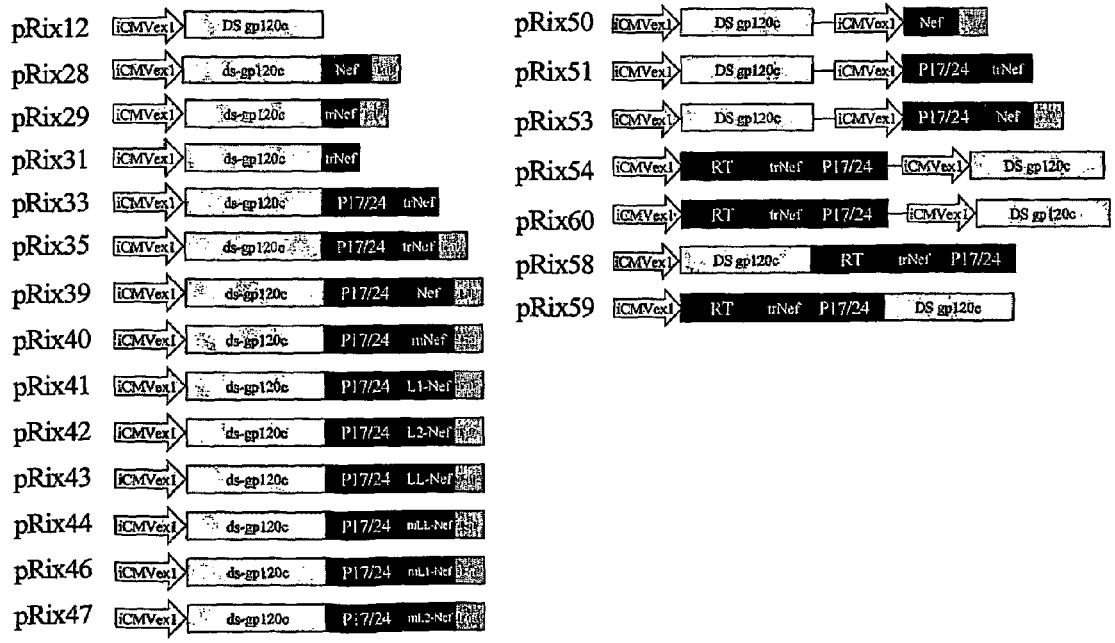

Figure 31
Expression data (anti-Nef) for dsgp120/Gag/Nef/Tat fusions with mutations in Nef (pRix 40-47)
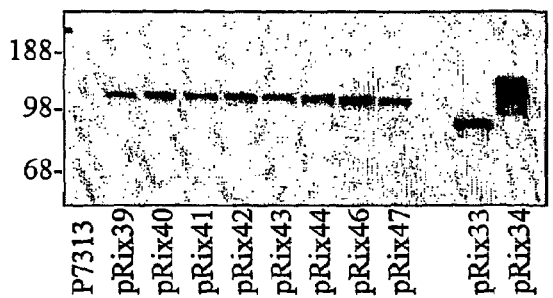
Expression data (anti-Nef and anti-gp120) for dual promoter vectors
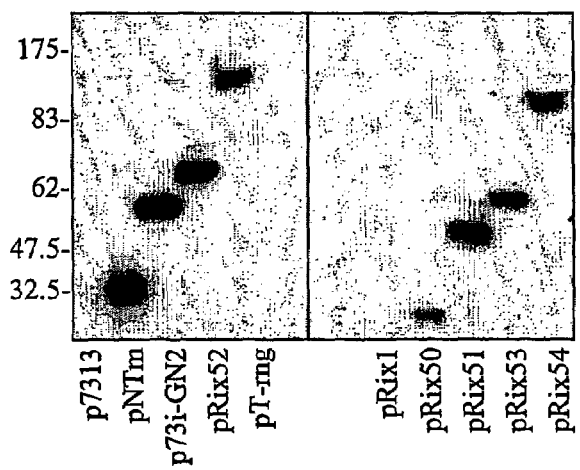 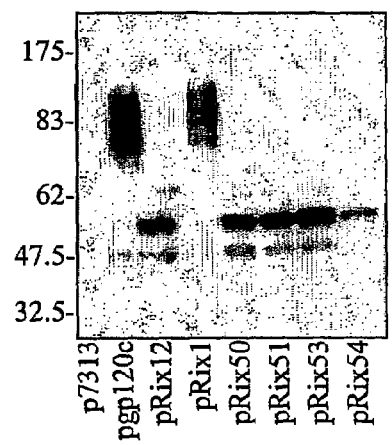
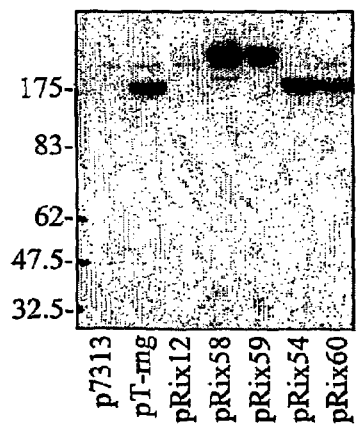 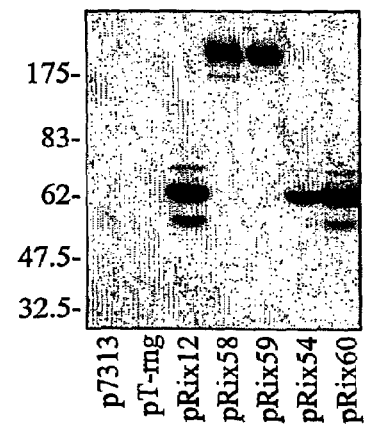

VACCINE

CROSS REFERENCE TO RELATED APPLICATION

This application is a 371 application of PCT/EP2003/012402 filed on 3 Nov. 2003.

FIELD OF THE INVENTION

This invention relates to nucleic acid constructs, vectors comprising such constructs, methods of preparing the vectors and constructs and their use in prophylaxis or therapy, in particular therapeutic vaccines. The invention further relates to host cells comprising the constructs and vectors and to polypeptides encoded by the constructs as well as to the polypeptides per se. The invention further relates to pharmaceutical formulations comprising the constructs and vectors and to the use of the constructs and vectors in medicine. The invention relates in particular to DNA vaccines that are useful in the prophylaxis and treatment of HIV infections, more particularly when administered by particle mediated delivery.

BACKGROUND TO THE INVENTION

HIV-1 is the primary cause of the acquired immune deficiency syndrome (AIDS) which is regarded as one of the world's major health problems. Although extensive research throughout the world has been conducted to produce a vaccine, such efforts thus far have not been successful.

The HIV envelope glycoprotein gp120 is the viral protein that is used for attachment to the host cell. This attachment is mediated by binding to two surface molecules of helper T cells and macrophages, known as CD4 and one of the two chemokine receptors CCR-4 or CXCR-5. The gp120 protein is first expressed as a larger precursor molecule (gp160), which is then cleaved post-translationally to yield gp120 and gp41. The gp120 protein is retained on the surface of the virion by linkage to the gp41 molecule, which is inserted into the viral membrane.

The gp120 protein is the principal target of neutralizing antibodies, but unfortunately the most immunogenic regions of the proteins (V3 loop) are also the most variable parts of the protein. Therefore, the use of gp120 (or its precursor gp 160) as a vaccine antigen to elicit neutralizing antibodies is thought to be of limited use for a broadly protective vaccine. The gp120 protein does also contain epitopes that are recognized by cytotoxic T lymphocytes (CTL). These effector cells are able to eliminate virus-infected cells, and therefore constitute a second major antiviral immune mechanism. In contrast to the target regions of neutralizing antibodies some CTL epitopes appear to be relatively conserved among different HIV strains. For this reason gp120 and gp160 maybe useful antigenic components in vaccines that aim at eliciting cell-mediated immune responses (particularly CTL).

Non-envelope proteins of HIV-1 have been described and include for example internal structural proteins such as the products of the gag and pol genes and other non-structural proteins such as Rev, Nef, Vif and Tat (Green et al., New England J. Med, 324, 5, 308 et seq (1991) and Bryant et al. (Ed. Pizzo), Pediatr. Infect. Dis. J., 11, 5, 390 et seq (1992).

HIV Tat and Nef proteins are early proteins, that is they are expressed early in infection and in the absence of structural protein.

BRIEF DESCRIPTION OF THE DRAWINGS

FIG. 2 is a map of pgp120c, including the amino acid and codon optimized DNA sequence of the W61D gp120 gene.
FIG. 4 is a map of Plasmid pNTm, including the DNA sequence of the insert and amino acid sequence of the antigen.
FIG. 5 is a map of Plasmid ptrNTm, including the DNA sequence of the insert and amino acid sequence of the antigen.
FIG. 6 is a map of Plasmid pRix12, including the DNA sequence of the insert and amino acid sequence of the antigen.
FIG. 7 is a map of Plasmid pRix28, including the DNA sequence of the insert and amino acid sequence of the antigen.
FIG. 8 is a map of Plasmid pRix29, including the DNA sequence of the insert and amino acid sequence of the antigen.
FIG. 9 is a map of Plasmid pRix31, including the DNA sequence of the insert and amino acid sequence of the antigen.
FIG. 10 is a map of p73i-Gn2, including the DNA sequence of the insert.
FIG. 11 is a map of Plasmid pRix33, including the DNA sequence of the insert and amino acid sequence of the antigen.
FIG. 12 is a map of Plasmid pRix35, including the DNA sequence of the insert and amino acid sequence of the antigen.
FIG. 13 is a map of Plasmid pRix39, including the DNA sequence of the insert and amino acid sequence of the antigen.
FIG. 14 is a map of Plasmid pRix40, including the DNA sequence of the insert and amino acid sequence of the antigen.
FIG. 15 is a map of Plasmid pRix41, including the DNA sequence of the insert and amino acid sequence of the antigen.
FIG. 16 is a map of Plasmid pRix42, including the DNA sequence of the insert and amino acid sequence of the antigen.
FIG. 17 is a map of Plasmid pRix43, including the DNA sequence of the insert and amino acid sequence of the antigen.
FIG. 18 is a map of Plasmid pRix44, including the DNA sequence of the insert and amino acid sequence of the antigen.
FIG. 19 is a map of Plasmid pRix46, including the DNA sequence of the insert and amino acid sequence of the antigen.
FIG. 20 is a map of Plasmid pRix47, including the DNA sequence of the insert and amino acid sequence of the antigen.
FIG. 21 is a map of Plasmid pRix58, including the DNA sequence of the insert and amino acid sequence of the antigen.
FIG. 22 is a map of Plasmid pRix59, including the DNA sequence of the insert and amino acid sequence of the antigen.
FIG. 28 is a map of Plasmid pT-RNG, including the DNA sequence of the insert and amino acid sequence of the antigen.
FIG. 29 is a schematic representation of constructs and associated expression data.
FIG. 30 is a schematic representation of constructs and associated expression data.
FIG. 31 is expression data (anti-Nef) for dsgp120/Gag/Nef/Tat fusions with mutations in Nef (pRix40-47).

DETAILED DESCRIPTION

Figure 1:
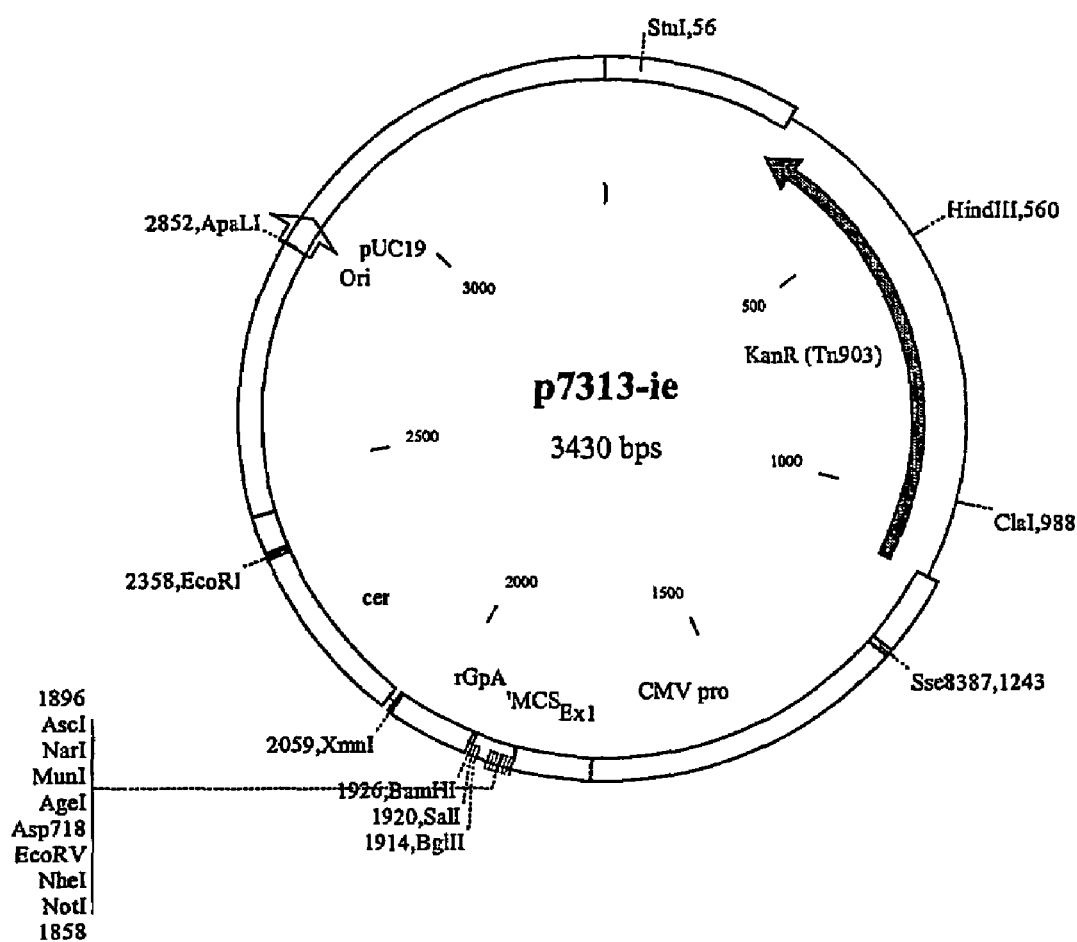
FIG. 1 is a map of P7313-ie.

The Nef protein is known to cause the removal of CD4, the HIV receptor, from the cell surface, but the biological importance of this function is debated. Additionally Nef interacts with the signal pathway of T cells and induces an active state, which in turn may promote more efficient gene expression. Some HIV isolates have mutations in this region, which cause them not to encode functional protein and are severely compromised in their replication and pathogenesis in vivo.

The Tat gene gives rise to a number of differentially spliced transcripts at different times during infection. The first exon encodes an 86 amino acid protein which dominates early in infection. The second exon encodes an additional 14 amino acids, and this partially spliced form of Tat is found late in infection. Both forms are fully functional transactivators, but the longer form also contains an RGD motif important for binding to $\alpha_v\beta_3$ and $\alpha_5\beta_1$ integrins. Tat binds to a short-stem loop structure, known as the transactivation response element (TAR), that is located at the 5' terminus of HIV RNAs, and up-regulates transcription from the HIV LTR at least 1000-fold. Tat has a role in promoting the elongation phase of HIV infection and stimulates the production of full-length viral transcripts. Tat can affect the expression of a number of cellular genes and can activate the expression of a number of cellular genes including TNF, IL-2 and IL-6, and regulates expression of p53 and Bcl-2. Tat is produced in excess and is secreted from infected cells. This extra-cellular Tat can enter other cells and may prime cells for infection by HIV or accelerate the rate of HIV replication in newly infected cells.

In a conference presentation (C. David Pauza, Immunization with Tat toxoid attenuates SHIV89.6PD infection in rhesus macaques, 12$^{th}$ Cent Gardes meeting, Marnes-La-Coquette, 26.10.1999), experiments were described in which rhesus macaques were immunised with Tat toxoid alone or in combination with an envelope glycoprotein gp160 vaccine combination (one dose recombinant vaccinia virus and one dose recombinant protein). The results observed showed that the presence of the envelope glycoprotein gave no advantage over experiments performed with Tat alone.

The Gag gene is translated from the full-length RNA to yield a precursor polyprotein which is subsequently cleaved into 3-5 capsid proteins; the matrix protein, capsid protein and nucleic acid binding protein and protease. (1. Fundamental Virology, Fields B N, Knipe D M and Howley M 1996 2. Fields Virology vol 2 1996).

The gag gene gives rise to the 55-kilodalton (kD) Gag precursor protein, also called p55, which is expressed from the unspliced viral mRNA. During translation, the N terminus of p55 is myristoylated, triggering its association with the cytoplasmic aspect of cell membranes. The membrane-associated Gag polyprotein recruits two copies of the viral genomic RNA along with other viral and cellular proteins that triggers the budding of the viral particle from the surface of an infected cell. After budding, p55 is cleaved by the virally encoded protease (a product of the pol gene) during the process of viral maturation into four smaller proteins designated MA (matrix [p17]), CA (capsid [p24]), NC (nucleocapsid [p9]), and p6.(4).

In addition to the 3 major Gag proteins, all Gag precursors contain several other regions, which are cleaved out and remain in the virion as peptides of various sizes. These proteins have different roles e.g. the p2 protein has a proposed role in regulating activity of the protease and contributes to the correct timing of proteolytic processing.

The MA polypeptide is derived from the N-terminal, myristoylated end of p55. Most MA molecules remain attached to the inner surface of the virion lipid bilayer, stabilizing the particle. A subset of MA is recruited inside the deeper layers of the virion where it becomes part of the complex which escorts the viral DNA to the nucleus. These MA molecules facilitate the nuclear transport of the viral genome because a karyophilic signal on MA is recognized by the cellular nuclear import machinery. This phenomenon allows HIV to infect non-dividing cells, an unusual property for a retrovirus.

The p24 (CA) protein forms the conical core of viral particles. Cyclophilin A has been demonstrated to interact with the p24 region of p55 leading to its incorporation into HIV particles. The interaction between Gag and cyclophilin A is essential because the disruption of this interaction by cyclosporin A inhibits viral replication.

The NC region of Gag is responsible for specifically recognizing the so-called packaging signal of HIV. The packaging signal consists of four stem loop structures located near the 5' end of the viral RNA, and is sufficient to mediate the incorporation of a heterologous RNA into HIV-1 virions. NC binds to the packaging signal through interactions mediated by two zinc-finger motifs. NC also facilitates reverse transcription.

The p6 polypeptide region mediates interactions between p55 Gag and the accessory protein Vpr, leading to the incorporation of Vpr into assembling virions. The p6 region also contains a so-called late domain which is required for the efficient release of budding virions from an infected cell.

The Pol gene encodes two proteins containing the two activities needed by the virus in early infection, the RT and the integrase protein needed for integration of viral DNA into cell DNA. The primary product of Pol is cleaved by the virion protease to yield the amino terminal RT peptide which contains activities necessary for DNA synthesis (RNA and DNA directed DNA polymerase, ribouclease H) and carboxy terminal integrase protein. HIV RT is a heterodimer of full-length RT (p66) and a cleavage product (p51) lacking the carboxy terminal Rnase integrase domain.

RT is one of the most highly conserved proteins encoded by the retroviral genome. Two major activities of RT are the DNA Pol and Ribonuclease H. The DNA Pol activity of RT uses RNA and DNA as templates interchangeably and like all DNA polymerases known is unable to initiate DNA synthesis de novo, but requires a pre existing molecule to serve as a primer (RNA).

The Rnase H activity inherent in all RT proteins plays the essential role early in replication of removing the RNA genome as DNA synthesis proceeds. It selectively degrades the RNA from all RNA-DNA hybrid molecules. Structurally the polymerase and ribo H occupy separate, non-overlapping domains with the Pol covering the amino two thirds of the Pol.

The p66 catalytic subunit is folded into 5 distinct subdomains. The amino terminal 23 of these have the portion with RT activity. Carboxy terminal to these is the Rnase H Domain.

After infection of the host cell, the retroviral RNA genome is copied into linear ds DNA by the reverse transcriptase that is present in the infecting particle. The integrase (reviewed in Skalka AM '99 Adv in Virus Res 52 271-273) recognises the ends of the viral DNA, trims them and accompanies the viral DNA to a host chromosomal site to catalyse integration. Many sites in the host DNA can be targets for integration. Although the integrase is sufficient to catalyse integration in vitro, it is not the only protein associated with the viral DNA in vivo—the large protein—viral DNA complex isolated from the infected cells has been denoted the pre integration complex. This facilitates the acquisition of the host cell genes by progeny viral genomes.

The integrase is made up of 3 distinct domains, the N terminal domain, the catalytic core and the C terminal domain. The catalytic core domain contains all of the requirements for the chemistry of polynucleotidyl transfer.

DNA vaccines usually consist of a bacterial plasmid vector into which is inserted a strong promoter, the gene of interest which encodes an antigenic peptide and a polyadenylation/transcriptional termination sequence. The gene of interest may encode a full protein or simply an antigenic peptide sequence relating to the pathogen, tumour or other agent which it is intended to protect against. The plasmid can be grown in bacteria, such as for example E. coli and then isolated and prepared in an appropriate medium, depending upon the intended route of administration, before being administered to the host. Following administration the plasmid is taken up by cells of the host, or delivered directly into the host cells, where the encoded peptide is produced. The plasmid vector will preferably be made without an origin of replication functional in eukaryotic cells, in order to prevent plasmid replication in the mammalian host and integration within chromosomal DNA of the animal concerned.

There are a number of advantages of DNA vaccination relative to traditional vaccination techniques. First, it is predicted that because the proteins that are encoded by the DNA sequence are synthesised in the host, the structure or conformation of the protein will be similar to the native protein associated with the disease state. It is also likely that DNA vaccination will offer protection against different strains of a virus, by generating a cytotoxic T lymphocyte response that recognises epitopes from conserved proteins. The technology also offers the possibility of combining diverse immunogens into a single preparation to facilitate simultaneous immunisation in relation to a number of disease states.

Helpful background information in relation to DNA vaccination is provided in Donnelly et al "DNA vaccines" Ann. Rev Immunol. 1997 15: 617-648, the disclosure of which is included herein in its entirety by way of reference.

Doe et al (1994) Eur J Immunol, 24: 2369-2376 investigated how variations in glycosylation affected the CD8+ CTL response to gp120 and found that gp120 produced in mammalian CHO cells had a reduced ability to prime CTL responses when compared with insect or yeast cell-derived envelope proteins unnless N-linked oligosaccharides were removed prior to immunization.

It has now been discovered that there are benefits to be gained by employing a polynucleotide encoding a non-glycosylated HIV envelope protein in a vaccine for HIV. Surprisingly, a DNA vector expressing gp120 without a secretion signal and which is thus not glycosylated or secreted from the cell is a more effective stimulator of CTL responses than a DNA vector expressing gp120 with its native secretion signal. Since the secretion signal is responsible for directing the gp120 to the intracellular site where glycosylation takes place, gp120 which lacks its native secretion signal is not glycosylated. Moreover, with the presence of a non-structural HIV protein such as Tat in a fusion protein with the non-glycosylated gp120, CTL responses to the gp120 are augmented. In contrast, Tat in a fusion protein with normal gp120 prevents secretion but does not result in an augmented immune response. The non-glycosylated gp120 can also be successfully expressed in a fusion protein with other HIV antigens, both structural and non-structural.

SUMMARY OF THE INVENTION

The present invention therefore provides novel constructs for use in nucleic acid or polypeptide vaccines for the prophylaxis and treatment of HIV infections and AIDS. In one aspect the invention provides a polynucleotide which comprises a sequence encoding an HIV envelope protein or fragment or immunogenic derivative thereof which is non- or substantially non-glycosylated when expressed in a mammalian target cell, operably linked to a heterologous promoter.

Preferably the HIV envelope protein is gp120. Alternatively it may be other forms of the envelope protein such as gp160 or gp140.

HIV envelope proteins such as gp120 expressed in a mammalian cell will normally be glycosylated. According to the present invention the gp120 encoding sequence is adapted to reduce or prevent glycosylation in a mammalian target cell, particularly a human target cell. Glycosylation may be reduced or prevented in a number of different ways, for example by removal of or mutation of the glycosylation sites or by removing the native secretion signal. Preferably in the polynucleotide construct according to the invention the gp120 or other form of HIV envelope protein lacks a functional secretion signal. The secretion signal may vary in length between HIV isolates, for example it is 30 amino acids long in the W61D isolate described herein, but may be more or less than that for different isolates. Generally the secretion signal is clearly delineated and will be removed in its entirety, although this is not necessarily the case. A sufficient amount of the signal will be removed to prevent its function of taking the envelope protein to the cellular machinery responsible for glycosylation. This can be easily tested for.

It will be understood that although the envelope protein does not have a functional secretion signal, there may still be a small amount of glycosylation taking place and this is not excluded from the invention. Thus the envelope protein according to the invention is substantially non-glycosylated in mammalian cells such that the majority of the envelope protein, for example greater than 50%, or preferably greater than 75%, or more preferably greater than 90%, or most preferably 95% or more of the envelope protein is not secreted from the cells.

The HIV envelope protein, particularly gp120 is preferably expressed as a fusion protein, preferably comprising at least one HIV protein selected from a non-structural protein such as Nef, Tat, and reverse transcriptase (RT) and a structural protein in particular a capsid protein such as Gag, or a fragment or immunogenic derivative of any of these.

In one embodiment the fusion protein is a gp120 and RT-containing fusion protein, optionally also comprising Gag and/or Nef.

In another embodiment the fusion protein is a gp120 and Gag-containing fusion protein optionally also comprising RT and/or Nef.

In a further embodiment the fusion protein is a gp120 and Nef-containing fusion protein optionally also comprising RT and/or Gag.

In the following preferred embodiments the fusion protein is a fusion of gp120, RT, Nef and Gag or fragments or immunogenic derivatives thereof:

gp120-RT-Nef-Gag

RT-Nef-Gag-gp120

Another embodiment is a fusion comprising gp120 and Tat or fragments or immunogenic derivatives thereof. In such an embodiment the polynucleotide according to the invention comprises a gp120 encoding sequence linked to a Tat encoding sequence to encode a gp120 and Tat-containing fusion protein.

In a particular embodiment the gp120 and Tat sequence is further linked to a Nef encoding sequence to encode a gp120, Tat and Nef-containing fusion protein, most preferably a gp120-Nef-Tat fusion.

Additional HIV sequences may be included such as a Gag encoding sequence.

In another particular embodiment the fusion encoded by the polynucleotide according to the invention is a gp120-Gag-Nef-Tat fusion.

Preferably the Tat sequence for use in the invention is mutated so that it encodes a biologically inactive Tat which lacks transactivation activity but which maintains its immunogenic epitopes. Tat transactivation activity can be measured for example by an HIV LTR reporter system such as a CAT assay system in which the chloramphenicol-acetyl transferase reporter gene is under the control of the long terminal repeat of HIV-1. One specific CAT assay which is suitable uses the HL3T1 cell line which is described in Felber and Pavlakis (1988) Science 239: 184-187 and also used in Mischiati et al (2001) Antisense Nucleic Acid Drug Dev Aug 11 (4): 209-17. HL3T1 is a HeLa cell line which contains stably integrated silent copies of HIV-1 LTR promoter linked to the CAT gene. These cells are transfected with DNA vectors containing the Tat gene, modified or not. CAT is produced upon presence of an active Tat and measured by ELISA.

One preferred mutated Tat sequence (originating from BH10 molecular clone) bears mutations in the active site region (Lys41→Ala) and in the RGD motif (Arg78→Lys and Asp80→Glu) (Virology 235: 48-64, 1997).

Optionally the Nef sequence for use in the invention is truncated to remove the sequence encoding the N terminal region i.e. removal of 30-85, preferably 60-85, preferably the N terminal 65 amino acids (the latter truncation is referred to herein as trNef). Advantageously the Nef may be modified to remove one or more myristylation sites. For example the Gly 2 myristylation site may be removed by deletion or substitution. Alternatively or additionally the Nef may be modified to alter the dileucine motif of Leu 174 and Leu 175 by deletion or substitution of one or both leucines. The importance of the dileucine motif in CD4 downregulation is described e.g. in Bresnahan P. A. et al (1998) Current Biology, 8(22): 1235-8.

Preferably the Gag for use in the invention does not encode the Gag p6 polypeptide. Preferred Gag sequences for use in the invention comprise P17 and/or 24.

The RT polynucleotide for use in the invention preferably encodes a mutation to substantially inactivate any reverse transcription activity. A preferred inactive mutant involves the substitution of W tryptophan 229 for K lysine. See WO 03/025003.

Preferably one or more of the HIV sequences included in the polynucleotide according to the invention encoding e.g. gp120, Nef, Tat, Gag or RT is or are codon optimised for mammalian cells, most preferably such that it/they resemble a highly expressed human gene in their codon use.

The fusion may contain further HIV sequences. It will be understood that for all of the HIV sequences included in the invention, these do not necessarily represent sequences encoding the full length or native proteins. Immunogenic derivatives such as truncated or otherwise altered e.g. mutated proteins are also contemplated, as are fragments which encode at least one HIV epitope, preferably a CTL epitope, typically a peptide of at least 8 amino acids. Immunogenic derivatives of the fragments are also contemplated. Immunogenic derivatives cross react with the native antigen or fragment thereof. Polynucleotides which encode a fragment of at least 8, for example 8-10 amino acids or up to 20, 50, 60, 70, 100, 150 or 200 amino acids in length are considered to fall within the scope of the invention as long as the encoded oligo or polypeptide demonstrates HIV antigenicity. The HIV polypeptide molecules encoded by the polynucleotide sequences according to the invention preferably represent a fragment of at least 50% of the length of the native protein, which fragment may contain mutations but which retains at least one HIV epitope and demonstrates HIV antigenicity. Similarly, immunogenic derivatives according to the invention must demonstrate HIV antigenicity. Preferred immunogenic derivatives provide some potential advantage over the native protein such as reduction or removal of a function of the native protein which is undesirable in a vaccine antigen such as an enzyme activity (RT), transactivating activity (Tat), or CD4 downregulation (Nef). The polynucleotide sequences are preferably codon optimised for mammalian cells, in line with preferred aspects of the invention.

Preferred polynucleotide sequences are selected from the group:

1. gp120 codon optimised, minus secretion signal
2. gp120 codon optimised, minus secretion signal–tr Nef
3. gp120 codon optimised, minus secretion signal–tr Nef-mTat
4. gp120 codon optimised, minus secretion signal–Nef-mTat
5. gp120 codon optimised, minus secretion signal–p17/24 Gag-tr Nef
6. gp120 codon optimised, minus secretion signal–p17/24 Gag-tr Nef-mTat
7. gp120 codon optimised, minus secretion signal–p17/24 Gag-Nef-mTat
8. gp120 codon optimised, minus secretion signal–p17/24 Gag-mNef-mTat
9. gp120 codon optimised, minus secretion signal–p17/24 Gag-L1Nef-mTat
10. gp120 codon optimised, minus secretion signal–p17/24 Gag-L2Nef-mTat
11. gp120 codon optimised, minus secretion signal–p17/24 Gag-LLNef-mTat
12. gp120 codon optimised, minus secretion signal–p17/24 Gag-mLLNef-mTat
13. gp120 codon optimised, minus secretion signal–p17/24 Gag-mL1Nef-mTat
14. gp120 codon optimised, minus secretion signal–p17/24 Gag-mL2Nef-mTat
15. gp120 codon optimised, minus secretion signal–mRT-trNef-p17/24 Gag
16. mRT-trNef-p17/24 Gag-gp120 codon optimised, minus secretion signal mNef=deletion of G2 to give non-myristoylated Nef L1 Nef=L174A mutation in Nef L2Nef=L175A mutation in Nef LLNef=L174A and L175A mutations in Nef TrNef=Nef devoid of nucleotides encoding terminal amino acids 1-65 mRT=Reverse Transcriptase mutated to remove biological activity (W229K). RT is codon optimised Gag=Gag codon optimised.

The invention preferably relates to HIV-1. It is preferred that the constructs described herein are derived from an HIV clade B or clade C, particularly clade B.

Preferably the promoter is the promoter from HCMV IE gene, more particularly wherein the 5' untranslated region of the HCMV IE gene comprising exon 1 is included as described in WO 02/36792.

In another aspect the invention provides a vector comprising the polynucleotide sequences described herein. The polynucleotide sequence is preferably DNA and is preferably contained within a vector which is a double stranded DNA plasmid. Alternative vectors are described hereinbelow and include in particular adenovirus vectors such as chimp derived adenovirus vectors Pan 9 or Pan 5, 6 and 7, preferably where these are replication defective such that they cannot replicate in the target cells.

Another aspect of the invention relates to a set of polynucleotides encoding an HIV envelope protein or fragment or immunogenic derivative thereof, particularly gp120, and separately one or more other HIV proteins such as RT, Gag, Nef, Tat or fragments or immunogenic derivatives thereof.

Thus the invention provides a set of polynucleotides comprising a polynucleotide as described herein for gp120 or another form of the HIV envelope protein, and at least one further polynucleotide encoding at least one of HIV Nef, Gag, RT or Tat or fragment or immunogenic derivative thereof, optionally linked to an additional promoter.

Preferably the set of polynucleotides is contained on a single vector, in particular a DNA plasmid, although other vectors such as adenovirus as described herein are also contemplated. Preferably the polynucleotides are under the control of two or more separate promoters. Alternatively the two polynucleotides may be under the control of a single promoter, and optionally translation of the second polynucleotide may be enhanced by inclusion of an internal ribosome entry site between the polynucleotides.

Preferably the set of polynucleotides comprises a gp120 polynucleotide as described herein and a further polynucleotide encoding a fusion of RT-Nef-Gag or of fragments or immunogenic derivatives thereof.

Preferred sets of polynucleotides are selected from the group:
1. gp120 codon optimised, minus secretion signal+tr Nef-mTat
2. gp120 codon optimised, minus secretion signal+P17/24 Gag-tr Nef
3. gp120 codon optimised, minus secretion signal+P17/24 Gag-Nef-mTat
4. mRT-tr Nef-P17/24 Gag+gp120 codon optimised, minus secretion signal
5. gp120 codon optimised, minus secretion signal+mRT-tr Nef-P17/24 Gag Where these preferred sets of two polynucleotides are contained on a single vector under the control of two separate promoters, this may be referred to as a dual promoter vector.

The preferred promoter for one or both of the protein or fusion proteins in a set of polynucleotides according to the invention is the promoter from HCMV IE gene, more particularly wherein the 5' untranslated leader sequence comprises exon 1 as described in WO 02/36792, as described herein.

In yet another aspect the invention provides polypeptides encoded by the polynucleotides and vectors described herein.

In one embodiment the invention provides a fusion protein comprising substantially non-glycosylated HIV envelope protein or a fragment or immunogenic derivative thereof and at least one additional HIV protein or fragment or immunogenic derivative thereof said additional HIV protein selected from Nef, Gag, RT and Tat.

In another embodiment the invention provides a composition comprising a substantially non-glycosylated HIV envelope protein or a fragment or immunogenic derivative thereof and at least one additional HIV protein or fragment or immunogenic derivative thereof said at least one additional HIV protein selected from Nef, Gag, RT and Tat. Preferably the at least one additional HIV protein is a fusion protein of two or more of Nef, Gag, RT and Tat or fragments or immunogenic derivatives thereof.

In yet another embodiment the invention provides a substantially non-glycosylated HIV envelope protein or a fragment or immunogenic derivative thereof, expressed from a polynucleotide which is codon optimised for mammalian cells.

In a further aspect the invention provides pharmaceutical compositions comprising the nucleotide sequences and vectors and polypeptides described herein, together with a pharmaceutically acceptable excipient, diluent, carrier or adjuvant. In a preferred embodiment the polynucleotide, preferably in the form of a DNA vector and preferably comprising at least one codon optimised HIV sequence, is present in a composition comprising a plurality of particles, preferably beads such as gold beads, onto which the DNA is coated.

Delivery of polynucleotides according to the invention is preferably carried out by particle mediated delivery, particularly via a bombardment approach.

It is envisaged that the vectors according to the invention may be utilised with immunostimulatory agents, preferably but not necessarily administered at the same time as the vectors and preferably formulated together in the compositions according to the invention.

Immunostimulatory agents for use in the invention include, but this list is by no means exhaustive and does not preclude other agents: synthetic imidazoquinolines such as imiquimod [S-26308, R-837], (Harrison, et al. 'Reduction of recurrent HSV disease using imiquimod alone or combined with a glycoprotein vaccine', Vaccine 19: 1820-1826, (2001)); and resiquimod [S-28463, R-848] (Vasilakos, et al. 'Adjuvant activites of immune response modifier R-848: Comparison with CpG ODN', Cellular immunology 204: 64-74 (2000).), Schiff bases of carbonyls and amines that are constitutively expressed on antigen presenting cell and T-cell surfaces, such as tucaresol (Rhodes, J. et al. 'Therapeutic potentiation of the immune system by costimulatory Schiff-base-forming drugs', Nature 377: 71-75 (1995)), cytokine, chemokine and co-stimulatory molecules as either protein or peptide or DNA, this would include pro-inflammatory cytokines such as GM-CSF, IL-1 alpha, IL-1 beta, TGF-alpha and TGF-beta, Th1 inducers such as interferon gamma, IL-2, IL-12, IL-15 and IL-18, Th2 inducers such as IL-4, IL-5, IL-6, IL-10 and IL-13 and other chemokine and co-stimulatory genes such as MCP-1, MIP-1 alpha, MIP-1 beta, RANTES, TCA-3, CD80, CD86 and CD40L, other immunostimulatory targeting ligands such as CTLA-4 and L-selectin, apoptosis stimulating proteins and peptides such as Fas, (49), synthetic lipid based adjuvants, such as vaxfectin, (Reyes et al., 'Vaxfectin enhances antigen specific antibody titres and maintains Th1 type immune responses to plasmid DNA immunization', Vaccine 19: 3778-3786) squalene, alpha-tocopherol, polysorbate 80, DOPC and cholesterol, endotoxin, [LPS], Beutler, B., 'Endotoxin, 'Toll-like receptor 4, and the afferent limb of innate immunity', Current Opinion in Microbiology 3: 23-30 (2000)); CpG oligo- and di-nucleotides, Sato, Y. et al., 'Immunostimulatory DNA sequences necessary for effective intradermal gene immunization', Science 273 (5273): 352-354 (1996). Hemmi, H. et al., 'A Toll-like receptor recognizes bacterial DNA', Nature 408: 740-745, (2000) and other potential ligands that trigger Toll receptors to produce appropriate Th1-inducing cytokines, such as synthetic Mycobacterial lipoproteins, Mycobacterial protein p19, peptidoglycan, teichoic acid and lipid A.

A preferred immunostimulatory agent for use with the invention is GM-CSF. This may be employed in the form of a polynucleotide expressing GM-CSF which is co-administered with the DNA vaccine of the invention. A DNA plasmid encoding GM-CSF may be present in a pharmaceutical composition comprising the polynucleotide(s) according to the invention.

Certain preferred adjuvants for eliciting a predominantly Th1-type response include, for example, a Lipid A derivative such as monophosphoryl lipid A, or preferably 3-de-O-acylated monophosphoryl lipid A. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, MA); Escin; Digitonin; or *Gypsophila* or *Chenopodium quinoa* saponins.

According to a further aspect of the invention, a host cell comprising a polynucleotide sequence according to the invention, or an expression vector according to the invention, is provided. The host cell may be for example bacterial e.g. *E. coli*, mammalian e.g. human, or may be an insect cell. Mammalian cells comprising a vector according to the present invention may be cultured cells transfected in vitro or may be cells transfected in vivo by administration of the vector to the mammal.

By codon optimisation is meant that the DNA sequence is optimised to resemble the codon usage of genes in mammalian cells. In particular, the codon usage in the sequence is optimised to resemble that of highly expressed human genes.

The DNA code has 4 letters (A, T, C and G) and uses these to spell three letter "codons" which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons.

Where more than one codon is available to code for a given amino acid, it has been observed that the codon usage patterns of organisms are highly non-random. Different species show a different bias in their codon selection and, furthermore, utilisation of codons may be markedly different in a single species between genes which are expressed at high and low levels. This bias is different in viruses, plants, bacteria and mammalian cells, and some species show a stronger bias away from a random codon selection than others. For example, humans and other mammals are less strongly biased than certain bacteria or viruses. For these reasons, there is a significant probability that a mammalian gene expressed in *E. coli* or a foreign or recombinant gene expressed in mammalian cells will have an inappropriate distribution of codons for efficient expression. It is believed that the presence in a heterologous DNA sequence of clusters of codons or an abundance of codons which are rarely observed in the host in which expression is to occur, is predictive of low heterologous expression levels in that host.

In an embodiment of the present invention there is provided a gp120 polynucleotide sequence which encodes a substantially non-glycosylated gp120 amino acid sequence, wherein the codon usage pattern of the polynucleotide sequence resembles that of highly expressed mammalian genes. Preferably the polynucleotide sequence is a DNA sequence. Desirably the codon usage pattern of the polynucleotide sequence is typical of highly expressed human genes.

In the polynucleotides of the present invention, the codon usage pattern is altered from that typical of human immunodeficiency viruses to more closely represent the codon bias of the target organism, e.g. a mammal, especially a human. The "codon usage coefficient" is a measure of how closely the codon pattern of a given polynucleotide sequence resembles that of a target species. Codon frequencies can be derived from literature sources for the highly expressed genes of many species (see e.g. Nakamura et. al. Nucleic Acids Research 1996, 24:214-215). The codon frequencies for each of the 61 codons (expressed as the number of occurrences occurrence per 1000 codons of the selected class of genes) are normalised for each of the twenty natural amino acids, so that the value for the most frequently used codon for each amino acid is set to 1 and the frequencies for the less common codons are scaled to lie between zero and 1. Thus each of the 61 codons is assigned a value of 1 or lower for the highly expressed genes of the target species. In order to calculate a codon usage coefficient for a specific polynucleotide, relative to the highly expressed genes of that species, the scaled value for each codon of the specific polynucleotide are noted and the geometric mean of all these values is taken (by dividing the sum of the natural logs of these values by the total number of codons and take the anti-log). The coefficient will have a value between zero and 1 and the higher the coefficient the more codons in the polynucleotide are frequently used codons. If a polynucleotide sequence has a codon usage coefficient of 1, all of the codons are "most frequent" codons for highly expressed genes of the target species.

According to the present invention, the codon usage pattern of the polynucleotide will preferably exclude rare codons. Rare codons can be defined as codons representing <20% or more preferably representing <10% of the codons used for a particular amino acid in highly expressed genes of the target organism. Alternatively rare codons may be defined as codons with a relative synonymous codon usage (RSCU) value of <0.3 or more preferably <0.2 in highly expressed genes of the target organism. An RSCU value is the observed number of codons divided by the number expected if all codons for that amino acid were used equally frequently. An appropriate definition of a rare codon would be apparent to a person skilled in the art.

A polynucleotide of the present invention will generally have a codon usage coefficient for highly expressed human genes of greater than 0.3, preferably greater than 0.4, most preferably greater than 0.5. Preferably also the codon usage coefficient will be less than 1.0, preferably less than 0.9 and more preferably less than 0.8. Thus a codon usage coefficient between 0.5 and 0.9 or between 0.5 and 0.8 is most preferred. Codon usage tables for human can also be found in Genbank.

In comparison, a highly expressed beta actin gene has a codon usage coefficient of 0.747.

The codon usage table for a *homo sapiens* is set out below:

| AmAcid | Codon | Number | /1000 | Fraction | ... |
|---|---|---|---|---|---|
| Gly | GGG | 905.00 | 18.76 | 0.24 | |
| Gly | GGA | 525.00 | 10.88 | 0.14 | |
| Gly | GGT | 441.00 | 9.14 | 0.12 | |
| Gly | GGC | 1867.00 | 38.70 | 0.50 | |
| Glu | GAG | 2420.00 | 50.16 | 0.75 | |
| Glu | GAA | 792.00 | 16.42 | 0.25 | |
| Asp | GAT | 592.00 | 12.27 | 0.25 | |
| Asp | GAC | 1821.00 | 37.75 | 0.75 | |
| Val | GTG | 1866.00 | 38.68 | 0.64 | |
| Val | GTA | 134.00 | 2.78 | 0.05 | |
| Val | GTT | 198.00 | 4.10 | 0.07 | |
| Val | GTC | 728.00 | 15.09 | 0.25 | |
| Ala | GCG | 652.00 | 13.51 | 0.17 | |
| Ala | GCA | 488.00 | 10.12 | 0.13 | |
| Ala | GCT | 654.00 | 13.56 | 0.17 | |
| Ala | GCC | 2057.00 | 42.64 | 0.53 | |
| Arg | AGG | 512.00 | 10.61 | 0.18 | |
| Arg | AGA | 298.00 | 6.18 | 0.10 | |
| Ser | AGT | 354.00 | 7.34 | 0.10 | |
| Ser | AGC | 1171.00 | 24.27 | 0.34 | |
| Lys | AAG | 2117.00 | 43.88 | 0.82 | |
| Lys | AAA | 471.00 | 9.76 | 0.18 | |
| Asn | AAT | 314.00 | 6.51 | 0.22 | |
| Asn | AAC | 1120.00 | 23.22 | 0.78 | |
| Met | ATG | 1077.00 | 22.32 | 1.00 | |
| Ile | ATA | 88.00 | 1.82 | 0.05 | |
| Ile | ATT | 315.00 | 6.53 | 0.18 | |
| Ile | ATC | 1369.00 | 28.38 | 0.77 | |
| Thr | ACG | 405.00 | 8.40 | 0.15 | |
| Thr | ACA | 373.00 | 7.73 | 0.14 | |
| Thr | ACT | 358.00 | 7.42 | 0.14 | |
| Thr | ACC | 1502.00 | 31.13 | 0.57 | |
| Trp | TGG | 652.00 | 13.51 | 1.00 | |
| End | TGA | 109.00 | 2.26 | 0.55 | |
| Cys | TGT | 325.00 | 6.74 | 0.32 | |
| Cys | TGC | 706.00 | 14.63 | 0.68 | |
| End | TAG | 42.00 | 0.87 | 0.21 | |
| End | TAA | 46.00 | 0.95 | 0.23 | |
| Tyr | TAT | 360.00 | 7.46 | 0.26 | |
| Tyr | TAC | 1042.00 | 21.60 | 0.74 | |
| Leu | TTG | 313.00 | 6.49 | 0.06 | |
| Leu | TTA | 76.00 | 1.58 | 0.02 | |
| Phe | TTT | 336.00 | 6.96 | 0.20 | |
| Phe | TTC | 1377.00 | 28.54 | 0.80 | |
| Ser | TCG | 325.00 | 6.74 | 0.09 | |
| Ser | TCA | 165.00 | 3.42 | 0.05 | |
| Ser | TCT | 450.00 | 9.33 | 0.13 | |
| Ser | TCC | 958.00 | 19.86 | 0.28 | |
| Arg | CGG | 611.00 | 12.67 | 0.21 | |
| Arg | CGA | 183.00 | 3.79 | 0.06 | |
| Arg | CGT | 210.00 | 4.35 | 0.07 | |
| Arg | CGC | 1086.00 | 22.51 | 0.37 | |
| Gln | CAG | 2020.00 | 41.87 | 0.88 | |
| Gln | CAA | 283.00 | 5.87 | 0.12 | |
| His | CAT | 234.00 | 4.85 | 0.21 | |
| His | CAC | 870.00 | 18.03 | 0.79 | |
| Leu | CTG | 2884.00 | 59.78 | 0.58 | |
| Leu | CTA | 166.00 | 3.44 | 0.03 | |
| Leu | CTT | 238.00 | 4.93 | 0.05 | |
| Leu | CTC | 1276.00 | 26.45 | 0.26 | |
| Pro | CCG | 482.00 | 9.99 | 0.17 | |
| Pro | CCA | 456.00 | 9.45 | 0.16 | |
| Pro | CCT | 568.00 | 11.77 | 0.19 | |
| Pro | CCC | 1410.00 | 29.23 | 0.48 | |

Codon usage for human (highly expressed) genes Jan. 24, 1991 (human_high.cod)

According to a further aspect of the invention, an expression vector is provided which comprises and is capable of directing the expression of a polynucleotide sequence according to the first aspect of the invention, in particular wherein the codon usage pattern of the gp120 polynucleotide sequence is typical of highly expressed mammalian genes, preferably highly expressed human genes. The vector may be suitable for driving expression of heterologous DNA in bacterial insect or mammalian cells, particularly human cells. In one embodiment, the expression vector is p7313 (see FIG. 1).

In a further aspect the invention provides a method of treating or preventing HIV infections, any symptoms or diseases associated therewith, comprising administering a safe and effective amount of a polynucleotide, a vector, a polypeptide or a pharmaceutical composition according to the invention.

Administration of the pharmaceutical composition may take the form of one or of more than one individual doses, for example as repeat doses of the same DNA plasmid, or in a heterologous "prime-boost" vaccination regime, particularly a therapeutic vaccination regime. A heterologous prime-boost regime uses administration of different forms of vaccine in the prime and the boost, each of which may itself include two or more administrations. Preferably but not necessarily the priming and boosting composition comprise the same antigens or different forms of the same antigens. The priming composition and the boosting composition will anyway have at least one antigen in common, although it is not necessarily an identical form of the antigen, it may be a different form of the same antigen. An example of different forms of the same antigen is in the case of a polynucleotide encoding a gp120 which lacks a functional signal sequence and is substantially non-glycosylated in mammalian cells, and a polypeptide which is gp120 with its signal sequence and which is glycosylated. A full length and a truncated version of the same protein, or a mutated and a non-mutated form of the same protein, may also be considered different forms of the same antigen for the purposes of a prime-boost format according to the invention.

In one example of a prime-boost regime the "prime" vaccination may be via particle mediated DNA delivery of a priming composition which comprises a polynucleotide or set of polynucleotides according to the present invention, preferably incorporated into a plasmid vector, while the "boost" administration may be of a boosting composition comprising a recombinant viral vector comprising the same polynucleotide sequence or a polynucleotide encoding at least one of the same antigens encoded by the priming composition. Alternatively the boosting may be carried out with at least one of the same antigens in the form of the protein in adjuvant. Conversely the priming may be with a priming composition comprising the viral vector or with a protein formulation typically a protein formulated in adjuvant, and the boost a DNA vaccine of the present invention.

A preferred prime-boost format for use with the polynucleotides according to the present invention is selected from:

Protein prime/live vector boost
Live vector prime/protein boost
Protein prime/DNA plasmid boost
DNA plasmid prime/protein boost
Live vector prime/DNA plasmid boost
DNA plasmid prime/live vector boost Preferred live vectors include live virus vectors in particular adenovirus vectors as described herein.

Preferably the priming and boosting compositions comprise, in addition to the antigen(s) a suitable adjuvant, which may be different according to the particular composition.

Both the priming composition and the boosting composition may be delivered in more than one dose. Furthermore the initial priming and boosting doses may be followed up with further doses which may be alternated to result in e.g. a DNA plasmid prime/protein boost/further DNA plasmid dose/further protein dose.

The invention further provides a process for the production of a polynucleotide as described herein comprising linking a nucleotide sequence encoding a substantially non-glycosylated HIV envelope molecule, preferably gp120 or fragment or immunogenic derivative thereof and optionally a sequence encoding an additional HIV protein for example an HIV non-structural protein such as Tat or an HIV capsid protein such as Gag, or fragments or immunogenic derivatives thereof, to a heterologous promoter sequence.

As discussed above, the present invention includes expression vectors that comprise the nucleotide sequences of the invention. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors and how to construct them would be apparent to persons skilled in the art. By way of further example in this regard we refer to Sambrook et al. Molecular Cloning: a Laboratory Manual. 2$^{nd}$ Edition. CSH Laboratory Press. (1989).

Preferably, a polynucleotide of the invention, or for use in the invention in a vector, is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

A nucleic acid sequence of the present invention may be administered by means of specialised delivery vectors useful in gene therapy. Gene therapy approached are discussed for example by Verme et al, Nature 1997, 389:239-242. Both viral and non-viral vector systems can be used. The vectors may be, for example, plasmids, artificial chromosomes (e.g. BAC, PAC, YAC), virus or phage vectors provided with a origin of replication, optionally a promoter for the expression of the polynucleotide and optionally a regulator of the promoter. The vectors may contain one or more selectable marker genes, for example an ampicillin or kanamycin resistance gene in the case of a bacterial plasmid or a resistance gene for a fungal vector. Vectors may be used in vitro, for example for the production of DNA or RNA or used to transfect or transform a host cell, for example, a mammalian host cell e.g. for the production of protein encoded by the vector. The vectors may also be adapted to be used in vivo, for example in a method of DNA vaccination or of gene therapy.

Examples of suitable viral vectors include retroviral, lentiviral, adenoviral, adeno-associated viral, herpes viral including herpes simplex viral, alpha-viral, pox viral such as Canarypox and vaccinia-viral based systems. Gene transfer techniques using these viruses are known to those skilled in the art. Retrovirus vectors for example may be used to stably integrate the polynucleotide of the invention into the host genome, although such recombination is not preferred. Replication-defective adenovirus vectors by contrast remain episomal and therefore allow transient expression. Vectors capable of driving expression in insect cells (for example baculovirus vectors), in human cells, yeast or in bacteria may be employed in order to produce quantities of the HIV protein encoded by the polynucleotides of the present invention, for example for use as subunit vaccines or in immunoassays.

In a preferred embodiment the adenovirus used as a live vector is a replication defective simian adenovirus. Typically these viruses contain an E1 deletion and can be grown on cell lines that are transformed with an E1 gene. Preferred Simian adenoviruses are viruses isolated from Chimpanzee. In particular C68 (also known as Pan 9) (See U.S. Pat. No. 6,083,716) and Pan 5, 6 and Pan 7 (WO 03/046124) are preferred for use in the present invention. Thus these vectors can be manipulated to insert a heterologous gene of the invention such that the gene product maybe expressed. The use, formulation and manufacture of such recombinant adenoviral vectors is set forth in detail in WO 03/046142.

Promoters and other expression regulation signals may be selected to be compatible with the host cell for which expression is designed. For example, mammalian promoters include the metallothionein promoter which can be induced in response to heavy metals such as cadmium, and the β-actin promoter. Viral promoters such as the SV40 large T antigen promoter, human cytomegalovirus (CMV) immediate early (1E) promoter, rous sarcoma virus LTR promoter, adenovirus promoter, or a HPV promoter, particularly the HPV upstream regulatory region (URR) may also be used. All these promoters are well described and readily available in the art.

A preferred promoter element is the CMV immediate early promoter devoid of intron A, but including exon 1. Accordingly there is provided a vector comprising a polynucleotide of the invention under the control of HCMV IE early promoter. A suitable HCMV IE promoter is described in WO 02/36792.

Non-viral based systems include direct administration of nucleic acids, microsphere encapsulation technology, poly (lactide-co-glycolide) and liposome-based systems.

The polynucleotides according to the invention have utility in the production by expression of the encoded proteins, which expression may take place in vitro, in vivo or ex vivo. The nucleotides may therefore be involved in recombinant protein synthesis, for example to increase yields, or indeed may find use as therapeutic agents in their own right, utilised in DNA vaccination techniques. Where the polynucleotides of the present invention are used in the production of the encoded proteins in vitro or ex vivo, cells, for example in cell culture, will be modified to include the polynucleotide to be expressed. Such cells include transient, or preferably stable mammalian cell lines. Particular examples of cells which may be modified by insertion of vectors encoding for a polypeptide according to the invention include mammalian HEK293T, CHO, HeLa, 293 and COS cells. Preferably the cell line selected will be one which is stable. Expression may be achieved in transformed oocytes. A polypeptide may be expressed from a polynucleotide of the present invention, in cells of a transgenic non-human animal, preferably a mouse. A transgenic non-human animal expressing a polypeptide from a polynucleotide of the invention is included within the scope of the invention.

The invention further provides a method of vaccinating a mammalian subject which comprises administering thereto an effective amount of a vaccine or vaccine composition according to the invention. Preferably, expression vectors for use in DNA vaccines, vaccine compositions and immunotherapeutics will be plasmid vectors or live viral vectors.

DNA vaccines may be administered in the form of "naked DNA", for example in a liquid formulation administered using a syringe or high pressure jet, or DNA formulated with liposomes or an irritant transfection enhancer, or by particle mediated DNA delivery (PMDDor particle mediated immunotherapeutic delivery PMID) as described in more detail herein. All of these delivery systems are well known in the art.

The vector may be introduced to a mammal for example by means of a viral vector delivery system.

The compositions of the present invention can be delivered by a number of routes such as intramuscularly, subcutaneously, intraperitonally, intravenously or mucosally.

The invention further provides an intradermal delivery device comprising a pharmaceutical composition described herein.

In a preferred embodiment, the composition is delivered intradermally. In particular, the composition is delivered by means of a gene gun particularly using particle bombardment administration techniques which involve coating the vector on to beads (eg gold beads) which are then administered under high pressure into the epidermis. This is described, for example, in Haynes et al, J Biotechnology 44: 37-42 (1996).

Numerous methods of carrying out a particle bombardment approach are known, see for example WO 91/07487. In one illustrative example, gas-driven particle acceleration can be achieved with devices such as those manufactured by Powderject Pharmaceuticals PLC (Oxford, UK) and Powdeiject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide, are accelerated to high speed within a helium gas jet generated by a hand held device, propelling the particles into a target tissue of interest, typically the skin. The particles are preferably gold beads of a 0.4-4.0 μm, more preferably 0.6-2.0 μm diameter and the DNA conjugate coated onto these and then encased in a cartridge or cassette for placing into the delivery device.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

The vectors which comprise the nucleotide sequences encoding antigenic peptides are administered in such amount as will be prophylactically or therapeutically effective. The quantity to be administered, is generally in the range of one picogram to 1 milligram, preferably 1 picogram to 10 micrograms for particle-mediated delivery, and 100 nanograms to 10 milligrams for other routes of nucleotide per dose. The exact quantity may vary considerably depending on the weight of the patient being immunised and the route of administration.

It is possible for the immunogen component comprising the nucleotide sequence encoding the antigenic peptide, to be administered on a one off basis or to be administered repeatedly, for example, between 1 and 7 times, preferably between 1 and 4 times, at intervals between about 1 day and about 18 months. Further administrations may also be given as necessary to maintain immune responses for the lifetime of the patient. However, this treatment regime will be significantly varied depending upon the size of the patient concerned, the amount of nucleotide sequence administered, the route of administration, and other factors which would be apparent to a skilled medical practitioner. The patient may receive one or more other anti HIV retroviral drugs as part of their overall treatment regime. Additionally the nucleic acid immunogen may be administered with an adjuvant.

The adjuvant component specified herein can similarly be administered via a variety of different administration routes, such as for example, via the oral, nasal, pulmonary, intramuscular, subcutaneous, intradermal or topical routes. Preferably, the adjuvant component is administered via the intradermal or topical route, most preferably by a topical route. This administration may take place between about 14 days prior to and about 14 days post administration of the nucleotide sequence, preferably between about 1 day prior to and about 3 days post administration of the nucleotide sequence.

The adjuvant component is, in one embodiment, administered substantially simultaneously with the administration of the nucleotide sequence. By "substantially simultaneous" what is meant is that administration of the adjuvant component is preferably at the same time as administration of the nucleotide sequence, or if not, it is at least within a few hours either side of nucleotide sequence administration. In the most preferred treatment protocol, the adjuvant component will be administered substantially simultaneously with administration of the nucleotide sequence. Obviously, this protocol can be varied as necessary, in accordance with the type of variables referred to above. It is preferred that the adjuvant is a 1H-imidazo[4,5c] quinoline-4-amine derivative such as imiquimod. Typically imiquimod will be presented as a topical cream formulation and will be administered according to the above protocol.

Once again, depending upon such variables, the dose of administration of the derivative will also vary, but may, for example, range between about 0.1 mg per kg to about 100 mg per kg, where "per kg" refers to the body weight of the mammal concerned. This administration of the 1H-imidazo[4,5-c]quinolin-4-amine derivative would preferably be repeated with each subsequent or booster administration of the nucleotide sequence. Most preferably, the administration dose will be between about 1 mg per kg to about 50 mg per kg. In the case of a "prime-boost" scheme as described herein, the imiquimod or other 1H-imidazo[4,5-c]quinolin-4-amine derivative may be administered with either the prime or the boost or with both the prime and the boost.

While it is possible for the adjuvant component to comprise only 1H-imidazo[4,5-c]quinolin-4-amine derivatives to be administered in the raw chemical state, it is preferable for administration to be in the form of a pharmaceutical formulation. That is, the adjuvant component will preferably comprise the 1H-imidazo[4,5-c]quinolin-4-amine combined with one or more pharmaceutically acceptable carriers, and optionally other therapeutic ingredients. The carrier(s) must be "acceptable" in the sense of being compatible with other ingredients within the formulation, and not deleterious to the recipient thereof. The nature of the formulations will naturally vary according to the intended administration route, and may be prepared by methods well known in the pharmaceutical art. All methods include the step of bringing into association a 1H-imidazo[4,5-c]quinolin-4-amine derivative with an appropriate carrier or carriers. In general, the formulations are prepared by uniformly and intimately bringing into association the derivative with liquid carriers or finely divided solid carriers, or both, and then, if necessary, shaping the product into the desired formulation. Formulations of the present invention suitable for oral administration may be presented as discrete units such as capsules, cachets or tablets each containing a pre-determined amount of the active ingredient; as a powder or granules; as a solution or a suspension in an aqueous liquid or a non-aqueous liquid; or as an oil-in-water liquid emulsion or a water-in-oil emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent.

The tablets may optionally be coated or scored and may be formulated so as to provide slow or controlled release of the active ingredient.

Formulations for injection via, for example, the intramuscular, intraperitoneal, intradermal, or subcutaneous administration routes include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilised) condition requiring only the addition of the sterile liquid carrier, for example, water for injections, immediately prior to use. Extemporaneous injection solutions and suspensions may be prepared from sterile powders, granules and tablets of the kind previously described. Formulations suitable for pulmonary administration via the buccal or nasal cavity are presented such that particles containing the active ingredient, desirably having a diameter in the range of 0.5 to 7 microns, are delivered into the bronchial tree of the recipient. Possibilities for such formulations are that they are in the form of finely comminuted powders which may conveniently be presented either in a piercable capsule, suitably of, for example, gelatine, for use in an inhalation device, or alternatively, as a self-propelling formulation comprising active ingredient, a suitable liquid propellant and optionally, other ingredients such as surfactant and/or a solid diluent. Self-propelling formulations may also be employed wherein the active ingredient is dispensed in the form of droplets of a solution or suspension. Such self-propelling formulations are analogous to those known in the art and may be prepared by established procedures. They are suitably provided with either a manually-operable or automatically functioning valve having the desired spray characteristics; advantageously the valve is of a metered type delivering a fixed volume, for example, 50 to 100 µL, upon each operation thereof.

In a further possibility, the adjuvant component may be in the form of a solution for use in an atomiser or nebuliser whereby an accelerated airstream or ultrasonic agitation is employed to produce a find droplet mist for inhalation.

Formulations suitable for intranasal administration generally include presentations similar to those described above for pulmonary administration, although it is preferred for such formulations to have a particle diameter in the range of about 10 to about 200 microns, to enable retention within the nasal cavity. This may be achieved by, as appropriate, use of a powder of a suitable particle size, or choice of an appropriate valve. Other suitable formulations include coarse powders having a particle diameter in the range of about 20 to about 500 microns, for administration by rapid inhalation through the nasal passage from a container held close up to the nose, and nasal drops comprising about 0.2 to 5% w/w of the active ingredient in aqueous or oily solutions. In one embodiment of the invention, it is possible for the vector which comprises the nucleotide sequence encoding the antigenic peptide to be administered within the same formulation as the 1H-imidazo[4,5-c]quinolin-4-amine derivative. Hence in this embodiment, the immunogenic and the adjuvant component are found within the same formulation.

In one embodiment the adjuvant component is prepared in a form suitable for biolistic administration, and is administered via that route substantially simultaneously with administration of the nucleotide sequence. For preparation of formulations suitable for use in this manner, it may be necessary for the 1H-imidazo[4,5-c]quinolin-4-amine derivative to be lyophilised and adhered onto, for example, particles such as gold beads which are suited for biolistic administration.

In an alternative embodiment, the adjuvant component may be administered as a dry powder, via high pressure gas propulsion.

Even if not formulated together, it may be appropriate for the adjuvant component to be administered at or about the same administration site as the nucleotide sequence.

Other details of pharmaceutical preparations can be found in Remington's Pharmaceutical Sciences, Mack Publishing Company, Easton, Pennysylvania (1985), the disclosure of which is included herein in its entirety, by way of reference.

Suitable techniques for introducing the naked polynucleotide or vector into a patient also include topical application with an appropriate vehicle. The nucleic acid may be administered topically to the skin, or to mucosal surfaces for example by intranasal, oral, intravaginal or intrarectal administration. The naked polynucleotide or vector may be present together with a pharmaceutically acceptable excipient, such as phosphate buffered saline (PBS). DNA uptake may be further facilitated by use of facilitating agents such as bupivacaine, either separately or included in the DNA formulation. Other methods of administering the nucleic acid directly to a recipient include ultrasound, electrical stimulation, electroporation and microseeding which is described in U.S. Pat. No. 5,697,901.

Uptake of nucleic acid constructs may be enhanced by several known transfection techniques, for example those including the use of transfection agents. Examples of these agents include cationic agents, for example calcium phosphate and DEAE-Dextran and lipofectants, for example lipofectam and transfectam. The dosage of the nucleic acid to be administered can be altered.

A nucleic acid sequence of the present invention may also be administered by means of specialised delivery vectors useful in gene therapy. Gene therapy approaches are discussed for example by Verme et al, Nature 1997, 389:239-242. Both viral and non-viral vector systems can be used and are described above. Viral and non-viral delivery systems may be combined where it is desirable to provide booster injections after an initial vaccination, for example an initial "prime" DNA vaccination using a non-viral vector such as a plasmid followed by one or more "boost" vaccinations using a viral vector or non-viral based system. Similarly the invention contemplates prime boost systems with the polynucleotide of the invention, followed by boosting with protein in adjuvant or vice versa.

A nucleic acid sequence of the present invention may also be administered by means of transformed cells. Such cells include cells harvested from a subject. The naked polynucleotide or vector of the present invention can be introduced into such cells in vitro and the transformed cells can later be returned to the subject. The polynucleotide of the invention may integrate into nucleic acid already present in a cell by homologous recombination events. A transformed cell may, if desired, be grown up in vitro and one or more of the resultant cells may be used in the present invention. Cells can be provided at an appropriate site in a patient by known surgical or microsurgical techniques (e.g. grafting, micro-injection, etc.)

The pharmaceutical compositions of the present invention may include adjuvant compounds as detailed above, or other substances which may serve to increase the immune response induced by the protein which is encoded by the DNA. These may be encoded by the DNA, either separately from or as a fusion with the antigen, or may be included as non-DNA elements of the formulation. Examples of adjuvant-type substances which may be included in the formulations of the present invention include ubiquitin, lysosomal associated membrane protein (LAMP), hepatitis B virus core antigen, FLT3-ligand (a cytokine important in the generation of professional antigen presenting cells, particularly dentritic cells) and other cytokines such as IFN-γ and GMCSF. Other preferred adjuvants include imiquimod and resimquimod and tucarasol, imiquimod being particularly preferred.

In a particular embodiment of the invention there is provided the use of a nucleic acid molecule as herein described for the treatment or prophylaxis of HIV infection, administered with imiquimod. The imiquimod is preferably administered topically, whereas the nucleic acid molecule is preferably administered by means of particle mediated delivery.

Accordingly the present invention also provides a method of treating a subject suffering from or susceptible to HIV infection, comprising administering a nucleic acid molecule as herein described and imiquimod.

The present invention will now be described by reference to the following examples:

EXAMPLES

Example 1

Plasmid Construction 1.1 Construction of gp120 Containing Plasmid

Recombinant gp120 glycoprotein described in the following examples is a synthetic form of the gp120 envelope protein of HIV-1 isolate W61D.

Codon Optimised (pgp120c):

The gene sequence was based on the gp120 sequence from the HIV-1 isolate W61D. This has a Codon Usage Coefficient of 0.297. Optimisation was performed using SynGene 2d, resulting in a CUC of 0.749 (Ertl, P F., Thomsen, L L. Technical issues in construction of nucleic acid vaccines. (2003) Methods 31(3); 199-206. SynGene uses a mathematical method for codon optimisation based on the relative frequencies of use. Briefly, codons are assigned value ranges according to their frequencies, so that more frequent codons have wider ranges, and placed in ascending frequency order. The value ranges are expressed as >=0.000, >=0.0??, >=0.??? And so on. A random number is generated between 0 and 0.99999. This is then used to select a codon, which will be the codon allocated the range within which the random number falls. To exclude rare codons the value 0.1 is added to the random number, so that it falls in the range 0.1-1.09999.

The gp120 sequence was split into 40 overlapping oligonucleotides, PCR assembled and recovered using the end primers. The gene was cloned into vector p7313-ie (shown in FIG. 1) as a NotI-BamHI fragment and sequenced. Restriction fragments from three initial clones were combined to generate a single correct clone. The amino acid sequence and codon optimised DNA sequence are given in FIG. 2.

1.2 Generation of Nef/Tat Containing Plasmids

Nef/Tat (pNTm and ptrNTm)

Figure 3:
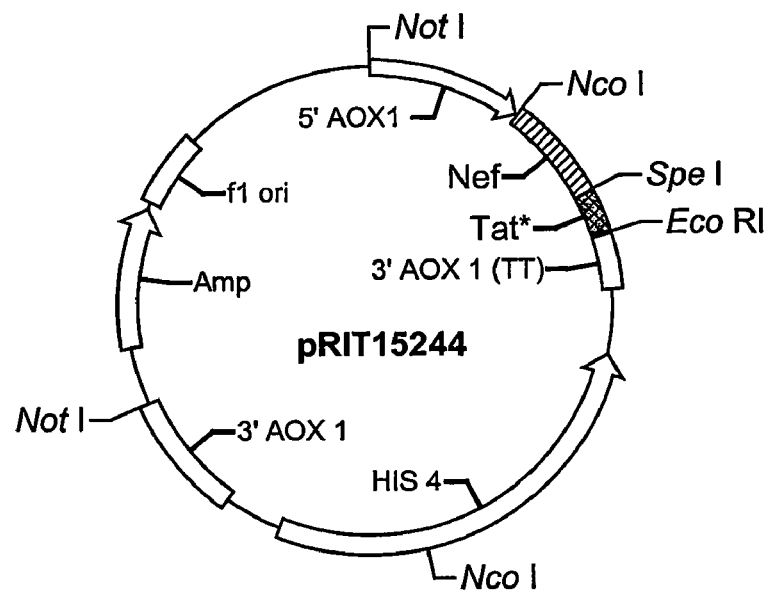
FIG. 3 is a map of pRix15244.
Figure 23:
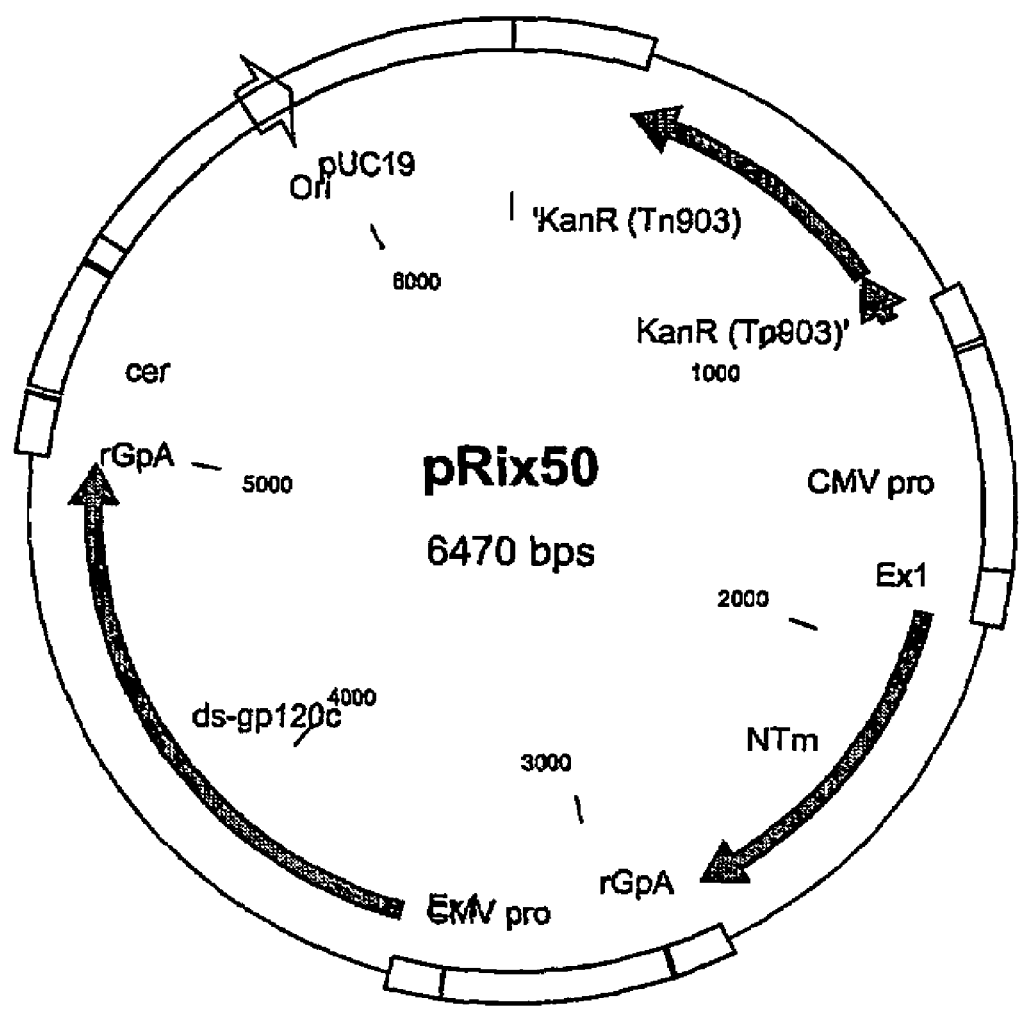
FIG. 23 is a map of Plasmid pRix50.
Figure 24:
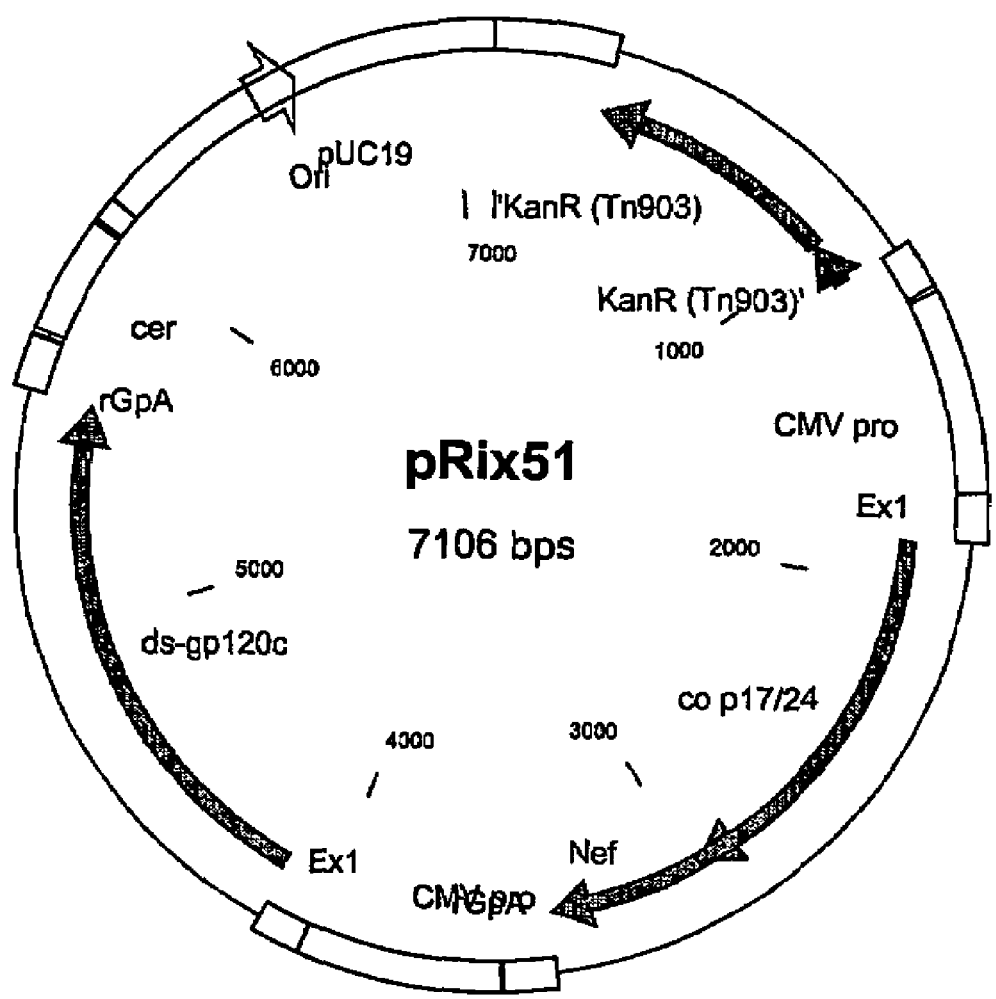
FIG. 24 is a map of Plasmid pRix51.
Figure 25:
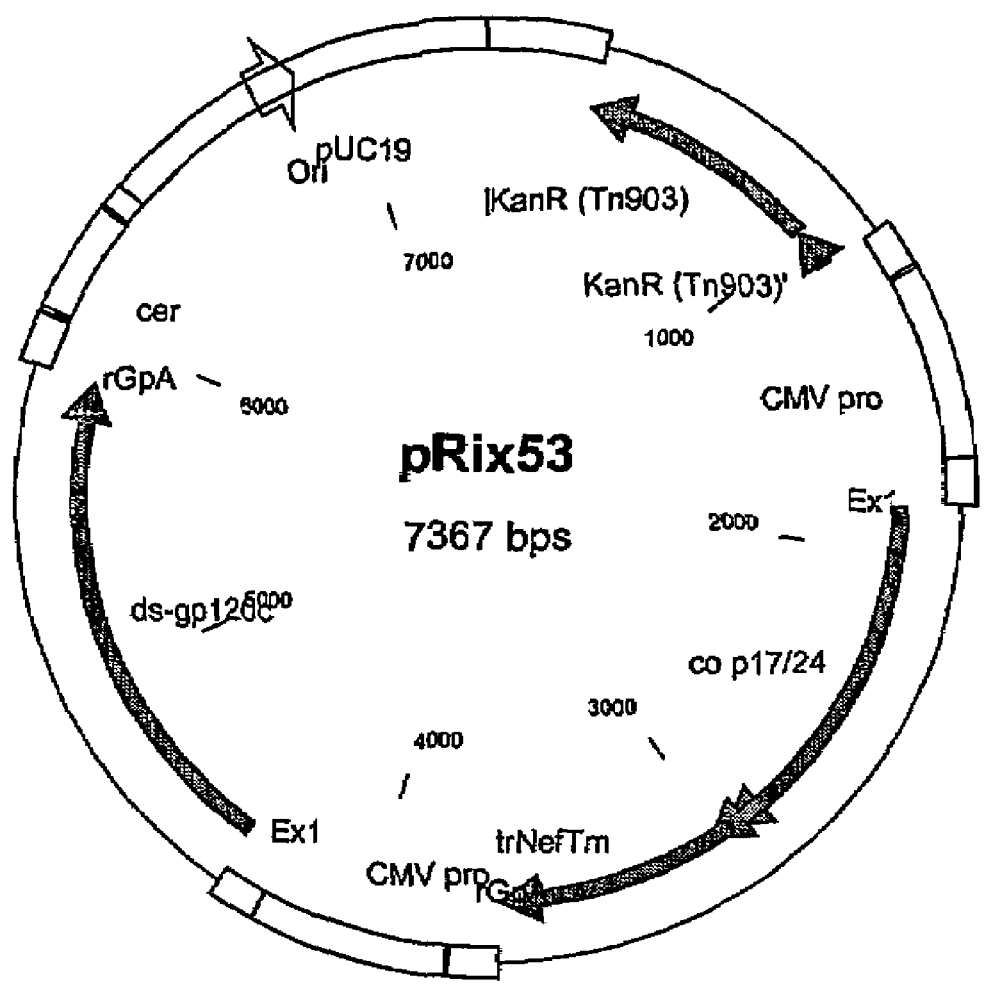
FIG. 25 is a map of Plasmid pRix53.
Figure 26:
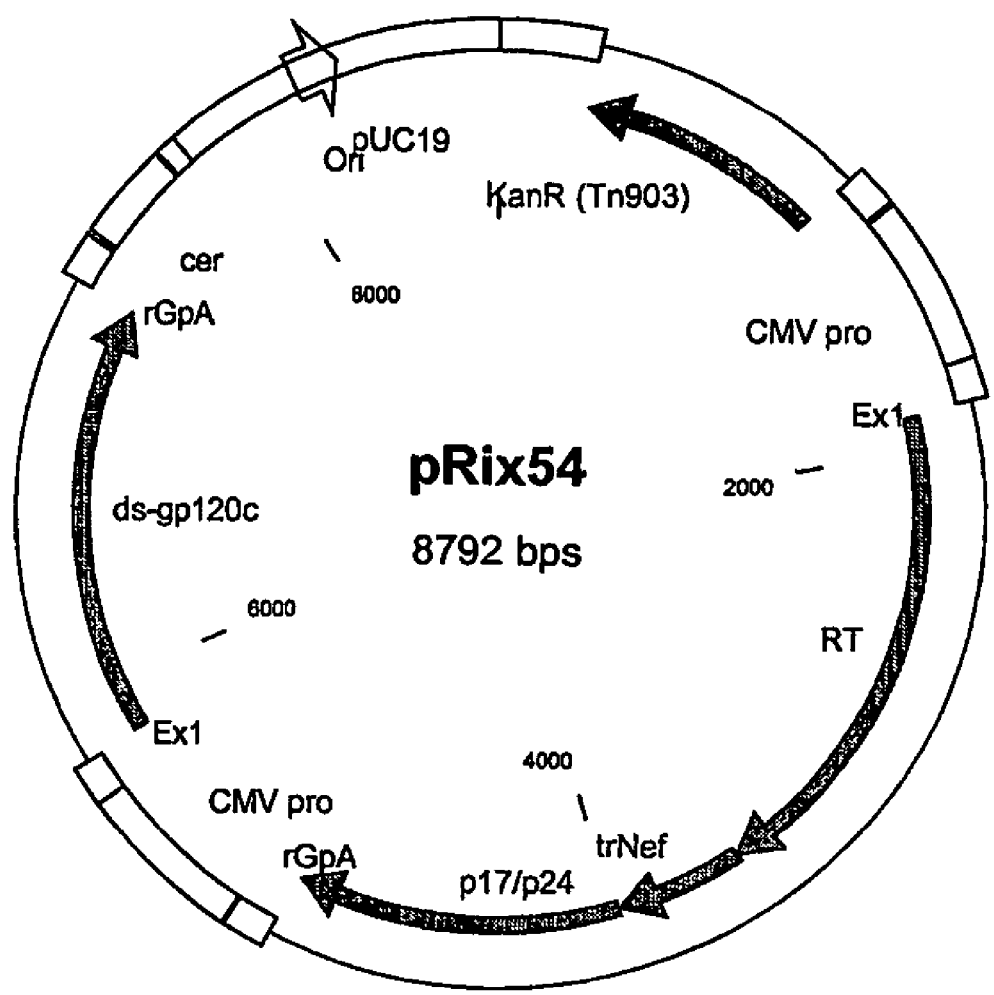
FIG. 26 is a map of Plasmid pRix54.
Figure 27:
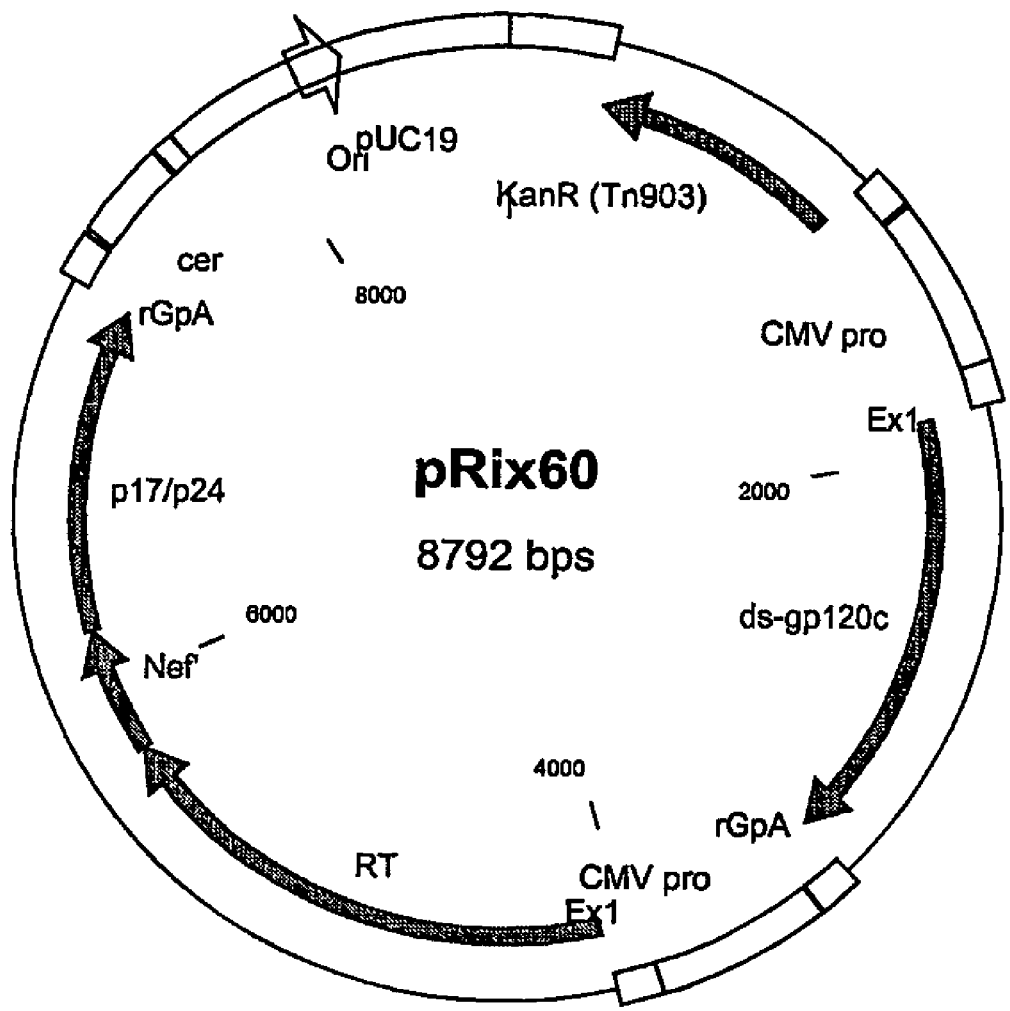
FIG. 27 is a map of Plasmid pRix60.

The gene for the Nef/Tat fusion protein was provided in plasmid pRIT15244 (FIG. 3). The plasmid pRIT 15244 is identical to pRIT 14913 described below except that the His tail has been deleted.

General

The Nef gene from the Bru/Lai isolate (Cell 40: 9-17, 1985) was selected for the constructs since this gene is among those that are most closely related to the consensus Nef.

The starting material for the Bru/Lai Nef gene was a 1170 bp DNA fragment cloned on the mammalian expression vector pcDNA3 (pcDNA3/Nef).

The Tat gene originates from the BH10 molecular clone. This gene was received as an HTLV III cDNA clone named pCV1 and described in Science, 229, p69-73, 1985. This tat gene bears mutations in the active site region (Lys41→GAla) and in RGD motif (Arg78→Lys and Asp80→Glu) (Virology 235: 48-64, 1997).

The mutant tat gene was received as a cDNA fragment subcloned between the EcoRI and HindIII sites within a CMV expression plasmid (pCMVLys41/KGE)

Construction of Vector pRIT14597 (Encoding Nef-His Protein).

The nef gene was amplified by PCR from the pcDNA3/Nef plasmid with primers 01 and 02.

```
                                              [SEQ ID NO: 1]
                     NcoI
PRIMER 01: 5'ATCGTCCATG.GGT.GGC.AAG.TGG.T 3'
```

```
                                              [SEQ ID NO: 2]
                     SpeI
PRIMER 02: 5'CGGCTACTAGTGCAGTTCTTGAA 3'
```

The integrative vector PHIL-D2 (INVITROGEN) was used. This vector was modified in such a way that expression of heterologous protein starts immediately after the native ATG codon of the AOX1 gene and will produce recombinant protein with a tail of one glycine and six histidines residues. This PHIL-D2-MOD vector was constructed by cloning an oligonucleotide linker between the adjacent AsuII and EcoRI sites of PHIL-D2 vector. In addition to the His tail, this linker carries NcoI, SpeI and XbaI restriction sites between which nef, tat and nef-tat fusion were inserted.

The nefPCR fragment obtained and the integrative PHIL-D2-MOD vector were both restricted by NcoI and SpeI, purified on agarose gel and ligated to create the integrative plasmid pRIT14597.

Construction of Vector pRIT14913 (Encoding Fusion Nef-Tat Mutant-His).

To construct pRIT14913, the tat mutant gene was amplified by PCR from the pCMVLys41/KGE plasmid with primers 03 and 04.

```
                                              [SEQ ID NO: 3]
                     SpeI
PRIMER 03: 5' ATCGTACTAGT.GAG.CCA.GTA.GAT.C 3'
```

```
                                              [SEQ ID NO: 4]
                     SpeI
PRIMER 04: 5' CGGCTACTAGTTTCCTTCGGGCCT 3'
```

The PCR fragment obtained and the plasmid pRIT14597 (expressing Nef-His protein) were both digested by SpeI restriction enzyme, purified on agarose gel and ligated to create the integrative plasmid pRIT14913.

1.3 Generation of PMID Vectors for gp120 and Nef/Tat:

gp120: Codon-optimised gp120 was provided as described above.

Nef/Tat (pNTm and ptrNTm):

The gene for the Nef/Tat fusion protein was provided in plasmid pRIT15244 described above. The Tat in this plasmid contains three mutations to inactivate the transactivation function. The fusion contains full length Nef which has an immune modulatory function (Collins and Baltimore (1999)) that may be abrogated by N-terminal truncation. Therefore constructs were generated for both full length Nef/mutant Tat(pNTm) and truncated Nef/mutant Tat(ptrNTm), in which the first 65 amino acids of Nef were removed. These sequences were PCR amplified from pRIT15244 using primers:

```
                                    [SEQ ID NOS: 5, 6, 7]
5'Nef     GAATTCGCGGCCGCCATGGGTGGCAAGTGGTCAAAAAG

5'trNef   GAATTCGCGGCCGCCATGGTGGGTTTTCCAGTCACACC

3'Tat     GAATTCGGATCCTTATTCCTTCGGGCCTGTCGGG
```

The genes were cloned into vector p7313-ie as NotI-BamHI fragments and sequenced. PNTm and ptrNTm and the Nef/Tat and truncated Nef/Tat sequences are shown in FIGS. 4 and 5.

Dual Expression Vectors: (pRIX1 and pRIX2)

The Nef/Tat and trNef/Tat expression cassettes were excised as ClaI-XmnI restriction fragments, and ligated into the ClaI and blunted Sse8387 I sites of the vector containing the codon optimised gp120 (pgp120c) to provide single plasmids for expression of both proteins (pRIX1 and pRIX2 respectively).

Composition of Plasmid p7313-ie (FIG. 1)

The plasmid was constructed by replacing the beta-lactamase gene containing Eam11051-Pst1 fragment of pUC19 (available from Amersham Pharmacia Biotech UK Ltd., Amersham Place, Little Chalfont, Bucks, HP7 9NA) with an EcoRI fragment of pUC4K (Amersham-Pharmacia) containing the Kanamycin resistance gene, following blunt ending of both fragments using T4 DNA polymerase. The human Cytomegalovirus IE1 promoter/enhancer, Intron A, was derived from plasmid JW4303 obtained from Dr Harriet Robinson, University of Massachusetts, and inserted into the SalI site of pUC19 as a XhoI-SalI fragment, incorporating the bovine growth hormone polyadenylation signal. Deletion of the 5' SalI-BanI fragment from the promoter generated the minimal promoter used in the vector (WO00/23592-Powderject Vaccines Inc.). HBV Surface antigen 3'UTR was derived from Hepatitis B Virus, serotype adw, in the vector pAM6 (Moriarty et al., Proc. Natl. Acad. Sci. USA, 78, 2606-10, 1981). pAM6 (pBR322 based vector) was obtained from the American Type Culture Collection, catalogue number ATCC 45020. The 3'UTR was inserted 5' to the polyadenylation signal as a 1.4 kb BamHI fragment, blunt ended for insertion to remove the BamHI sites. In a series of steps (including digestion with Bgl II, Klenow polymerase treatment, digestion with BstXI, digestion with NcoI, treatment with mung bean nuclease to remove overhang and further digestion with BstXI), modifications were made to the region between the 3'untranslated enhancer region of the HBV S gene and bGHpA signal to remove all open reading frames of greater than 5 codons between the X gene promoter and the bGHpA signal. This resulted in deletion of sequence encoding the translatable portion of the X protein (9 amino acids) and the X gene start codon. The bovine growth hormone polyadenylation signal was substituted with the rabbit beta globin polyadenylation signal. The 5'non-coding and coding sequences of the S antigen were excised and replaced with an oligonucleotide linker to provide multiple cloning sites as shown to produce plasmid p7313-PL.

```
                                              [SEQ ID NO: 8]
Hind---NotI--   EcoRV-     -NdeI-    -BamHI
AGCTTGCGGCCGCTAGCGATATCGGTACCATATGTCGACGGATCC....

....ACGCCGGCGATCGCTATAGCCATGGTCTACAGCTGCCTAGGCCGG
            -NheI-     -KpnI-     -SalI-    ΔNotI
```

This polylinker was further extended by insertion of an additional oligonucleotide linker between the KpnI and SalI sites:

```
                                              [SEQ ID NO: 9]
AspI-   -MunI-  NaeI-     NdeI--    BglII-
GTACCGGTCAATTGGCGCCGGCGCGCCATATGACGTCAGATCTG----

----GCCAGTTAACCGCGGCCGCGCGGTATACTGCAGTCTAGACAGCT
--AgeI-     -NarI--           AatII-       SalI
```

The ColEI cer sequence was obtained from a subclone from plasmid pDAH212 from David Hodgeson (Warwick University) and amplified by PCR using primers to place EcoRI restriction sites at the ends of the sequence. The cer sequence was then inserted into the EcoRI site of p7313-PL to produce plasmid p7313-PLc. The sequence of the amplified cer was verified against the Genbank entry M11411.

The HBV 3'UTR sequence between the promoter and polyadenylation signal was removed by PCR amplification of the polyadenylation signal using primers:

```
sense:
CCATGGATCCGATCTTTTTCCCTCTGCC        [SEQ ID NO: 10]

antisense:
GTTAGGGTGAAAAGCTTCCGAGTGAGAGACAC    [SEQ ID NO: 11]
```

The resulting product was cut with BamHI and XmnI and used to replace the corresponding fragment containing both the polyadenylation signal and the 3'UTR. The Intron A sequence was removed from the plasmid by PCR amplification of the CMV promoter/enhancer using primers:

```
sense:
GCTAGCCTGCAGGCTGACCGCCCAACGAC       [SEQ ID NO: 12]

antisense:
GTTCTCCATCGCGGCCGCACTCTTGGCACGGGG   [SEQ ID NO: 13]
```

The resulting product was cut with Sse8387 I and NotI, and inserted back into the Sse8387 I and NotI sites of the parental vector.

Example 2

Modification of pp 120 and NeVTat(mut) Expression Vectors gp120 constructs were modified to reduce secretion of the protein.

Generation of Constructs:

gp120 Without a Secretion Signal (dsgp120, pRix12—see FIGS. 2 and 6)

The gp120 gene was PCR amplified from pgp120c using the following primers:

5'120ds:
5'GAATTCGCGGCCGCCATGGCCGAGCAGCTGTG [SEQ ID NO: 14]
GGTCACC

L01:
5'GAATTCGGATCCTCATCTCTGCACGACGCGGC [SEQ ID NO: 15]
GCTTGGCCCGGGTGGGGGCCACG

Fragments were amplified using PWO DNA polymerase (Roche) and the cycle:

95° C.(30 s)95° C.(30 s)50° C.(30 s)72° C.(90 s)72° C.(120 s)4° C.(hold)
repeat x20

The products were cut with NotI and BamHI and cloned into p7313-ie to give pRix12 (FIG. 6).

Results

In 293T cells the vector pRIX12, which lacks the secretion signal, makes a good amount of a 60 kDa non-glycosylated protein that is not secreted (FIGS. 29 and 30).

Example 3

Construction of Vectors for Expression of ep120 and Nef/Tat(mut) from a Single Plasmid Vector Construction:

The gp120 Nef/Tat(m) constructs were generated by PCR stitching the gp120 and Nef/Tat(m) or trNef/Tat(m) orfs.

5' and 3' Gp120, 5' and 3' Nef/Tat(m) and 5'trNef/Tat were amplified from pRix1. 3'trNef/Tat(m) was amplified from pNTm. The following primers were used:

3'120: (antisense to):
GCCAAGCGCCGCGTCGTGCAGAGA                    [SEQ ID NO: 16]

5'120/NT:
GCCAAGCGCCGCGTCGTGCAGAGAATGGGTGGCA          [SEQ ID NO: 17]
AGTGGTGAAAAAGT

3'NT (antisense to):
GGGGAGCCGACAGGCCCGAAGGAA                    [SEQ ID NO: 18]

5'NT/120:
GGGGAGCCGACAGGCCCGAAGGAAATGAAGGTCA          [SEQ ID NO: 19]
AGGAGACCAGAAAG

5'120/trN:
GCCAAGCGCCGCGTCGTGCAGAGAATGGTGGGTT          [SEQ ID NO: 20]
TTCCAGTCAC

5'trNef:
GAATTCGCGGCCGCCATGGTGGGTTTTCCAGTCA          [SEQ ID NO: 21]
CACC

L01:
GAATTCGGATCCTCATCTCTGCACGACGCGGCGC          [SEQ ID NO: 22]
TTGGCCCGGGTGGGGGCCACG

L02:
ACCACCTTGTACTTGTACAGCTCGCTCCGCCAGT          [SEQ ID NO: 23]
TATCCCTCATGTCGCCGCCGCGGGC

Fragments were amplified using PWO DNA polymerase (Roche) and the cycle:

95° C.(60 s)95° C.(30 s)55° C.(30 s)72° C.(120 s)72°(120 s)4° C.(hold)
repeat x20

Primer L1 was used as the 3' primer for 3'gp120. However there were problems using this primer when stitching Nef/Tat or trNef/T to the 5' end of gp120 so primer L2 was used instead.

The stitched gp120-N/Tm and gp120-trN/Tm fragments were cut with NotI and BamHI and cloned into similarly cut p7313-ie. Due to the use of primer L2 rather than L1 the N/Tm-gp120 and trN/Tm-gp120 fragments lacked a BamHI site, so these were cut with NotI and AccI, and cloned into similarly cut pgp120c. All inserts were fully verified by sequencing. The plasmids were designated pRix6 (gp120c NefTat''') and pRix11 (gp120c trNefTat''').

Example 4

Construction of Vectors to Investigate the Effects of Glycosylation and Secretion, Inclusion of Tat and Inclusion of Gag (p17/24) and Nef and RT on gp120 and gp120 Fusions Vectors were constructed as shown in FIGS. 29 and 30 (schematic).

pRix28 and pRix29 (FIGS. 7 and 8)

pRix28 and 29 containing ds gp120c NefTat''' and ds gp120c trNefTat were generated by transferring the AccI-BamHI fragments from pRix6 (2315 bp) and pRix11 (2123 bp) into similarly cut pRix12 (ds gp120c).

pRix30 and pRix31 (FIG. 9)

To generate glycosylated and non-glycosylated fusion vectors of gp120c Nef without Tat, the NotI-KpnI fragment was transferred from pRix11 (1580 bp) or pRix29 (1496 bp) into similarly cut pRix15, a vector containing Tat/trNef.

(pRix15)-Tat(mut)trNef

The genes for Tat and trNef were PCR amplified from pNTm using the following primers:

[SEQ ID NO: 24]
5'Tat:   5'GAATTCGCGGCCGCCATGGAGCCAGTAGATCCTAGAC

[SEQ ID NO: 25]
3'Tat:   5'TTCCTTCGGGCCTGTCGGC

[SEQ ID NO: 26]
5'trTN:  GCCGACAGGCCCGAAGGAAATGGTGGGTTTTCCAGTCACAC

[SEQ ID NO: 27]
3'Nef:   GAATTCGGATCCTTAGCAGTTCTTGAAGTACTCCGG

The individual genes were gel purified and then PCR stitched to give TmtrN using the end primers. The fusion was then digested with NotI and BamHI and cloned into p7313-ie.

pRix32

To generate the fusion containing p17/24, gp120 was PCR amplified from pgp120c using primers U1 and 3'120, p17/24-Nef was amplified from p73I-GN2 using primers 5'120G and 3'Nef, and the two were PCR stitched using U1 and 3'Nef. p731-GN2 contained a synthetic codon optimised sequence of p17/p24 based on the sequence of HXB2 (GenBank entry K03455) and designed using SynGene and assembled from overlapping oligonucleotides as described for codon optimised gp120 above, fused to HXB2 Nef, which had been obtained from plasmid pHXBΔPr (B. Maschera, E Furfine and E. D. Blair 1995 J. Virol 69 5431-5436) by PCR. Since the HXB2 nef gene in this plasmid contains a premature termination codon two overlapping PCRs were used to repair the codon (TGA [stop] to TGG [Trp]). The position of the repaired codon is underlined in the sequence. The p17/p24/Nef gene was inserted into the NotI and BamHI sites of plasmid p7313ie. The coding sequence and map is given in FIG. 10. A * marks the p24/trNefjunction.

Primers:

```
U1:                                       [SEQ ID NO: 28]
GAATTCGCGGCCGCAATGAAGGTCAAGGAGACCAGAAAGAACTACCAGC
ATCTGTG

3'120:                                    [SEQ ID NO: 29]
TCTCTGCACGACGCGGCGCTTGGC

5'120G:                                   [SEQ ID NO: 30]
GCCAAGCGCCGCGTCGTGGAGAGAATGGGTGCCCGAGCTTCGGTAC

3'Nef:                                    [SEQ ID NO: 31]
GAATTCGGATCCTTAGCAGTTCTTGAAGTACTCCGG
```

Initial Cycle:
94° C.(30 s) 20×[94° C. (30 s) 50° C. (30 s) 68° C. (180 s)] 68° C. (120 s) 4° C. (0 s)

Using pfx polymerase with 1× enhancer.

Stitch:
94° C.(30 s) 20×[94° C. (30 s) 50° C. (30 s) 72° C. (180 s)] 72° C. (120 s) 4° C. (0 s)

Using Vent polymerase in standard conditions+2 mM $MgCl_2$.

The product was cut with NotI and BamHI and cloned into p7313-ie.

On sequencing the construct was found to have a error in the signal peptide, which was corrected by transferring the 2560 bp BstEII-KpnI fragment containing the back of gp120 to the front of Nef into pRix30.

pRix33 (FIG. 11), pRix34, and pRix35 (FIG. 12)

The 2560 bp BstEII-KpnI fragment containing the back of gp120 to the front of Nef was transferred to pRix31, pRix11 and pRix29 to make vectors pRix33 (FIG. 11), 34 and 35 (FIG. 12) respectively.

pRix39 (gp120 Codon Optimised, Minus Secretion Signal—p17/24 gag-Nef-Tat—FIG. 13) and pRix40-47 (Constructs pRix40-47 Contain Non-Glycosylated gp120, gag-p17/24, Nef and Tat(m) Fusions with Mutations in the Miristoylation Site and/or Dileucine Motif of Nef)

A fragment containing gag p17/24 was PCR amplified from vector pRix35 using primers:

```
5'120G:                                   [SEQ ID NO: 32]
GCCAAGCGCCGCGTCGTGGAGAGAATGGGTGCCCGAGCTTCGGTAC and p24AS:                                    [SEQ ID NO: 33]
CAACACTCTGGCTTTGTGTCC
```

Full length Nef was PCR amplified from pNTm using primers:

```
5'p24-N:                                  [SEQ ID NO:34]
GGACACAAAGCCAGAGTGTTGATGGGCAAGTGGTCAAAAAGTAG and 3'Nef:                                    [SEQ ID NO:35]
GAATTCGGATCCTTAGCAGTTCTTGAAGTACTCCGG
```

The two fragments were PCR stitched together using the end primers (5'120G and 3'Nef). The product was cut with SalI and KpnI, and the 423 bp fragment containing part of p24 and Nef was used to replace the corresponding fragment in pRix35 to make pRix39 (FIG. 13).

pRix40 (FIG. 14) was similarly constructed except primer 5'p24-N was replaced with primer:

```
5'p24-Ndm:                                [SEQ ID NO: 36]
GGACACAAAGCCAGAGTGTTGATGGGCAAGTGGTCAAAAAGTAG
```

This primer deletes the one G to destroy the miristoylation site at the start of Nef.

pRix41-44, 46 and 47 (FIGS. 15 to 20)

Mutations to the dileucine motif in Nef (L174L175) were made by PCR:

To insert the mutations, the portion of Nef 5' to the LL motif was PCR amplified using the 5'Nef primer and asNefLL

```
5'Nef                                     [SEQ ID NO: 37]
GAATTCGCGGCCGCCATGGGTGGCAAGTGGTCAAAAAG asNefLL (Antisense to)                    [SEQ ID NO: 38]
GCCAATAAAGGAGAGAACACCAGC
```

Mutations to L174, L175 or both 174 and 175 were generated using forward primers

```
sNefL1 (L174A)                            [SEQ ID NO: 39]
GCCAATAAAGGAGAGAACACCAGCGCCTTACACCCTGTGAGCCTGCATG sNefL2 (L175A)                            [SEQ ID NO: 40]
GCCAATAAAGGAGAGAACACCAGCTTGGCACACCCTGTGAGCCTGCATG

SnefLL (LL174/5AA)                        [SEQ ID NO: 41]
GCCAATAAAGGAGAGAACACCAGCGCCGCACACCCTGTGAGCCTGCATG
``` and the 3'NT primer:

```
3'NT (antisense to):                      [SEQ ID NO: 42]
GGGGAGCCGACAGGCCCGAAGGAA
``` to amplify the 3' portion of Nef. The 5' and each of the 3' products were PCR stitched using the 5Nef and 3'NT primers. These were cut with KpnI and SpeI and inserted into similarly cut pRix39 to generate pRix41 (L174A), pRix42 (L175A), and pRix43 (LL174/175A) in the absence of the myristoylation site mutation, or into pRix40 to generate pRix44 (mLL174/175AA) pRix46 (mL174A) and pRix47 (mL175A) with the myristoylation site mutation.

pRix50, 51 and 52 and 53, 54 and 60 (FIGS. 23 to 27)

To generate dual promoter vectors containing non-glycosylated gp120 initially pRix12 was cut with Sse8387I, blunt ended with T4 DNA polymerase to remove the overhangs, and cut with ClaI. The 4573 bp product was gel purified (Fragment A)

pRix50: the plasmid pN™ was cut with ClaI and XmnI and the 1897 bp fragment was gel purified and ligated with Fragment A.

pRix51: the plasmid p73i-GN2 was cut with ClaI and XmnI and the 2533 bp fragment was gel purified and ligated with Fragment A.

pRix52: Plasmids p73i-GN2 and pNTm were cut with BglII and EcoRI, and the 4090 bp and 1060 bp fragments were isolated. From the respective digests. These fragments were ligated to produce the vector pRix52.

pRix53: the plasmid pRix52 was cut with ClaI and XmnI and ApaLI and the 2794 bp fragment was gel purified and ligated with Fragment A.

pRix54: the plasmid pT-mg (described in PG5035) was cut with ClaI and XmnI and the 4219 bp fragment was gel purified and ligated with Fragment A.

pRix60: pT-mg was cut with Sse8387I, blunt ended with T4 DNA polymerase to remove the overhangs, and cut with ClaI. The large fragment was gel purified. The plasmid pRix12 was cut with ClaI and XmnI and DraI and the 2476 bp fragment was gel purified and ligated with the fragment from pT-rng.

pRix58 (FIG. 21)

The gp120 fragment without signal sequence was PCR amplified from pgp120c using the primers:

```
                                            [SEQ ID NO: 43]
5'ds120:    GAATTCGCGGCCGCCATGGCCGAGCAGCTGTGGGTCACC

[SEQ ID NO: 44]
3'120:      GCCAAGCGCCGCGTCGTGCAGAGA
(antisense
to):
``` the 5' end of RT (codon optimised and containing the W229K inactivating mutation) was PCR amplified from pt-mg (FIG. 28—see also WO 03/025003) using a 5' primer to insert a sequence homologous to 3'120, and a primer within RT

```
    120RTf:                                 [SEQ ID NO: 45]
    GCCAAGCGCCGCGTCGTGCAGAGAATGGGCCCCATCAGTCCCATC

RT3SR1:                                 [SEQ ID NO: 46]
    CGTCACGATGTTCACCTCCAGGCC
```

The two products were PCR stitched using the end primers, and cut with NotI and NheI. The fragment was gel purified and used to replace the NotI-NheI fragment from pT-mg.

pRix59 (FIG. 22): the 3'Gag fragment was PCR amplified from pT-rng using a primer 5' to the MunI site in p24 and a 3' primer encoding the start of dsgp120, covering the position of the BstEII site near the 5' end:

```
GagMunf                                     [SEQ ID NO: 47]
GTGGCCCGAGAGCTGCATCCG GAG120R (Antisense to:)                     [SEQ ID NO: 48]
Gag-----------------ds120
GGACACAAAGCCAGAGTGTTGATGGCCGAGCAGCTGTGGGTCACCGTC
```

The product was cut with MunI and BstEII, and inserted into the 7113 bp fragment from MunI-BstEII cut pRix54.

Results

Expression Data is Shown in FIGS. 29, 30 and 31.

293T cell monolayers in 24 well plates were transfected with 1 µg of each DNA indicated using Lipofectamine 2000 following the manufacturer's supplied protocol. After 24 hours the cells were detached and separated from the culture medium by centrifugation. Samples equivalent to $1\times10^4$ cells or 12 µl of medium were examined by PAGE and Western blot.

The gp120c construct gave a highly glycosylated well secreted protein. Addition of c-terminal Nef/Tat fusions (pRix6 and pRix11) resulted in a reduction of the intracellular protein levels and loss of secretion. Removal of the secretion signal from gp120c (pRix12) gave a non-glycosylated non-secreted form of the protein.

As expected, fusion constructs with no secretion signal pRix28, 29, 31, 33 and 35, made non-glycosylated intracellular proteins in similar amounts, though expression from pRix35 was somewhat reduced. Surprisingly, when the secretion signal was present in constructs pRix30, 32 and 34, only pRix34 failed to be secreted. It appears that the presence of Tat in the fusion inhibits secretion of the protein. The initial pRix32.1 construct had a point mutation resulting in poor expression. This was corrected in pRix32.7, which showed greatly improved expression.

For pRix40-47 the western blot in FIG. 31 shows the expression of the dsgp120/GagNef/Tat fusions with mutations in Nef in 293T cells 24 hours post transfection with the plasmids indicated. Total cell extracts equivalent to ~$1\times10^4$ cells were loaded onto the gel. The blot was probed with an anti-nef antiserum.

For pRix50, 51, 53, 54, 58, 59 and 60 the two sets of western blots in FIG. 31 show the expression of the products of the dual promoter vectors indicated. Total cell extracts equivalent to ~$1\times10^4$ 293T cells, 24 hours post transfection, were loaded onto the gel. The left blot was probed with an anti-nef antiserum, and the right blot was probed with anti-gp120 antiserum.

REFS

Andre S. Seed B. Eberle J. Schraut W. Bultmann A. Haas J. (1998) Increased immune response elicited by DNA vaccination with a synthetic gp120 sequence with optimized codon usage. Journal of Virology. 72(2):1497-503.

Vinner L. Nielsen H V. Bryder K. Corbet S, Nielsen C. Fomsgaard A. (1999) Gene gun DNA vaccination with Rev-independent synthetic HIV-1 gp160 envelope gene using mammalian codons. Vaccine. 17(17):2166-75

Collins K L. Baltimore D.(1999) HIV's evasion of the cellular immune response. Immunological Reviews. 168:65-74.

Example 5

Preparation of Plasmid-Coated 'Gold Slurry' for 'Gene Gun' DNA Cartridges

Plasmid DNA (approximately 1 µg/µl), eg. 100 ug, and 2 µm gold particles, eg. 50 mg, (PowderJect), were suspended in 0.05M spermidine, eg. 100 ul, (Sigma). The DNA was precipitated on to the gold particles by addition of 1M $CaCl_2$, eg. 100 ul (American Pharmaceutical Partners, Inc., USA). The DNA/gold complex was incubated for 10 minutes at room temperature, washed 3 times in absolute ethanol, eg. 3×1 ml, (previously dried on molecular sieve 3A (BDH)). Samples were resuspended in absolute ethanol containing 0.05 mg/ml of polyvinylpyrrolidone (PVP, Sigma), and split into three equal aliquots in 1.5 ml microfuge tubes, (Eppendorf). The aliquots were for analysis of (a) 'gold slurry', (b) eluate-plasmid eluted from (a) and (c) for preparation of gold/plasmid coated Tefzel cartridges for the 'gene gun', (see Example 3 below). For preparation of samples (a) and (b), the tubes containing plasmid DNA/'gold slurry' in ethanol/PVP were spun for 2 minutes at top speed in an Eppendorf 5418 microfuge, the supernatant was removed and the 'gold slurry' dried for 10 minutes at room temperature. Sample (a) was resuspended to 0.5-1.0 ug/ul of plasmid DNA in TE pH 8.0, assuming approx. 50% coating. For elution, sample (b) was resuspended to 0.5-1.0 ug/ul of plasmid DNA in TE pH 8.0 and incubated at 37° C. for 30 minutes, shaking vigorously, and then spun for 2 minutes at top speed in an Eppendorf 5418 microfuge and the supernatant, eluate, was removed and stored at −20° C. The exact DNA concentration eluted was determined by spectrophotometric quantitation using a Genequant II (Pharmacia Biotech).

Example 6

Preparation of Cartridges for DNA Immunisation

Preparation of Cartridges for the Accell Gene Transfer Device was as Previously described (Eisenbraun et al DNA and Cell Biology, 1993 Vol 12 No 9 pp 791-797; Pertner et al). Briefly, plasmid DNA was coated onto 2 μm gold particles (DeGussa Corp., South Plainfield, N.J., USA) and loaded into Tefzel tubing, which was subsequently cut into 1.27 cm lengths to serve as cartridges and stored desiccated at 4° C. until use. In a typical vaccination, each cartridge contained 0.5 mg gold coated with a total of 0.5 μg DNA/cartridge.

Example 7

PMID Immunisations Including Using gp120-Nef-Tat Triple Fusion Lacking gp120 Secretion Signal Protocol: For PMID immunisations (DNA) cartridges were prepared for using standard methods as described in Examples 5 and 6. A DNA loading rate of 2, which will give approximately 0.5 μg DNA/cartridge was used and each immunisation consisted of two shots. Balb/c mice were given a primary immunisation of DNA (using PMID). The mice were boosted 28 days later with DNA (using PMID). Mice were culled 7 days later and serum and spleens were collected. The splenocytes were harvested by teasing out the spleen cells and erythrocytes were lysed. The splenocytes were washed and counted. Specialised ELIspot plates (coated with interferon-gamma capture antibody and blocked) were used. Splenocytes were transferred to these plates and incubated overnight at 37° C./5% $CO_2$ in the presence of a gp120 peptide, RT peptide or Gag peptide. The splenocytes were lysed and the plate developed using standard procedures to demonstrate the number of interferon-gamma secreting cells present. Serum was analysed by ELISA assay to detect for specific antibodies. Results are shown in FIGS. 32-34.

CONCLUSION

Figure 32:
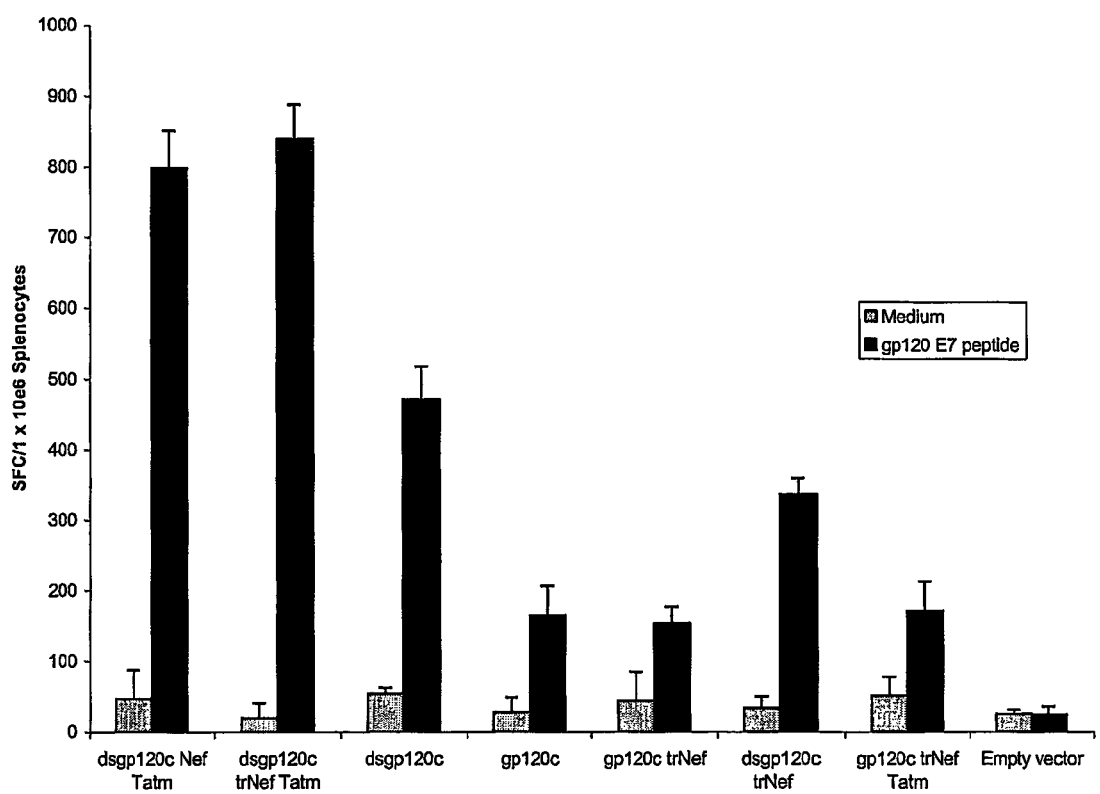
FIG. 32 is a bar graph depicting IFN-γ responses to gp120 peptide.
Figure 33:
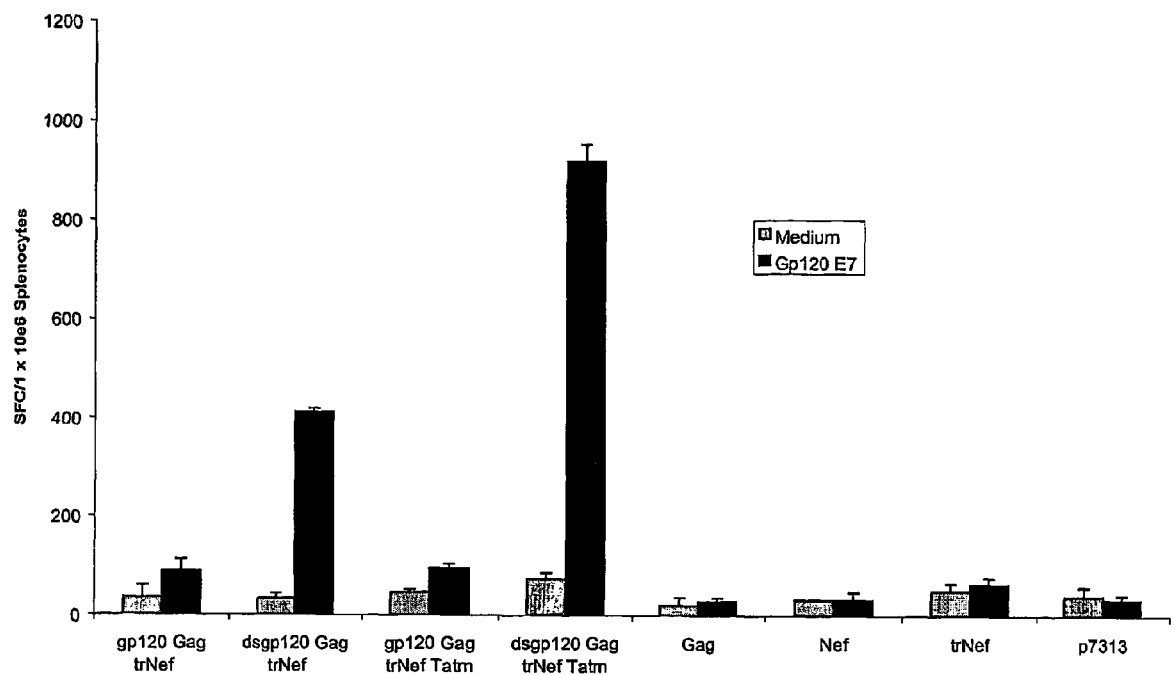
FIG. 33 is a bar graph depicting IFN-γ responses to gp120 peptide.
Figure 34:
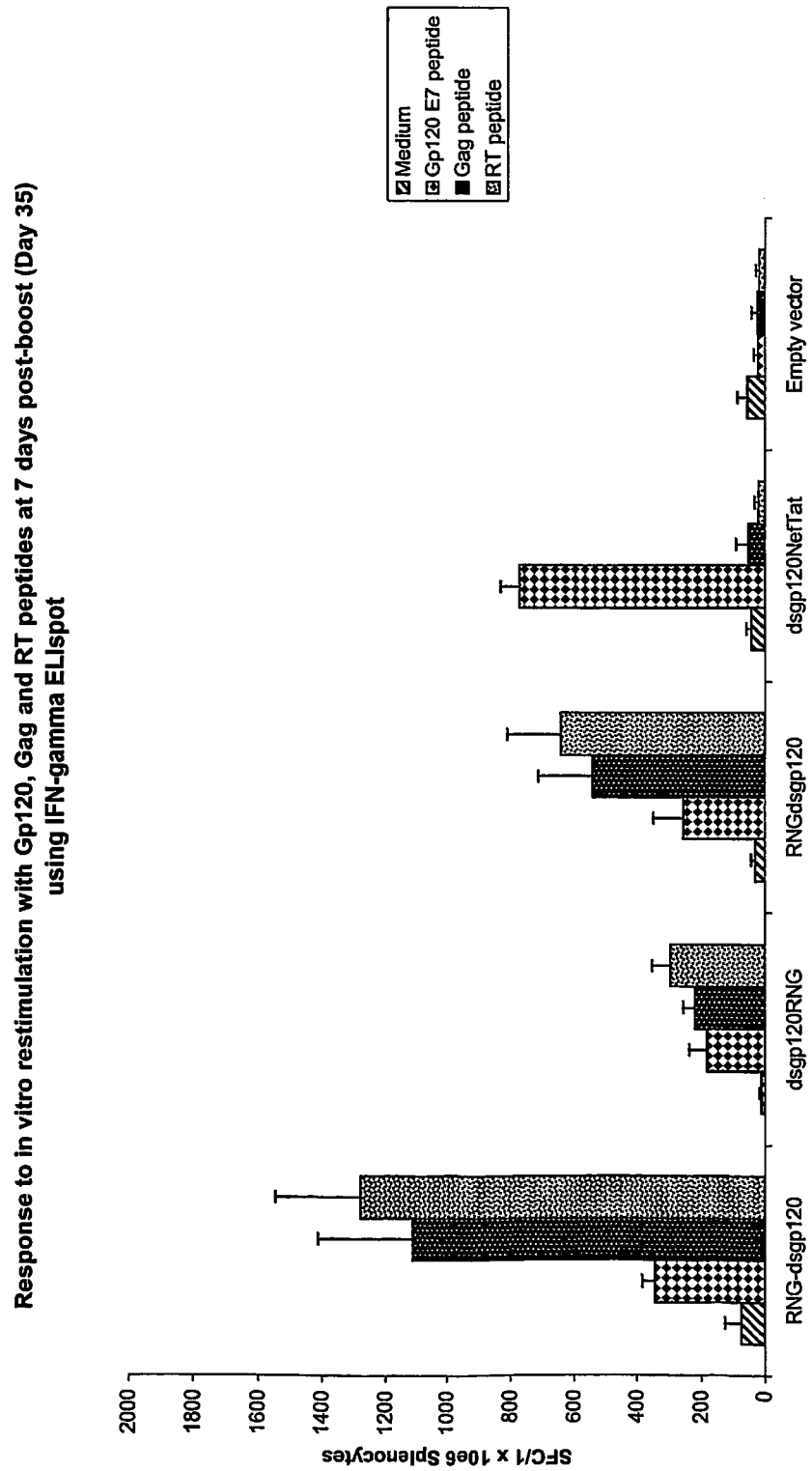
FIG. 34 is a bar graph depicting the response to in vitro restimulation with gp120, Gag and RT peptides.

Unexpectedly, the cellular immune response of mice immunised with dsgp120 (gp120 lacking secretion signal) expressing constructs was approximately double that of mice immunised with gp120 constructs (see FIGS. 32 and 33). This was consistent with the observation that in in vitro transfection studies the expression of dsgp120 had remained largely cell associated, whereas gp120 had been excreted.

Inclusion of Tat (mutated Tat) in the dsgp120 constructs increased the cellular immune response to twice that of the dsgp120 constructs without Tat (FIGS. 32 and 33). Tat on its own did not affect the immune response to gp120, but acted synergistically with dsgp120 to optimise the cellular response.

The inclusion of other HIV antigens in the constructs or dual promoter vectors produced a balanced cellular response to all the different antigens included and thus broadened the immune response compared to the gp120 only vectors (FIG. 34).

The invention claimed is:

1. An immunogenic composition comprising:
   (a) a polynucleotide that comprises a sequence encoding an HIV gp120 envelope protein operably linked to a heterologous promoter, wherein the gp120 encoding sequence is linked to a sequence encoding HIV RT and a sequence encoding HIV Gag and a sequence encoding HIV Nef, such that said polynucleotide encodes a fusion protein containing gp120, RT, Gag and Nef, and wherein the encoded HIV gp120 envelope protein lacks a functional secretion signal and is substantially non-glycosylated when expressed in a mammalian target cell, and
   (b) at least one pharmaceutically acceptable exipient, diluent, or carrier.

2. The immunogenic composition of claim 1, wherein the polynucleotide encodes a fusion protein selected from the group consisting of:
   a fusion protein comprising in the 5' to 3' direction: gp120-RT-Nef-Gag, and
   a fusion protein comprising in the 5' to 3' direction: RT-Nef-Gag-gp120.

3. The immunogenic composition of claim 1, wherein the polynucleotide encodes HIV Gag comprising one or both of P17 and P24.

4. The immunogenic composition of claim 1, wherein at least one of the sequences encoding gp120, Nef, Gag, and RT is codon optimised to resemble codon usage in a highly expressed human gene.

5. An immunogenic composition comprising:
   (a) a nucleic acid molecule encoding a fusion protein comprising in the 5' to 3' direction gp120-RT-Nef-Gag:
   wherein the nucleic acid sequences encoding gp120, RT and Gag are codon optimized, wherein the encoded gp120 lacks a functional secretion signal;

wherein the encoded RT comprises a mutation that substantially inactivates reverse transcriptase activity;

wherein the encoded Nef is a truncated Nef lacking N-terminal amino acids 1-65;

wherein the encoded Gag comprises p17 and p24; and (b) at least one pharmaceutically acceptable excipient, diluent, or carrier.

6. The immunogenic composition of claim 1, wherein the promoter is from an HCMV IE gene.

7. The immunogenic composition of claim 6, wherein a 5' untranslated region comprising exon 1 of the HCMV IE gene is between the promoter and the coding sequences.

8. An immunogenic composition according to claim 1, further comprising a polynucleotide encoding Tat.

9. The immunogenic composition of claim 8, wherein the polynucleotide encoding the fusion protein and the polynucleotide encoding Tat are contained on a single vector and are under the control of a single promoter.

10. The immunogenic composition of claim 1, wherein the polynucleotide sequence encoding the fusion protein is in a vector.

11. The immunogenic composition of claim 10, wherein the vector is a double stranded DNA plasmid.

12. The immunogenic composition of claim 10, wherein the vector is a replication defective adenovirus vector.

13. The immunogenic composition of claim 12, wherein the replication defective vector is selected from the group consisting of: Pan 9, Pan 5, Pan 6 and Pan 7.

14. The immunogenic composition of claim 1, further comprising an adjuvant.

15. The immunogenic composition of claim 1 comprising a carrier, wherein the carrier is a plurality of particles.

16. The immunogenic composition of claim 1, wherein the immunogenic composition is suitable for delivery in a prime boost format.

17. An intradermal delivery device comprising the immunogenic composition of claim 1.

18. The immunogenic composition of claim 15, wherein the carrier is gold beads.

19. The immunogenic composition of claim 8, wherein the polynucleotide encoding the fusion protein and the polynucleotide encoding Tat are contained on a single vector and are under the control of separate promoters.

20. The immunogenic composition of claim 1, wherein the sequence encoding HIV Gag encodes both p17 and p24.

21. The immunogenic composition of claim 1, wherein the sequence encoding RT comprises a mutation that substantially inactivates reverse transcriptase activity in the encoded RT.

22. The immunogenic composition of claim 1, wherein the sequence encoding Nef encodes a truncated Nef lacking N-terminal amino acids 1-65.

23. An immunogenic composition comprising:

(a) a nucleic acid molecule encoding a fusion protein comprising in the 5' to 3' direction RT-Nef-Gag-gp120; wherein the sequences encoding gp120, RT and Gag are codon optimized; wherein the encoded RT comprises a mutation that substantially inactivates reverse transcriptase activity; wherein the encoded Nef is a truncated Nef lacking N-terminal amino acids 1-65; wherein the encoded Gag comprises p17 and p24; and wherein the encoded gp120 lacks a functional secretion signal; and (b) at least one pharmaceutically acceptable excipient, diluent, or carrier.

24. The immunogenic composition of claim 23, further comprising a polynucleotide encoding Tat.

25. The immunogenic composition of claim 5, further comprising a polynucleotide encoding Tat.

26. The immunogenic composition of claim 5, wherein the polynucleotide sequence encoding the fusion protein is in a vector.

27. The immunogenic composition of claim 23, wherein the polynucleotide sequence encoding the fusion protein is in a vector.

28. The immunogenic composition of claim 5, wherein the vector is a replication defective adenovirus vector.

29. The immunogenic composition of claim 5, wherein the vector is a replication defective adenovirus vector.

30. The immunogenic composition of claim 23, further comprising an adjuvant.

31. The immunogenic composition of claim 23, further comprising an adjuvant.

* * * * *

SEQUENCE LISTING

```
<160> NUMBER OF SEQ ID NOS: 89

<210> SEQ ID NO 1
<211> LENGTH: 23
<212> TYPE: DNA
<213> ORGANISM: Artificial Sequence
<220> FEATURE:
<223> OTHER INFORMATION: Synthetic DNA primer

<400> SEQUENCE: 1
atcgtccatg ggtggcaagt ggt                                             23

<210> SEQ ID NO 2
<211> LENGTH: 23
<212> TYPE: DNA
<213> ORGANISM: Artificial Sequence
<220> FEATURE:
<223> OTHER INFORMATION: Synthetic DNA primer

<400> SEQUENCE: 2
cggctactag tgcagttctt gaa                                             23

<210> SEQ ID NO 3
<211> LENGTH: 24
<212> TYPE: DNA
```

```
<213> ORGANISM: Artificial Sequence
<220> FEATURE:
<223> OTHER INFORMATION: Synthetic DNA primer

<400> SEQUENCE: 3
atcgtactag tgagccagta gatc                                          24

<210> SEQ ID NO 4
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 4
cggctactag tttccttcgg gcct                                          24

<210> SEQ ID NO 5
<211> LENGTH: 38
<212> TYPE: DNA
<213> ORGANISM: Artificial Sequence
<220> FEATURE:
<223> OTHER INFORMATION: Synthetic DNA primer

<400> SEQUENCE: 5
gaattcgcgg ccgccatggg tggcaagtgg tcaaaaag                           38

<210> SEQ ID NO 6
<211> LENGTH: 38
<212> TYPE: DNA
<213> ORGANISM: Artificial Sequence
<220> FEATURE:
<223> OTHER INFORMATION: Synthetic DNA primer

<400> SEQUENCE: 6
gaattcgcgg ccgccatggt gggttttcca gtcacacc                           38

<210> SEQ ID NO 7
<211> LENGTH: 34
<212> TYPE: DNA
<213> ORGANISM: Artificial Sequence
<220> FEATURE:
<223> OTHER INFORMATION: Synthetic DNA primer

<400> SEQUENCE: 7
gaattcggat ccttattcct tcgggcctgt cggg                               34

<210> SEQ ID NO 8
<211> LENGTH: 45
<212> TYPE: DNA
<213> ORGANISM: Artificial Sequence
<220> FEATURE:
<223> OTHER INFORMATION: Synthetic polylinker

<400> SEQUENCE: 8
agcttgcggc cgctagcgat atcggtacca tatgtcgacg gatcc                   45

<210> SEQ ID NO 9
<211> LENGTH: 44
<212> TYPE: DNA
<213> ORGANISM: Artificial Sequence
<220> FEATURE:
<223> OTHER INFORMATION: Synthetic polylinker

<400> SEQUENCE: 9
gtaccggtca attggcgccg gcgcgccata tgacgtcaga tctg                    44
```

<210> SEQ ID NO 10
<211> LENGTH: 28
<212> TYPE: DNA
<213> ORGANISM: Artificial Sequence
<220> FEATURE:
<223> OTHER INFORMATION: Synthetic primer

<400> SEQUENCE: 10
ccatggatcc gatcttttc cctctgcc                                          28

<210> SEQ ID NO 11
<211> LENGTH: 32
<212> TYPE: DNA
<213> ORGANISM: Artificial Sequence
<220> FEATURE:
<223> OTHER INFORMATION: Synthetic primer

<400> SEQUENCE: 11
gttagggtga aaagcttccg agtgagagac ac                                    32

<210> SEQ ID NO 12
<211> LENGTH: 32
<212> TYPE: DNA
<213> ORGANISM: Artificial Sequence
<220> FEATURE:
<223> OTHER INFORMATION: Synthetic primer

<400> SEQUENCE: 12
gttagggtga aaagcttccg agtgagagac ac                                    32

<210> SEQ ID NO 13
<211> LENGTH: 33
<212> TYPE: DNA
<213> ORGANISM: Artificial Sequence
<220> FEATURE:
<223> OTHER INFORMATION: Synthetic primer

<400> SEQUENCE: 13
gttctccatc gcggccgcac tcttggcacg ggg                                   33

<210> SEQ ID NO 14
<211> LENGTH: 39
<212> TYPE: DNA
<213> ORGANISM: Artificial Sequence
<220> FEATURE:
<223> OTHER INFORMATION: Synthetic primer

<400> SEQUENCE: 14
gaattcgcgg ccgccatggc cgagcagctg tgggtcacc                             39

<210> SEQ ID NO 15
<211> LENGTH: 55
<212> TYPE: DNA
<213> ORGANISM: Artificial Sequence
<220> FEATURE:
<223> OTHER INFORMATION: Synthetic primer

<400> SEQUENCE: 15
gaattcggat cctcatctct gcacgacgcg gcgcttggcc cgggtggggg ccacg           55

<210> SEQ ID NO 16
<211> LENGTH: 24
<212> TYPE: DNA
<213> ORGANISM: Artificial Sequence
<220> FEATURE:

```
<223> OTHER INFORMATION: Synthetic primer

<400> SEQUENCE: 16
gccaagcgcc gcgtcgtgca gaga                                          24

<210> SEQ ID NO 17
<211> LENGTH: 48
<212> TYPE: DNA
<213> ORGANISM: Artificial Sequence
<220> FEATURE:
<223> OTHER INFORMATION: Synthetic primer

<400> SEQUENCE: 17
gccaagcgcc gcgtcgtgca gagaatgggt ggcaagtggt caaaaagt               48

<210> SEQ ID NO 18
<211> LENGTH: 24
<212> TYPE: DNA
<213> ORGANISM: Artificial Sequence
<220> FEATURE:
<223> OTHER INFORMATION: Synthetic primer

<400> SEQUENCE: 18
ggggagccga caggcccgaa ggaa                                          24

<210> SEQ ID NO 19
<211> LENGTH: 48
<212> TYPE: DNA
<213> ORGANISM: Artificial Sequence
<220> FEATURE:
<223> OTHER INFORMATION: Synthetic primer

<400> SEQUENCE: 19
ggggagccga caggcccgaa ggaaatgaag gtcaaggaga ccagaaag               48

<210> SEQ ID NO 20
<211> LENGTH: 44
<212> TYPE: DNA
<213> ORGANISM: Artificial Sequence
<220> FEATURE:
<223> OTHER INFORMATION: Synthetic primer

<400> SEQUENCE: 20
gccaagcgcc gcgtcgtgca gagaatggtg ggttttccag tcac                    44

<210> SEQ ID NO 21
<211> LENGTH: 38
<212> TYPE: DNA
<213> ORGANISM: Artificial Sequence
<220> FEATURE:
<223> OTHER INFORMATION: Synthetic primer

<400> SEQUENCE: 21
gaattcgcgg ccgccatggt gggttttcca gtcacacc                           38

<210> SEQ ID NO 22
<211> LENGTH: 55
<212> TYPE: DNA
<213> ORGANISM: Artificial Sequence
<220> FEATURE:
<223> OTHER INFORMATION: Synthetic primer

<400> SEQUENCE: 22
gaattcggat cctcatctct gcacgacgcg gcgcttggcc cgggtggggg ccacg        55
```

<210> SEQ ID NO 23
<211> LENGTH: 60
<212> TYPE: DNA
<213> ORGANISM: Artificial Sequence
<220> FEATURE:
<223> OTHER INFORMATION: Synthetic primer

<400> SEQUENCE: 23
accaccttgt acttgtacag ctcgctccgc cagttatccc tcatgtcgcc gccgccgggc    60

<210> SEQ ID NO 24
<211> LENGTH: 37
<212> TYPE: DNA
<213> ORGANISM: Artificial Sequence
<220> FEATURE:
<223> OTHER INFORMATION: Synthetic primer

<400> SEQUENCE: 24
gaattcgcgg ccgccatgga gccagtagat cctagac                             37

<210> SEQ ID NO 25
<211> LENGTH: 19
<212> TYPE: DNA
<213> ORGANISM: Artificial Sequence
<220> FEATURE:
<223> OTHER INFORMATION: Synthetic primer

<400> SEQUENCE: 25
ttccttcggg cctgtcggc                                                 19

<210> SEQ ID NO 26
<211> LENGTH: 41
<212> TYPE: DNA
<213> ORGANISM: Artificial Sequence
<220> FEATURE:
<223> OTHER INFORMATION: Synthetic primer

<400> SEQUENCE: 26
gccgacaggc ccgaaggaaa tggtgggttt ccagtcaca c                         41

<210> SEQ ID NO 27
<211> LENGTH: 36
<212> TYPE: DNA
<213> ORGANISM: Artificial Sequence
<220> FEATURE:
<223> OTHER INFORMATION: Synthetic primer

<400> SEQUENCE: 27
gaattcggat ccttagcagt tcttgaagta ctccgg                              36

<210> SEQ ID NO 28
<211> LENGTH: 56
<212> TYPE: DNA
<213> ORGANISM: Artificial Sequence
<220> FEATURE:
<223> OTHER INFORMATION: Synthetic primer

<400> SEQUENCE: 28
gaattcgcgg ccgcaatgaa ggtcaaggag accagaaaga actaccagca tctgtg        56

<210> SEQ ID NO 29
<211> LENGTH: 24
<212> TYPE: DNA
<213> ORGANISM: Artificial Sequence
<220> FEATURE:
<223> OTHER INFORMATION: Synthetic primer

```
<400> SEQUENCE: 29
tctctgcacg acgcggcgct tggc                                    24

<210> SEQ ID NO 30
<211> LENGTH: 46
<212> TYPE: DNA
<213> ORGANISM: Artificial Sequence
<220> FEATURE:
<223> OTHER INFORMATION: Synthetic primer

<400> SEQUENCE: 30
gccaagcgcc gcgtcgtgga gagaatgggt gcccgagctt cggtac            46

<210> SEQ ID NO 31
<211> LENGTH: 36
<212> TYPE: DNA
<213> ORGANISM: Artificial Sequence
<220> FEATURE:
<223> OTHER INFORMATION: Synthetic primer

<400> SEQUENCE: 31
gaattcggat ccttagcagt tcttgaagta ctccgg                       36

<210> SEQ ID NO 32
<211> LENGTH: 46
<212> TYPE: DNA
<213> ORGANISM: Artificial Sequence
<220> FEATURE:
<223> OTHER INFORMATION: Synthetic primer

<400> SEQUENCE: 32
gccaagcgcc gcgtcgtgga gagaatgggt gcccgagctt cggtac            46

<210> SEQ ID NO 33
<211> LENGTH: 21
<212> TYPE: DNA
<213> ORGANISM: Artificial Sequence
<220> FEATURE:
<223> OTHER INFORMATION: Synthetic primer

<400> SEQUENCE: 33
caacactctg gctttgtgtc c                                       21

<210> SEQ ID NO 34
<211> LENGTH: 44
<212> TYPE: DNA
<213> ORGANISM: Artificial Sequence
<220> FEATURE:
<223> OTHER INFORMATION: Synthetic primer

<400> SEQUENCE: 34
ggacacaaag ccagagtgtt gatgggcaag tggtcaaaaa gtag              44

<210> SEQ ID NO 35
<211> LENGTH: 36
<212> TYPE: DNA
<213> ORGANISM: Artificial Sequence
<220> FEATURE:
<223> OTHER INFORMATION: Synthetic primer

<400> SEQUENCE: 35
gaattcggat ccttagcagt tcttgaagta ctccgg                       36

<210> SEQ ID NO 36
<211> LENGTH: 44
```

<210> SEQ ID NO 36
<211> LENGTH: 44 (implied)
<212> TYPE: DNA
<213> ORGANISM: Artificial Sequence
<220> FEATURE:
<223> OTHER INFORMATION: Synthetic primer

<400> SEQUENCE: 36
ggacacaaag ccagagtgtt gatgggcaag tggtcaaaaa gtag        44

<210> SEQ ID NO 37
<211> LENGTH: 38
<212> TYPE: DNA
<213> ORGANISM: Artificial Sequence
<220> FEATURE:
<223> OTHER INFORMATION: Synthetic primer

<400> SEQUENCE: 37
gaattcgcgg ccgccatggg tggcaagtgg tcaaaaag             38

<210> SEQ ID NO 38
<211> LENGTH: 24
<212> TYPE: DNA
<213> ORGANISM: Artificial Sequence
<220> FEATURE:
<223> OTHER INFORMATION: Synthetic primer

<400> SEQUENCE: 38
gccaataaag gagagaacac cagc                           24

<210> SEQ ID NO 39
<211> LENGTH: 49
<212> TYPE: DNA
<213> ORGANISM: Artificial Sequence
<220> FEATURE:
<223> OTHER INFORMATION: Synthetic primer

<400> SEQUENCE: 39
gccaataaag gagagaacac cagcgcctta caccctgtga gcctgcatg   49

<210> SEQ ID NO 40
<211> LENGTH: 49
<212> TYPE: DNA
<213> ORGANISM: Artificial Sequence
<220> FEATURE:
<223> OTHER INFORMATION: Synthetic primer

<400> SEQUENCE: 40
gccaataaag gagagaacac cagcttggca caccctgtga gcctgcatg   49

<210> SEQ ID NO 41
<211> LENGTH: 49
<212> TYPE: DNA
<213> ORGANISM: Artificial Sequence
<220> FEATURE:
<223> OTHER INFORMATION: Synthetic primer

<400> SEQUENCE: 41
gccaataaag gagagaacac cagcgccgca caccctgtga gcctgcatg   49

<210> SEQ ID NO 42
<211> LENGTH: 24
<212> TYPE: DNA
<213> ORGANISM: Artificial Sequence
<220> FEATURE:
<223> OTHER INFORMATION: Synthetic primer

<400> SEQUENCE: 42

```
ggggagccga caggcccgaa ggaa                                          24
```

<210> SEQ ID NO 43
<211> LENGTH: 39
<212> TYPE: DNA
<213> ORGANISM: Artificial Sequence
<220> FEATURE:
<223> OTHER INFORMATION: Synthetic primer

<400> SEQUENCE: 43

```
gaattcgcgg ccgccatggc cgagcagctg tgggtcacc                          39
```

<210> SEQ ID NO 44
<211> LENGTH: 24
<212> TYPE: DNA
<213> ORGANISM: Artificial Sequence
<220> FEATURE:
<223> OTHER INFORMATION: Synthetic primer

<400> SEQUENCE: 44

```
gccaagcgcc gcgtcgtgca gaga                                          24
```

<210> SEQ ID NO 45
<211> LENGTH: 45
<212> TYPE: DNA
<213> ORGANISM: Artificial Sequence
<220> FEATURE:
<223> OTHER INFORMATION: Synthetic primer

<400> SEQUENCE: 45

```
gccaagcgcc gcgtcgtgca gagaatgggc cccatcagtc ccatc                   45
```

<210> SEQ ID NO 46
<211> LENGTH: 24
<212> TYPE: DNA
<213> ORGANISM: Artificial Sequence
<220> FEATURE:
<223> OTHER INFORMATION: Synthetic primer

<400> SEQUENCE: 46

```
cgtcacgatg ttcacctcca ggcc                                          24
```

<210> SEQ ID NO 47
<211> LENGTH: 21
<212> TYPE: DNA
<213> ORGANISM: Artificial Sequence
<220> FEATURE:
<223> OTHER INFORMATION: Synthetic primer

<400> SEQUENCE: 47

```
gtggcccgag agctgcatcc g                                             21
```

<210> SEQ ID NO 48
<211> LENGTH: 48
<212> TYPE: DNA
<213> ORGANISM: Artificial Sequence
<220> FEATURE:
<223> OTHER INFORMATION: Synthetic primer

<400> SEQUENCE: 48

```
ggacacaaag ccagagtgtt gatggccgag cagctgtggg tcaccgtc                48
```

<210> SEQ ID NO 49
<211> LENGTH: 514
<212> TYPE: PRT
<213> ORGANISM: HIV-1

<400> SEQUENCE: 49

```
Met Lys Val Lys Glu Thr Arg Lys Asn Tyr Gln His Leu Trp Arg Trp
 1               5                  10                  15
Gly Thr Met Leu Leu Gly Met Leu Met Ile Cys Ser Ala Ala Glu Gln
             20                  25                  30
Leu Trp Val Thr Val Tyr Tyr Gly Val Pro Val Trp Lys Glu Ala Thr
         35                  40                  45
Thr Thr Leu Phe Cys Ala Ser Asp Ala Lys Ala Tyr Asp Thr Glu Val
     50                  55                  60
His Asn Val Trp Ala Thr His Ala Cys Val Pro Thr Asp Pro Asn Pro
 65                  70                  75                  80
Gln Glu Val Val Leu Gly Asn Val Thr Glu Tyr Phe Asn Met Trp Lys
                 85                  90                  95
Asn Asn Met Val Asp Gln Met His Glu Asp Ile Ile Ser Leu Trp Asp
            100                 105                 110
Gln Ser Leu Lys Pro Cys Val Lys Leu Thr Pro Leu Cys Val Thr Leu
        115                 120                 125
Asp Cys Asp Asp Val Asn Thr Thr Asn Ser Thr Thr Thr Thr Ser Asn
    130                 135                 140
Gly Trp Thr Gly Glu Ile Arg Lys Gly Glu Ile Lys Asn Cys Ser Phe
145                 150                 155                 160
Asn Ile Thr Thr Ser Ile Arg Asp Lys Val Gln Lys Glu Tyr Ala Leu
                165                 170                 175
Phe Tyr Asn Leu Asp Val Val Pro Ile Asp Asp Asn Ala Thr Thr
            180                 185                 190
Lys Asn Lys Thr Thr Arg Asn Phe Arg Leu Ile His Cys Asn Ser Ser
        195                 200                 205
Val Met Thr Gln Ala Cys Pro Lys Val Ser Phe Glu Pro Ile Pro Ile
    210                 215                 220
His Tyr Cys Ala Pro Ala Gly Phe Ala Ile Leu Lys Cys Asn Asn Lys
225                 230                 235                 240
Thr Phe Asp Gly Lys Gly Leu Cys Thr Asn Val Ser Thr Val Gln Cys
                245                 250                 255
Thr His Gly Ile Arg Pro Val Val Ser Thr Gln Leu Leu Asn Gly
            260                 265                 270
Ser Leu Ala Glu Glu Glu Val Val Ile Arg Ser Asp Asn Phe Met Asp
        275                 280                 285
Asn Thr Lys Thr Ile Ile Val Gln Leu Asn Glu Ser Val Ala Ile Asn
    290                 295                 300
Cys Thr Arg Pro Asn Asn Asn Thr Arg Lys Gly Ile His Ile Gly Pro
305                 310                 315                 320
Gly Arg Ala Phe Tyr Ala Ala Arg Lys Ile Ile Gly Asp Ile Arg Gln
                325                 330                 335
Ala His Cys Asn Leu Ser Arg Ala Gln Trp Asn Asn Thr Leu Lys Gln
            340                 345                 350
Ile Val Ile Lys Leu Arg Glu His Phe Gly Asn Lys Thr Ile Lys Phe
        355                 360                 365
Asn Gln Ser Ser Gly Gly Asp Pro Glu Ile Val Arg His Ser Phe Asn
    370                 375                 380
Cys Gly Gly Glu Phe Phe Tyr Cys Asp Thr Thr Gln Leu Phe Asn Ser
385                 390                 395                 400
Thr Trp Asn Gly Thr Glu Gly Asn Asn Thr Glu Gly Asn Ser Thr Ile
```

```
                    405                 410                 415
Thr Leu Pro Cys Arg Ile Lys Gln Ile Ile Asn Met Trp Gln Glu Val
            420                 425                 430

Gly Lys Ala Met Tyr Ala Pro Pro Ile Gly Gly Gln Ile Arg Cys Ser
        435                 440                 445

Ser Asn Ile Thr Gly Leu Leu Leu Thr Arg Asp Gly Gly Thr Glu Gly
    450                 455                 460

Asn Gly Thr Glu Asn Glu Thr Glu Ile Phe Arg Pro Gly Gly Gly Asp
465                 470                 475                 480

Met Arg Asp Asn Trp Arg Ser Glu Leu Tyr Lys Tyr Lys Val Val Lys
            485                 490                 495

Val Glu Pro Leu Gly Val Ala Pro Thr Arg Ala Lys Arg Arg Val Val
        500                 505                 510

Gln Arg

<210> SEQ ID NO 50
<211> LENGTH: 1545
<212> TYPE: DNA
<213> ORGANISM: Artificial Sequence
<220> FEATURE:
<223> OTHER INFORMATION: Codon optimised DNA for gp120

<400> SEQUENCE: 50
atgaaggtca aggagaccag aaagaactac cagcatctgt ggcgctgggg caccatgctc      60
ctgggaatgc tgatgatctg ctccgccgcc gagcagctgt gggtcaccgt ctactacggc    120
gtgcctgtgt ggaaggaggc cacgaccacc ctcttctgcg cgagcgacgc caaggcctac    180
gacacggaag tgcataacgt gtgggcgacg catgcttgcg tgcctacgga ccccaacccc    240
caggaggtgg tgctgggaaa cgtgaccgag tacttcaaca tgtggaagaa taacatggtg    300
gatcagatgc acgaggacat catctctctg tgggaccagt ccctgaagcc tgcgtgaag     360 ctgacgcctc tctgcgtgac actggactgt gacgacgtca caccaccaa cagcactacc     420 accaccagca acggctggac cggagagatt cggaagggcg agatcaagaa ctgctccttc    480
aatatcacga cctcgatcag agacaaggtg cagaaggaat acgcgctgtt ttataatctc    540
gatgtggtcc ccatcgacga cgacaatgcc accaccaaga acaagacgac gcgtaatttc    600
agactcattc actgcaacag cagcgtcatg acgcaggcct gccccaaggt gtccttcgaa    660
ccaatcccga tccattactg tgcccctgcc ggattcgcga tcctcaagtg taacaacaag    720
accttcgacg ggaagggcct gtgcaccaac gtcagcacgg tgcagtgcac ccatggcatc    780
cgccccgtcg tgagcaccca gctgctgctg aacgggtccc tggctgagga ggaggtggtg    840
atccggtcgg acaacttcat ggacaacacc aagacaatca tcgtccagct gaacgagtct    900
gtggcgatta actgtacccg gcctaacaac aacacccgta agggcatcca tatcgggcct    960
ggacgggcct ctatgccgc ccgcaagatc atcggcgaca tccggcaggc cattgcaac    1020 ctctcccgcg cccagtggaa taacaccctg aagcagatcg tgatcaagct gagagagcac   1080
tttggaaaca agaccatcaa gttcaatcag agttctggcg agacccccga gatcgtgcgg   1140
cactccttca actgcggggg cgagttcttc tactgcgata cgacacagct cttcaactcc   1200
acctggaacg gcaccgaggg caacaacaca gagggaaact ccactatcac cctcccttgc   1260
cgcatcaagc agatcatcaa catgtggcag gaggtgggaa aggccatgta tgcccccccc   1320
atcgggggcc agatccgctg ctcctccaac atcaccggcc tgctgctcac cagagacggg   1380
ggcaccgagg gcaacggcac ggagaacgag acggagatct tcaggcccgg cggcggcgac   1440
```

```
atgagggata actggcggag cgagctgtac aagtacaagg tggtgaaggt ggagccgctc    1500
ggcgtggccc ccacccgggc caagcgccgc gtcgtgcaga gatga                    1545

<210> SEQ ID NO 51
<211> LENGTH: 882
<212> TYPE: DNA
<213> ORGANISM: Artificial Sequence
<220> FEATURE:
<223> OTHER INFORMATION: HIV-1 Nef-Tatm fusion

<400> SEQUENCE: 51
atgggtggca gtggtcaaaa agtagtgtg gttggatggc ctactgtaag ggaaagaatg      60
agacgagctg agccagcagc agatgggggtg ggagcagcat ctcgagacct ggaaaaacat   120
ggagcaatca caagtagcaa tacagcagct accaatgctg cttgtgcctg gctagaagca    180
caagaggagg aggaggtggg ttttccagtc acacctcagg taccttttaag accaatgact   240 tacaaggcag ctgtagatct tagccacttt ttaaaagaaa aggggggact ggaagggcta    300
attcactccc aacgaagaca agatatcctt gatctgtgga tctaccacac acaaggctac    360
ttccctgatt ggcagaacta cacaccaggg ccaggggtca gatatccact gacctttgga    420
tggtgctaca agctagtacc agttgagcca gataaggtag aagaggccaa taaaggagag    480
aacaccagct tgttacaccc tgtgagcctg catggaatgg atgaccctga gagaagtg     540 ttagagtgga ggtttgacag ccgcctagca tttcatcacg tggcccgaga gctgcatccg    600
gagtacttca agaactgcac tagtgagcca gtagatccta gactagagcc ctggaagcat    660
ccaggaagtc agcctaaaac tgcttgtacc aattgctatt gtaaaaagtg ttgctttcat    720
tgccaagttt gtttcataac agctgccttaa ggcatctcct atggcaggaa gaagcggaga    780
cagcgacgaa gacctcctca aggcagtcag actcatcaag tttctctatc aaagcaaccc    840
acctcccaat ccaaggggga gccgacaggc ccgaaggaat aa                       882

<210> SEQ ID NO 52
<211> LENGTH: 293
<212> TYPE: PRT
<213> ORGANISM: Artificial Sequence
<220> FEATURE:
<223> OTHER INFORMATION: HIV-1 Nef-Tatm fusion

<400> SEQUENCE: 52

Met Gly Gly Lys Trp Ser Lys Ser Ser Val Val Gly Trp Pro Thr Val
  1               5                  10                  15

Arg Glu Arg Met Arg Arg Ala Glu Pro Ala Ala Asp Gly Val Gly Ala
                 20                  25                  30

Ala Ser Arg Asp Leu Glu Lys His Gly Ala Ile Thr Ser Ser Asn Thr
             35                  40                  45

Ala Ala Thr Asn Ala Ala Cys Ala Trp Leu Glu Ala Gln Glu Glu Glu
         50                  55                  60

Glu Val Gly Phe Pro Val Thr Pro Gln Val Pro Leu Arg Pro Met Thr
 65                  70                  75                  80

Tyr Lys Ala Ala Val Asp Leu Ser His Phe Leu Lys Glu Lys Gly Gly
                 85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
            115                 120                 125
```

```
Pro Gly Pro Gly Val Arg Tyr Pro Leu Thr Phe Gly Trp Cys Tyr Lys
    130                 135                 140
Leu Val Pro Val Glu Pro Asp Lys Val Glu Glu Ala Asn Lys Gly Glu
145                 150                 155                 160
Asn Thr Ser Leu Leu His Pro Val Ser Leu His Gly Met Asp Asp Pro
                165                 170                 175
Glu Arg Glu Val Leu Glu Trp Arg Phe Asp Ser Arg Leu Ala Phe His
            180                 185                 190
His Val Ala Arg Glu Leu His Pro Glu Tyr Phe Lys Asn Cys Thr Ser
        195                 200                 205
Glu Pro Val Asp Pro Arg Leu Glu Pro Trp Lys His Pro Gly Ser Gln
    210                 215                 220
Pro Lys Thr Ala Cys Thr Asn Cys Tyr Cys Lys Lys Cys Cys Phe His
225                 230                 235                 240
Cys Gln Val Cys Phe Ile Thr Ala Ala Leu Gly Ile Ser Tyr Gly Arg
                245                 250                 255
Lys Lys Arg Arg Gln Arg Arg Pro Pro Gln Gly Ser Gln Thr His
            260                 265                 270
Gln Val Ser Leu Ser Lys Gln Pro Thr Ser Gln Ser Lys Gly Glu Pro
        275                 280                 285
Thr Gly Pro Lys Glu
    290

<210> SEQ ID NO 53
<211> LENGTH: 690
<212> TYPE: DNA
<213> ORGANISM: Artificial Sequence
<220> FEATURE:
<223> OTHER INFORMATION: HIV-1 trNef-Tatm fusion

<400> SEQUENCE: 53
atggtgggtt ttccagtcac acctcaggta cctttaagac caatgactta caaggcagct     60
gtagatctta gccacttttt aaaagaaaag gggggactgg aagggctaat tcactcccaa    120
cgaagacaag atatccttga tctgtggatc taccacacac aaggctactt ccctgattgg    180
cagaactaca caccagggcc aggggtcaga tatccactga cctttggatg gtgctacaag    240
ctagtaccag ttgagccaga taaggtagaa gaggccaata aggagagaa caccagcttg    300 ttacaccctg tgagcctgca tggaatggat gaccctgaga gagaagtgtt agagtggagg    360
tttgacagcc gcctagcatt tcatcacgtg cccgagagc tgcatccgga gtacttcaag    420
aactgcacta gtgagccagt agatcctaga ctagagccct ggaagcatcc aggaagtcag    480
cctaaaactg cttgtaccaa ttgctattgt aaaaagtgtt gctttcattg ccaagtttgt    540
ttcataacag ctgccttagg catctcctat ggcaggaaga agcggagaca gcgacgaaga    600
cctcctcaag cagtcagact catcaagtt tctctatcaa agcaacccac ctcccaatcc    660 aaagggagc cgacaggccc gaaggaataa                                      690

<210> SEQ ID NO 54
<211> LENGTH: 229
<212> TYPE: PRT
<213> ORGANISM: Artificial Sequence
<220> FEATURE:
<223> OTHER INFORMATION: HIV-1 trNef-Tatm fusion

<400> SEQUENCE: 54

Met Val Gly Phe Pro Val Thr Pro Gln Val Pro Leu Arg Pro Met Thr
1               5                   10                  15
```

-continued

```
Tyr Lys Ala Ala Val Asp Leu Ser His Phe Leu Lys Glu Lys Gly Gly
            20                  25                  30

Leu Glu Gly Leu Ile His Ser Gln Arg Arg Gln Asp Ile Leu Asp Leu
        35                  40                  45

Trp Ile Tyr His Thr Gln Gly Tyr Phe Pro Asp Trp Gln Asn Tyr Thr
    50                  55                  60

Pro Gly Pro Gly Val Arg Tyr Pro Leu Thr Phe Gly Trp Cys Tyr Lys
65                  70                  75                  80

Leu Val Pro Val Glu Pro Asp Lys Val Glu Glu Ala Asn Lys Gly Glu
                85                  90                  95

Asn Thr Ser Leu Leu His Pro Val Ser Leu His Gly Met Asp Asp Pro
            100                 105                 110

Glu Arg Glu Val Leu Glu Trp Arg Phe Asp Ser Arg Leu Ala Phe His
        115                 120                 125

His Val Ala Arg Glu Leu His Pro Glu Tyr Phe Lys Asn Cys Thr Ser
    130                 135                 140

Glu Pro Val Asp Pro Arg Leu Glu Pro Trp Lys His Pro Gly Ser Gln
145                 150                 155                 160

Pro Lys Thr Ala Cys Thr Asn Cys Tyr Cys Lys Lys Cys Cys Phe His
                165                 170                 175

Cys Gln Val Cys Phe Ile Thr Ala Ala Leu Gly Ile Ser Tyr Gly Arg
            180                 185                 190

Lys Lys Arg Arg Gln Arg Arg Arg Pro Pro Gln Gly Ser Gln Thr His
        195                 200                 205

Gln Val Ser Leu Ser Lys Gln Pro Thr Ser Gln Ser Lys Gly Glu Pro
    210                 215                 220

Thr Gly Pro Lys Glu
225
```

<210> SEQ ID NO 55
<211> LENGTH: 1461
<212> TYPE: DNA
<213> ORGANISM: Artificial Sequence
<220> FEATURE:
<223> OTHER INFORMATION: HIV-1 ds-gp120c

<400> SEQUENCE: 55

```
atggccgagc agctgtgggt caccgtctac tacggcgtgc ctgtgtggaa ggaggccacg      60
accaccctct tctgcgcgag cgacgccaag gcctacgaca cggaagtgca taacgtgtgg     120
gcgacgcatg cttgcgtgcc tacggacccc aacccccagg aggtggtgct gggaaacgtg     180
accgagtact tcaacatgtg gaagaataac atggtggatc agatgcacga ggacatcatc     240
tctctgtggg accagtccct gaagccctgc gtgaagctga cgcctctctg cgtgacactg     300
gactgtgacg acgtcaacac caccaacagc actaccacca ccagcaacgg ctggaccgga     360
gagattcgga agggcgagat caagaactgc tccttcaata tcacgacctc gatcagagac     420
aaggtgcaga aggaatacgc gctgttttat aatctcgatg tggtccccat cgacgacgac     480
aatgccacca ccaagaacaa gacgacgcgt aatttcagac tcattcactg caacagcagc     540
gtcatgacgc aggcctgccc caaggtgtcc ttcgaaccaa tcccgatcca ttactgtgcc     600
cctgccggat tcgcgatcct caagtgtaac aacaagacct tcgacgggaa gggcctgtgc     660
accaacgtca gcacggtgca gtgcacccat ggcatccgcc ccgtcgtgag cacccagctg     720
ctgctgaacg ggtccctggc tgaggaggag gtggtgatcc ggtcggacaa cttcatggac     780
```

-continued

```
aacaccaaga caatcatcgt ccagctgaac gagtctgtgg cgattaactg tacccggcct    840
aacaacaaca cccgtaaggg catccacatc gggcctggac gggccttcta tgccgcccgc    900
aagatcatcg cgacatccg gcaggccat tgcaacctct cccgcgccca gtggaataac    960
accctgaagc agatcgtgat caagctgaga gagcactttg aaacaagac catcaagttc   1020 aatcagagtt ctggcggaga ccccgagatc gtgcggcact ccttcaactg cggggggcgag   1080 ttcttctact gcgatacgac acagctcttc aactccacct ggaacggcac cgagggcaac   1140
aacacagagg gaaactccac tatcaccctc ccttgccgca tcaagcagat catcaacatg   1200
tggcaggagt gggaaaggc catgtatgcc ccccccatcg ggggccagat ccgctgctcc   1260
tccaacatca ccggcctgct gctcaccaga gacgggggca ccgagggcaa cggcacggag   1320
aacgagacgg agatcttcag gcccggcggc ggcgacatga gggataactg gcggagcgag   1380
ctgtacaagt acaaggtggt gaaggtggag ccgctcggcg tggcccccac ccgggccaag   1440
cgccgcgtcg tgcagagatg a                                            1461
```

<210> SEQ ID NO 56
<211> LENGTH: 486
<212> TYPE: PRT
<213> ORGANISM: Artificial Sequence
<220> FEATURE:
<223> OTHER INFORMATION: HIV-1 ds-gp120c

<400> SEQUENCE: 56

```
Met Ala Glu Gln Leu Trp Val Thr Val Tyr Tyr Gly Val Pro Val Trp
 1               5                  10                  15

Lys Glu Ala Thr Thr Thr Leu Phe Cys Ala Ser Asp Ala Lys Ala Tyr
                20                  25                  30

Asp Thr Glu Val His Asn Val Trp Ala Thr His Ala Cys Val Pro Thr
            35                  40                  45

Asp Pro Asn Pro Gln Glu Val Val Leu Gly Asn Val Thr Glu Tyr Phe
        50                  55                  60

Asn Met Trp Lys Asn Asn Met Val Asp Gln Met His Glu Asp Ile Ile
65                  70                  75                  80

Ser Leu Trp Asp Gln Ser Leu Lys Pro Cys Val Lys Leu Thr Pro Leu
                85                  90                  95

Cys Val Thr Leu Asp Cys Asp Asp Val Asn Thr Thr Asn Ser Thr Thr
            100                 105                 110

Thr Thr Ser Asn Gly Trp Thr Gly Glu Ile Arg Lys Gly Glu Ile Lys
        115                 120                 125

Asn Cys Ser Phe Asn Ile Thr Thr Ser Ile Arg Asp Lys Val Gln Lys
    130                 135                 140

Glu Tyr Ala Leu Phe Tyr Asn Leu Asp Val Val Pro Ile Asp Asp Asp
145                 150                 155                 160

Asn Ala Thr Thr Lys Asn Lys Thr Arg Asn Phe Arg Leu Ile His
                165                 170                 175

Cys Asn Ser Ser Val Met Thr Gln Ala Cys Pro Lys Val Ser Phe Glu
            180                 185                 190

Pro Ile Pro Ile His Tyr Cys Ala Pro Ala Gly Phe Ala Ile Leu Lys
        195                 200                 205

Cys Asn Asn Lys Thr Phe Asp Gly Lys Gly Leu Cys Thr Asn Val Ser
    210                 215                 220

Thr Val Gln Cys Thr His Gly Ile Arg Pro Val Val Ser Thr Gln Leu
225                 230                 235                 240
```

-continued

```
Leu Leu Asn Gly Ser Leu Ala Glu Glu Glu Val Val Ile Arg Ser Asp
                245                 250                 255

Asn Phe Met Asp Asn Thr Lys Thr Ile Ile Val Gln Leu Asn Glu Ser
            260                 265                 270

Val Ala Ile Asn Cys Thr Arg Pro Asn Asn Asn Thr Arg Lys Gly Ile
        275                 280                 285

His Ile Gly Pro Gly Arg Ala Phe Tyr Ala Ala Arg Lys Ile Ile Gly
    290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
                325                 330                 335

Thr Ile Lys Phe Asn Gln Ser Ser Gly Gly Asp Pro Glu Ile Val Arg
            340                 345                 350

His Ser Phe Asn Cys Gly Gly Glu Phe Phe Tyr Cys Asp Thr Thr Gln
        355                 360                 365

Leu Phe Asn Ser Thr Trp Asn Gly Thr Glu Gly Asn Asn Thr Glu Gly
    370                 375                 380

Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
                405                 410                 415

Ile Arg Cys Ser Ser Asn Ile Thr Gly Leu Leu Leu Thr Arg Asp Gly
            420                 425                 430

Gly Thr Glu Gly Asn Gly Thr Glu Asn Glu Thr Glu Ile Phe Arg Pro
        435                 440                 445

Gly Gly Gly Asp Met Arg Asp Asn Trp Arg Ser Glu Leu Tyr Lys Tyr
    450                 455                 460

Lys Val Val Lys Val Glu Pro Leu Gly Val Ala Pro Thr Arg Ala Lys
465                 470                 475                 480

Arg Arg Val Val Gln Arg
                485
```

<210> SEQ ID NO 57
<211> LENGTH: 2340
<212> TYPE: DNA
<213> ORGANISM: Artificial Sequence
<220> FEATURE:
<223> OTHER INFORMATION: HIV-1 ds-gp120c'

<400> SEQUENCE: 57

```
atggccgagc agctgtgggt caccgtctac tacggcgtgc ctgtgtggaa ggaggccacg      60
accaccctct tctgcgcgag cgacgccaag gcctacgaca cggaagtgca taacgtgtgg     120
gcgacgcatg cttgcgtgcc tacggacccc aacccccagg aggtggtgct gggaaacgtg     180
accgagtact tcaacatgtg gaagaataac atggtggatc agatgcacga ggacatcatc     240
tctctgtggg accagtccct gaagccctgc gtgaagctga cgcctctctg cgtgacactg     300
gactgtgacg acgtcaacac caccaacagc actaccacca ccagcaacgg ctggaccgga     360
gagattcgga agggcgagat caagaactgc tccttcaata tcacgacctc gatcagagac     420
aaggtgcaga aggaatacgc gctgttttat aatctcgatg tggtccccat cgacgacgac     480
aatgccacca ccaagaacaa gacgacgcgt aatttcagac tcattcactg caacagcagc     540
gtcatgacgc aggcctgccc caaggtgtcc ttcgaaccaa tcccgatcca ttactgtgcc     600
cctgccggat tcgcgatcct caagtgtaac aacaagacct tcgacgggaa gggcctgtgc     660
```

```
accaacgtca gcacggtgca gtgcacccat ggcatccgcc ccgtcgtgag cacccagctg    720
ctgctgaacg ggtccctggc tgaggaggag gtggtgatcc ggtcggacaa cttcatggac    780
aacaccaaga caatcatcgt ccagctgaac gagtctgtgg cgattaactg tacccggcct    840
aacaacaaca cccgtaaggg catccacatc gggcctggac gggccttcta tgccgcccgc    900
aagatcatcg gcgacatccg gcaggccat  tgcaacctct cccgcgccca gtggaataac    960
accctgaagc agatcgtgat caagctgaga gagcactttg aaacaagac  catcaagttc   1020 aatcagagtt ctggcggaga ccccgagatc gtgcggcact ccttcaactg cggggcgag   1080 ttcttctact gcgatacgac acagctcttc aactccacct ggaacggcac cgagggcaac   1140
aacacagagg gaaactccac tatcaccctc ccttgccgca tcaagcagat catcaacatg   1200
tggcaggagg tgggaaaggc catgtatgcc ccccccatcg ggggccagat ccgctgctcc   1260
tccaacatca ccggcctgct gctcaccaga cgggggggca ccgagggcaa cggcacggag   1320
aacgagacgg agatcttcag gcccggcggc ggcgacatga gggataactg gcggagcgag   1380
ctgtacaagt acaaggtggt gaaggtggag ccgctcggcg tggcccccac ccgggccaag   1440
cgccgcgtcg tgcagagaat gggtggcaag tggtcaaaaa gtagtgtggt tggatggcct   1500
actgtaaggg aaagaatgag acgagctgag ccagcagcag atgggggtgg agcagcatct   1560
cgagacctgg aaaaacatgg agcaatcaca agtagcaata cagcagctac caatgctgct   1620
tgtgcctggc tagaagcaca agaggaggag gaggtggggtt ttccagtcac acctcaggta   1680
cctttaagac caatgactta caaggcagct gtagatctta gccacttttt aaaagaaaag   1740
gggggactgg aagggctaat tcactcccaa cgaagacaag atatccttga tctgtggatc   1800
taccacacac aaggctactt ccctgattgg cagaactaca caccagggcc aggggtcaga   1860
tatccactga cctttggatg gtgctacaag ctagtaccag ttgagccaga taaggtagaa   1920
gaggccaata aaggagagaa caccagcttg ttacaccctg tgagcctgca tggaatggat   1980
gaccctgaga gagaagtgtt agagtggagg tttgacagcc gcctagcatt tcatcacgtg   2040
gcccgagagc tgcatccgga gtacttcaag aactgcacta gtgagccagt agatcctaga   2100
ctagagccct ggaagcatcc aggaagtcag cctaaaactg cttgtaccaa ttgctattgt   2160
aaaaagtgtt gctttcattg ccaagtttgt ttcataacag ctgccttagg catctcctat   2220
ggcaggaaga agcggagaca gcgacgaaga cctcctcaag gcagtcagac tcatcaagtt   2280
tctctatcaa agcaacccac ctcccaatcc aaaggggagc cgacaggccc gaaggaataa   2340
```

<210> SEQ ID NO 58
<211> LENGTH: 779
<212> TYPE: PRT
<213> ORGANISM: Artificial Sequence
<220> FEATURE:
<223> OTHER INFORMATION: HIV-1 ds-gp120c'

<400> SEQUENCE: 58

```
Met Ala Glu Gln Leu Trp Val Thr Val Tyr Tyr Gly Val Pro Val Trp
 1               5                  10                  15

Lys Glu Ala Thr Thr Thr Leu Phe Cys Ala Ser Asp Ala Lys Ala Tyr
                20                  25                  30

Asp Thr Glu Val His Asn Val Trp Ala Thr His Ala Cys Val Pro Thr
            35                  40                  45

Asp Pro Asn Pro Gln Glu Val Val Leu Gly Asn Val Thr Glu Tyr Phe
        50                  55                  60
```

-continued

```
Asn Met Trp Lys Asn Asn Met Val Asp Gln Met His Glu Asp Ile Ile
 65                  70                  75                  80

Ser Leu Trp Asp Gln Ser Leu Lys Pro Cys Val Lys Leu Thr Pro Leu
                 85                  90                  95

Cys Val Thr Leu Asp Cys Asp Val Asn Thr Thr Asn Ser Thr Thr
            100                 105                 110

Thr Thr Ser Asn Gly Trp Thr Gly Glu Ile Arg Lys Gly Glu Ile Lys
            115                 120                 125

Asn Cys Ser Phe Asn Ile Thr Thr Ser Ile Arg Asp Lys Val Gln Lys
130                 135                 140

Glu Tyr Ala Leu Phe Tyr Asn Leu Asp Val Val Pro Ile Asp Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
            180                 185                 190

Pro Ile Pro Ile His Tyr Cys Ala Pro Ala Gly Phe Ala Ile Leu Lys
            195                 200                 205

Cys Asn Asn Lys Thr Phe Asp Gly Lys Gly Leu Cys Thr Asn Val Ser
210                 215                 220

Thr Val Gln Cys Thr His Gly Ile Arg Pro Val Val Ser Thr Gln Leu
225                 230                 235                 240

Leu Leu Asn Gly Ser Leu Ala Glu Glu Val Val Ile Arg Ser Asp
                245                 250                 255

Asn Phe Met Asp Asn Thr Lys Thr Ile Ile Val Gln Leu Asn Glu Ser
            260                 265                 270

Val Ala Ile Asn Cys Thr Arg Pro Asn Asn Asn Thr Arg Lys Gly Ile
            275                 280                 285

His Ile Gly Pro Gly Arg Ala Phe Tyr Ala Ala Arg Lys Ile Ile Gly
            290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
                325                 330                 335

Thr Ile Lys Phe Asn Gln Ser Ser Gly Gly Asp Pro Glu Ile Val Arg
            340                 345                 350

His Ser Phe Asn Cys Gly Gly Glu Phe Phe Tyr Cys Asp Thr Thr Gln
            355                 360                 365

Leu Phe Asn Ser Thr Trp Asn Gly Thr Glu Gly Asn Asn Thr Glu Gly
            370                 375                 380

Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
                405                 410                 415

Ile Arg Cys Ser Ser Asn Ile Thr Gly Leu Leu Leu Thr Arg Asp Gly
            420                 425                 430

Gly Thr Glu Gly Asn Gly Thr Glu Asn Glu Thr Glu Ile Phe Arg Pro
            435                 440                 445

Gly Gly Gly Asp Met Arg Asp Asn Trp Arg Ser Glu Leu Tyr Lys Tyr
            450                 455                 460

Lys Val Val Lys Val Glu Pro Leu Gly Val Ala Pro Thr Arg Ala Lys
465                 470                 475                 480

Arg Arg Val Val Gln Arg Met Gly Gly Lys Trp Ser Lys Ser Ser Val
```

-continued

```
                485                 490                 495

Val Gly Trp Pro Thr Val Arg Glu Arg Met Arg Arg Ala Glu Pro Ala
            500                 505                 510

Ala Asp Gly Val Gly Ala Ala Ser Arg Asp Leu Glu Lys His Gly Ala
        515                 520                 525

Ile Thr Ser Ser Asn Thr Ala Ala Thr Asn Ala Ala Cys Ala Trp Leu
    530                 535                 540

Glu Ala Gln Glu Glu Glu Glu Val Gly Phe Pro Val Thr Pro Gln Val
545                 550                 555                 560
Pro Leu Arg Pro Met Thr Tyr Lys Ala Ala Val Asp Leu Ser His Phe
                565                 570                 575
Leu Lys Glu Lys Gly Gly Leu Glu Gly Leu Ile His Ser Gln Arg Arg
            580                 585                 590

Gln Asp Ile Leu Asp Leu Trp Ile Tyr His Thr Gln Gly Tyr Phe Pro
        595                 600                 605

Asp Trp Gln Asn Tyr Thr Pro Gly Pro Gly Val Arg Tyr Pro Leu Thr
    610                 615                 620

Phe Gly Trp Cys Tyr Lys Leu Val Pro Val Glu Pro Asp Lys Val Glu
625                 630                 635                 640
Glu Ala Asn Lys Gly Glu Asn Thr Ser Leu Leu His Pro Val Ser Leu
                645                 650                 655
His Gly Met Asp Asp Pro Glu Arg Glu Val Leu Glu Trp Arg Phe Asp
            660                 665                 670

Ser Arg Leu Ala Phe His His Val Ala Arg Glu Leu His Pro Glu Tyr
        675                 680                 685

Phe Lys Asn Cys Thr Ser Glu Pro Val Asp Pro Arg Leu Glu Pro Trp
    690                 695                 700

Lys His Pro Gly Ser Gln Pro Lys Thr Ala Cys Thr Asn Cys Tyr Cys
705                 710                 715                 720
Lys Lys Cys Cys Phe His Cys Gln Val Cys Phe Ile Thr Ala Ala Leu
                725                 730                 735

Gly Ile Ser Tyr Gly Arg Lys Lys Arg Arg Gln Arg Arg Arg Pro Pro
            740                 745                 750

Gln Gly Ser Gln Thr His Gln Val Ser Leu Ser Lys Gln Pro Thr Ser
        755                 760                 765

Gln Ser Lys Gly Glu Pro Thr Gly Pro Lys Glu
    770                 775
```

<210> SEQ ID NO 59
<211> LENGTH: 2148
<212> TYPE: DNA
<213> ORGANISM: Artificial Sequence
<220> FEATURE:
<223> OTHER INFORMATION: HIV-1 ds-gp120c Nef-Tatm fusion

<400> SEQUENCE: 59

```
atggccgagc agctgtgggt caccgtctac tacggcgtgc ctgtgtggaa ggaggccacg      60
accaccctct tctgcgcgag cgacgccaag gcctacgaca cggaagtgca taacgtgtgg     120
gcgacgcatg cttgcgtgcc tacggacccc aacccccagg aggtggtgct gggaaacgtg     180
accgagtact tcaacatgtg gaagaataac atggtggatc agatgcacga ggacatcatc     240
tctctgtggg accagtccct gaagccctgc gtgaagctga cgcctctctg cgtgacactg     300
gactgtgacg acgtcaacac caccaacagc actaccacca ccagcaacgg ctggaccgga     360
gagattcgga agggcgagat caagaactgc tccttcaata tcacgacctc gatcagagac     420
```

-continued

```
aaggtgcaga aggaatacgc gctgttttat aatctcgatg tggtcoccat cgacgacgac    480
aatgccacca ccaagaacaa gacgacgcgt aatttcagac tcattcactg caacagcagc    540
gtcatgacgc aggcctgccc caaggtgtcc ttcgaaccaa tcccgatcca ttactgtgcc    600
cctgccggat tcgcgatcct caagtgtaac aacaagacct tcgacgggaa gggcctgtgc    660
accaacgtca gcacggtgca gtgcacccat ggcatccgcc ccgtcgtgag cacccagctg    720
ctgctgaacg gtccctggc tgaggaggag gtggtgatcc ggtcggacaa cttcatggac    780
aacaccaaga caatcatcgt ccagctgaac gagtctgtgg cgattaactg tacccggcct    840
aacaacaaca cccgtaaggg catccacatc gggcctggac gggccttcta tgccgcccgc    900
aagatcatcg gcgacatccg gcaggcccat tgcaacctct cccgcgccca gtggaataac    960
accctgaagc agatcgtgat caagctgaga gagcactttg aaacaagac catcaagttc    1020
aatcagagtt ctggcggaga ccccgagatc gtgcggcact ccttcaactg cggggggcgag    1080
ttcttctact gcgatacgac acagctcttc aactccacct ggaacggcac cgagggcaac    1140
aacacagagg gaaactccac tatcaccctc ccttgccgca tcaagcagat catcaacatg    1200
tggcaggagg tgggaaaggc catgtatgcc ccccccatcg ggggccagat ccgctgctcc    1260
tccaacatca ccggcctgct gctcaccaga gacgggggca ccgagggcaa cggcacggag    1320
aacgagacgg agatcttcag gcccggcggc ggcgacatga gggataactg gcggagcgag    1380
ctgtacaagt acaaggtggt gaaggtggag ccgtcggcg tggcccccac ccgggccaag    1440
cgccgcgtcg tgcagagaat ggtgggtttt ccagtcacac ctcaggtacc tttaagacca    1500
atgacttaca aggcagctgt agatcttagc cacttttaa agaaaaggg gggactggaa    1560
gggctaattc actcccaacg aagacaagat atccttgatc tgtggatcta ccacacacaa    1620
ggctacttcc ctgattggca gaactacaca ccagggccag gggtcagata tccactgacc    1680
tttggatggt gctacaagct agtaccagtt gagccagata aggtagaaga ggccaataaa    1740
ggagagaaca ccagcttgtt acaccctgtg agcctgcatg gaatggatga ccctgagaga    1800
gaagtgttag agtggaggtt tgacagccgc ctagcatttc atcacgtggc ccgagagctg    1860
catccggagt acttcaagaa ctgcactagt gagccagtag atcctagact agagccctgg    1920
aagcatccag gaagtcagcc taaaactgct tgtaccaatt gctattgtaa aaagtgttgc    1980
tttcattgcc aagtttgttt cataacagct gccttaggca tctcctatgg caggaagaag    2040
cggagacagc gacgaagacc tcctcaaggc agtcagactc atcaagtttc tctatcaaag    2100
caacccacct cccaatccaa agggagccg acaggcccga aggaataa                 2148
```

<210> SEQ ID NO 60
<211> LENGTH: 715
<212> TYPE: PRT
<213> ORGANISM: Artificial Sequence
<220> FEATURE:
<223> OTHER INFORMATION: HIV-1 ds-gp120c Nef-Tatm fusion

<400> SEQUENCE: 60

```
Met Ala Glu Gln Leu Trp Val Thr Val Tyr Tyr Gly Val Pro Val Trp
  1

```
                50                    55                    60
Asn Met Trp Lys Asn Asn Met Val Asp Gln Met His Glu Asp Ile Ile
 65                  70                  75                  80

Ser Leu Trp Asp Gln Ser Leu Lys Pro Cys Val Lys Leu Thr Pro Leu
                     85                  90                  95

Cys Val Thr Leu Asp Cys Asp Val Asn Thr Thr Asn Ser Thr Thr
                100                 105                 110

Thr Thr Ser Asn Gly Trp Thr Gly Glu Ile Arg Lys Gly Glu Ile Lys
                115                 120                 125

Asn Cys Ser Phe Asn Ile Thr Thr Ser Ile Arg Asp Lys Val Gln Lys
130                 135                 140

Glu Tyr Ala Leu Phe Tyr Asn Leu Asp Val Val Pro Ile Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
                180                 185                 190

Pro Ile Pro Ile His Tyr Cys Ala Pro Ala Gly Phe Ala Ile Leu Lys
                195                 200                 205

Cys Asn Asn Lys Thr Phe Asp Gly Lys Gly Leu Cys Thr Asn Val Ser
210                 215                 220

Thr Val Gln Cys Thr His Gly Ile Arg Pro Val Val Ser Thr Gln Leu
225                 230                 235                 240

Leu Leu Asn Gly Ser Leu Ala Glu Glu Val Val Ile Arg Ser Asp
                245                 250                 255

Asn Phe Met Asp Asn Thr Lys Thr Ile Ile Val Gln Leu Asn Glu Ser
                260                 265                 270

Val Ala Ile Asn Cys Thr Arg Pro Asn Asn Asn Thr Arg Lys Gly Ile
                275                 280                 285

His Ile Gly Pro Gly Arg Ala Phe Tyr Ala Ala Arg Lys Ile Ile Gly
                290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
                325                 330                 335

Thr Ile Lys Phe Asn Gln Ser Ser Gly Gly Asp Pro Glu Ile Val Arg
                340                 345                 350

His Ser Phe Asn Cys Gly Gly Glu Phe Phe Tyr Cys Asp Thr Thr Gln
                355                 360                 365

Leu Phe Asn Ser Thr Trp Asn Gly Thr Glu Gly Asn Asn Thr Glu Gly
                370                 375                 380

Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
                405                 410                 415

Ile Arg Cys Ser Ser Asn Ile Thr Gly Leu Leu Leu Thr Arg Asp Gly
                420                 425                 430

Gly Thr Glu Gly Asn Gly Thr Glu Asn Glu Thr Glu Ile Phe Arg Pro
                435                 440                 445

Gly Gly Gly Asp Met Arg Asp Asn Trp Arg Ser Glu Leu Tyr Lys Tyr
                450                 455                 460

Lys Val Val Lys Val Glu Pro Leu Gly Val Ala Pro Thr Arg Ala Lys
465                 470                 475                 480
```

-continued

```
Arg Arg Val Val Gln Arg Met Val Gly Phe Pro Val Thr Pro Gln Val
                485                 490                 495

Pro Leu Arg Pro Met Thr Tyr Lys Ala Ala Val Asp Leu Ser His Phe
            500                 505                 510

Leu Lys Glu Lys Gly Gly Leu Glu Gly Leu Ile His Ser Gln Arg Arg
        515                 520                 525

Gln Asp Ile Leu Asp Leu Trp Ile Tyr His Thr Gln Gly Tyr Phe Pro
    530                 535                 540

Asp Trp Gln Asn Tyr Thr Pro Gly Pro Gly Val Arg Tyr Pro Leu Thr
545                 550                 555                 560

Phe Gly Trp Cys Tyr Lys Leu Val Pro Val Glu Pro Asp Lys Val Glu
                565                 570                 575

Glu Ala Asn Lys Gly Glu Asn Thr Ser Leu Leu His Pro Val Ser Leu
            580                 585                 590

His Gly Met Asp Asp Pro Glu Arg Glu Val Leu Glu Trp Arg Phe Asp
        595                 600                 605

Ser Arg Leu Ala Phe His His Val Ala Arg Glu Leu His Pro Glu Tyr
    610                 615                 620

Phe Lys Asn Cys Thr Ser Glu Pro Val Asp Pro Arg Leu Glu Pro Trp
625                 630                 635                 640

Lys His Pro Gly Ser Gln Pro Lys Thr Ala Cys Thr Asn Cys Tyr Cys
                645                 650                 655

Lys Lys Cys Cys Phe His Cys Gln Val Cys Phe Ile Thr Ala Ala Leu
            660                 665                 670

Gly Ile Ser Tyr Gly Arg Lys Lys Arg Arg Gln Arg Arg Arg Pro Pro
        675                 680                 685

Gln Gly Ser Gln Thr His Gln Val Ser Leu Ser Lys Gln Pro Thr Ser
    690                 695                 700

Gln Ser Lys Gly Glu Pro Thr Gly Pro Lys Glu
705                 710                 715
```

<210> SEQ ID NO 61
<211> LENGTH: 1887
<212> TYPE: DNA
<213> ORGANISM: Artificial Sequence
<220> FEATURE:
<223> OTHER INFORMATION: HIV-1 ds-gp120c trNef fusion

<400> SEQUENCE: 61

```
atggccgagc agctgtgggt caccgtctac tacggcgtgc ctgtgtggaa ggaggccacg      60
accaccctct tctgcgcgag cgacgccaag gcctacgaca cggaagtgca taacgtgtgg     120
gcgacgcatg cttgcgtgcc tacggacccc aacccccagg aggtggtgct gggaaacgtg     180
accgagtact tcaacatgtg gaagaataac atggtggatc agatgcacga ggacatcatc     240
tctctgtggg accagtccct gaagccctgc gtgaagctga cgcctctctg cgtgacactg     300
gactgtgacg acgtcaacac caccaacagc actaccacca ccagcaacgg ctggaccgga     360
gagattcgga agggcgagat caagaactgc tccttcaata tcacgacctc gatcagagac     420
aaggtgcaga aggaatacgc gctgttttat aatctcgatg tggtccccat cgacgacgac     480
aatgccacca ccaagaacaa gacgacgcgt aatttcagac tcattcactg caacagcagc     540
gtcatgacgc aggcctgccc caaggtgtcc ttcgaaccaa tcccgatcca ttactgtgcc     600
cctgccggat tcgcgatcct caagtgtaac aacaagacct tcgacgggaa gggcctgtgc     660
accaacgtca gcacggtgca gtgcacccat ggcatccgcc ccgtcgtgag cacccagctg     720
```

```
ctgctgaacg gtcctggc tgaggaggag gtggtgatcc ggtcggacaa cttcatggac    780
aacaccaaga caatcatcgt ccagctgaac gagtctgtgg cgattaactg tacccggcct    840
aacaacaaca cccgtaaggg catccacatc gggcctggac gggccttcta tgccgcccgc    900
aagatcatcg gcgacatccg gcaggcccat tgcaacctct cccgcgccca gtggaataac    960
accctgaagc agatcgtgat caagctgaga gagcactttg aaacaagac catcaagttc   1020 aatcagagtt ctggcggaga ccccgagatc gtgcggcact ccttcaactg cggggcgag    1080 ttcttctact gcgatacgac acagctcttc aactccacct ggaacggcac cgagggcaac   1140
aacacagagg gaaactccac tatcaccctc ccttgccgca tcaagcagat catcaacatg   1200 tgcaggagg tgggaaaggc catgtatgcc cccccatcg ggggccagat ccgctgctcc    1260
tccaacatca ccggcctgct gctcaccaga gacgggggca ccgagggcaa cggcacggag   1320
aacgagacgg agatcttcag gcccggcggc ggcgacatga gggataactg gcggagcgag   1380
ctgtacaagt acaaggtggt gaaggtggag ccgctcggcg tggcccccac ccgggccaag   1440
cgccgcgtcg tgcagagaat ggtgggtttt ccagtcacac ctcaggtacc tttaagacca   1500
atgacttaca aggcagctgt agatcttagc cacttttaa aagaaaaggg gggactggaa    1560
gggctaattc actcccaacg aagacaagat atccttgatc tgtggatcta ccacacacaa   1620
ggctacttcc ctgattggca gaactacaca ccagggccag gggtcagata tccactgacc   1680
tttggatggt gctacaagct agtaccagtt gagccagata aggtagaaga ggccaataaa   1740
ggagagaaca ccagcttgtt acaccctgtg agcctgcatg gaatggatga ccctgagaga   1800
gaagtgttag agtggaggtt tgacagccgc ctagcatttc atcacgtggc ccgagagctg   1860
catccggagt acttcaagaa ctgctaa                                      1887
```

<210> SEQ ID NO 62
<211> LENGTH: 628
<212> TYPE: PRT
<213> ORGANISM: Artificial Sequence
<220> FEATURE:
<223> OTHER INFORMATION: HIV-1 ds-gp120c trNef fusion

<400> SEQUENCE: 62

```
Met Ala Glu Gln Leu Trp Val Thr Val Tyr Tyr Gly Val Pro Val Trp
 1               5                  10                  15

Lys Glu Ala Thr Thr Thr Leu Phe Cys Ala Ser Asp Ala Lys Ala Tyr
            20                  25                  30

Asp Thr Glu Val His Asn Val Trp Ala Thr His Ala Cys Val Pro Thr
        35                  40                  45

Asp Pro Asn Pro Gln Glu Val Val Leu Gly Asn Val Thr Glu T

-continued

```
                145                 150                 155                 160
Asn Ala Thr Thr Lys Asn Lys Thr Thr Arg Asn Phe Arg Leu Ile His
                    165                 170                 175
Cys Asn Ser Ser Val Met Thr Gln Ala Cys Pro Lys Val Ser Phe Glu
                180                 185                 190
Pro Ile Pro Ile His Tyr Cys Ala Pro Ala Gly Phe Ala Ile Leu Lys
            195                 200                 205
Cys Asn Asn Lys Thr Phe Asp Gly Lys Gly Leu Cys Thr Asn Val Ser
210                 215                 220
Thr Val Gln Cys Thr His Gly Ile Arg Pro Val Val Ser Thr Gln Leu
225                 230                 235                 240
Leu Leu Asn Gly Ser Leu Ala Glu Glu Val Val Ile Arg Ser Asp
                    245                 250                 255
Asn Phe Met Asp Asn Thr Lys Thr Ile Ile Val Gln Leu Asn Glu Ser
                260                 265                 270
Val Ala Ile Asn Cys Thr Arg Pro Asn Asn Asn Thr Arg Lys Gly Ile
            275                 280                 285
His Ile Gly Pro Gly Arg Ala Phe Tyr Ala Ala Arg Lys Ile Ile Gly
        290                 295                 300
Asp Ile Arg Gln Ala His Cys Asn Leu Ser Arg Ala Gln Trp Asn Asn
305                 310                 315                 320
Thr Leu Lys Gln Ile Val Ile Lys Leu Arg Glu His Phe Gly Asn Lys
                    325                 330                 335
Thr Ile Lys Phe Asn Gln Ser Ser Gly Gly Asp Pro Glu Ile Val Arg
                340                 345                 350
His Ser Phe Asn Cys Gly Gly Glu Phe Phe Tyr Cys Asp Thr Thr Gln
            355                 360                 365
Leu Phe Asn Ser Thr Trp Asn Gly Thr Glu Gly Asn Asn Thr Glu Gly
        370                 375                 380
Asn Ser Thr Ile Thr Leu Pro Cys Arg Ile Lys Gln Ile Ile Asn Met
385                 390                 395                 400
Trp Gln Glu Val Gly Lys Ala Met Tyr Ala Pro Pro Ile Gly Gly Gln
                    405                 410                 415
Ile Arg Cys Ser Ser Asn Ile Thr Gly Leu Leu Leu Thr Arg Asp Gly
                420                 425                 430
Gly Thr Glu Gly Asn Gly Thr Glu Asn Glu Thr Glu Ile Phe Arg Pro
            435                 440                 445
Gly Gly Gly Asp Met Arg Asp Asn Trp Arg Ser Glu Leu Tyr Lys Tyr
        450                 455                 460
Lys Val Val Lys Val Glu Pro Leu Gly Val Ala Pro Thr Arg Ala Lys
465                 470                 475                 480
Arg Arg Val Val Gln Arg Met Val Gly Phe Pro Val Thr Pro Gln Val
                    485                 490                 495
Pro Leu Arg Pro Met Thr Tyr Lys Ala Ala Val Asp Leu Ser His Phe
                500                 505                 510
Leu Lys Glu Lys Gly Gly Leu Glu Gly Leu Ile His Ser Gln Arg Arg
            515                 520                 525
Gln Asp Ile Leu Asp Leu Trp Ile Tyr His Thr Gln Gly Tyr Phe Pro
        530                 535                 540
Asp Trp Gln Asn Tyr Thr Pro Gly Pro Gly Val Arg Tyr Pro Leu Thr
545                 550                 555                 560
Phe Gly Trp Cys Tyr Lys Leu Val Pro Val Glu Pro Asp Lys Val Glu
                    565                 570                 575
```

```
Glu Ala Asn Lys Gly Glu Asn Thr Ser Leu Leu His Pro Val Ser Leu
                580                 585                 590

His Gly Met Asp Asp Pro Glu Arg Glu Val Leu Glu Trp Arg Phe Asp
        595                 600                 605

Ser Arg Leu Ala Phe His His Val Ala Arg Glu Leu His Pro Glu Tyr
    610                 615                 620

Phe Lys Asn Cys
625

<210> SEQ ID NO 63
<211> LENGTH: 1517
<212> TYPE: DNA
<213> ORGANISM: Artificial Sequence
<220> FEATURE:
<223> OTHER INFORMATION: HIV-1 Nef p17/24 fusion

<400> SEQUENCE: 63
tgggtgcccg agcttcggta ctgtctggtg gagagctgga cagatgggag aaaattaggc      60
tgcgcccggg aggcaaaaag aaatacaagc tcaagcatat cgtgtgggcc tcgagggagc     120
ttgaacggtt tgccgtgaac ccaggcctgc tggaaacatc tgagggatgt cgccagatcc     180
tggggcaatt gcagccatcc ctccagaccg ggagtgaaga gctgaggtcc ttgtataaca     240
cagtggctac cctctactgc gtacaccaga ggatcgagat taaggatacc aaggaggcct     300
tggacaaaat tgaggaggag caaaacaaga gcaagaagaa ggcccagcag gcagctgctg     360
acactgggca tagcaaccag gtatcacaga actatcctat tgtccaaaac attcagggcc     420
agatggttca tcaggccatc agcccccgga cgctcaatgc ctgggtgaag gttgtcgaag     480
agaaggcctt ttctcctgag gttatcccca tgttctccgc tttgagtgag gggccactc      540 ctcaggacct caatacaatg cttaataccg tgggcggcca tcaggccgcc atgcaaatgt     600
tgaaggagac tatcaacgag gaggcagccg agtgggacag tgcatcccc gtccacgctg      660 gcccaatcgc gcccggacag atgcgggagc ctcgcggctc tgacattgcc ggcaccacct     720
ctacactgca agagcaaatc ggatggatga ccaacaatcc tcccatccca gttggagaaa     780
tctataaacg gtggatcatt ctcggtctca ataaaattgt tagaatgtac tctccgacat     840
ccatccttga cattagacag ggacccaaag agccttttag ggattacgtc gaccggtttt     900
ataagaccct gcgagcagag caggcctctc aggaggtcaa aaactggatg acggagacac     960
tcctggtaca gaacgctaac cccgactgca aacaatcttg aaggcactaa ggcccggctg    1020
ccaccctgga agagatgatg accgcctgtc agggagtagg cggacccgga cacaaagcca    1080
gagtgttgat ggtgggtttt ccagtcacac tcaggtacc tttaagacca atgacttaca     1140
aggcagctgt agatcttagc cacttttta aagaaaaggg gggactggaa gggctaattc     1200
actcccaaag aagacaagat atccttgatc tgtggatcta ccacacacaa ggctacttcc    1260
ctgattggca gaactacaca ccagggccag gggtcagata tccactgacc tttggatggt    1320
gctacaagct agtaccagtt gagccagata aggtagaaga ggccaataaa ggagagaaca    1380
ccagcttgtt acaccctgtg agcctgcatg ggatggatga cccggagaga gaagtgttag    1440
agtggaggtt tgacagccgc ctagcatttc atcacgtggc ccgagagctg catccggagt    1500
acttcaagaa ctgctga                                                  1517

<210> SEQ ID NO 64
<211> LENGTH: 2976
<212> TYPE: DNA
```

-continued

<213> ORGANISM: Artificial Sequence
<220> FEATURE:
<223> OTHER INFORMATION: HIV-1 ds-gp120c p17/24 trNef fusion

<400> SEQUENCE: 64

```
atggccgagc agctgtgggt caccgtctac tacggcgtgc ctgtgtggaa ggaggccacg 60
accaccctct tctgcgcgag cgacgccaag gcctacgaca cggaagtgca taacgtgtgg 120
gcgacgcatg cttgcgtgcc tacggacccc aacccccagg aggtggtgct gggaaacgtg 180
accgagtact tcaacatgtg gaagaataac atggtggatc agatgcacga ggacatcatc 240
tctctgtggg accagtccct gaagccctgc gtgaagctga cgcctctctg cgtgacactg 300
gactgtgacg acgtcaacac caccaacagc actaccacca ccagcaacgg ctggaccgga 360
gagattcgga agggcgagat caagaactgc tccttcaata tcacgacctc gatcagagac 420
aaggtgcaga aggaatacgc gctgttttat aatctcgatg tggtccccat cgacgacgac 480
aatgccacca ccaagaacaa gacgacgcgt aatttcagac tcattcactg caacagcagc 540
gtcatgacgc aggcctgccc caaggtgtcc ttcgaaccaa tcccgatcca ttactgtgcc 600
cctgccggat tcgcgatcct caagtgtaac aacaagacct tcgacgggaa gggcctgtgc 660
accaacgtca gcacggtgca gtgcacccat ggcatccgcc ccgtcgtgag cacccagctg 720
ctgctgaacg ggtccctggc tgaggaggag gtggtgatcc ggtcggacaa cttcatggac 780
aacaccaaga caatcatcgt ccagctgaac gagtctgtgg cgattaactg tacccggcct 840
aacaacaaca cccgtaaggg catccacatc gggcctggac gggccttcta tgccgcccgc 900
aagatcatcg gcgacatccg gcaggcccat tgcaacctct cccgcgccca gtggaataac 960
accctgaagc agatcgtgat caagctgaga gagcactttg gaaacaagac catcaagttc 1020
aatcagagtt ctggcggaga ccccgagatc gtgcggcact ccttcaactg cgggggcgag 1080
ttcttctact gcgatacgac acagctcttc aactccacct ggaacggcac cgagggcaac 1140
aacacagagg gaaactccac tatcaccctc ccttgccgca tcaagcagat catcaacatg 1200
tggcaggagg tgggaaaggc catgtatgcc ccccccatcg gggccagat ccgctgctcc 1260
tccaacatca ccggcctgct gctcaccaga gacgggggca ccgagggcaa cggcacggag 1320
aacgagacgg agatcttcag gcccggcggc ggcgacatga gggataactg gcggagcgag 1380
ctgtacaagt acaaggtggt gaaggtggag ccgctcggcg tggcccccac ccgggccaag 1440
cgccgcgtcg tgcagagaat gggtgcccga gcttcggtac tgtctggtgg agagctggac 1500
agatgggaga aaattaggct gcgcccggga ggcaaaaaga aatacaagct caagcatatc 1560
gtgtgggcct cgagggagct tgaacggttt gccgtgaacc caggcctgct ggaaacatct 1620
gagggatgtc gccagatcct ggggcaattg cagccatccc tccagaccgg gagtgaagag 1680
ctgaggtcct tgtataacac agtggctacc ctctactgcg tacaccagag gatcgagatt 1740
aaggatacca aggaggcctt ggacaaaatt gaggaggagc aaaacaagag caagaagaag 1800
gcccagcagg cagctgctga cactgggcat agcaaccagg tatcacagaa ctatcctatt 1860
gtccaaaaca ttcagggcca gatggttcat caggccatca gcccccggac gctcaatgcc 1920
tgggtgaagg ttgtcgaaga gaaggccttt tctcctgagg ttatccccat gttctccgct 1980
ttgagtgagg gggccactcc tcaggacctc aatacaatgc ttaataccgt gggcggccat 2040
caggccgcca tgcaaatgtt gaaggagact atcaacgagg aggcagccga gtgggacaga 2100
gtgcatcccg tccacgctgg cccaatcgcg cccggacaga tgcgggagcc tcgcggctct 2160
gacattgccg gcaccacctc tacactgcaa gagcaaatcg gatggatgac caacaatcct 2220
```

```
cccatcccag ttggagaaat ctataaacgg tggatcattc tcggtctcaa taaaattgtt      2280
agaatgtact ctccgacatc catccttgac attagacagg gacccaaaga gccttttagg      2340
gattacgtcg accggtttta taagaccctg cgagcagagc aggcctctca ggaggtcaaa      2400
aactggatga cggagacact cctggtacag aacgctaacc ccgactgcaa acaatcttg       2460 aaggcactag gccggctgc caccctggaa gagatgatga ccgcctgtca gggagtaggc       2520
ggacccggac acaaagccag agtgttgatg gtgggttttc cagtcacacc tcaggtacct      2580
ttaagaccaa tgacttacaa gcagctgta gatcttagcc acttttaaa agaaaagggg        2640 ggactggaag ggctaattca ctcccaacga agacaagata tccttgatct gtggatctac      2700
cacacacaag ctacttccc tgattggcag aactacacac cagggccagg ggtcagatat       2760
ccactgacct ttggatggtg ctacaagcta gtaccagttg agccagataa ggtagaagag      2820
gccaataaag gagagaacac cagcttgtta caccctgtga gcctgcatgg aatggatgac      2880
cctgagagag aagtgttaga gtggaggttt gacagccgcc tagcatttca tcacgtggcc      2940
cgagagctgc atccggagta cttcaagaac tgctaa                                2976

<210> SEQ ID NO 65
<211> LENGTH: 991
<212> TYPE: PRT
<213> ORGANISM: Artificial Sequence
<220> FEATURE:
<223> OTHER INFORMATION: HIV-1 ds-gp120c p17/24 trNef fusion

<400> SEQUENCE: 65

Met Ala Glu Gln Leu Trp Val Thr Val Tyr Tyr Gly Val Pro Val Trp
1               5                   10                  15

Lys Glu Ala Thr Thr Thr Leu Phe Cys Ala Ser Asp Ala Lys Ala Tyr
            20                  25                  30

Asp Thr Glu Val His Asn Val Trp Ala Thr His Ala Cys Val Pro Thr
        35                  40                  45

Asp Pro Asn Pro Gln Glu Val Val Leu Gly Asn Val Thr Glu Tyr Phe
    50                  55                  60

Asn Met Trp Lys Asn Asn Met Val Asp Gln Met His Glu Asp Ile Ile
65                  70                  75                  80

Ser Leu Trp Asp Gln Ser Leu Lys Pro Cys Val Lys Leu Thr Pro Leu
                85                  90                  95

Cys Val Thr Leu Asp Cys Asp Asp Val Asn Thr Thr Asn Ser Thr Thr
            100                 105                 110

Thr Thr Ser Asn Gly Trp Thr Gly Glu Ile Arg Lys Gly Glu Ile Lys
        115                 120                 125

Asn Cys Ser Phe Asn Ile Thr Thr Ser Ile Arg Asp Lys Val Gln Lys
    130                 135                 140

Glu Tyr Ala Leu Phe Tyr Asn Leu Asp Val Val Pro Ile Asp Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
            180                 185                 190

Pro Ile Pro Ile His Tyr Cys Ala Pro Ala Gly Phe Ala Ile Leu Lys
        195                 200                 205

Cys Asn Asn Lys Thr Phe Asp Gly Lys Gly Leu Cys Thr Asn Val Ser
    210                 215                 220
```

-continued

```
Thr Val Gln Cys Thr His Gly Ile Arg Pro Val Ser Thr Gln Leu
225                 230                 235                 240

Leu Leu Asn Gly Ser Leu Ala Glu Glu Val Val Ile Arg Ser Asp
            245                 250                 255

Asn Phe Met Asp Asn Thr Lys Thr Ile Ile Val Gln Leu Asn Glu Ser
        260                 265                 270

Val Ala Ile Asn Cys Thr Arg Pro Asn Asn Asn Thr Arg Lys Gly Ile
            275                 280                 285

His Ile Gly Pro Gly Arg Ala Phe Tyr Ala Ala Arg Lys Ile Ile Gly
        290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
            325                 330                 335

Thr Ile Lys Phe Asn Gln Ser Ser Gly Gly Asp Pro Glu Ile Val Arg
            340                 345                 350

His Ser Phe Asn Cys Gly Gly Glu Phe Phe Tyr Cys Asp Thr Thr Gln
        355                 360                 365

Leu Phe Asn Ser Thr Trp Asn Gly Thr Glu Gly Asn Asn Thr Glu Gly
    370                 375                 380

Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
            405                 410                 415

Ile Arg Cys Ser Ser Asn Ile Thr Gly Leu Leu Leu Thr Arg Asp Gly
            420                 425                 430

Gly Thr Glu Gly Asn Gly Thr Glu Asn Glu Thr Glu Ile Phe Arg Pro
        435                 440                 445

Gly Gly Gly Asp Met Arg Asp Asn Trp Arg Ser Glu Leu Tyr Lys Tyr
    450                 455                 460

Lys Val Val Lys Val Glu Pro Leu Gly Val Ala Pro Thr Arg Ala Lys
465                 470                 475                 480

Arg Arg Val Val Gln Arg Met Gly Ala Arg Ala Ser Val Leu Ser Gly
            485                 490                 495

Gly Glu Leu Asp Arg Trp Glu Lys Ile Arg Leu Arg Pro Gly Gly Lys
        500                 505                 510

Lys Lys Tyr Lys Leu Lys His Ile Val Trp Ala Ser Arg Glu Leu Glu
    515                 520                 525

Arg Phe Ala Val Asn Pro Gly Leu Leu Glu Thr Ser Glu Gly Cys Arg
530                 535                 540

Gln Ile Leu Gly Gln Leu Gln Pro Ser Leu Gln Thr Gly Ser Glu Glu
545                 550                 555                 560

Leu Arg Ser Leu Tyr Asn Thr Val Ala Thr Leu Tyr Cys Val His Gln
            565                 570                 575

Arg Ile Glu Ile Lys Asp Thr Lys Glu Ala Leu Asp Lys Ile Glu Glu
            580                 585                 590

Glu Gln Asn Lys Ser Lys Lys Ala Gln Gln Ala Ala Ala Asp Thr
        595                 600                 605

Gly His Ser Asn Gln Val Ser Gln Asn Tyr Pro Ile Val Gln Asn Ile
        610                 615                 620

Gln Gly Gln Met Val His Gln Ala Ile Ser Pro Arg Thr Leu Asn Ala
625                 630                 635                 640

Trp Val Lys Val Val Glu Glu Lys Ala Phe Ser Pro Glu Val Ile Pro
```

```
                    645                 650                 655
Met Phe Ser Ala Leu Ser Glu Gly Ala Thr Pro Gln Asp Leu Asn Thr
                660                 665                 670

Met Leu Asn Thr Val Gly Gly His Gln Ala Ala Met Gln Met Leu Lys
            675                 680                 685

Glu Thr Ile Asn Glu Glu Ala Ala Glu Trp Asp Arg Val His Pro Val
        690                 695                 700

His Ala Gly Pro Ile Ala Pro Gly Gln Met Arg Glu Pro Arg Gly Ser
705                 710                 715                 720

Asp Ile Ala Gly Thr Thr Ser Thr Leu Gln Glu Gln Ile Gly Trp Met
                725                 730                 735

Thr Asn Asn Pro Pro Ile Pro Val Gly Glu Ile Tyr Lys Arg Trp Ile
            740                 745                 750

Ile Leu Gly Leu Asn Lys Ile Val Arg Met Tyr Ser Pro Thr Ser Ile
        755                 760                 765

Leu Asp Ile Arg Gln Gly Pro Lys Glu Pro Phe Arg Asp Tyr Val Asp
770                 775                 780

Arg Phe Tyr Lys Thr Leu Arg Ala Glu Gln Ala Ser Gln Glu Val Lys
785                 790                 795                 800

Asn Trp Met Thr Glu Thr Leu Leu Val Gln Asn Ala Asn Pro Asp Cys
                805                 810                 815

Lys Thr Ile Leu Lys Ala Leu Gly Pro Ala Ala Thr Leu Glu Glu Met
            820                 825                 830

Met Thr Ala Cys Gln Gly Val Gly Gly Pro Gly His Lys Ala Arg Val
        835                 840                 845

Leu Met Val Gly Phe Pro Val Thr Pro Gln Val Pro Leu Arg Pro Met
850                 855                 860

Thr Tyr Lys Ala Ala Val Asp Leu Ser His Phe Leu Lys Glu Lys Gly
865                 870                 875                 880

Gly Leu Glu Gly Leu Ile His Ser Gln Arg Arg Gln Asp Ile Leu Asp
                885                 890                 895

Leu Trp Ile Tyr His Thr Gln Gly Tyr Phe Pro Asp Trp Gln Asn Tyr
            900                 905                 910

Thr Pro Gly Pro Gly Val Arg Tyr Pro Leu Thr Phe Gly Trp Cys Tyr
        915                 920                 925

Lys Leu Val Pro Val Glu Pro Asp Lys Val Glu Glu Ala Asn Lys Gly
930                 935                 940

Glu Asn Thr Ser Leu Leu His Pro Val Ser Leu His Gly Met Asp Asp
945                 950                 955                 960

Pro Glu Arg Glu Val Leu Glu Trp Arg Phe Asp Ser Arg Leu Ala Phe
                965                 970                 975

His His Val Ala Arg Glu Leu His Pro Glu Tyr Phe Lys Asn Cys
            980                 985                 990

<210> SEQ ID NO 66
<211> LENGTH: 3237
<212> TYPE: DNA
<213> ORGANISM: Artificial Sequence
<220> FEATURE:
<223> OTHER INFORMATION: HIV-1 ds-gp120c p17/24 trNef Tatm fusion

<400> SEQUENCE: 66
atggccgagc agctgtgggt caccgtctac tacggcgtgc ctgtgtggaa ggaggccacg      60
accaccctct tctgcgcgag cgacgccaag gcctacgaca cggaagtgca taacgtgtgg     120
```

```
gcgacgcatg cttgcgtgcc tacggacccc aaccccagg aggtggtgct gggaaacgtg      180
accgagtact tcaacatgtg aagaataac atggtggatc agatgcacga ggacatcatc      240
tctctgtggg accagtccct gaagccctgc gtgaagctga cgcctctctg cgtgacactg     300
gactgtgacg acgtcaacac caccaacagc actaccacca ccagcaacgg ctggaccgga    360
gagattcgga agggcgagat caagaactgc tccttcaata tcacgacctc gatcagagac    420
aaggtgcaga aggaatacgc gctgttttat aatctcgatg tggtccccat cgacgacgac    480
aatgccacca ccaagaacaa gacgacgcgt aatttcagac tcattcactg caacagcagc    540
gtcatgacgc aggcctgccc caaggtgtcc ttcgaaccaa tcccgatcca ttactgtgcc    600
cctgccggat cgcgatcct caagtgtaac aacaagacct cgacgggaa gggcctgtgc      660 accaacgtca gcacggtgca gtgcacccat ggcatccgcc ccgtcgtgag cacccagctg    720
ctgctgaacg ggtccctggc tgaggaggag gtggtgatcc ggtcggacaa cttcatggac    780
aacaccaaga caatcatcgt ccagctgaac gagtctgtgg cgattaactg tacccggcct    840
aacaacaaca cccgtaaggg catccacatc gggcctggac gggccttcta tgccgcccgc    900
aagatcatcg cgacatccg gcaggcccat tgcaacctct cccgcgccca gtggaataac    960
accctgaagc agatcgtgat caagctgaga gagcactttg aaacaagac catcaagttc     1020 aatcagagtt ctggcggaga ccccgagatc gtgcggcact ccttcaactg cggggggcgag  1080 ttcttctact gcgatacgac acagctcttc aactccacct ggaacggcac cgagggcaac   1140
aacacagagg gaaactccac tatcaccctc ccttgccgca tcaagcagat catcaacatg   1200
tggcaggagg tgggaaaggc catgtatgcc ccccccatcg ggggccagat ccgctgctcc   1260
tccaacatca ccggcctgct gctcaccaga gacgggggca ccgagggcaa cggcacggag   1320
aacgagacgg agatcttcag gcccggcggc ggcgacatga gggataactg gcggagcgag   1380
ctgtacaagt acaaggtggt gaaggtggag ccgctcggcg tggcccccac ccgggccaag   1440
cgccgcgtcg tgcagagaat gggtgcccga gcttcggtac tgtctggtgg agagctggac   1500
agatgggaga aaattaggct cgcccggga ggcaaaaaga aatacaagct caagcatatc    1560
gtgtgggcct cgagggagct tgaacggttt gccgtgaacc caggcctgct ggaaacatct   1620
gagggatgtc gccagatcct ggggcaattg cagccatccc tccagaccgg gagtgaagag   1680
ctgaggtcct tgtataacac agtggctacc ctctactgcg tacaccagag gatcgagatt    1740
aaggatacca aggaggcctt ggacaaaatt gaggaggagc aaaacaagag caagaagaag   1800
gcccagcagg cagctgctga cactgggcat agcaaccagg tatcacagaa ctatcctatt     1860
gtccaaaaca ttcagggcca gatggttcat caggccatca gccccggac gctcaatgcc    1920 tgggtgaagg ttgtcgaaga aaggcctttt tctcctgagg ttatcccat gttctccgct    1980 ttgagtgagg gggccactcc tcaggacctc aatacaatgc ttaataccgt gggcggccat   2040
caggccgcca tgcaaatgtt gaaggagact atcaacgagg aggcagccga gtgggacaga   2100
gtgcatcccg tccacgctgg cccaatcgcg cccggacaga tgcgggagcc tcgcggctct   2160
gacattgccg gcaccacctc tacactgcaa gagcaaatcg gatggatgac caacaatcct   2220
cccatcccag ttggagaaat ctataaacgg tggatcattc tcggtctcaa taaaattgtt    2280
agaatgtact ctccgacatc catccttgac attagacagg acccaaaga gccttttagg    2340 gattacgtcg accggtttta taagaccctg cgagcagagc aggcctctca ggaggtcaaa    2400
aactggatga cggagacact cctggtacag aacgctaacc ccgactgcaa acaatcttg    2460 aaggcactag gcccggctgc cacccctggaa gagatgatga ccgcctgtca gggagtaggc  2520
```

-continued

```
ggacccggac acaaagccag agtgttgatg gtgggttttc cagtcacacc tcaggtacct   2580
ttaagaccaa tgacttacaa ggcagctgta gatcttagcc acttttaaa agaaaagggg    2640 ggactggaag ggctaattca ctcccaacga agacaagata tccttgatct gtggatctac   2700
cacacacaag gctacttccc tgattggcag aactacacac cagggccagg gtcagatat    2760 ccactgacct ttggatggtg ctacaagcta gtaccagttg agccagataa ggtagaagag   2820
gccaataaag gagagaacac cagcttgtta caccctgtga gcctgcatgg aatggatgac   2880
cctgagagag aagtgttaga gtggaggttt gacagccgcc tagcatttca tcacgtggcc   2940
cgagagctgc atccggagta cttcaagaac tgcactagtg agccagtaga tcctagacta   3000
gagccctgga agcatccagg aagtcagcct aaaactgctt gtaccaattg ctattgtaaa   3060
aagtgttgct ttcattgcca gtttgtttc ataacagctg ccttaggcat ctcctatggc    3120
aggaagaagc ggagacagcg acgaagacct cctcaaggca gtcagactca tcaagtttct   3180
ctatcaaagc aacccacctc ccaatccaaa ggggagccga caggcccgaa ggaataa      3237
```

<210> SEQ ID NO 67
<211> LENGTH: 1078
<212> TYPE: PRT
<213> ORGANISM: Artificial Sequence
<220> FEATURE:
<223> OTHER INFORMATION: HIV-1 ds-gp120c p17/24 trNef Tatm fusion

<400> SEQUENCE: 67

```
Met Ala Glu Gln Leu Trp Val Thr Val Tyr Tyr Gly Val Pro Val Trp
 1               5                  10                  15

Lys Glu Ala Thr Thr Thr Leu Phe Cys Ala Ser Asp Ala Lys Ala Tyr
            20                  25                  30

Asp Thr Glu Val His Asn Val Trp Ala Thr His Ala Cys Val Pro Thr
        35                  40                  45

Asp Pro Asn Pro Gln Glu Val Val Leu Gly Asn Val Thr Glu Tyr Phe
    50                  55                  60

Asn Met Trp Lys Asn Asn Met Val Asp Gln Met His Glu Asp Ile Ile
65                  70                  75                  80

Ser Leu Trp Asp Gln Ser Leu Lys Pro Cys Val Lys Leu Thr Pro Leu
                85                  90                  95

Cys Val Thr Leu Asp Cys Asp Asp Val Asn Thr Thr Asn Ser Thr Thr
            100                 105                 110

Thr Thr Ser Asn Gly Trp Thr Gly Glu Ile Arg Lys Gly Glu Ile Lys
        115                 120                 125

Asn Cys Ser Phe Asn Ile Thr Thr Ser Ile Arg Asp Lys Val Gln Lys
    130                 135                 140

Glu Tyr Ala Leu Phe Tyr Asn Leu Asp Val Val Pro Ile Asp Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
            180                 185                 190

Pro Ile Pro Ile His Tyr Cys Ala Pro Ala Gly Phe Ala Ile Leu Lys
        195                 200                 205

Cys Asn Asn Lys Thr Phe Asp Gly Lys Gly Leu Cys Thr Asn Val Ser
    210                 215                 220

Thr Val Gln Cys Thr His Gly Ile Arg Pro Val Val Ser Thr Gln Leu
225                 230                 235                 240
```

```
Leu Leu Asn Gly Ser Leu Ala Glu Glu Val Val Ile Arg Ser Asp
                245                 250                 255

Asn Phe Met Asp Asn Thr Lys Thr Ile Ile Val Gln Leu Asn Glu Ser
            260                 265                 270

Val Ala Ile Asn Cys Thr Arg Pro Asn Asn Asn Thr Arg Lys Gly Ile
        275                 280                 285

His Ile Gly Pro Gly Arg Ala Phe Tyr Ala Ala Arg Lys Ile Ile Gly
    290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
                325                 330                 335

Thr Ile Lys Phe Asn Gln Ser Ser Gly Gly Asp Pro Glu Ile Val Arg
            340                 345                 350

His Ser Phe Asn Cys Gly Gly Glu Phe Phe Tyr Cys Asp Thr Thr Gln
        355                 360                 365

Leu Phe Asn Ser Thr Trp Asn Gly Thr Glu Gly Asn Asn Thr Glu Gly
    370                 375                 380

Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
                405                 410                 415

Ile Arg Cys Ser Ser Asn Ile Thr Gly Leu Leu Leu Thr Arg Asp Gly
            420                 425                 430

Gly Thr Glu Gly Asn Gly Thr Glu Asn Glu Thr Glu Ile Phe Arg Pro
        435                 440                 445

Gly Gly Gly Asp Met Arg Asp Asn Trp Arg Ser Glu Leu Tyr Lys Tyr
    450                 455                 460

Lys Val Val Lys Val Glu Pro Leu Gly Val Ala Pro Thr Arg Ala Lys
465                 470                 475                 480

Arg Arg Val Val Gln Arg Met Gly Ala Arg Ala Ser Val Leu Ser Gly
                485                 490                 495

Gly Glu Leu Asp Arg Trp Glu Lys Ile Arg Leu Arg Pro Gly Gly Lys
            500                 505                 510

Lys Lys Tyr Lys Leu Lys His Ile Val Trp Ala Ser Arg Glu Leu Glu
        515                 520                 525

Arg Phe Ala Val Asn Pro Gly Leu Leu Glu Thr Ser Glu Gly Cys Arg
    530                 535                 540

Gln Ile Leu Gly Gln Leu Gln Pro Ser Leu Gln Thr Gly Ser Glu Glu
545                 550                 555                 560

Leu Arg Ser Leu Tyr Asn Thr Val Ala Thr Leu Tyr Cys Val His Gln
                565                 570                 575

Arg Ile Glu Ile Lys Asp Thr Lys Glu Ala Leu Asp Lys Ile Glu Glu
            580                 585                 590

Glu Gln Asn Lys Ser Lys Lys Ala Gln Gln Ala Ala Ala Asp Thr
        595                 600                 605

Gly His Ser Asn Gln Val Ser Gln Asn Tyr Pro Ile Val Gln Asn Ile
    610                 615                 620

Gln Gly Gln Met Val His Gln Ala Ile Ser Pro Arg Thr Leu Asn Ala
625                 630                 635                 640

Trp Val Lys Val Val Glu Glu Lys Ala Phe Ser Pro Glu Val Ile Pro
                645                 650                 655
```

-continued

```
Met Phe Ser Ala Leu Ser Glu Gly Ala Thr Pro Gln Asp Leu Asn Thr
                660                 665                 670

Met Leu Asn Thr Val Gly Gly His Gln Ala Ala Met Gln Met Leu Lys
                675                 680                 685

Glu Thr Ile Asn Glu Glu Ala Ala Glu Trp Asp Arg Val His Pro Val
            690                 695                 700

His Ala Gly Pro Ile Ala Pro Gly Gln Met Arg Glu Pro Arg Gly Ser
705                 710                 715                 720

Asp Ile Ala Gly Thr Thr Ser Thr Leu Gln Glu Gln Ile Gly Trp Met
                725                 730                 735

Thr Asn Asn Pro Pro Ile Pro Val Gly Glu Ile Tyr Lys Arg Trp Ile
                740                 745                 750

Ile Leu Gly Leu Asn Lys Ile Val Arg Met Tyr Ser Pro Thr Ser Ile
                755                 760                 765

Leu Asp Ile Arg Gln Gly Pro Lys Glu Pro Phe Arg Asp Tyr Val Asp
                770                 775                 780

Arg Phe Tyr Lys Thr Leu Arg Ala Glu Gln Ala Ser Gln Glu Val Lys
785                 790                 795                 800

Asn Trp Met Thr Glu Thr Leu Leu Val Gln Asn Ala Asn Pro Asp Cys
                805                 810                 815

Lys Thr Ile Leu Lys Ala Leu Gly Pro Ala Ala Thr Leu Glu Glu Met
                820                 825                 830

Met Thr Ala Cys Gln Gly Val Gly Gly Pro Gly His Lys Ala Arg Val
                835                 840                 845

Leu Met Val Gly Phe Pro Val Thr Pro Gln Val Pro Leu Arg Pro Met
                850                 855                 860

Thr Tyr Lys Ala Ala Val Asp Leu Ser His Phe Leu Lys Glu Lys Gly
865                 870                 875                 880

Gly Leu Glu Gly Leu Ile His Ser Gln Arg Arg Gln Asp Ile Leu Asp
                885                 890                 895

Leu Trp Ile Tyr His Thr Gln Gly Tyr Phe Pro Asp Trp Gln Asn Tyr
                900                 905                 910

Thr Pro Gly Pro Gly Val Arg Tyr Pro Leu Thr Phe Gly Trp Cys Tyr
                915                 920                 925

Lys Leu Val Pro Val Glu Pro Asp Lys Val Glu Glu Ala Asn Lys Gly
                930                 935                 940

Glu Asn Thr Ser Leu Leu His Pro Val Ser Leu His Gly Met Asp Asp
945                 950                 955                 960

Pro Glu Arg Glu Val Leu Glu Trp Arg Phe Asp Ser Arg Leu Ala Phe
                965                 970                 975

His His Val Ala Arg Glu Leu His Pro Glu Tyr Phe Lys Asn Cys Thr
                980                 985                 990

Ser Glu Pro Val Asp Pro Arg Leu Glu Pro Trp Lys His Pro Gly Ser
            995                 1000                1005

Gln Pro Lys Thr Ala Cys Thr Asn Cys Tyr Cys Lys Lys Cys Cys Phe
        1010                1015                1020

His Cys Gln Val Cys Phe Ile Thr Ala Ala Leu Gly Ile Ser Tyr Gly
1025                1030                1035                1040

Arg Lys Lys Arg Arg Gln Arg Arg Pro Pro Gln Gly Ser Gln Thr
                1045                1050                1055

His Gln Val Ser Leu Ser Lys Gln Pro Thr Ser Gln Ser Lys Gly Glu
        1060                1065                1070

Pro Thr Gly Pro Lys Glu
```

<210> SEQ ID NO 68
<211> LENGTH: 3429
<212> TYPE: DNA
<213> ORGANISM: Artificial Sequence
<220> FEATURE:
<223> OTHER INFORMATION: HIV-1 ds-gp120c p17/24 Nef Tatm fusion

<400> SEQUENCE: 68

```
atggccgagc agctgtgggt caccgtctac tacggcgtgc ctgtgtggaa ggaggccacg      60
accaccctct tctgcgcgag cgacgccaag gcctacgaca cggaagtgca taacgtgtgg     120
gcgacgcatg cttgcgtgcc tacggacccc aaccccagg aggtggtgct gggaaacgtg      180
accgagtact tcaacatgtg gaagaataac atggtggatc agatgcacga ggacatcatc     240
tctctgtggg accagtccct gaagccctgc gtgaagctga cgcctctctg cgtgacactg     300
gactgtgacg acgtcaacac caccaacagc actaccacca ccagcaacgg ctggaccgga     360
gagattcgga agggcgagat caagaactgc tccttcaata tcacgacctc gatcagagac     420
aaggtgcaga aggaatacgc gctgttttat aatctcgatg tggtccccat cgacgacgac     480
aatgccacca ccaagaacaa gacgacgcgt aatttcagac tcattcactg caacagcagc     540
gtcatgacgc aggcctgccc caaggtgtcc ttcgaaccaa tcccgatcca ttactgtgcc     600
cctgccggat cgcgatcct caagtgtaac aacaagacct cgacgggaa gggcctgtgc      660
accaacgtca gcacggtgca gtgcacccat ggcatccgcc ccgtcgtgag cacccagctg     720
ctgctgaacg gtccctggc tgaggaggag gtggtgatcc ggtcggacaa cttcatggac      780
aacaccaaga caatcatcgt ccagctgaac gagtctgtgg cgattaactg tacccggcct     840
aacaacaaca cccgtaaggg catccacatc gggcctggac gggccttcta tgccgcccgc     900
aagatcatcg cgacatccg gcaggcccat tgcaacctct cccgcgccca gtggaataac     960
accctgaagc agatcgtgat caagctgaga gagcactttg aaacaagac catcaagttc    1020
aatcagagtt ctggcggaga ccccgagatc gtgcggcact ccttcaactg cggggggcgag 1080
ttcttctact gcgatacgac acagctcttc aactccacct ggaacggcac cgagggcaac    1140
aacacagagg gaaactccac tatcaccctc ccttgccgca tcaagcagat catcaacatg    1200
tggcaggagg tgggaaaggc catgtatgcc ccccccatcg ggggccagat ccgctgctcc    1260
tccaacatca ccggcctgct gctcaccaga cacgggggca ccgagggcaa cggcacggag    1320
aacgagacgg agatcttcag gcccggcggc ggcgacatga gggataactg gcggagcgag    1380
ctgtacaagt acaaggtggt gaaggtggag ccgctcggcg tggcccccac ccgggccaag    1440
cgccgcgtcg tgcagagaat gggtgcccga gcttcggtac tgtctggtgg agagctggac    1500
agatgggaga aaattaggct gcgcccggga ggcaaaaaga atacaagct caagcatatc    1560
gtgtgggcct cgagggagct tgaacggttt gccgtgaacc caggcctgct ggaaacatct    1620
gagggatgtc gccagatcct ggggcaattg cagccatccc tccagaccgg gagtgaagag    1680
ctgaggtcct tgtataacac agtggctacc ctctactgcg tacaccagag gatcgagatt    1740
aaggatacca aggaggcctt ggacaaaatt gaggaggagc aaaacaagag caagaagaag    1800
gcccagcagc agctgctga cactgggcat agcaaccagg tatcacagaa ctatcctatt    1860
gtccaaaaca ttcagggcca gatggttcat caggccatca gccccggac gctcaatgcc    1920
tgggtgaagg ttgtcgaaga aaggcctttt tctcctgagg ttatcccat gttctccgct    1980
ttgagtgagg gggccactcc tcaggacctc aatacaatgc ttaataccgt gggcggccat    2040
```

-continued

```
caggccgcca tgcaaatgtt gaaggagact atcaacgagg aggcagccga gtgggacaga   2100
gtgcatcccg tccacgctgg cccaatcgcg cccggacaga tgcgggagcc tcgcggctct   2160
gacattgccg gcaccacctc tacactgcaa gagcaaatcg gatggatgac caacaatcct   2220
cccatcccag ttggagaaat ctataaacgg tggatcattc tcggtctcaa taaaattgtt   2280
agaatgtact ctccgacatc catccttgac attagacagg gacccaaaga gccttttagg   2340
gattacgtcg accggtttta taagaccctg cgagcagagc aggcctctca ggaggtcaaa   2400
aactggatga cggagacact cctggtacag aacgctaacc ccgactgcaa aacaatcttg   2460
aaggcactag gcccggctgc caccctggaa gagatgatga ccgcctgtca gggagtaggc   2520
ggacccggac acaaagccag agtgttgatg ggtggcaagt ggtcaaaaag tagtgtggtt   2580
ggatggccta ctgtaaggga aagaatgaga cgagctgagc cagcagcaga tggggtggga   2640
gcagcatctc gagacctgga aaaacatgga gcaatcacaa gtagcaatac agcagctacc   2700
aatgctgctt gtgcctggct agaagcacaa gaggaggagg aggtgggttt tccagtcaca   2760
cctcaggtac ctttaagacc aatgacttac aaggcagctg tagatcttag ccactttta    2820
aaagaaaagg ggggactgga agggctaatt cactcccaac gaagacaaga tatccttgat   2880
ctgtggatct accacacaca aggctacttc cctgattggc agaactacac accagggcca   2940
ggggtcagat atccactgac ctttggatgg tgctacaagc tagtaccagt tgagccagat   3000
aaggtagaag aggccaataa aggagagaac accagcttgt tacaccctgt gagcctgcat   3060
ggaatggatg accctgagag agaagtgtta gagtggaggt ttgacagccg cctagcattt   3120
catcacgtgg cccgagagct gcatccggag tacttcaaga actgcactag tgagccagta   3180
gatcctagac tagagccctg gaagcatcca ggaagtcagc ctaaaactgc ttgtaccaat   3240
tgctattgta aaaagtgttg ctttcattgc caagtttgtt tcataacagc tgccttaggc   3300
atctcctatg gcaggaagaa gcggagacag cgacgaagac ctcctcaagg cagtcagact   3360
catcaagttt ctctatcaaa gcaacccacc tcccaatcca aaggggagcc gacaggcccg   3420
aaggaataa                                                            3429
```

```

<210> SEQ ID NO 69
<211> LENGTH: 1142
<212> TYPE: PRT
<213> ORGANISM: Artificial Sequence
<220> FEATURE:
<223> OTHER INFORMATION: HIV-1 ds-gp120c p17/24 Nef Tatm fusion

<400> SEQUENCE: 69

Met Ala Glu Gln Leu Trp Val Thr Val Tyr Tyr Gly Val Pro Val Trp
 1               5                  10                  15

Lys Glu Ala Thr Thr Thr Leu Phe Cys Ala Ser Asp Ala Lys Ala Tyr
            20                  25                  30

Asp Thr Glu Val His Asn Val Trp Ala Thr His Ala Cys Val Pro Thr
        35                  40                  45

Asp Pro Asn Pro Gln Glu Val Val Leu Gly Asn Val Thr Glu Tyr Phe
    50                  55                  60

Asn Met Trp Lys Asn Asn Met Val Asp Gln Met His Glu Asp Ile Ile
65                  70                  75                  80

Ser Leu Trp Asp Gln Ser Leu Lys Pro Cys Val Lys Leu Thr Pro Leu
                85                  90                  95

Cys Val Thr Leu Asp Cys Asp Asp Val Asn Thr Thr Asn Ser Thr Thr
            100                 105                 110
```

```
Thr Thr Ser Asn Gly Trp Thr Gly Glu Ile Arg Lys Gly Glu Ile Lys
        115                 120                 125

Asn Cys Ser Phe Asn Ile Thr Thr Ser Ile Arg Asp Lys Val Gln Lys
130                 135                 140

Glu Tyr Ala Leu Phe Tyr Asn Leu Asp Val Val Pro Ile Asp Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
                180                 185                 190

Pro Ile Pro Ile His Tyr Cys Ala Pro Ala Gly Phe Ala Ile Leu Lys
            195                 200                 205

Cys Asn Asn Lys Thr Phe Asp Gly Lys Gly Leu Cys Thr Asn Val Ser
            210                 215                 220

Thr Val Gln Cys Thr His Gly Ile Arg Pro Val Val Ser Thr Gln Leu
225                 230                 235                 240

Leu Leu Asn Gly Ser Leu Ala Glu Glu Val Val Ile Arg Ser Asp
                245                 250                 255

Asn Phe Met Asp Asn Thr Lys Thr Ile Ile Val Gln Leu Asn Glu Ser
                260                 265                 270

Val Ala Ile Asn Cys Thr Arg Pro Asn Asn Thr Arg Lys Gly Ile
            275                 280                 285

His Ile Gly Pro Gly Arg Ala Phe Tyr Ala Ala Arg Lys Ile Ile Gly
            290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
                325                 330                 335

Thr Ile Lys Phe Asn Gln Ser Ser Gly Gly Asp Pro Glu Ile Val Arg
                340                 345                 350

His Ser Phe Asn Cys Gly Gly Glu Phe Phe Tyr Cys Asp Thr Thr Gln
            355                 360                 365

Leu Phe Asn Ser Thr Trp Asn Gly Thr Glu Gly Asn Asn Thr Glu Gly
            370                 375                 380

Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
                405                 410                 415

Ile Arg Cys Ser Ser Asn Ile Thr Gly Leu Leu Leu Thr Arg Asp Gly
            420                 425                 430

Gly Thr Glu Gly Asn Gly Thr Glu Asn Glu Thr Glu Ile Phe Arg Pro
            435                 440                 445

Gly Gly Gly Asp Met Arg Asp Asn Trp Arg Ser Glu Leu Tyr Lys Tyr
            450                 455                 460

Lys Val Val Lys Val Glu Pro Leu Gly Val Ala Pro Thr Arg Ala Lys
465                 470                 475                 480

Arg Arg Val Val Gln Arg Met Gly Ala Arg Ala Ser Val Leu Ser Gly
                485                 490                 495

Gly Glu Leu Asp Arg Trp Glu Lys Ile Arg Leu Arg Pro Gly Gly Lys
                500                 505                 510

Lys Lys Tyr Lys Leu Lys His Ile Val Trp Ala Ser Arg Glu Leu Glu
            515                 520                 525
```

-continued

```
Arg Phe Ala Val Asn Pro Gly Leu Leu Glu Thr Ser Glu Gly Cys Arg
    530                 535                 540
Gln Ile Leu Gly Gln Leu Gln Pro Ser Leu Gln Thr Gly Ser Glu Glu
545                 550                 555                 560
Leu Arg Ser Leu Tyr Asn Thr Val Ala Thr Leu Tyr Cys Val His Gln
                565                 570                 575
Arg Ile Glu Ile Lys Asp Thr Lys Glu Ala Leu Asp Lys Ile Glu Glu
            580                 585                 590
Glu Gln Asn Lys Ser Lys Lys Ala Gln Gln Ala Ala Ala Asp Thr
        595                 600                 605
Gly His Ser Asn Gln Val Ser Gln Asn Tyr Pro Ile Val Gln Asn Ile
    610                 615                 620
Gln Gly Gln Met Val His Gln Ala Ile Ser Pro Arg Thr Leu Asn Ala
625                 630                 635                 640
Trp Val Lys Val Val Glu Glu Lys Ala Phe Ser Pro Glu Val Ile Pro
                645                 650                 655
Met Phe Ser Ala Leu Ser Glu Gly Ala Thr Pro Gln Asp Leu Asn Thr
            660                 665                 670
Met Leu Asn Thr Val Gly Gly His Gln Ala Ala Met Gln Met Leu Lys
        675                 680                 685
Glu Thr Ile Asn Glu Glu Ala Ala Glu Trp Asp Arg Val His Pro Val
    690                 695                 700
His Ala Gly Pro Ile Ala Pro Gly Gln Met Arg Glu Pro Arg Gly Ser
705                 710                 715                 720
Asp Ile Ala Gly Thr Thr Ser Thr Leu Gln Glu Gln Ile Gly Trp Met
                725                 730                 735
Thr Asn Asn Pro Pro Ile Pro Val Gly Glu Ile Tyr Lys Arg Trp Ile
            740                 745                 750
Ile Leu Gly Leu Asn Lys Ile Val Arg Met Tyr Ser Pro Thr Ser Ile
        755                 760                 765
Leu Asp Ile Arg Gln Gly Pro Lys Glu Pro Phe Arg Asp Tyr Val Asp
    770                 775                 780
Arg Phe Tyr Lys Thr Leu Arg Ala Glu Gln Ala Ser Gln Glu Val Lys
785                 790                 795                 800
Asn Trp Met Thr Glu Thr Leu Leu Val Gln Asn Ala Asn Pro Asp Cys
                805                 810                 815
Lys Thr Ile Leu Lys Ala Leu Gly Pro Ala Ala Thr Leu Glu Glu Met
            820                 825                 830
Met Thr Ala Cys Gln Gly Val Gly Gly Pro Gly His Lys Ala Arg Val
        835                 840                 845
Leu Met Gly Gly Lys Trp Ser Lys Ser Ser Val Val Gly Trp Pro Thr
    850                 855                 860
Val Arg Glu Arg Met Arg Arg Ala Glu Pro Ala Ala Asp Gly Val Gly
865                 870                 875                 880
Ala Ala Ser Arg Asp Leu Glu Lys His Gly Ala Ile Thr Ser Ser Asn
                885                 890                 895
Thr Ala Ala Thr Asn Ala Ala Cys Ala Trp Leu Glu Ala Gln Glu Glu
            900                 905                 910
Glu Glu Val Gly Phe Pro Val Thr Pro Gln Val Pro Leu Arg Pro Met
        915                 920                 925
Thr Tyr Lys Ala Ala Val Asp Leu Ser His Phe Leu Lys Glu Lys Gly
    930                 935                 940
Gly Leu Glu Gly Leu Ile His Ser Gln Arg Arg Gln Asp Ile Leu Asp
```

-continued 945 950 955 960

Leu Trp Ile Tyr His Thr Gln Gly Tyr Phe Pro Asp Trp Gln Asn Tyr
965 970 975

Thr Pro Gly Pro Gly Val Arg Tyr Pro Leu Thr Phe Gly Trp Cys Tyr
980 985 990

Lys Leu Val Pro Val Glu Pro Asp Lys Val Glu Glu Ala Asn Lys Gly
995 1000 1005

Glu Asn Thr Ser Leu Leu His Pro Val Ser Leu His Gly Met Asp Asp
1010 1015 1020

Pro Glu Arg Glu Val Leu Glu Trp Arg Phe Asp Ser Arg Leu Ala Phe
1025 1030 1035 1040

His His Val Ala Arg Glu Leu His Pro Glu Tyr Phe Lys Asn Cys Thr
1045 1050 1055

Ser Glu Pro Val Asp Pro Arg Leu Glu Pro Trp Lys His Pro Gly Ser
1060 1065 1070

Gln Pro Lys Thr Ala Cys Thr Asn Cys Tyr Cys Lys Lys Cys Cys Phe
1075 1080 1085

His Cys Gln Val Cys Phe Ile Thr Ala Ala Leu Gly Ile Ser Tyr Gly
1090 1095 1100

Arg Lys Lys Arg Arg Gln Arg Arg Arg Pro Pro Gln Gly Ser Gln Thr
1105 1110 1115 1120

His Gln Val Ser Leu Ser Lys Gln Pro Thr Ser Gln Ser Lys Gly Glu
1125 1130 1135

Pro Thr Gly Pro Lys Glu
1140

<210> SEQ ID NO 70
<211> LENGTH: 3426
<212> TYPE: DNA
<213> ORGANISM: Artificial Sequence
<220> FEATURE:
<223> OTHER INFORMATION: HIV-1 ds-gp120c p17/24 mNef Tatm fusion

<400> SEQUENCE: 70
atggccgagc agctgtgggt caccgtctac tacggcgtgc ctgtgtggaa ggaggccacg 60
accaccctct tctgcgcgag cgacgccaag gcctacgaca cggaagtgca taacgtgtgg 120
gcgacgcatg cttgcgtgcc tacggacccc aacccccagg aggtggtgct gggaaacgtg 180
accgagtact tcaacatgtg gaagaataac atggtggatc agatgcacga ggacatcatc 240
tctctgtggg accagtccct gaagccctgc gtgaagctga cgcctctctg cgtgacactg 300
gactgtgacg acgtcaacac caccaacagc actaccacca ccagcaacgg ctggaccgga 360
gagattcgga agggcgagat caagaactgc tccttcaata tcacgacctc gatcagagac 420
aaggtgcaga aggaatacgc gctgttttat aatctcgatg tggtccccat cgacgacgac 480
aatgccacca ccaagaacaa gacgacgcgt aatttcagac tcattcactg caacagcagc 540
gtcatgacgc aggcctgccc caaggtgtcc ttcgaaccaa tcccgatcca ttactgtgcc 600
cctgccggat tcgcgatcct caagtgtaac aacaagacct tcgacgggaa gggcctgtgc 660
accaacgtca gcacggtgca gtgcacccat ggcatccgcc ccgtcgtgag cacccagctg 720
ctgctgaacg ggtccctggc tgaggaggag gtggtgatcc ggtcggacaa cttcatggac 780
aacaccaaga caatcatcgt ccagctgaac gagtctgtgg cgattaactg tacccggcct 840
aacaacaaca cccgtaaggg catccacatc gggcctggac gggccttcta tgccgcccgc 900
aagatcatcg gcgacatccg gcaggcccat tgcaacctct cccgcgccca gtggaataac 960

```
accctgaagc agatcgtgat caagctgaga gagcactttg gaaacaagac catcaagttc    1020
aatcagagtt ctggcggaga ccccgagatc gtgcggcact ccttcaactg cggggggcgag    1080 ttcttctact gcgatacgac acagctcttc aactccacct ggaacggcac cgagggcaac    1140
aacacagagg gaaactccac tatcaccctc ccttgccgca tcaagcagat catcaacatg    1200
tggcaggagg tgggaaaggc catgtatgcc cccccatcg ggggccagat ccgctgctcc    1260
tccaacatca ccggcctgct gctcaccaga gacggggca ccgagggcaa cggcacggag    1320
aacgagacgg agatcttcag gcccggcggc ggcgacatga gggataactg gcggagcgag    1380
ctgtacaagt acaaggtggt gaaggtggag ccgctcggcg tggcccccac ccgggccaag    1440
cgccgcgtcg tgcagagaat gggtgcccga gcttcggtac tgtctggtgg agagctggac    1500
agatgggaga aaattaggct gcgcccggga ggcaaaaaga aatacaagct caagcatatc    1560
gtgtgggcct cgagggagct tgaacggttt gccgtgaacc caggcctgct ggaaacatct    1620
gagggatgtc gccagatcct ggggcaattg cagccatccc tccagaccgg gagtgaagag    1680
ctgaggtcct tgtataacac agtggctacc ctctactgcg tacaccagag gatcgagatt    1740
aaggatacca aggaggcctt ggacaaaatt gaggaggagc aaaacaagag caagaagaag    1800
gcccagcagg cagctgctga cactgggcat agcaaccagg tatcacagaa ctatcctatt    1860
gtccaaaaca ttcagggcca gatggttcat caggccatca gcccccggac gctcaatgcc    1920
tgggtgaagg ttgtcgaaga aaggcctttt tctcctgagg ttatccccat gttctccgct    1980
ttgagtgagg gggccactcc tcaggacctc aatacaatgc ttaataccgt gggcggccat    2040
caggccgcca tgcaaatgtt gaaggagact atcaacgagg aggcagccga gtgggacaga    2100
gtgcatcccg tccacgctgg cccaatcgcg cccggacaga tgcgggagcc tcgcggctct    2160
gacattgccg gcaccacctc tacactgcaa gagcaaatcg gatggatgac caacaatcct    2220
cccatcccag ttggagaaat ctataaacgg tggatcattc tcggtctcaa taaaattgtt    2280
agaatgtact ctccgacatc catccttgac attagacagg gacccaaaga gccttttagg    2340
gattacgtcg accggtttta taagaccctg cgagcagagc aggcctctca ggaggtcaaa    2400
aactggatga cggagacact cctggtacag aacgctaacc ccgactgcaa aacaatcttg    2460
aaggcactag gccggctgc caccctggaa gagatgatga ccgcctgtca gggagtaggc    2520
ggacccggac acaaagccag agtgttgatg ggcaagtggt caaaaagtag tgtggttgga    2580
tggcctactg taagggaaag aatgagacga gctgagccag cagcagatgg ggtgggagca    2640
gcatctcgag acctggaaaa acatggagca atcacaagta gcaatacagc agctaccaat    2700
gctgcttgtg cctggctaga agcacaagag gaggaggagg tgggttttcc agtcacacct    2760
caggtacctt taagaccaat gacttacaag gcagctgtag atcttagcca ctttttaaaa    2820
gaaaaggggg gactggaagg gctaattcac tcccaacgaa gacaagatat ccttgatctg    2880
tggatctacc acacacaagg ctacttccct gattggcaga actacacacc agggccaggg    2940
gtcagatatc cactgacctt tggatggtgc tacaagctag taccagttga gccagataag    3000
gtagaagagg ccaataaagg agagaacacc agcttgttac accctgtgag cctgcatgga    3060
atggatgacc ctgagagaga agtgttagag tggaggtttg acagccgcct agcatttcat    3120
cacgtggccc gagagctgca tccggagtac ttcaagaact gcactagtga gccagtagat    3180
cctagactag agccctggaa gcatccagga agtcagccta aaactgcttg taccaattgc    3240
tattgtaaaa agtgttgctt tcattgccaa gtttgtttca taacagctgc cttaggcatc    3300
```

-continued

```
tcctatggca ggaagaagcg gagacagcga cgaagacctc ctcaaggcag tcagactcat    3360
caagtttctc tatcaaagca acccacctcc caatccaaag gggagccgac aggcccgaag    3420
gaataa                                                               3426
```

<210> SEQ ID NO 71
<211> LENGTH: 1141
<212> TYPE: PRT
<213> ORGANISM: Artificial Sequence
<220> FEATURE:
<223> OTHER INFORMATION: HIV-1 ds-gp120c p17/24 mNef Tatm fusion

<400> SEQUENCE: 71

```
Met Ala Glu Gln Leu Trp Val Thr Val Tyr Tyr Gly Val Pro Val Trp
 1               5                  10                  15

Lys Glu Ala Thr Thr Thr Leu Phe Cys Ala Ser Asp Ala Lys Ala Tyr
             20                  25                  30

Asp Thr Glu Val His Asn Val Trp Ala Thr His Ala Cys Val Pro Thr
         35                  40                  45

Asp Pro Asn Pro Gln Glu Val Val Leu Gly Asn Val Thr Glu Tyr Phe
     50                  55                  60

Asn Met Trp Lys Asn Asn Met Val Asp Gln Met His Glu Asp Ile Ile
 65                  70                  75                  80

Ser Leu Trp Asp Gln Ser Leu Lys Pro Cys Val Lys Leu Thr Pro Leu
                 85                  90                  95

Cys Val Thr Leu Asp Cys Asp Asp Val Asn Thr Thr Asn Ser Thr Thr
            100                 105                 110

Thr Thr Ser Asn Gly Trp Thr Gly Glu Ile Arg Lys Gly Glu Ile Lys
        115                 120                 125

Asn Cys Ser Phe Asn Ile Thr Thr Ser Ile Arg Asp Lys Val Gln Lys
    130                 135                 140

Glu Tyr Ala Leu Phe Tyr Asn Leu Asp Val Val Pro Ile Asp Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
            180                 185                 190

Pro Ile Pro Ile His Tyr Cys Ala Pro Ala Gly Phe Ala Ile Leu Lys
        195                 200                 205

Cys Asn Asn Lys Thr Phe Asp Gly Lys Gly Leu Cys Thr Asn Val Ser
    210                 215                 220

Thr Val Gln Cys Thr His Gly Ile Arg Pro Val Val Ser Thr Gln Leu
225                 230                 235                 240

Leu Leu Asn Gly Ser Leu Ala Glu Glu Val Val Ile Arg Ser Asp
                245                 250                 255

Asn Phe Met Asp Asn Thr Lys Thr Ile Ile Val Gln Leu Asn Glu Ser
            260                 265                 270

Val Ala Ile Asn Cys Thr Arg Pro Asn Asn Asn Thr Arg Lys Gly Ile
        275                 280                 285

His Ile Gly Pro Gly Arg Ala Phe Tyr Ala Ala Arg Lys Ile Ile Gly
    290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
                325                 330                 335
```

```
             -continued
Thr Ile Lys Phe Asn Gln Ser Ser Gly Gly Asp Pro Glu Ile Val Arg
            340                 345                 350

His Ser Phe Asn Cys Gly Gly Glu Phe Phe Tyr Cys Asp Thr Thr Gln
        355                 360                 365

Leu Phe Asn Ser Thr Trp Asn Gly Thr Glu Gly Asn Asn Thr Glu Gly
    370                 375                 380

Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
                405                 410                 415

Ile Arg Cys Ser Ser Asn Ile Thr Gly Leu Leu Leu Thr Arg Asp Gly
            420                 425                 430

Gly Thr Glu Gly Asn Gly Thr Glu Asn Glu Thr Glu Ile Phe Arg Pro
        435                 440                 445

Gly Gly Gly Asp Met Arg Asp Asn Trp Arg Ser Glu Leu Tyr Lys Tyr
    450                 455                 460

Lys Val Val Lys Val Glu Pro Leu Gly Val Ala Pro Thr Arg Ala Lys
465                 470                 475                 480

Arg Arg Val Val Gln Arg Met Gly Ala Arg Ala Ser Val Leu Ser Gly
                485                 490                 495

Gly Glu Leu Asp Arg Trp Glu Lys Ile Arg Leu Arg Pro Gly Gly Lys
            500                 505                 510

Lys Lys Tyr Lys Leu Lys His Ile Val Trp Ala Ser Arg Glu Leu Glu
        515                 520                 525

Arg Phe Ala Val Asn Pro Gly Leu Leu Glu Thr Ser Glu Gly Cys Arg
    530                 535                 540

Gln Ile Leu Gly Gln Leu Gln Pro Ser Leu Gln Thr Gly Ser Glu Glu
545                 550                 555                 560

Leu Arg Ser Leu Tyr Asn Thr Val Ala Thr Leu Tyr Cys Val His Gln
                565                 570                 575

Arg Ile Glu Ile Lys Asp Thr Lys Glu Ala Leu Asp Lys Ile Glu Glu
            580                 585                 590

Glu Gln Asn Lys Ser Lys Lys Lys Ala Gln Gln Ala Ala Ala Asp Thr
        595                 600                 605

Gly His Ser Asn Gln Val Ser Gln Asn Tyr Pro Ile Val Gln Asn Ile
    610                 615                 620

Gln Gly Gln Met Val His Gln Ala Ile Ser Pro Arg Thr Leu Asn Ala
625                 630                 635                 640

Trp Val Lys Val Val Glu Glu Lys Ala Phe Ser Pro Glu Val Ile Pro
                645                 650                 655

Met Phe Ser Ala Leu Ser Glu Gly Ala Thr Pro Gln Asp Leu Asn Thr
            660                 665                 670

Met Leu Asn Thr Val Gly Gly His Gln Ala Ala Met Gln Met Leu Lys
        675                 680                 685

Glu Thr Ile Asn Glu Glu Ala Ala Glu Trp Asp Arg Val His Pro Val
    690                 695                 700

His Ala Gly Pro Ile Ala Pro Gly Gln Met Arg Glu Pro Arg Gly Ser
705                 710                 715                 720

Asp Ile Ala Gly Thr Thr Ser Thr Leu Gln Glu Gln Ile Gly Trp Met
                725                 730                 735

Thr Asn Asn Pro Pro Ile Pro Val Gly Glu Ile Tyr Lys Arg Trp Ile
            740                 745                 750

Ile Leu Gly Leu Asn Lys Ile Val Arg Met Tyr Ser Pro Thr Ser Ile
```

```
                755                 760                 765
Leu Asp Ile Arg Gln Gly Pro Lys Glu Pro Phe Arg Asp Tyr Val Asp
770                 775                 780

Arg Phe Tyr Lys Thr Leu Arg Ala Glu Gln Ala Ser Gln Glu Val Lys
785                 790                 795                 800

Asn Trp Met Thr Glu Thr Leu Val Gln Asn Ala Asn Pro Asp Cys
                805                 810                 815

Lys Thr Ile Leu Lys Ala Leu Gly Pro Ala Ala Thr Leu Glu Glu Met
            820                 825                 830

Met Thr Ala Cys Gln Gly Val Gly Gly Pro Gly His Lys Ala Arg Val
                835                 840                 845

Leu Met Gly Lys Trp Ser Lys Ser Ser Val Val Gly Trp Pro Thr Val
850                 855                 860

Arg Glu Arg Met Arg Arg Ala Glu Pro Ala Ala Asp Gly Val Gly Ala
865                 870                 875                 880

Ala Ser Arg Asp Leu Glu Lys His Gly Ala Ile Thr Ser Ser Asn Thr
                885                 890                 895

Ala Ala Thr Asn Ala Ala Cys Ala Trp Leu Glu Ala Gln Glu Glu Glu
                900                 905                 910

Glu Val Gly Phe Pro Val Thr Pro Gln Val Pro Leu Arg Pro Met Thr
            915                 920                 925

Tyr Lys Ala Ala Val Asp Leu Ser His Phe Leu Lys Glu Lys Gly Gly
            930                 935                 940

Leu Glu Gly Leu Ile His Ser Gln Arg Arg Gln Asp Ile Leu Asp Leu
945                 950                 955                 960

Trp Ile Tyr His Thr Gln Gly Tyr Phe Pro Asp Trp Gln Asn Tyr Thr
                965                 970                 975

Pro Gly Pro Gly Val Arg Tyr Pro Leu Thr Phe Gly Trp Cys Tyr Lys
            980                 985                 990

Leu Val Pro Val Glu Pro Asp Lys Val Glu Glu Ala Asn Lys Gly Glu
            995                 1000                1005

Asn Thr Ser Leu Leu His Pro Val Ser Leu His Gly Met Asp Asp Pro
1010                1015                1020

Glu Arg Glu Val Leu Glu Trp Arg Phe Asp Ser Arg Leu Ala Phe His
1025                1030                1035                1040

His Val Ala Arg Glu Leu His Pro Glu Tyr Phe Lys Asn Cys Thr Ser
                1045                1050                1055

Glu Pro Val Asp Pro Arg Leu Glu Pro Trp Lys His Pro Gly Ser Gln
            1060                1065                1070

Pro Lys Thr Ala Cys Thr Asn Cys Tyr Cys Lys Lys Cys Cys Phe His
            1075                1080                1085

Cys Gln Val Cys Phe Ile Thr Ala Ala Leu Gly Ile Ser Tyr Gly Arg
            1090                1095                1100

Lys Lys Arg Arg Gln Arg Arg Arg Pro Pro Gln Gly Ser Gln Thr His
1105                1110                1115                1120

Gln Val Ser Leu Ser Lys Gln Pro Thr Ser Gln Ser Lys Gly Glu Pro
                1125                1130                1135

Thr Gly Pro Lys Glu
            1140

<210> SEQ ID NO 72
<211> LENGTH: 3429
<212> TYPE: DNA
<213> ORGANISM: Artificial Sequence
```

<220> FEATURE:
<223> OTHER INFORMATION: HIV-1 ds-gp120c p17/24 L1-Nef Tatm fusion

<400> SEQUENCE: 72

```
atggccgagc agctgtgggt caccgtctac tacggcgtgc ctgtgtggaa ggaggccacg     60
accaccctct tctgcgcgag cgacgccaag gcctacgaca cggaagtgca taacgtgtgg    120
gcgacgcatg cttgcgtgcc tacggacccc aacccccagg aggtggtgct gggaaacgtg    180
accgagtact tcaacatgtg gaagaataac atggtggatc agatgcacga ggacatcatc    240
tctctgtggg accagtccct gaagccctgc gtgaagctga cgcctctctg cgtgacactg    300
gactgtgacg acgtcaacac caccaacagc actaccacca ccagcaacgg ctggaccgga    360
gagattcgga agggcgagat caagaactgc tccttcaata tcacgacctc gatcagagac    420
aaggtgcaga aggaatacgc gctgttttat aatctcgatg tggtccccat cgacgacgac    480
aatgccacca ccaagaacaa gacgacgcgt aatttcagac tcattcactg caacagcagc    540
gtcatgacgc aggcctgccc caaggtgtcc ttcgaaccaa tcccgatcca ttactgtgcc    600
cctgccggat tcgcgatcct caagtgtaac aacaagacct tcgacgggaa gggcctgtgc    660
accaacgtca gcacggtgca gtgcacccat ggcatccgcc ccgtcgtgag cacccagctg    720
ctgctgaacg ggtccctggc tgaggaggag gtggtgatcc ggtcggacaa cttcatggac    780
aacaccaaga caatcatcgt ccagctgaac gagtctgtgg cgattaactg tacccggcct    840
aacaacaaca cccgtaaggg catccacatc gggcctggac gggccttcta tgccgcccgc    900
aagatcatcg gcgacatccg gcaggcccat tgcaacctct cccgcgccca gtggaataac    960
accctgaagc agatcgtgat caagctgaga gagcactttg gaaacaagac catcaagttc   1020
aatcagagtt ctggcggaga ccccgagatc gtgcggcact ccttcaactg cgggggcgag   1080
ttcttctact gcgatacgac acagctcttc aactccacct ggaacggcac cgagggcaac   1140
aacacagagg gaaactccac tatcaccctc ccttgccgca tcaagcagat catcaacatg   1200
tggcaggagg tgggaaaggc catgtatgcc ccccccatcg gggccagat ccgctgctcc    1260
tccaacatca ccggcctgct gctcaccaga gacgggggca ccgagggcaa cggcacggag   1320
aacgagacgg agatcttcag gcccggcggc ggcgacatga gggataactg gcggagcgag   1380
ctgtacaagt acaaggtggt gaaggtggag ccgctcggcg tggcccccac ccgggccaag   1440
cgccgcgtcg tgcagagaat gggtgcccga gcttcggtac tgtctggtgg agagctggac   1500
agatgggaga aaattaggct gcgcccggga ggcaaaaaga aatacaagct caagcatatc   1560
gtgtgggcct cgagggagct tgaacggttt gccgtgaacc caggcctgct ggaaacatct   1620
gagggatgtc gccagatcct ggggcaattg cagccatccc tccagaccgg gagtgaagag   1680
ctgaggtcct tgtataacac agtggctacc ctctactgcg tacaccagag gatcgagatt   1740
aaggatacca aggaggcctt ggacaaaatt gaggaggagc aaaacaagag caagaagaag   1800
gcccagcagg cagctgctga cactgggcat agcaaccagg tatcacagaa ctatcctatt   1860
gtccaaaaca ttcagggcca gatggttcat caggccatca gcccccggac gctcaatgcc   1920
tgggtgaagg ttgtcgaaga gaaggccttt tctcctgagg ttatccccat gttctccgct   1980
ttgagtgagg gggccactcc tcaggacctc aatacaatgc ttaataccgt gggcggccat   2040
caggccgcca tgcaaatgtt gaaggagact atcaacgagg aggcagccga gtgggacaga   2100
gtgcatcccg tccacgctgg cccaatcgcg cccggacaga tgcgggagcc tcgcggctct   2160
gacattgccg gcaccacctc tacactgcaa gagcaaatcg gatggatgac caacaatcct   2220
```

-continued

```
cccatcccag ttggagaaat ctataaacgg tggatcattc tcggtctcaa taaaattgtt   2280
agaatgtact ctccgacatc catccttgac attagacagg gacccaaaga gccttttagg   2340
gattacgtcg accggtttta taagaccctg cgagcagagc aggcctctca ggaggtcaaa   2400
aactggatga cggagacact cctggtacag aacgctaacc ccgactgcaa aacaatcttg   2460
aaggcactag gcccggctgc caccctggaa gagatgatga ccgcctgtca gggagtaggc   2520
ggacccggac acaaagccag agtgttgatg ggtggcaagt ggtcaaaaag tagtgtggtt   2580
ggatggccta ctgtaaggga aagaatgaga cgagctgagc cagcagcaga tggggtggga   2640
gcagcatctc gagacctgga aaaacatgga gcaatcacaa gtagcaatac agcagctacc   2700
aatgctgctt gtgcctggct agaagcacaa gaggaggagg aggtgggttt tccagtcaca   2760
cctcaggtac ctttaagacc aatgacttac aaggcagctg tagatcttag ccacttttta   2820
aaagaaaagg ggggactgga agggctaatt cactcccaac gaagacaaga tatccttgat   2880
ctgtggatct accacacaca aggctacttc cctgattggc agaactacac accagggcca   2940
ggggtcagat atccactgac ctttggatgg tgctacaagc tagtaccagt tgagccagat   3000
aaggtagaag aggccaataa aggagagaac accagcgcct tacaccctgt gagcctgcat   3060
ggaatggatg accctgagag agaagtgtta gagtggaggt ttgacagccg cctagcattt   3120
catcacgtgg cccgagagct gcatccggag tacttcaaga actgcactag tgagccagta   3180
gatcctagac tagagccctg gaagcatcca ggaagtcagc ctaaaactgc ttgtaccaat   3240
tgctattgta aaaagtgttg ctttcattgc caagtttgtt tcataacagc tgccttaggc   3300
atctcctatg gcaggaagaa gcggagacag cgacgaagac ctcctcaagg cagtcagact   3360
catcaagttt ctctatcaaa gcaacccacc tcccaatcca aaggggagcc gacaggcccg   3420
aaggaataa                                                           3429
```

<210> SEQ ID NO 73
<211> LENGTH: 1142
<212> TYPE: PRT
<213> ORGANISM: Artificial Sequence
<220> FEATURE:
<223> OTHER INFORMATION: HIV-1 ds-gp120c p17/24 L1-Nef Tatm fusion

<400> SEQUENCE: 73

```
Met Ala Glu Gln Leu Trp Val Thr Val Tyr Tyr Gly Val Pro Val Trp
 1               5                  10                  15

Lys Glu Ala Thr Thr Thr Leu Phe Cys Ala Ser Asp Ala Lys Ala Tyr
            20                  25                  30

Asp Thr Glu Val His Asn Val Trp Ala Thr His Ala Cys Val Pro Thr
        35                  40                  45

Asp Pro Asn Pro Gln Glu Val Val Leu Gly Asn Val Thr Glu Tyr Phe
    50                  55                  60

Asn Met Trp Lys Asn Asn Met Val Asp Gln Met His Glu Asp Ile Ile
65                  70                  75                  80

Ser Leu Trp Asp Gln Ser Leu Lys Pro Cys Val Lys Leu Thr Pro Leu
                85                  90                  95

Cys Val Thr Leu Asp Cys Asp Asp Val Asn Thr Thr Asn Ser Thr Thr
            100                 105                 110

Thr Thr Ser Asn Gly Trp Thr Gly Glu Ile Arg Lys Gly Glu Ile Lys
        115                 120                 125

Asn Cys Ser Phe Asn Ile Thr Thr Ser Ile Arg Asp Lys Val Gln Lys
    130                 135                 140
```

-continued

```
Glu Tyr Ala Leu Phe Tyr Asn Leu Asp Val Val Pro Ile Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
            180                 185                 190

Pro Ile Pro Ile His Tyr Cys Ala Pro Ala Gly Phe Ala Ile Leu Lys
        195                 200                 205

Cys Asn Asn Lys Thr Phe Asp Gly Lys Gly Leu Cys Thr Asn Val Ser
210                 215                 220

Thr Val Gln Cys Thr His Gly Ile Arg Pro Val Val Ser Thr Gln Leu
225                 230                 235                 240

Leu Leu Asn Gly Ser Leu Ala Glu Glu Val Val Ile Arg Ser Asp
                245                 250                 255

Asn Phe Met Asp Asn Thr Lys Thr Ile Ile Val Gln Leu Asn Glu Ser
            260                 265                 270

Val Ala Ile Asn Cys Thr Arg Pro Asn Asn Asn Thr Arg Lys Gly Ile
        275                 280                 285

His Ile Gly Pro Gly Arg Ala Phe Tyr Ala Ala Arg Lys Ile Ile Gly
290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
                325                 330                 335

Thr Ile Lys Phe Asn Gln Ser Ser Gly Gly Asp Pro Glu Ile Val Arg
            340                 345                 350

His Ser Phe Asn Cys Gly Gly Glu Phe Phe Tyr Cys Asp Thr Thr Gln
        355                 360                 365

Leu Phe Asn Ser Thr Trp Asn Gly Thr Glu Gly Asn Asn Thr Glu Gly
370                 375                 380

Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
                405                 410                 415

Ile Arg Cys Ser Ser Asn Ile Thr Gly Leu Leu Leu Thr Arg Asp Gly
            420                 425                 430

Gly Thr Glu Gly Asn Gly Thr Glu Asn Glu Thr Glu Ile Phe Arg Pro
        435                 440                 445

Gly Gly Gly Asp Met Arg Asp Asn Trp Arg Ser Glu Leu Tyr Lys Tyr
450                 455                 460

Lys Val Val Lys Val Glu Pro Leu Gly Val Ala Pro Thr Arg Ala Lys
465                 470                 475                 480

Arg Arg Val Val Gln Arg Met Gly Ala Arg Ala Ser Val Leu Ser Gly
                485                 490                 495

Gly Glu Leu Asp Arg Trp Glu Lys Ile Arg Leu Arg Pro Gly Gly Lys
            500                 505                 510

Lys Lys Tyr Lys Leu Lys His Ile Val Trp Ala Ser Arg Glu Leu Glu
        515                 520                 525

Arg Phe Ala Val Asn Pro Gly Leu Leu Glu Thr Ser Glu Gly Cys Arg
530                 535                 540

Gln Ile Leu Gly Gln Leu Gln Pro Ser Leu Gln Thr Gly Ser Glu Glu
545                 550                 555                 560

Leu Arg Ser Leu Tyr Asn Thr Val Ala Thr Leu Tyr Cys Val His Gln
```

-continued

```
                565                 570                 575
Arg Ile Glu Ile Lys Asp Thr Lys Glu Ala Leu Asp Lys Ile Glu Glu
            580                 585                 590
Glu Gln Asn Lys Ser Lys Lys Ala Gln Gln Ala Ala Ala Asp Thr
        595                 600                 605
Gly His Ser Asn Gln Val Ser Gln Asn Tyr Pro Ile Val Gln Asn Ile
    610                 615                 620
Gln Gly Gln Met Val His Gln Ala Ile Ser Pro Arg Thr Leu Asn Ala
625                 630                 635                 640
Trp Val Lys Val Val Glu Glu Lys Ala Phe Ser Pro Glu Val Ile Pro
                645                 650                 655
Met Phe Ser Ala Leu Ser Glu Gly Ala Thr Pro Gln Asp Leu Asn Thr
            660                 665                 670
Met Leu Asn Thr Val Gly Gly His Gln Ala Ala Met Gln Met Leu Lys
        675                 680                 685
Glu Thr Ile Asn Glu Glu Ala Ala Glu Trp Asp Arg Val His Pro Val
    690                 695                 700
His Ala Gly Pro Ile Ala Pro Gly Gln Met Arg Glu Pro Arg Gly Ser
705                 710                 715                 720
Asp Ile Ala Gly Thr Thr Ser Thr Leu Gln Glu Gln Ile Gly Trp Met
                725                 730                 735
Thr Asn Asn Pro Pro Ile Pro Val Gly Glu Ile Tyr Lys Arg Trp Ile
            740                 745                 750
Ile Leu Gly Leu Asn Lys Ile Val Arg Met Tyr Ser Pro Thr Ser Ile
        755                 760                 765
Leu Asp Ile Arg Gln Gly Pro Lys Glu Pro Phe Arg Asp Tyr Val Asp
    770                 775                 780
Arg Phe Tyr Lys Thr Leu Arg Ala Glu Gln Ala Ser Gln Glu Val Lys
785                 790                 795                 800
Asn Trp Met Thr Glu Thr Leu Leu Val Gln Asn Ala Asn Pro Asp Cys
                805                 810                 815
Lys Thr Ile Leu Lys Ala Leu Gly Pro Ala Ala Thr Leu Glu Glu Met
            820                 825                 830
Met Thr Ala Cys Gln Gly Val Gly Gly Pro Gly His Lys Ala Arg Val
        835                 840                 845
Leu Met Gly Gly Lys Trp Ser Lys Ser Ser Val Val Gly Trp Pro Thr
    850                 855                 860
Val Arg Glu Arg Met Arg Arg Ala Glu Pro Ala Ala Asp Gly Val Gly
865                 870                 875                 880
Ala Ala Ser Arg Asp Leu Glu Lys His Gly Ala Ile Thr Ser Ser Asn
                885                 890                 895
Thr Ala Ala Thr Asn Ala Ala Cys Ala Trp Leu Glu Ala Gln Glu Glu
            900                 905                 910
Glu Glu Val Gly Phe Pro Val Thr Pro Gln Val Pro Leu Arg Pro Met
        915                 920                 925
Thr Tyr Lys Ala Ala Val Asp Leu Ser His Phe Leu Lys Glu Lys Gly
    930                 935                 940
Gly Leu Glu Gly Leu Ile His Ser Gln Arg Arg Gln Asp Ile Leu Asp
945                 950                 955                 960
Leu Trp Ile Tyr His Thr Gln Gly Tyr Phe Pro Asp Trp Gln Asn Tyr
                965                 970                 975
Thr Pro Gly Pro Gly Val Arg Tyr Pro Leu Thr Phe Gly Trp Cys Tyr
            980                 985                 990
```

```
Lys Leu Val Pro Val Glu Pro Asp Lys Val Glu Glu Ala Asn Lys Gly
        995                 1000                1005
Glu Asn Thr Ser Ala Leu His Pro Val Ser Leu His Gly Met Asp Asp
    1010                1015                1020
Pro Glu Arg Glu Val Leu Glu Trp Arg Phe Asp Ser Arg Leu Ala Phe
1025                1030                1035                1040
His His Val Ala Arg Glu Leu His Pro Glu Tyr Phe Lys Asn Cys Thr
                1045                1050                1055
Ser Glu Pro Val Asp Pro Arg Leu Glu Pro Trp Lys His Pro Gly Ser
            1060                1065                1070
Gln Pro Lys Thr Ala Cys Thr Asn Cys Tyr Cys Lys Cys Cys Phe
        1075                1080                1085
His Cys Gln Val Cys Phe Ile Thr Ala Ala Leu Gly Ile Ser Tyr Gly
            1090                1095                1100
Arg Lys Lys Arg Arg Gln Arg Arg Pro Pro Gln Gly Ser Gln Thr
1105                1110                1115                1120
His Gln Val Ser Leu Ser Lys Gln Pro Thr Ser Gln Ser Lys Gly Glu
                1125                1130                1135
Pro Thr Gly Pro Lys Glu
            1140
```

<210> SEQ ID NO 74
<211> LENGTH: 3429
<212> TYPE: DNA
<213> ORGANISM: Artificial Sequence
<220> FEATURE:
<223> OTHER INFORMATION: HIV-1 ds-gp120c p17/24 L2-Nef Tatm fusion

<400> SEQUENCE: 74

```
atggccgagc agctgtgggt caccgtctac tacggcgtgc ctgtgtggaa ggaggccacg      60
accaccctct tctgcgcgag cgacgccaag gcctacgaca cggaagtgca taacgtgtgg     120
gcgacgcatg cttgcgtgcc tacggacccc aaccccagg aggtggtgct gggaaacgtg      180
accgagtact tcaacatgtg gaagaataac atggtggatc agatgcacga ggacatcatc     240
tctctgtggg accagtccct gaagccctgc gtgaagctga cgcctctctg cgtgacactg     300
gactgtacg acgtcaacac caccaacagc actaccacca ccagcaacgg ctggaccgga     360
gagattcgga agggcgagat caagaactgc tccttcaata tcacgacctc gatcagagac     420
aaggtgcaga aggaatacgc gctgttttat aatctcgatg tggtccccat cgacgacgac     480
aatgccacca ccaagaacaa gacgacgcgt aatttcagac tcattcactg caacagcagc     540
gtcatgacgc aggcctgccc caaggtgtcc ttcgaaccaa tcccgatcca ttactgtgcc     600
cctgccggat cgcgatcct caagtgtaac aacaagacct cgacgggaa gggcctgtgc      660
accaacgtca gcacggtgca gtgcacccat ggcatccgcc cgtcgtgag cacccagctg     720
ctgctgaacg gtccctggc tgaggaggag gtggtgatcc ggtcggacaa cttcatggac     780
aacaccaaga caatcatcgt ccagctgaac gagtctgtgg cgattaactg tacccggcct     840
aacaacaaca cccgtaaggg catccacatc gggcctggac gggccttcta tgccgcccgc     900
aagatcatcg cgacatccg gcaggcccat tgcaacctct cccgcgccca gtggaataac     960
accctgaagc agatcgtgat caagctgaga gagcactttg aaacaagac catcaagttc    1020
aatcagagtt ctggcggaga ccccgagatc gtgcggcact ccttcaactg cggggcgag    1080
ttcttctact gcgatacgac acagctcttc aactccacct ggaacggcac cgagggcaac    1140
```

```
aacacagagg gaaactccac tatcaccctc ccttgccgca tcaagcagat catcaacatg    1200
tggcaggagg tgggaaaggc catgtatgcc cccccatcg ggggccagat ccgctgctcc     1260
tccaacatca ccggcctgct gctcaccaga cacgggggca ccgagggcaa cggcacggag    1320
aacgagacgg agatcttcag gcccggcggc ggcgacatga gggataactg gcggagcgag    1380
ctgtacaagt acaaggtggt gaaggtggag ccgctcggcg tggcccccac ccgggccaag    1440
cgccgcgtcg tgcagagaat gggtgcccga gcttcggtac tgtctggtgg agagctggac    1500
agatgggaga aaattaggct gcgcccggga ggcaaaaaga aatacaagct caagcatatc    1560
gtgtgggcct cgagggagct tgaacggttt gccgtgaacc caggcctgct ggaaacatct    1620
gagggatgtc gccagatcct ggggcaattg cagccatccc tccagaccgg gagtgaagag    1680
ctgaggtcct tgtataacac agtggctacc ctctactgcg tacaccagag gatcgagatt    1740
aaggatacca aggaggcctt ggacaaaatt gaggaggagc aaaacaagag caagaagaag    1800
gcccagcagc cagctgctga cactgggcat agcaaccagg tatcacagaa ctatcctatt    1860
gtccaaaaca ttcagggcca gatggttcat caggccatca gcccccggac gctcaatgcc    1920
tgggtgaagg ttgtcgaaga aaggcctttt tctcctgagg ttatccccat gttctccgct    1980
ttgagtgagg gggccactcc tcaggacctc aatacaatgc ttaataccgt gggcggccat    2040
caggccgcca tgcaaatgtt gaaggagact atcaacgagg aggcagccga gtgggacaga    2100
gtgcatcccg tccacgctgg cccaatcgcg cccggacaga tgcgggagcc tcgcggctct    2160
gacattgccg gcaccacctc tacactgcaa gagcaaatcg gatggatgac caacaatcct    2220
cccatcccag ttggagaaat ctataaacgg tggatcattc tcggtctcaa taaaattgtt    2280
agaatgtact ctccgacatc catccttgac attagacagg gacccaaaga gccttttagg    2340
gattacgtcg accggtttta taagaccctg cgagcagagc aggcctctca ggaggtcaaa    2400
aactggatga cggagacact cctggtacag aacgctaacc ccgactgcaa acaatcttg     2460 aaggcactag gcccggctgc caccctggaa gagatgatga ccgcctgtca gggagtaggc    2520
ggacccggac acaaagccag agtgttgatg ggtggcaagt ggtcaaaaag tagtgtggtt    2580
ggatggccta ctgtaaggga aagaatgaga cgagctgagc cagcagcaga tggggtggga    2640
gcagcatctc gagacctgga aaaacatgga gcaatcacaa gtagcaatac agcagctacc    2700
aatgctgctt gtgcctggct agaagcacaa gaggaggagg aggtgggttt tccagtcaca    2760
cctcaggtac cttttaagacc aatgacttac aaggcagctg tagatcttag ccacttttta    2820
aaagaaaagg ggggactgga agggctaatt cactcccaac gaagacaaga tatccttgat    2880
ctgtggatct accacacaca aggctacttc cctgattggc agaactacac accagggcca    2940
ggggtcagat atccactgac ctttggatgg tgctacaagc tagtaccagt tgagccagat    3000
aaggtagaag aggccaataa aggagagaac accagcttgg cacaccctgt gagcctgcat    3060
ggaatggatg accctgagag agaagtgtta gagtggaggt ttgacagccg cctagcattt    3120
catcacgtgg cccgagagct gcatccggag tacttcaaga actgcactag tgagccagta    3180
gatcctagac tagagccctg gaagcatcca ggaagtcagc ctaaaactgc ttgtaccaat    3240
tgctattgta aaaagtgttg ctttcattgc caagtttgtt tcataacagc tgccttaggc    3300
atctcctatg gcaggaagaa gcggagacag cgacgaagac ctcctcaagg cagtcagact    3360
catcaagttt ctctatcaaa gcaacccacc tcccaatcca aggggagcc gacaggcccg    3420 aaggaataa                                                            3429
```

-continued

```
<210> SEQ ID NO 75
<211> LENGTH: 1142
<212> TYPE: PRT
<213> ORGANISM: Artificial Sequence
<220> FEATURE:
<223> OTHER INFORMATION: HIV-1 ds-gp120c p17/24 L2-Nef Tatm fusion

<400> SEQUENCE: 75

Met Ala Glu Gln Leu Trp Val Thr Val Tyr Tyr Gly Val Pro Val Trp
 1               5                  10                  15

Lys Glu Ala Thr Thr Thr Leu Phe Cys Ala Ser Asp Ala Lys Ala Tyr
            20                  25                  30

Asp Thr Glu Val His Asn Val Trp Ala Thr His Ala Cys Val Pro Thr
        35                  40                  45

Asp Pro Asn Pro Gln Glu Val Val Leu Gly Asn Val Thr Glu Tyr Phe
    50                  55                  60

Asn Met Trp Lys Asn Asn Met Val Asp Gln Met His Glu Asp Ile Ile
65                  70                  75                  80

Ser Leu Trp Asp Gln Ser Leu Lys Pro Cys Val Lys Leu Thr Pro Leu
                85                  90                  95

Cys Val Thr Leu Asp Cys Asp Asp Val Asn Thr Thr Asn Ser Thr Thr
            100                 105                 110

Thr Thr Ser Asn Gly Trp Thr Gly Glu Ile Arg Lys Gly Glu Ile Lys
        115                 120                 125

Asn Cys Ser Phe Asn Ile Thr Thr Ser Ile Arg Asp Lys Val Gln Lys
    130                 135                 140

Glu Tyr Ala Leu Phe Tyr Asn Leu Asp Val Val Pro Ile Asp Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
            180                 185                 190

Pro Ile Pro Ile His Tyr Cys Ala Pro Ala Gly Phe Ala Ile Leu Lys
        195                 200                 205

Cys Asn Asn Lys Thr Phe Asp Gly Lys Gly Leu Cys Thr Asn Val Ser
    210                 215                 220

Thr Val Gln Cys Thr His Gly Ile Arg Pro Val Val Ser Thr Gln Leu
225                 230                 235                 240

Leu Leu Asn Gly Ser Leu Ala Glu Glu Glu Val Val Ile Arg Ser Asp
                245                 250                 255

Asn Phe Met Asp Asn Thr Lys Thr Ile Ile Val Gln Leu Asn Glu Ser
            260                 265                 270

Val Ala Ile Asn Cys Thr Arg Pro Asn Asn Asn Thr Arg Lys Gly Ile
        275                 280                 285

His Ile Gly Pro Gly Arg Ala Phe Tyr Ala Ala Arg Lys Ile Ile Gly
    290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
                325                 330                 335

Thr Ile Lys Phe Asn Gln Ser Ser Gly Gly Asp Pro Glu Ile Val Arg
            340                 345                 350

His Ser Phe Asn Cys Gly Gly Glu Phe Phe Tyr Cys Asp Thr Thr Gln
        355                 360                 365

Leu Phe Asn Ser Thr Trp Asn Gly Thr Glu Gly Asn Asn Thr Glu Gly
```

-continued

```
            370                 375                 380
Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
                405                 410                 415

Ile Arg Cys Ser Ser Asn Ile Thr Gly Leu Leu Thr Arg Asp Gly
            420                 425                 430

Gly Thr Glu Gly Asn Gly Thr Glu Asn Glu Thr Glu Ile Phe Arg Pro
            435                 440                 445

Gly Gly Gly Asp Met Arg Asp Asn Trp Arg Ser Glu Leu Tyr Lys Tyr
450                 455                 460

Lys Val Lys Val Glu Pro Leu Gly Val Ala Pro Thr Arg Ala Lys
465                 470                 475                 480

Arg Arg Val Val Gln Arg Met Gly Ala Arg Ala Ser Val Leu Ser Gly
                485                 490                 495

Gly Glu Leu Asp Arg Trp Glu Lys Ile Arg Leu Arg Pro Gly Gly Lys
                500                 505                 510

Lys Lys Tyr Lys Leu Lys His Ile Val Trp Ala Ser Arg Glu Leu Glu
            515                 520                 525

Arg Phe Ala Val Asn Pro Gly Leu Leu Glu Thr Ser Glu Gly Cys Arg
            530                 535                 540

Gln Ile Leu Gly Gln Leu Gln Pro Ser Leu Gln Thr Gly Ser Glu Glu
545                 550                 555                 560

Leu Arg Ser Leu Tyr Asn Thr Val Ala Thr Leu Tyr Cys Val His Gln
                565                 570                 575

Arg Ile Glu Ile Lys Asp Thr Lys Glu Ala Leu Asp Lys Ile Glu Glu
            580                 585                 590

Glu Gln Asn Lys Ser Lys Lys Ala Gln Gln Ala Ala Ala Asp Thr
            595                 600                 605

Gly His Ser Asn Gln Val Ser Gln Asn Tyr Pro Ile Val Gln Asn Ile
            610                 615                 620

Gln Gly Gln Met Val His Gln Ala Ile Ser Pro Arg Thr Leu Asn Ala
625                 630                 635                 640

Trp Val Lys Val Val Glu Glu Lys Ala Phe Ser Pro Glu Val Ile Pro
                645                 650                 655

Met Phe Ser Ala Leu Ser Glu Gly Ala Thr Pro Gln Asp Leu Asn Thr
                660                 665                 670

Met Leu Asn Thr Val Gly Gly His Gln Ala Ala Met Gln Met Leu Lys
            675                 680                 685

Glu Thr Ile Asn Glu Glu Ala Ala Glu Trp Asp Arg Val His Pro Val
690                 695                 700

His Ala Gly Pro Ile Ala Pro Gly Gln Met Arg Glu Pro Arg Gly Ser
705                 710                 715                 720

Asp Ile Ala Gly Thr Thr Ser Thr Leu Gln Glu Ile Gly Trp Met
                725                 730                 735

Thr Asn Asn Pro Pro Ile Pro Val Gly Glu Ile Tyr Lys Arg Trp Ile
                740                 745                 750

Ile Leu Gly Leu Asn Lys Ile Val Arg Met Tyr Ser Pro Thr Ser Ile
            755                 760                 765

Leu Asp Ile Arg Gln Gly Pro Lys Glu Pro Phe Arg Asp Tyr Val Asp
            770                 775                 780

Arg Phe Tyr Lys Thr Leu Arg Ala Glu Gln Ala Ser Gln Glu Val Lys
785                 790                 795                 800
```

Asn Trp Met Thr Glu Thr Leu Leu Val Gln Asn Ala Asn Pro Asp Cys
            805                 810                 815
Lys Thr Ile Leu Lys Ala Leu Gly Pro Ala Ala Thr Leu Glu Glu Met
            820                 825                 830
Met Thr Ala Cys Gln Gly Val Gly Gly Pro Gly His Lys Ala Arg Val
            835                 840                 845
Leu Met Gly Gly Lys Trp Ser Lys Ser Ser Val Gly Trp Pro Thr
        850                 855                 860
Val Arg Glu Arg Met Arg Arg Ala Glu Pro Ala Ala Asp Gly Val Gly
865                 870                 875                 880
Ala Ala Ser Arg Asp Leu Glu Lys His Gly Ala Ile Thr Ser Ser Asn
                885                 890                 895
Thr Ala Ala Thr Asn Ala Ala Cys Ala Trp Leu Glu Ala Gln Glu Glu
                900                 905                 910
Glu Glu Val Gly Phe Pro Val Thr Pro Gln Val Pro Leu Arg Pro Met
            915                 920                 925
Thr Tyr Lys Ala Ala Val Asp Leu Ser His Phe Leu Lys Glu Lys Gly
        930                 935                 940
Gly Leu Glu Gly Leu Ile His Ser Gln Arg Arg Gln Asp Ile Leu Asp
945                 950                 955                 960
Leu Trp Ile Tyr His Thr Gln Gly Tyr Phe Pro Asp Trp Gln Asn Tyr
                965                 970                 975
Thr Pro Gly Pro Gly Val Arg Tyr Pro Leu Thr Phe Gly Trp Cys Tyr
                980                 985                 990
Lys Leu Val Pro Val Glu Pro Asp Lys Val Glu Glu Ala Asn Lys Gly
            995                 1000                 1005
Glu Asn Thr Ser Leu Ala His Pro Val Ser Leu His Gly Met Asp Asp
            1010                 1015                 1020
Pro Glu Arg Glu Val Leu Glu Trp Arg Phe Asp Ser Arg Leu Ala Phe
1025                 1030                 1035                 1040
His His Val Ala Arg Glu Leu His Pro Glu Tyr Phe Lys Asn Cys Thr
                1045                 1050                 1055
Ser Glu Pro Val Asp Pro Arg Leu Glu Pro Trp Lys His Pro Gly Ser
            1060                 1065                 1070
Gln Pro Lys Thr Ala Cys Thr Asn Cys Tyr Cys Lys Lys Cys Cys Phe
            1075                 1080                 1085
His Cys Gln Val Cys Phe Ile Thr Ala Ala Leu Gly Ile Ser Tyr Gly
            1090                 1095                 1100
Arg Lys Lys Arg Arg Gln Arg Arg Pro Pro Gln Gly Ser Gln Thr
1105                 1110                 1115                 1120
His Gln Val Ser Leu Ser Lys Gln Pro Thr Ser Gln Ser Lys Gly Glu
                1125                 1130                 1135
Pro Thr Gly Pro Lys Glu
            1140

<210> SEQ ID NO 76
<211> LENGTH: 3429
<212> TYPE: DNA
<213> ORGANISM: Artificial Sequence
<220> FEATURE:
<223> OTHER INFORMATION: HIV-1 ds-gp120c p17/24 LL-Nef Tatm fusion

<400> SEQUENCE: 76
atggccgagc agctgtgggt caccgtctac tacggcgtgc ctgtgtggaa ggaggccacg      60

```
accaccctct tctgcgcgag cgacgccaag gcctacgaca cggaagtgca taacgtgtgg    120
gcgacgcatg cttgcgtgcc tacggacccc aaccccagg aggtggtgct gggaaacgtg    180
accgagtact tcaacatgtg gaagaataac atggtggatc agatgcacga ggacatcatc    240
tctctgtggg accagtccct gaagccctgc gtgaagctga cgcctctctg cgtgacactg    300
gactgtgacg acgtcaacac caccaacagc actaccacca ccagcaacgg ctggaccgga    360
gagattcgga agggcgagat caagaactgc tccttcaata tcacgacctc gatcagagac    420
aaggtgcaga aggaatacgc gctgttttat aatctcgatg tggtccccat cgacgacgac    480
aatgccacca ccaagaacaa gacgacgcgt aatttcagac tcattcactg caacagcagc    540
gtcatgacgc aggcctgccc caaggtgtcc ttcgaaccaa tcccgatcca ttactgtgcc    600
cctgccggat tcgcgatcct caagtgtaac aacaagacct tcgacgggaa gggcctgtgc    660
accaacgtca gcacggtgca gtgcacccat ggcatccgcc cgtcgtgag cacccagctg    720 ctgctgaacg ggtccctggc tgaggaggag gtggtgatcc ggtcggacaa cttcatggac    780
aacaccaaga caatcatcgt ccagctgaac gagtctgtgg cgattaactg tacccggcct    840
aacaacaaca cccgtaaggg catccacatc gggcctggac gggccttcta tgccgcccgc    900
aagatcatcg gcgacatccg gcaggcccat tgcaacctct cccgcgccca gtggaataac    960
accctgaagc agatcgtgat caagctgaga gagcactttg gaaacaagac catcaagttc   1020
aatcagagtt ctggcggaga ccccgagatc gtgcggcact ccttcaactg cggggcgag    1080 ttcttctact gcgatacgac acagctcttc aactccacct ggaacggcac cgagggcaac   1140
aacacagagg gaaactccac tatcaccctc ccttgccgca tcaagcagat catcaacatg   1200
tggcaggagg tgggaaaggc catgtatgcc ccccccatcg ggggccagat ccgctgctcc   1260
tccaacatca ccggcctgct gctcaccaga gacggggca ccgagggcaa cggcacggag    1320
aacgagacgg agatcttcag gcccggcggc ggcgacatga gggataactg gcggagcgag   1380
ctgtacaagt acaaggtggt gaaggtggag ccgctcggcg tggcccccac ccgggccaag   1440
cgccgcgtcg tgcagagaat gggtgcccga gcttcggtac tgtctggtgg agagctggac   1500
agatgggaga aaattaggct gcgcccggga ggcaaaaaga aatacaagct caagcatatc   1560
gtgtgggcct cgagggagct tgaacggttt gccgtgaacc caggcctgct ggaaacatct   1620
gagggatgtc gccagatcct ggggcaattg cagccatccc tccagaccgg gagtgaagag   1680
ctgaggtcct tgtataacac agtggctacc ctctactgcg tacaccagag gatcgagatt   1740
aaggatacca aggaggcctt ggacaaaatt gaggaggagc aaaacaagag caagaagaag   1800
gcccagcagg cagctgctga cactgggcat agcaaccagg tatcacagaa ctatcctatt   1860
gtccaaaaca ttcagggcca gatggttcat caggccatca gccccggac gctcaatgcc    1920 tgggtgaagg ttgtcgaaga aaggcctttt tctcctgagg ttatccccat gttctccgct   1980
ttgagtgagg ggccactcc tcaggacctc aatacaatgc ttaataccgt gggcggccat    2040
caggccgcca tgcaaatgtt gaaggagact atcaacgagg aggcagccga gtgggacaga   2100
gtgcatcccg tccacgctgg cccaatcgcg cccggacaga tgcgggagcc tcgcggctct   2160
gacattgccg gcaccacctc tacactgcaa gagcaaatcg gatggatgac caacaatcct   2220
cccatcccag ttggagaaat ctataaacgg tggatcattc tcggtctcaa taaaattgtt   2280
agaatgtact ctccgacatc catccttgac attagacagg gacccaaaga gccttttagg   2340
gattacgtcg accggtttta taagacccctg cgagcagagc aggcctctca ggaggtcaaa   2400
aactggatga cggagacact cctggtacag aacgctaacc ccgactgcaa aacaatcttg   2460
```

```
aaggcactag gcccggctgc caccctggaa gagatgatga ccgcctgtca gggagtaggc   2520
ggacccggac acaaagccag agtgttgatg ggtggcaagt ggtcaaaaag tagtgtggtt   2580
ggatggccta ctgtaaggga agaatgaga cgagctgagc cagcagcaga tggggtggga   2640
gcagcatctc gagacctgga aaaacatgga gcaatcacaa gtagcaatac agcagctacc   2700
aatgctgctt gtgcctggct agaagcacaa gaggaggag aggtgggttt tccagtcaca   2760
cctcaggtac ctttaagacc aatgacttac aaggcagctg tagatcttag ccactttta   2820 aaagaaaagg ggggactgga agggctaatt cactcccaac gaagacaaga tatccttgat   2880
ctgtggatct accacacaca aggctacttc cctgattggc agaactacac accagggcca   2940
ggggtcagat atccactgac ctttggatgg tgctacaagc tagtaccagt tgagccagat   3000
aaggtagaag aggccaataa aggagagaac accagcgccg cacaccctgt gagcctgcat   3060
ggaatggatg accctgagag agaagtgtta gagtggaggt ttgacagccg cctagcattt   3120
catcacgtgg cccgagagct gcatccggag tacttcaaga actgcactag tgagccagta   3180
gatcctagac tagagccctg gaagcatcca ggaagtcagc ctaaaactgc ttgtaccaat   3240
tgctattgta aaaagtgttg ctttcattgc caagtttgtt tcataacagc tgccttaggc   3300
atctcctatg gcaggaagaa gcggagacag cgacgaagac ctcctcaagg cagtcagact   3360
catcaagttt ctctatcaaa gcaacccacc tcccaatcca aggggagcc gacaggcccg   3420 aaggaataa                                                           3429
```

<210> SEQ ID NO 77
<211> LENGTH: 1142
<212> TYPE: PRT
<213> ORGANISM: Artificial Sequence
<220> FEATURE:
<223> OTHER INFORMATION: HIV-1 ds-gp120c p17/24 LL-Nef Tatm fusion

<400> SEQUENCE: 77

```
Met Ala Glu Gln Leu Trp Val Thr Val Tyr Tyr Gly Val Pro Val Trp
 1               5                  10                  15

Lys Glu Ala Thr Thr Thr Leu Phe Cys Ala Ser Asp Ala Lys Ala Tyr
            20                  25                  30

Asp Thr Glu Val His Asn Val Trp Ala Thr His Ala Cys Val Pro Thr
        35                  40                  45

Asp Pro Asn Pro Gln Glu Val Val Leu Gly Asn Val Thr Glu Tyr Phe
    50                  55                  60

Asn Met Trp Lys Asn Asn Met Val Asp Gln Met His Glu Asp Ile Ile
65                  70                  75                  80

Ser Leu Trp Asp Gln Ser Leu Lys Pro Cys Val Lys Leu Thr Pro Leu
                85                  90                  95

Cys Val Thr Leu Asp Cys Asp Asp Val Asn Thr Thr Asn Ser Thr Thr
            100                 105                 110

Thr Thr Ser Asn Gly Trp Thr Gly Glu Ile Arg Lys Gly Glu Ile Lys
        115                 120                 125

Asn Cys Ser Phe Asn Ile Thr Thr Ser Ile Arg Asp Lys Val Gln Lys
    130                 135                 140

Glu Tyr Ala Leu Phe Tyr Asn Leu Asp Val Val Pro Ile Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
```

-continued

```
                180                 185                 190
Pro Ile Pro Ile His Tyr Cys Ala Pro Ala Gly Phe Ala Ile Leu Lys
            195                 200                 205
Cys Asn Asn Lys Thr Phe Asp Gly Lys Gly Leu Cys Thr Asn Val Ser
        210                 215                 220
Thr Val Gln Cys Thr His Gly Ile Arg Pro Val Val Ser Thr Gln Leu
225                 230                 235                 240
Leu Leu Asn Gly Ser Leu Ala Glu Glu Val Val Ile Arg Ser Asp
                245                 250                 255
Asn Phe Met Asp Asn Thr Lys Thr Ile Ile Val Gln Leu Asn Glu Ser
            260                 265                 270
Val Ala Ile Asn Cys Thr Arg Pro Asn Asn Asn Thr Arg Lys Gly Ile
        275                 280                 285
His Ile Gly Pro Gly Arg Ala Phe Tyr Ala Ala Arg Lys Ile Ile Gly
        290                 295                 300
Asp Ile Arg Gln Ala His Cys Asn Leu Ser Arg Ala Gln Trp Asn Asn
305                 310                 315                 320
Thr Leu Lys Gln Ile Val Ile Lys Leu Arg Glu His Phe Gly Asn Lys
                325                 330                 335
Thr Ile Lys Phe Asn Gln Ser Ser Gly Gly Asp Pro Glu Ile Val Arg
            340                 345                 350
His Ser Phe Asn Cys Gly Gly Glu Phe Phe Tyr Cys Asp Thr Thr Gln
        355                 360                 365
Leu Phe Asn Ser Thr Trp Asn Gly Thr Glu Gly Asn Asn Thr Glu Gly
        370                 375                 380
Asn Ser Thr Ile Thr Leu Pro Cys Arg Ile Lys Gln Ile Ile Asn Met
385                 390                 395                 400
Trp Gln Glu Val Gly Lys Ala Met Tyr Ala Pro Pro Ile Gly Gly Gln
                405                 410                 415
Ile Arg Cys Ser Ser Asn Ile Thr Gly Leu Leu Leu Thr Arg Asp Gly
            420                 425                 430
Gly Thr Glu Gly Asn Gly Thr Glu Asn Glu Thr Glu Ile Phe Arg Pro
        435                 440                 445
Gly Gly Gly Asp Met Arg Asp Asn Trp Arg Ser Glu Leu Tyr Lys Tyr
        450                 455                 460
Lys Val Val Lys Val Glu Pro Leu Gly Val Ala Pro Thr Arg Ala Lys
465                 470                 475                 480
Arg Arg Val Val Gln Arg Met Gly Ala Arg Ala Ser Val Leu Ser Gly
                485                 490                 495
Gly Glu Leu Asp Arg Trp Glu Lys Ile Arg Leu Arg Pro Gly Gly Lys
            500                 505                 510
Lys Lys Tyr Lys Leu Lys His Ile Val Trp Ala Ser Arg Glu Leu Glu
        515                 520                 525
Arg Phe Ala Val Asn Pro Gly Leu Leu Glu Thr Ser Glu Gly Cys Arg
        530                 535                 540
Gln Ile Leu Gly Gln Leu Gln Pro Ser Leu Gln Thr Gly Ser Glu Glu
545                 550                 555                 560
Leu Arg Ser Leu Tyr Asn Thr Val Ala Thr Leu Tyr Cys Val His Gln
                565                 570                 575
Arg Ile Glu Ile Lys Asp Thr Lys Glu Ala Leu Asp Lys Ile Glu Glu
            580                 585                 590
Glu Gln Asn Lys Ser Lys Lys Ala Gln Gln Ala Ala Ala Asp Thr
        595                 600                 605
```

-continued

Gly His Ser Asn Gln Val Ser Gln Asn Tyr Pro Ile Val Gln Asn Ile
    610                 615                 620

Gln Gly Gln Met Val His Gln Ala Ile Ser Pro Arg Thr Leu Asn Ala
625                 630                 635                 640

Trp Val Lys Val Val Glu Glu Lys Ala Phe Ser Pro Glu Val Ile Pro
                645                 650                 655

Met Phe Ser Ala Leu Ser Glu Gly Ala Thr Pro Gln Asp Leu Asn Thr
            660                 665                 670

Met Leu Asn Thr Val Gly Gly His Gln Ala Ala Met Gln Met Leu Lys
        675                 680                 685

Glu Thr Ile Asn Glu Glu Ala Ala Glu Trp Asp Arg Val His Pro Val
690                 695                 700

His Ala Gly Pro Ile Ala Pro Gly Gln Met Arg Glu Pro Arg Gly Ser
705                 710                 715                 720

Asp Ile Ala Gly Thr Thr Ser Thr Leu Gln Glu Gln Ile Gly Trp Met
                725                 730                 735

Thr Asn Asn Pro Pro Ile Pro Val Gly Glu Ile Tyr Lys Arg Trp Ile
            740                 745                 750

Ile Leu Gly Leu Asn Lys Ile Val Arg Met Tyr Ser Pro Thr Ser Ile
        755                 760                 765

Leu Asp Ile Arg Gln Gly Pro Lys Glu Pro Phe Arg Asp Tyr Val Asp
770                 775                 780

Arg Phe Tyr Lys Thr Leu Arg Ala Glu Gln Ala Ser Gln Glu Val Lys
785                 790                 795                 800

Asn Trp Met Thr Glu Thr Leu Leu Val Gln Asn Ala Asn Pro Asp Cys
                805                 810                 815

Lys Thr Ile Leu Lys Ala Leu Gly Pro Ala Ala Thr Leu Glu Glu Met
            820                 825                 830

Met Thr Ala Cys Gln Gly Val Gly Gly Pro Gly His Lys Ala Arg Val
        835                 840                 845

Leu Met Gly Gly Lys Trp Ser Lys Ser Ser Val Val Gly Trp Pro Thr
850                 855                 860

Val Arg Glu Arg Met Arg Arg Ala Glu Pro Ala Ala Asp Gly Val Gly
865                 870                 875                 880

Ala Ala Ser Arg Asp Leu Glu Lys His Gly Ala Ile Thr Ser Ser Asn
                885                 890                 895

Thr Ala Thr Asn Ala Ala Cys Ala Trp Leu Glu Ala Gln Glu Glu
            900                 905                 910

Glu Glu Val Gly Phe Pro Val Thr Pro Gln Val Pro Leu Arg Pro Met
        915                 920                 925

Thr Tyr Lys Ala Ala Val Asp Leu Ser His Phe Leu Lys Glu Lys Gly
930                 935                 940

Gly Leu Glu Gly Leu Ile His Ser Gln Arg Arg Gln Asp Ile Leu Asp
945                 950                 955                 960

Leu Trp Ile Tyr His Thr Gln Gly Tyr Phe Pro Asp Trp Gln Asn Tyr
                965                 970                 975

Thr Pro Gly Pro Gly Val Arg Tyr Pro Leu Thr Phe Gly Trp Cys Tyr
            980                 985                 990

Lys Leu Val Pro Val Glu Pro Asp Lys Val Glu Glu Ala Asn Lys Gly
        995                 1000                1005

Glu Asn Thr Ser Ala Ala His Pro Val Ser Leu His Gly Met Asp Asp
    1010                1015                1020

```
Pro Glu Arg Glu Val Leu Glu Trp Arg Phe Asp Ser Arg Leu Ala Phe
1025                1030                1035                1040

His His Val Ala Arg Glu Leu His Pro Glu Tyr Phe Lys Asn Cys Thr
            1045                1050                1055

Ser Glu Pro Val Asp Pro Arg Leu Glu Pro Trp Lys His Pro Gly Ser
        1060                1065                1070

Gln Pro Lys Thr Ala Cys Thr Asn Cys Tyr Cys Lys Lys Cys Cys Phe
            1075                1080                1085

His Cys Gln Val Cys Phe Ile Thr Ala Ala Leu Gly Ile Ser Tyr Gly
        1090                1095                1100

Arg Lys Lys Arg Arg Gln Arg Arg Pro Pro Gln Gly Ser Gln Thr
1105                1110                1115                1120

His Gln Val Ser Leu Ser Lys Gln Pro Thr Ser Gln Ser Lys Gly Glu
            1125                1130                1135

Pro Thr Gly Pro Lys Glu
        1140
```

<210> SEQ ID NO 78
<211> LENGTH: 3426
<212> TYPE: DNA
<213> ORGANISM: Artificial Sequence
<220> FEATURE:
<223> OTHER INFORMATION: HIV-1 ds-gp120c p17/24 mLL-Nef Tatm fusion

<400> SEQUENCE: 78

```
atggccgagc agctgtgggt caccgtctac tacggcgtgc tgtgtggaa ggaggccacg       60
accaccctct tctgcgcgag cgacgccaag gcctacgaca cggaagtgca taacgtgtgg     120
gcgacgcatg cttgcgtgcc tacgacccc aaccccagg aggtggtgct gggaaacgtg       180
accgagtact tcaacatgtg gaagaataac atggtggatc agatgcacga ggacatcatc     240
tctctgtggg accagtccct gaagccctgc gtgaagctga cgcctctctg cgtgacactg    300
gactgtacg acgtcaacac caccaacagc actaccacca ccagcaacgg ctggaccgga     360
gagattcgga agggcgagat caagaactgc tccttcaata tcacgacctc gatcagagac     420
aaggtgcaga aggaatacgc gctgttttat aatctcgatg tggtccccat cgacgacgac     480
aatgccacca ccaagaacaa gacgacgcgt aatttcagac tcattcactg caacagcagc     540
gtcatgacgc aggcctgccc caaggtgtcc ttcgaaccaa tcccgatcca ttactgtgcc    600
cctgccggat cgcgatcct caagtgtaac aacaagacct cgacgggaa gggcctgtgc      660
accaacgtca gcacggtgca gtgcacccat ggcatccgcc cgtcgtgag cacccagctg     720
ctgctgaacg gtccctggc tgaggaggag gtggtgatcc ggtcggacaa cttcatggac    780
aacaccaaga caatcatcgt ccagctgaac gagtctgtgg cgattaactg tacccggcct    840
aacaacaaca cccgtaaggg catccacatc gggcctggac gggccttcta tgccgcccgc    900
aagatcatcg cgacatccg gcaggcccat gcaacctct cccgcgccca gtggaataac    960
accctgaagc agatcgtgat caagctgaga gagcactttg aaacaagac catcaagttc    1020
aatcagagtt ctggcggaga ccccgagatc gtgcggcact ccttcaactg cggggccgag    1080
ttcttctact gcgatacgac acagctcttc aactccacct ggaacggcac cgagggcaac    1140
aacacagagg gaaactccac tatcacccctc ccttgccgca tcaagcagat catcaacatg    1200
tggcaggagg tgggaaaggc catgtatgcc ccccccatcg ggccagat ccgctgctcc    1260
tccaacatca ccggcctgct gctcaccaga gacggggca ccgagggcaa cggcacggag    1320
aacgagacgg agatcttcag gcccggcggc ggcgacatga gggataactg gcggagcgag    1380
```

```
ctgtacaagt acaaggtggt gaaggtggag ccgctcggcg tggcccccac ccgggccaag    1440
cgccgcgtcg tgcagagaat gggtgcccga gcttcggtac tgtctggtgg agagctggac    1500
agatgggaga aaattaggct gcgcccggga ggcaaaaaga aatacaagct caagcatatc    1560
gtgtgggcct cgagggagct tgaacggttt gccgtgaacc caggcctgct ggaaacatct    1620
gagggatgtc gccagatcct ggggcaattg cagccatccc tccagaccgg gagtgaagag    1680
ctgaggtcct tgtataacac agtggctacc ctctactgcg tacaccagag gatcgagatt    1740
aaggatacca aggaggcctt ggacaaaatt gaggaggagc aaaacaagag caagaagaag    1800
gcccagcagg cagctgctga cactgggcat agcaaccagg tatcacagaa ctatcctatt    1860
gtccaaaaca ttcagggcca gatggttcat caggccatca gccccggac gctcaatgcc     1920 tgggtgaagg ttgtcgaaga aaggcctttt tctcctgagg ttatccccat gttctccgct    1980
ttgagtgagg gggccactcc tcaggacctc aatacaatgc ttaataccgt gggcggccat    2040
caggccgcca tgcaaatgtt gaaggagact atcaacgagg aggcagccga gtgggacaga    2100
gtgcatcccg tccacgctgg cccaatcgcg cccggacaga tgcggagcc tcgcggctct     2160 gacattgccg gcaccacctc tacactgcaa gagcaaatcg gatggatgac caacaatcct    2220
cccatcccag ttggagaaat ctataaacgg tggatcattc tcggtctcaa taaaattgtt    2280
agaatgtact ctccgacatc catccttgac attagacagg acccaaaga gccttttagg     2340 gattacgtcg accggtttta taagaccctg cgagcagagc aggcctctca ggaggtcaaa    2400
aactggatga cggagacact cctggtacag aacgctaacc ccgactgcaa acaatcttg     2460 aaggcactag gccggctgc caccctggaa gagatgatga ccgcctgtca gggagtaggc    2520 ggaccccggac acaaagccag agtgttgatg ggcaagtggt caaaaagtag tgtggttgga   2580
tggcctactg taagggaaag aatgagacga gctgagccag cagcagatgg ggtgggagca    2640
gcatctcgag acctggaaaa acatggagca atcacaagta gcaatacagc agctaccaat    2700
gctgcttgtg cctggctaga agcacaagag gaggaggagg tgggttttcc agtcacacct    2760
caggtacctt taagaccaat gacttacaag gcagctgtag atcttagcca cttttttaaa    2820
gaaaaggggg gactggaagg gctaattcac tcccaacgaa gacaagatat ccttgatctg    2880
tggatctacc acacacaagg ctacttccct gattggcaga actacacacc agggccaggg    2940
gtcagatatc cactgaccct tggatggtgc tacaagctag taccagttga gccagataag    3000
gtagaagagg ccaataaagg agagaacacc agcgccgcac accctgtgag cctgcatgga    3060
atggatgacc ctgagagaga agtgttagag tggaggtttg acagccgcct agcatttcat    3120
cacgtggccc gagagctgca tccggagtac ttcaagaact gcactagtga gccagtagat    3180
cctagactag agccctggaa gcatccagga agtcagccta aaactgcttg taccaattgc    3240
tattgtaaaa agtgttgctt tcattgccaa gtttgtttca taacagctgc cttaggcatc    3300
tcctatggca ggaagaagcg gagacagcga cgaagacctc ctcaaggcag tcagactcat    3360
caagtttctc tatcaaagca acccacctcc caatccaaag ggagccgac aggcccgaag     3420 gaataa                                                               3426
```

<210> SEQ ID NO 79
<211> LENGTH: 1141
<212> TYPE: PRT
<213> ORGANISM: Artificial Sequence
<220> FEATURE:
<223> OTHER INFORMATION: HIV-1 ds-gp120c p17/24 mLL-Nef Tatm fusion

<400> SEQUENCE: 79

```
Met Ala Glu Gln Leu Trp Val Thr Val Tyr Tyr Gly Val Pro Val Trp
 1               5                  10                  15

Lys Glu Ala Thr Thr Thr Leu Phe Cys Ala Ser Asp Ala Lys Ala Tyr
                20                  25                  30

Asp Thr Glu Val His Asn Val Trp Ala Thr His Ala Cys Val Pro Thr
            35                  40                  45

Asp Pro Asn Pro Gln Glu Val Val Leu Gly Asn Val Thr Glu Tyr Phe
    50                  55                  60

Asn Met Trp Lys Asn Asn Met Val Asp Gln Met His Glu Asp Ile Ile
65                  70                  75                  80

Ser Leu Trp Asp Gln Ser Leu Lys Pro Cys Val Lys Leu Thr Pro Leu
                85                  90                  95

Cys Val Thr Leu Asp Cys Asp Asp Val Asn Thr Thr Asn Ser Thr Thr
            100                 105                 110

Thr Thr Ser Asn Gly Trp Thr Gly Glu Ile Arg Lys Gly Glu Ile Lys
        115                 120                 125

Asn Cys Ser Phe Asn Ile Thr Thr Ser Ile Arg Asp Lys Val Gln Lys
130                 135                 140

Glu Tyr Ala Leu Phe Tyr Asn Leu Asp Val Val Pro Ile Asp Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
            180                 185                 190

Pro Ile Pro Ile His Tyr Cys Ala Pro Ala Gly Phe Ala Ile Leu Lys
        195                 200                 205

Cys Asn Asn Lys Thr Phe Asp Gly Lys Gly Leu Cys Thr Asn Val Ser
210                 215                 220

Thr Val Gln Cys Thr His Gly Ile Arg Pro Val Val Ser Thr Gln Leu
225                 230                 235                 240

Leu Leu Asn Gly Ser Leu Ala Glu Glu Val Val Ile Arg Ser Asp
                245                 250                 255

Asn Phe Met Asp Asn Thr Lys Thr Ile Ile Val Gln Leu Asn Glu Ser
            260                 265                 270

Val Ala Ile Asn Cys Thr Arg Pro Asn Asn Asn Thr Arg Lys Gly Ile
        275                 280                 285

His Ile Gly Pro Gly Arg Ala Phe Tyr Ala Ala Arg Lys Ile Ile Gly
    290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
                325                 330                 335

Thr Ile Lys Phe Asn Gln Ser Ser Gly Gly Asp Pro Glu Ile Val Arg
            340                 345                 350

His Ser Phe Asn Cys Gly Gly Glu Phe Phe Tyr Cys Asp Thr Thr Gln
        355                 360                 365

Leu Phe Asn Ser Thr Trp Asn Gly Thr Glu Gly Asn Asn Thr Glu Gly
370                 375                 380

Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
                405                 410                 415
```

-continued

```
Ile Arg Cys Ser Ser Asn Ile Thr Gly Leu Leu Leu Thr Arg Asp Gly
            420                 425                 430
Gly Thr Glu Gly Asn Gly Thr Glu Asn Glu Thr Glu Ile Phe Arg Pro
        435                 440                 445
Gly Gly Gly Asp Met Arg Asp Asn Trp Arg Ser Glu Leu Tyr Lys Tyr
    450                 455                 460
Lys Val Lys Val Glu Pro Leu Gly Val Ala Pro Thr Arg Ala Lys
465                 470                 475                 480
Arg Arg Val Val Gln Arg Met Gly Ala Arg Ala Ser Val Leu Ser Gly
            485                 490                 495
Gly Glu Leu Asp Arg Trp Glu Lys Ile Arg Leu Arg Pro Gly Gly Lys
        500                 505                 510
Lys Lys Tyr Lys Leu Lys His Ile Val Trp Ala Ser Arg Glu Leu Glu
    515                 520                 525
Arg Phe Ala Val Asn Pro Gly Leu Leu Glu Thr Ser Glu Gly Cys Arg
530                 535                 540
Gln Ile Leu Gly Gln Leu Gln Pro Ser Leu Gln Thr Gly Ser Glu Glu
545                 550                 555                 560
Leu Arg Ser Leu Tyr Asn Thr Val Ala Thr Leu Tyr Cys Val His Gln
            565                 570                 575
Arg Ile Glu Ile Lys Asp Thr Lys Glu Ala Leu Asp Lys Ile Glu Glu
        580                 585                 590
Glu Gln Asn Lys Ser Lys Lys Ala Gln Gln Ala Ala Ala Asp Thr
    595                 600                 605
Gly His Ser Asn Gln Val Ser Gln Asn Tyr Pro Ile Val Gln Asn Ile
610                 615                 620
Gln Gly Gln Met Val His Gln Ala Ile Ser Pro Arg Thr Leu Asn Ala
625                 630                 635                 640
Trp Val Lys Val Val Glu Glu Lys Ala Phe Ser Pro Glu Val Ile Pro
            645                 650                 655
Met Phe Ser Ala Leu Ser Glu Gly Ala Thr Pro Gln Asp Leu Asn Thr
        660                 665                 670
Met Leu Asn Thr Val Gly Gly His Gln Ala Ala Met Gln Met Leu Lys
    675                 680                 685
Glu Thr Ile Asn Glu Glu Ala Ala Glu Trp Asp Arg Val His Pro Val
690                 695                 700
His Ala Gly Pro Ile Ala Pro Gly Gln Met Arg Glu Pro Arg Gly Ser
705                 710                 715                 720
Asp Ile Ala Gly Thr Thr Ser Thr Leu Gln Glu Gln Ile Gly Trp Met
            725                 730                 735
Thr Asn Asn Pro Pro Ile Pro Val Gly Glu Ile Tyr Lys Arg Trp Ile
        740                 745                 750
Ile Leu Gly Leu Asn Lys Ile Val Arg Met Tyr Ser Pro Thr Ser Ile
    755                 760                 765
Leu Asp Ile Arg Gln Gly Pro Lys Glu Pro Phe Arg Asp Tyr Val Asp
770                 775                 780
Arg Phe Tyr Lys Thr Leu Arg Ala Glu Gln Ala Ser Gln Glu Val Lys
785                 790                 795                 800
Asn Trp Met Thr Glu Thr Leu Leu Val Gln Asn Ala Asn Pro Asp Cys
            805                 810                 815
Lys Thr Ile Leu Lys Ala Leu Gly Pro Ala Ala Thr Leu Glu Glu Met
        820                 825                 830
```

-continued

```
Met Thr Ala Cys Gln Gly Val Gly Pro Gly His Lys Ala Arg Val
        835                 840                 845
Leu Met Gly Lys Trp Ser Lys Ser Ser Val Val Gly Trp Pro Thr Val
        850                 855                 860
Arg Glu Arg Met Arg Arg Ala Glu Pro Ala Ala Asp Gly Val Gly Ala
865                 870                 875                 880
Ala Ser Arg Asp Leu Glu Lys His Gly Ala Ile Thr Ser Ser Asn Thr
                885                 890                 895
Ala Ala Thr Asn Ala Ala Cys Ala Trp Leu Glu Ala Gln Glu Glu Glu
            900                 905                 910
Glu Val Gly Phe Pro Val Thr Pro Gln Val Pro Leu Arg Pro Met Thr
        915                 920                 925
Tyr Lys Ala Ala Val Asp Leu Ser His Phe Leu Lys Glu Lys Gly Gly
        930                 935                 940
Leu Glu Gly Leu Ile His Ser Gln Arg Arg Gln Asp Ile Leu Asp Leu
945                 950                 955                 960
Trp Ile Tyr His Thr Gln Gly Tyr Phe Pro Asp Trp Gln Asn Tyr Thr
                965                 970                 975
Pro Gly Pro Gly Val Arg Tyr Pro Leu Thr Phe Gly Trp Cys Tyr Lys
            980                 985                 990
Leu Val Pro Val Glu Pro Asp Lys Val Glu Glu Ala Asn Lys Gly Glu
        995                 1000                1005
Asn Thr Ser Ala Ala His Pro Val Ser Leu His Gly Met Asp Asp Pro
        1010                1015                1020
Glu Arg Glu Val Leu Glu Trp Arg Phe Asp Ser Arg Leu Ala Phe His
1025                1030                1035                1040
His Val Ala Arg Glu Leu His Pro Glu Tyr Phe Lys Asn Cys Thr Ser
                1045                1050                1055
Glu Pro Val Asp Pro Arg Leu Glu Pro Trp Lys His Pro Gly Ser Gln
            1060                1065                1070
Pro Lys Thr Ala Cys Thr Asn Cys Tyr Cys Lys Lys Cys Cys Phe His
        1075                1080                1085
Cys Gln Val Cys Phe Ile Thr Ala Ala Leu Gly Ile Ser Tyr Gly Arg
        1090                1095                1100
Lys Lys Arg Arg Gln Arg Arg Pro Pro Gln Gly Ser Gln Thr His
1105                1110                1115                1120
Gln Val Ser Leu Ser Lys Gln Pro Thr Ser Gln Ser Lys Gly Glu Pro
                1125                1130                1135
Thr Gly Pro Lys Glu
        1140
```

<210> SEQ ID NO 80
<211> LENGTH: 3426
<212> TYPE: DNA
<213> ORGANISM: Artificial Sequence
<220> FEATURE:
<223> OTHER INFORMATION: HIV-1 ds-gp120c p17/24 mL1-Nef Tatm fusion

<400> SEQUENCE: 80

| | | | | | |
|---|---|---|---|---|---|
| atggccgagc | agctgtgggt | caccgtctac | tacggcgtgc | ctgtgtggaa | ggaggccacg | 60 |
| accacccctct | tctgcgcgag | cgacgccaag | gcctacgaca | cggaagtgca | taacgtgtgg | 120 |
| gcgacgcatg | cttgcgtgcc | tacggacccc | aaccccagg | aggtggtgct | gggaaacgtg | 180 |
| accgagtact | tcaacatgtg | gaagaataac | atggtggatc | agatgcacga | ggacatcatc | 240 |
| tctctgtggg | accagtccct | gaagccctgc | gtgaagctga | cgcctctctg | cgtgacactg | 300 |

```
gactgtgacg acgtcaacac caccaacagc actaccacca ccagcaacgg ctggaccgga      360
gagattcgga agggcgagat caagaactgc tccttcaata tcacgacctc gatcagagac      420
aaggtgcaga aggaatacgc gctgttttat aatctcgatg tggtcccat cgacgacgac      480 aatgccacca ccaagaacaa gacgacgcgt aatttcagac tcattcactg caacagcagc     540
gtcatgacgc aggcctgccc caaggtgtcc ttcgaaccaa tcccgatcca ttactgtgcc      600
cctgccggat tcgcgatcct caagtgtaac aacaagacct tcgacgggaa gggcctgtgc     660
accaacgtca gcacggtgca gtgcacccat ggcatccgcc ccgtcgtgag cacccagctg     720
ctgctgaacg ggtccctggc tgaggaggag gtggtgatcc ggtcggacaa cttcatggac     780
aacaccaaga caatcatcgt ccagctgaac gagtctgtgg cgattaactg tacccggcct     840
aacaacaaca cccgtaaggg catccacatc gggcctggac gggccttcta tgccgcccgc     900
aagatcatcg cgacatccg gcaggcccat tgcaacctct cccgcgccca gtggaataac     960
accctgaagc agatcgtgat caagctgaga gagcactttg aaacaagac catcaagttc     1020 aatcagagtt ctggcggaga ccccgagatc gtgcggcact ccttcaactg cgggggcgag     1080
ttcttctact gcgatacgac acagctcttc aactccacct ggaacggcac cgagggcaac     1140
aacacagagg gaaactccac tatcaccctc ccttgccgca tcaagcagat catcaacatg     1200
tggcaggagg tgggaaaggc catgtatgcc ccccccatcg ggggcagat ccgctgctcc      1260 tccaacatca ccggcctgct gctcaccaga gacgggggca ccgagggcaa cggcacggag     1320
aacgagacgg agatcttcag gcccggcggc ggcgacatga gggataactg gcggagcgag     1380
ctgtacaagt acaaggtggt gaaggtggag ccgctcggcg tggccccac ccgggccaag      1440 cgccgcgtcg tgcagagaat gggtgcccga gcttcggtac tgtctggtgg agagctggac     1500
agatgggaga aaattaggct gcgcccggga ggcaaaaaga atacaagct caagcatatc      1560 gtgtgggcct cgagggagct tgaacggttt gccgtgaacc caggcctgct ggaaacatct     1620
gagggatgtc gccagatcct ggggcaattg cagccatccc tccagaccgg gagtgaagag     1680
ctgaggtcct tgtataacac agtggctacc ctctactgcg tacaccagag gatcgagatt     1740
aaggatacca aggaggcctt ggacaaaatt gaggaggagc aaaacaagag caagaagaag     1800
gcccagcagg cagctgctga cactgggcat agcaaccagg tatcacagaa ctatcctatt     1860
gtccaaaaca ttcagggcca gatggttcat caggccatca gcccccggac gctcaatgcc     1920
tgggtgaagg ttgtcgaaga aaggcctttt tctcctgagg ttatcccat gttctccgct      1980 ttgagtgagg gggccactcc tcaggacctc aatacaatgc ttaataccgt gggcggccat     2040
caggccgcca tgcaaatgtt gaaggagact atcaacgagg aggcagccga gtgggacaga     2100
gtgcatcccg tccacgctgg cccaatcgcg cccggacaga tgcgggagcc tcgcggctct     2160
gacattgccg gcaccacctc tacactgcaa gagcaaatcg gatggatgac caacaatcct     2220
cccatcccag ttggagaaat ctataaacgg tggatcattc tcggtctcaa taaaattgtt     2280
agaatgtact ctccgacatc catccttgac attagacagg gacccaaaga gcctttagg     2340 gattacgtcg accggttta taagaccctg cgagcagagc aggcctctca ggaggtcaaa      2400
aactggatga cggagacact cctggtacag aacgctaacc ccgactgcaa acaatcttg      2460 aaggcactag gcccggctgc caccctgaa gagatgatga ccgcctgtca gggagtaggc      2520
ggacccggac acaaagccag agtgttgatg ggcaagtggt caaaaagtag tgtggttgga     2580
tggcctactg taagggaaag aatgagacga gctgagccag cagcagatgg ggtgggagca     2640
```

-continued

```
gcatctcgag acctggaaaa acatggagca atcacaagta gcaatacagc agctaccaat   2700
gctgcttgtg cctggctaga agcacaagag gaggaggagg tgggttttcc agtcacacct   2760
caggtacctt taagaccaat gacttacaag gcagctgtag atcttagcca ctttttaaaa   2820
gaaaaggggg gactggaagg gctaattcac tcccaacgaa gacaagatat ccttgatctg   2880
tggatctacc acacacaagg ctacttccct gattggcaga actacacacc agggccaggg   2940
gtcagatatc cactgacctt tggatggtgc tacaagctag taccagttga gccagataag   3000
gtagaagagg ccaataaagg agagaacacc agcgccttac accctgtgag cctgcatgga   3060
atggatgacc ctgagagaga agtgttagag tggaggtttg acagccgcct agcatttcat   3120
cacgtggccc gagagctgca tccggagtac ttcaagaact gcactagtga gccagtagat   3180
cctagactag agccctggaa gcatccagga agtcagccta aaactgcttg taccaattgc   3240
tattgtaaaa agtgttgctt tcattgccaa gtttgtttca taacagctgc cttaggcatc   3300
tcctatggca ggaagaagcg gagacagcga cgaagacctc ctcaaggcag tcagactcat   3360
caagtttctc tatcaaagca acccacctcc caatccaaag gggagccgac aggcccgaag   3420
gaataa                                                              3426
```

<210> SEQ ID NO 81
<211> LENGTH: 1141
<212> TYPE: PRT
<213> ORGANISM: Artificial Sequence
<220> FEATURE:
<223> OTHER INFORMATION: HIV-1 ds-gp120c p17/24 mL1-Nef Tatm fusion

<400> SEQUENCE: 81

```
Met Ala Glu Gln Leu Trp Val Thr Val Tyr Tyr Gly Val Pro Val Trp
1               5                   10                  15

Lys Glu Ala Thr Thr Thr Leu Phe Cys Ala Ser Asp Ala Lys Ala Tyr
            20                  25                  30

Asp Thr Glu Val His Asn Val Trp Ala Thr His Ala Cys Val Pro Thr
        35                  40                  45

Asp Pro Asn Pro Gln Glu Val Val Leu Gly Asn Val Thr Glu Tyr Phe
    50                  55                  60

Asn Met Trp Lys Asn Asn Met Val Asp Gln Met His Glu Asp Ile Ile
65                  70                  75                  80

Ser Leu Trp Asp Gln Ser Leu Lys Pro Cys Val Lys Leu Thr Pro Leu
                85                  90                  95

Cys Val Thr Leu Asp Cys Asp Asp Val Asn Thr Thr Asn Ser Thr Thr
            100                 105                 110

Thr Thr Ser Asn Gly Trp Thr Gly Glu Ile Arg Lys Gly Glu Ile Lys
        115                 120                 125

Asn Cys Ser Phe Asn Ile Thr Thr Ser Ile Arg Asp Lys Val Gln Lys
    130                 135                 140

Glu Tyr Ala Leu Phe Tyr Asn Leu Asp Val Val Pro Ile Asp Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
            180                 185                 190

Pro Ile Pro Ile His Tyr Cys Ala Pro Ala Gly Phe Ala Ile Leu Lys
        195                 200                 205

Cys Asn Asn Lys Thr Phe Asp Gly Lys Gly Leu Cys Thr Asn Val Ser
    210                 215                 220
```

-continued

```
Thr Val Gln Cys Thr His Gly Ile Arg Pro Val Ser Thr Gln Leu
225                 230                 235                 240

Leu Leu Asn Gly Ser Leu Ala Glu Glu Val Val Ile Arg Ser Asp
            245                 250                 255

Asn Phe Met Asp Asn Thr Lys Thr Ile Ile Val Gln Leu Asn Glu Ser
                260                 265                 270

Val Ala Ile Asn Cys Thr Arg Pro Asn Asn Thr Arg Lys Gly Ile
                275                 280                 285

His Ile Gly Pro Gly Arg Ala Phe Tyr Ala Ala Arg Lys Ile Ile Gly
    290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
                325                 330                 335

Thr Ile Lys Phe Asn Gln Ser Ser Gly Gly Asp Pro Glu Ile Val Arg
                340                 345                 350

His Ser Phe Asn Cys Gly Gly Glu Phe Phe Tyr Cys Asp Thr Thr Gln
                355                 360                 365

Leu Phe Asn Ser Thr Trp Asn Gly Thr Glu Gly Asn Asn Thr Glu Gly
    370                 375                 380

Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
                405                 410                 415

Ile Arg Cys Ser Ser Asn Ile Thr Gly Leu Leu Leu Thr Arg Asp Gly
                420                 425                 430

Gly Thr Glu Gly Asn Gly Thr Glu Asn Glu Thr Glu Ile Phe Arg Pro
            435                 440                 445

Gly Gly Gly Asp Met Arg Asp Asn Trp Arg Ser Glu Leu Tyr Lys Tyr
    450                 455                 460

Lys Val Val Lys Val Glu Pro Leu Gly Val Ala Pro Thr Arg Ala Lys
465                 470                 475                 480

Arg Arg Val Val Gln Arg Met Gly Ala Arg Ala Ser Val Leu Ser Gly
                485                 490                 495

Gly Glu Leu Asp Arg Trp Glu Lys Ile Arg Leu Arg Pro Gly Gly Lys
                500                 505                 510

Lys Lys Tyr Lys Leu Lys His Ile Val Trp Ala Ser Arg Glu Leu Glu
            515                 520                 525

Arg Phe Ala Val Asn Pro Gly Leu Leu Glu Thr Ser Glu Gly Cys Arg
    530                 535                 540

Gln Ile Leu Gly Gln Leu Gln Pro Ser Leu Gln Thr Gly Ser Glu Glu
545                 550                 555                 560

Leu Arg Ser Leu Tyr Asn Thr Val Ala Thr Leu Tyr Cys Val His Gln
                565                 570                 575

Arg Ile Glu Ile Lys Asp Thr Lys Glu Ala Leu Asp Lys Ile Glu Glu
                580                 585                 590

Glu Gln Asn Lys Ser Lys Lys Lys Ala Gln Gln Ala Ala Ala Asp Thr
            595                 600                 605

Gly His Ser Asn Gln Val Ser Gln Asn Tyr Pro Ile Val Gln Asn Ile
    610                 615                 620

Gln Gly Gln Met Val His Gln Ala Ile Ser Pro Arg Thr Leu Asn Ala
625                 630                 635                 640
```

```
Trp Val Lys Val Val Glu Glu Lys Ala Phe Ser Pro Glu Val Ile Pro
                645                 650                 655
Met Phe Ser Ala Leu Ser Glu Gly Ala Thr Pro Gln Asp Leu Asn Thr
        660                 665                 670
Met Leu Asn Thr Val Gly Gly His Gln Ala Ala Met Gln Met Leu Lys
            675                 680                 685
Glu Thr Ile Asn Glu Glu Ala Ala Glu Trp Asp Arg Val His Pro Val
690                 695                 700
His Ala Gly Pro Ile Ala Pro Gly Gln Met Arg Glu Pro Arg Gly Ser
705                 710                 715                 720
Asp Ile Ala Gly Thr Thr Ser Thr Leu Gln Glu Gln Ile Gly Trp Met
                725                 730                 735
Thr Asn Asn Pro Pro Ile Pro Val Gly Glu Ile Tyr Lys Arg Trp Ile
            740                 745                 750
Ile Leu Gly Leu Asn Lys Ile Val Arg Met Tyr Ser Pro Thr Ser Ile
        755                 760                 765
Leu Asp Ile Arg Gln Gly Pro Lys Glu Pro Phe Arg Asp Tyr Val Asp
770                 775                 780
Arg Phe Tyr Lys Thr Leu Arg Ala Glu Gln Ala Ser Gln Glu Val Lys
785                 790                 795                 800
Asn Trp Met Thr Glu Thr Leu Leu Val Gln Asn Ala Asn Pro Asp Cys
                805                 810                 815
Lys Thr Ile Leu Lys Ala Leu Gly Pro Ala Ala Thr Leu Glu Glu Met
            820                 825                 830
Met Thr Ala Cys Gln Gly Val Gly Gly Pro Gly His Lys Ala Arg Val
        835                 840                 845
Leu Met Gly Lys Trp Ser Lys Ser Ser Val Val Gly Trp Pro Thr Val
850                 855                 860
Arg Glu Arg Met Arg Arg Ala Glu Pro Ala Ala Asp Gly Val Gly Ala
865                 870                 875                 880
Ala Ser Arg Asp Leu Glu Lys His Gly Ala Ile Thr Ser Ser Asn Thr
                885                 890                 895
Ala Ala Thr Asn Ala Ala Cys Ala Trp Leu Glu Ala Gln Glu Glu Glu
            900                 905                 910
Glu Val Gly Phe Pro Val Thr Pro Gln Val Pro Leu Arg Pro Met Thr
        915                 920                 925
Tyr Lys Ala Ala Val Asp Leu Ser His Phe Leu Lys Glu Lys Gly Gly
    930                 935                 940
Leu Glu Gly Leu Ile His Ser Gln Arg Arg Gln Asp Ile Leu Asp Leu
945                 950                 955                 960
Trp Ile Tyr His Thr Gln Gly Tyr Phe Pro Asp Trp Gln Asn Tyr Thr
                965                 970                 975
Pro Gly Pro Gly Val Arg Tyr Pro Leu Thr Phe Gly Trp Cys Tyr Lys
            980                 985                 990
Leu Val Pro Val Glu Pro Asp Lys Val Glu Glu Ala Asn Lys Gly Glu
        995                 1000                1005
Asn Thr Ser Ala Leu His Pro Val Ser Leu His Gly Met Asp Asp Pro
    1010                1015                1020
Glu Arg Glu Val Leu Glu Trp Arg Phe Asp Ser Arg Leu Ala Phe His
1025                1030                1035                1040
His Val Ala Arg Glu Leu His Pro Glu Tyr Phe Lys Asn Cys Thr Ser
                1045                1050                1055
Glu Pro Val Asp Pro Arg Leu Glu Pro Trp Lys His Pro Gly Ser Gln
```

```
                   1060             1065             1070
Pro Lys Thr Ala Cys Thr Asn Cys Tyr Cys Lys Cys Cys Phe His
        1075             1080             1085

Cys Gln Val Cys Phe Ile Thr Ala Ala Leu Gly Ile Ser Tyr Gly Arg
        1090             1095             1100

Lys Lys Arg Arg Gln Arg Arg Arg Pro Pro Gln Gly Ser Gln Thr His
1105             1110             1115             1120

Gln Val Ser Leu Ser Lys Gln Pro Thr Ser Gln Ser Lys Gly Glu Pro
                1125             1130             1135

Thr Gly Pro Lys Glu
        1140

<210> SEQ ID NO 82
<211> LENGTH: 3426
<212> TYPE: DNA
<213> ORGANISM: Artificial Sequence
<220> FEATURE:
<223> OTHER INFORMATION: HIV-1 ds-gp120c p17/24 mL2-Nef Tatm fusion

<400> SEQUENCE: 82
atggccgagc agctgtgggt caccgtctac tacggcgtgc ctgtgtggaa ggaggccacg     60
accaccctct tctgcgcgag cgacgccaag gcctacgaca cggaagtgca taacgtgtgg    120
gcgacgcatg cttgcgtgcc tacggacccc aaccccagg aggtggtgct gggaaacgtg    180
accgagtact tcaacatgtg gaagaataac atggtggatc agatgcacga ggacatcatc    240
tctctgtggg accagtccct gaagcccgtg cgtgaagctga cgcctctctg cgtgacactg    300
gactgtgacg acgtcaacac caccaacagc actaccacca ccagcaacgg ctggaccgga    360
gagattcgga agggcgagat caagaactgc tccttcaata tcacgacctc gatcagagac    420
aaggtgcaga aggaatacgc gctgttttat aatctcgatg tggtccccat cgacgacgac    480
aatgccacca ccaagaacaa gacgacgcgt aatttcagac tcattcactg caacagcagc    540
gtcatgacgc aggcctgccc caaggtgtcc ttcgaaccaa tcccgatcca ttactgtgcc    600
cctgccggat cgcgatcct caagtgtaac aacaagacct cgacgggaa gggcctgtgc    660 accaacgtca gcacggtgca gtgcacccat ggcatccgcc cgtcgtgag cacccagctg    720 ctgctgaacg gtcccctggc tgaggaggag gtggtgatcc ggtcggacaa cttcatggac    780
aacaccaaga caatcatcgt ccagctgaac gagtctgtgg cgattaactg tacccggcct    840
aacaacaaca cccgtaaggg catccacatc gggcctggac gggccttcta tgccgcccgc    900
aagatcatcg gcgacatccg gcaggcccat tgcaacctct cccgcgccca gtggaataac    960
accctgaagc agatcgtgat caagctgaga gagcactttg aaacaagac catcaagttc   1020 aatcagagtt ctggcggaga ccccgagatc gtgcggcact ccttcaactg cggggggcgag   1080 ttcttctact gcgatacgac acagctcttc aactccacct ggaacggcac cgagggcaac   1140
aacacagagg gaaactccac tatcaccctc ccttgccgca tcaagcagat catcaacatg   1200
tggcaggagg tgggaaaggc catgtatgcc ccccccatcg ggggccagat ccgctgctcc   1260
tccaacatca ccggcctgct gctcaccaga acgggggca ccgagggcaa cggcacggag   1320
aacgagacgg agatcttcag gcccggcggc ggcgacatga gggataactg gcggagcgag   1380
ctgtacaagt acaaggtggt gaaggtggag ccgctcggcg tggccccac ccgggccaag   1440 cgccgcgtcg tgcagagaat gggtgcccga gcttcggtac tgtctggtgg agagctggac   1500
agatgggaga aaattaggct gcgcccggga ggcaaaaaga aatacaagct caagcatatc   1560
```

-continued

```
gtgtgggcct cgagggagct tgaacggttt gccgtgaacc caggcctgct ggaaacatct    1620
gagggatgtc gccagatcct ggggcaattg cagccatccc tccagaccgg gagtgaagag    1680
ctgaggtcct tgtataacac agtggctacc ctctactgcg tacaccagag gatcgagatt    1740
aaggatacca aggaggcctt ggacaaaatt gaggaggagc aaaacaagag caagaagaag    1800
gcccagcagg cagctgctga cactgggcat agcaaccagg tatcacagaa ctatcctatt    1860
gtccaaaaca ttcagggcca gatggttcat caggccatca gccccggac gctcaatgcc     1920 tgggtgaagg ttgtcgaaga aaggcctttt tctcctgagg ttatccccat gttctccgct    1980
ttgagtgagg gggccactcc tcaggacctc aatacaatgc ttaataccgt gggcggccat    2040
caggccgcca tgcaaatgtt gaaggagact atcaacgagg aggcagccga gtgggacaga    2100
gtgcatcccg tccacgctgg cccaatcgcg cccggacaga tgcgggagcc tcgcggctct    2160
gacattgccg gcaccacctc tacactgcaa gagcaaatcg gatggatgac caacaatcct    2220
cccatcccag ttggagaaat ctataaacgg tggatcattc tcggtctcaa taaaattgtt    2280
agaatgtact ctccgacatc catccttgac attagacagg gacccaaaga gcctttagg     2340 gattacgtcg accggttta taagaccctg cgagcagagc aggcctctca ggaggtcaaa    2400
aactggatga cggagacact cctggtacag aacgctaacc ccgactgcaa aacaatcttg    2460
aaggcactag gccggctgc caccctggaa gagatgatga ccgcctgtca gggagtaggc    2520
ggacccggac acaaagccag agtgttgatg ggcaagtggt caaaaagtag tgtggttgga    2580
tggcctactg taagggaaag aatgagacga gctgagccag cagcagatgg ggtgggagca    2640
gcatctcgag acctggaaaa acatggagca atcacaagta gcaatacagc agctaccaat    2700
gctgcttgtg cctggctaga agcacaagag gaggaggagg tgggttttcc agtcacacct    2760
caggtacctt taagaccaat gacttacaag gcagctgtag atcttagcca cttttttaaaa   2820 gaaaaggggg gactgaagg gctaattcac tcccaacgaa gacaagatat ccttgatctg    2880
tggatctacc acacacaagg ctacttccct gattggcaga actacacacc agggccaggg   2940
gtcagatatc cactgacctt tggatggtgc tacaagctag taccagttga gccagataag   3000
gtagaagagg ccaataaagg agagaacacc agcttggcac accctgtgag cctgcatgga    3060
atggatgacc ctgagagaga agtgttagag tggaggtttg acagccgcct agcatttcat    3120
cacgtggccc gagagctgca tccggagtac ttcaagaact gcactagtga gccagtagat    3180
cctagactag agccctggaa gcatccagga agtcagccta aaactgcttg taccaattgc    3240
tattgtaaaa agtgttgctt tcattgccaa gtttgtttca taacagctgc cttaggcatc    3300
tcctatggca ggaagaagcg gagacagcga cgaagacctc ctcaaggcag tcagactcat    3360
caagtttctc tatcaaagca acccacctcc aatccaaag ggagccgac aggcccgaag     3420 gaataa                                                              3426
```

<210> SEQ ID NO 83
<211> LENGTH: 1141
<212> TYPE: PRT
<213> ORGANISM: Artificial Sequence
<220> FEATURE:
<223> OTHER INFORMATION: HIV-1 ds-gp120c p17/24 mL2-Nef Tatm fusion

<400> SEQUENCE: 83

```
Met Ala Glu Gln Leu Trp Val Thr Val Tyr Tyr Gly Val Pro Val Trp
1               5                   10                  15

Lys Glu Ala Thr Thr Thr Leu Phe Cys Ala Ser Asp Ala Lys Ala Tyr
            20                  25                  30
```

-continued

```
Asp Thr Glu Val His Asn Val Trp Ala Thr His Ala Cys Val Pro Thr
         35                  40                  45
Asp Pro Asn Pro Gln Glu Val Val Leu Gly Asn Val Thr Glu Tyr Phe
 50                  55                  60
Asn Met Trp Lys Asn Asn Met Val Asp Gln Met His Glu Asp Ile Ile
 65                  70                  75                  80
Ser Leu Trp Asp Gln Ser Leu Lys Pro Cys Val Lys Leu Thr Pro Leu
                 85                  90                  95
Cys Val Thr Leu Asp Cys Asp Asp Val Asn Thr Thr Asn Ser Thr Thr
             100                 105                 110
Thr Thr Ser Asn Gly Trp Thr Gly Glu Ile Arg Lys Gly Glu Ile Lys
         115                 120                 125
Asn Cys Ser Phe Asn Ile Thr Thr Ser Ile Arg Asp Lys Val Gln Lys
 130                 135                 140
Glu Tyr Ala Leu Phe Tyr Asn Leu Asp Val Val Pro Ile Asp Asp Asp
145                 150                 155                 160
Asn Ala Thr Thr Lys Asn Lys Thr Thr Arg Asn Phe Arg Leu Ile His
                 165                 170                 175
Cys Asn Ser Ser Val Met Thr Gln Ala Cys Pro Lys Val Ser Phe Glu
             180                 185                 190
Pro Ile Pro Ile His Tyr Cys Ala Pro Ala Gly Phe Ala Ile Leu Lys
         195                 200                 205
Cys Asn Asn Lys Thr Phe Asp Gly Lys Gly Leu Cys Thr Asn Val Ser
 210                 215                 220
Thr Val Gln Cys Thr His Gly Ile Arg Pro Val Val Ser Thr Gln Leu
225                 230                 235                 240
Leu Leu Asn Gly Ser Leu Ala Glu Glu Val Val Ile Arg Ser Asp
                 245                 250                 255
Asn Phe Met Asp Asn Thr Lys Thr Ile Ile Val Gln Leu Asn Glu Ser
             260                 265                 270
Val Ala Ile Asn Cys Thr Arg Pro Asn Asn Asn Thr Arg Lys Gly Ile
         275                 280                 285
His Ile Gly Pro Gly Arg Ala Phe Tyr Ala Ala Arg Lys Ile Ile Gly
 290                 295                 300
Asp Ile Arg Gln Ala His Cys Asn Leu Ser Arg Ala Gln Trp Asn Asn
305                 310                 315                 320
Thr Leu Lys Gln Ile Val Ile Lys Leu Arg Glu His Phe Gly Asn Lys
                 325                 330                 335
Thr Ile Lys Phe Asn Gln Ser Ser Gly Gly Asp Pro Glu Ile Val Arg
             340                 345                 350
His Ser Phe Asn Cys Gly Gly Glu Phe Phe Tyr Cys Asp Thr Thr Gln
         355                 360                 365
Leu Phe Asn Ser Thr Trp Asn Gly Thr Glu Gly Asn Asn Thr Glu Gly
 370                 375                 380
Asn Ser Thr Ile Thr Leu Pro Cys Arg Ile Lys Gln Ile Ile Asn Met
385                 390                 395                 400
Trp Gln Glu Val Gly Lys Ala Met Tyr Ala Pro Pro Ile Gly Gly Gln
                 405                 410                 415
Ile Arg Cys Ser Ser Asn Ile Thr Gly Leu Leu Leu Thr Arg Asp Gly
             420                 425                 430
Gly Thr Glu Gly Asn Gly Thr Glu Asn Glu Thr Glu Ile Phe Arg Pro
         435                 440                 445
```

-continued

```
Gly Gly Gly Asp Met Arg Asp Asn Trp Arg Ser Glu Leu Tyr Lys Tyr
450                 455                 460

Lys Val Val Lys Val Glu Pro Leu Gly Val Ala Pro Thr Arg Ala Lys
465                 470                 475                 480

Arg Arg Val Val Gln Arg Met Gly Ala Arg Ala Ser Val Leu Ser Gly
                485                 490                 495

Gly Glu Leu Asp Arg Trp Glu Lys Ile Arg Leu Arg Pro Gly Gly Lys
            500                 505                 510

Lys Lys Tyr Lys Leu Lys His Ile Val Trp Ala Ser Arg Glu Leu Glu
        515                 520                 525

Arg Phe Ala Val Asn Pro Gly Leu Leu Glu Thr Ser Glu Gly Cys Arg
    530                 535                 540

Gln Ile Leu Gly Gln Leu Gln Pro Ser Leu Gln Thr Gly Ser Glu Glu
545                 550                 555                 560

Leu Arg Ser Leu Tyr Asn Thr Val Ala Thr Leu Tyr Cys Val His Gln
                565                 570                 575

Arg Ile Glu Ile Lys Asp Thr Lys Glu Ala Leu Asp Lys Ile Glu Glu
            580                 585                 590

Glu Gln Asn Lys Ser Lys Lys Ala Gln Gln Ala Ala Ala Asp Thr
        595                 600                 605

Gly His Ser Asn Gln Val Ser Gln Asn Tyr Pro Ile Val Gln Asn Ile
    610                 615                 620

Gln Gly Gln Met Val His Gln Ala Ile Ser Pro Arg Thr Leu Asn Ala
625                 630                 635                 640

Trp Val Lys Val Val Glu Glu Lys Ala Phe Ser Pro Glu Val Ile Pro
                645                 650                 655

Met Phe Ser Ala Leu Ser Glu Gly Ala Thr Pro Gln Asp Leu Asn Thr
            660                 665                 670

Met Leu Asn Thr Val Gly Gly His Gln Ala Ala Met Gln Met Leu Lys
        675                 680                 685

Glu Thr Ile Asn Glu Glu Ala Ala Glu Trp Asp Arg Val His Pro Val
    690                 695                 700

His Ala Gly Pro Ile Ala Pro Gly Gln Met Arg Glu Pro Arg Gly Ser
705                 710                 715                 720

Asp Ile Ala Gly Thr Thr Ser Thr Leu Gln Glu Gln Ile Gly Trp Met
                725                 730                 735

Thr Asn Asn Pro Pro Ile Pro Val Gly Glu Ile Tyr Lys Arg Trp Ile
            740                 745                 750

Ile Leu Gly Leu Asn Lys Ile Val Arg Met Tyr Ser Pro Thr Ser Ile
        755                 760                 765

Leu Asp Ile Arg Gln Gly Pro Lys Glu Pro Phe Arg Asp Tyr Val Asp
    770                 775                 780

Arg Phe Tyr Lys Thr Leu Arg Ala Glu Gln Ala Ser Gln Glu Val Lys
785                 790                 795                 800

Asn Trp Met Thr Glu Thr Leu Leu Val Gln Asn Ala Asn Pro Asp Cys
                805                 810                 815

Lys Thr Ile Leu Lys Ala Leu Gly Pro Ala Ala Thr Leu Glu Glu Met
            820                 825                 830

Met Thr Ala Cys Gln Gly Val Gly Gly Pro Gly His Lys Ala Arg Val
        835                 840                 845

Leu Met Gly Lys Trp Ser Lys Ser Ser Val Val Gly Trp Pro Thr Val
    850                 855                 860

Arg Glu Arg Met Arg Arg Ala Glu Pro Ala Ala Asp Gly Val Gly Ala
```

-continued

```
865                 870                 875                 880
Ala Ser Arg Asp Leu Glu Lys His Gly Ala Ile Thr Ser Ser Asn Thr
                885                 890                 895

Ala Ala Thr Asn Ala Ala Cys Ala Trp Leu Glu Ala Gln Glu Glu Glu
            900                 905                 910
Glu Val Gly Phe Pro Val Thr Pro Gln Val Pro Leu Arg Pro Met Thr
        915                 920                 925

Tyr Lys Ala Ala Val Asp Leu Ser His Phe Leu Lys Glu Lys Gly Gly
    930                 935                 940

Leu Glu Gly Leu Ile His Ser Gln Arg Arg Gln Asp Ile Leu Asp Leu
945                 950                 955                 960
Trp Ile Tyr His Thr Gln Gly Tyr Phe Pro Asp Trp Gln Asn Tyr Thr
                965                 970                 975
Pro Gly Pro Gly Val Arg Tyr Pro Leu Thr Phe Gly Trp Cys Tyr Lys
            980                 985                 990

Leu Val Pro Val Glu Pro Asp Lys Val Glu Glu Ala Asn Lys Gly Glu
        995                 1000                1005

Asn Thr Ser Leu Ala His Pro Val Ser Leu His Gly Met Asp Asp Pro
    1010                1015                1020
Glu Arg Glu Val Leu Glu Trp Arg Phe Asp Ser Arg Leu Ala Phe His
1025                1030                1035                1040
His Val Ala Arg Glu Leu His Pro Glu Tyr Phe Lys Asn Cys Thr Ser
                1045                1050                1055
Glu Pro Val Asp Pro Arg Leu Glu Pro Trp Lys His Pro Gly Ser Gln
            1060                1065                1070
Pro Lys Thr Ala Cys Thr Asn Cys Tyr Cys Lys Lys Cys Cys Phe His
        1075                1080                1085

Cys Gln Val Cys Phe Ile Thr Ala Ala Leu Gly Ile Ser Tyr Gly Arg
    1090                1095                1100

Lys Lys Arg Arg Gln Arg Arg Arg Pro Pro Gln Gly Ser Gln Thr His
1105                1110                1115                1120
Gln Val Ser Leu Ser Lys Gln Pro Thr Ser Gln Ser Lys Gly Glu Pro
                1125                1130                1135

Thr Gly Pro Lys Glu
            1140
```

```
<210> SEQ ID NO 84
<211> LENGTH: 4662
<212> TYPE: DNA
<213> ORGANISM: Artificial Sequence
<220> FEATURE:
<223> OTHER INFORMATION: HIV-1 ds-gp120c RT trNef p17/24 fusion

<400> SEQUENCE: 84
atggccgagc agctgtgggt caccgtctac tacggcgtgc ctgtgtggaa ggaggccacg      60
accaccctct tctgcgcgag cgacgccaag gcctacgaca cggaagtgca taacgtgtgg     120
gcgacgcatg cttgcgtgcc tacggacccc aacccccagg aggtggtgct gggaaacgtg     180
accgagtact tcaacatgtg gaagaataac atggtggatc agatgcacga ggacatcatc     240
tctctgtggg accagtccct gaagccctgc gtgaagctga cgcctctctg cgtgacactg     300
gactgtgacg acgtcaacac caccaacagc actaccacca ccagcaacgg ctggaccgga     360
gagattcgga agggcgagat caagaactgc tccttcaata tcacgacctc gatcagagac     420
aaggtgcaga aggaatacgc gctgttttat aatctcgatg tggtccccat cgacgacgac     480
```

```
aatgccacca ccaagaacaa gacgacgcgt aatttcagac tcattcactg caacagcagc    540
gtcatgacgc aggcctgccc caaggtgtcc ttcgaaccaa tcccgatcca ttactgtgcc    600
cctgccggat tcgcgatcct caagtgtaac aacaagacct tcgacgggaa gggcctgtgc    660
accaacgtca gcacggtgca gtgcacccat ggcatccgcc ccgtcgtgag cacccagctg    720
ctgctgaacg ggtccctggc tgaggaggag gtggtgatcc ggtcggacaa cttcatggac    780
aacaccaaga caatcatcgt ccagctgaac gagtctgtgg cgattaactg tacccggcct    840
aacaacaaca cccgtaaggg catccacatc gggcctggac gggccttcta tgccgcccgc    900
aagatcatcg gcgacatccg gcaggcccat tgcaacctct cccgcgccca gtggaataac    960
accctgaagc agatcgtgat caagctgaga gagcactttg gaaacaagac catcaagttc   1020
aatcagagtt ctggcggaga ccccgagatc gtgcggcact ccttcaactg cggggggcgag   1080 ttcttctact gcgatacgac acagctcttc aactccacct ggaacggcac cgagggcaac   1140
aacacagagg gaaactccac tatcaccctc ccttgccgca tcaagcagat catcaacatg   1200
tggcaggagg tgggaaaggc catgtatgcc cccccatcg ggggccagat ccgctgctcc    1260
tccaacatca ccggcctgct gctcaccaga gacgggggca ccgagggcaa cggcacggag   1320
aacgagacgg agatcttcag gcccggcggc ggcgacatga gggataactg gcggagcgag   1380
ctgtacaagt acaaggtggt gaaggtggag ccgctcggcg tggcccccac ccgggccaag   1440
cgccgcgtcg tgcagagaat gggccccatc agtcccatcg agaccgtgcc ggtgaagctg   1500
aaacccggga tggacggccc caaggtcaag cagtggccac tcaccgagga gaagatcaag   1560
gccctggtgg agatctgcac cgagatggag aaagagggca gatcagcaa gatcgggcct   1620 gagaacccat acaacacccc cgtgtttgcc atcaagaaga aggacagcac caagtggcgc   1680
aagctggtgg atttccggga gctgaataag cggacccagg atttctggga ggtccagctg   1740
ggcatccccc atccggccgg cctgaagaag aagaagagcg tgaccgtgct ggacgtgggc   1800
gacgcttact tcagcgtccc tctggacgag gactttagaa agtacaccgc ctttaccatc   1860
ccatctatca caacgagac ccctggcatc agatatcagt acaacgtcct cccccagggc    1920
tggaagggct ctcccgccat tttccagagc tccatgacca agatcctgga gccgtttcgg    1980
aagcagaacc ccgatatcgt catctaccag tacatggacg acctgtacgt gggctctgac   2040
ctggaaatcg ggcagcatcg cacgaagatt gaggagctga ggcagcatct gctgagatgg   2100
ggcctgacca ctccggacaa gaagcatcag aaggagccgc cattcctgaa gatgggctac   2160
gagctccatc ccgacaagtg gaccgtgcag cctatcgtcc tccccgagaa ggacagctgg   2220
accgtgaacg acatccagaa gctggtgggc aagctcaact gggctagcca gatctatccc   2280
gggatcaagg tgcgccagct ctgcaagctg ctgcgcggca ccaaggccct gaccgaggtg   2340
attcccctca cggaggaagc cgagctcgag ctggctgaga accgggagat cctgaaggag   2400
cccgtgcacg gcgtgtacta tgacccctcc aaggacctga tcgccgaaat ccagaagcag   2460
ggccaggggc agtggacata ccagatttac caggagcctt tcaagaacct caagaccggc   2520
aagtacgccc gcatgagggg cgcccacacc aacgatgtca gcagctgac cgaggccgtc    2580 cagaagatca cgaccgagtc catcgtgatc tgggggaaga cacccaagtt caagctgcct   2640
atccagaagg agacctggga gacgtggtgg accgaatatt ggcaggccac ctggattccc   2700
gagtgggagt tcgtgaatac acctcctctg gtgaagctgt ggtaccagct cgagaaggag   2760
cccatcgtgg gcgcggagac attctacgtg gacggcgcgg ccaaccgcga aacaaagctc   2820
gggaaggccg ggtacgtcac caaccgggc cgccagaagg tcgtcaccct gaccgacacc    2880
```

```
accaaccaga agacggagct gcaggccatc tatctcgctc tccaggactc cggcctggag    2940
gtgaacatcg tgacggacag ccagtacgcg ctgggcatta ttcaggccca gccggaccag    3000
tccgagagcg aactggtgaa ccagattatc gagcagctga tcaagaaaga aaggtctac    3060 ctcgcctggg tcccggccca taagggcatt ggcggcaacg agcaggtcga caagctggtg    3120
agtgcgggga ttagaaaggt gctgatggtg ggttttccag tcacacctca ggtacccttta   3180 agaccaatga cttacaaggc agctgtagat cttagccact tttaaaaga aagggggga     3240 ctggaagggc taattcactc ccaaagaaga caagatatcc ttgatctgtg gatctaccac    3300
acacaaggct acttccctga ttggcagaac tacacaccag ggccagggt cagatatcca    3360 ctgacctttg gatggtgcta caagctagta ccagttgagc cagataaggt agaagaggcc    3420
aataaaggag agaacaccag cttgttacac cctgtgagcc tgcatgggat ggatgacccg    3480
gagagagaag tgttagagtg gaggtttgac agccgcctag catttcatca cgtggcccga    3540
gagctgcatc cggagtactt caagaactgc atgggtgccc gagcttcggt actgtctggt    3600
ggagagctgg acagatggga gaaaattagg ctgcgcccgg gaggcaaaaa gaaatacaag    3660
ctcaagcata tcgtgtgggc ctcgagggag cttgaacggt ttgccgtgaa cccaggcctg    3720
ctggaaacat ctgagggatg tcgccagatc ctggggcaat gcagccatc cctccagacc    3780 gggagtgaag agctgaggtc cttgtataac acagtggcta ccctctactg cgtacaccag    3840
aggatcgaga ttaaggatac caaggaggcc ttggacaaaa ttgaggagga gcaaaacaag    3900
agcaagaaga aggcccagca ggcagctgct gacactgggc atagcaacca ggtatcacag    3960
aactatccta ttgtccaaaa cattcagggc cagatggttc atcaggccat cagccccgg    4020 acgctcaatg cctgggtgaa ggttgtcgaa gagaaggcct tttctcctga ggttatcccc    4080
atgttctccg ctttgagtga ggggccact cctcaggacc tcaatacaat gcttaatacc    4140
gtgggcggcc atcaggccgc catgcaaatg ttgaaggaga ctatcaacga ggaggcagcc    4200
gagtgggaca gagtgcatcc cgtccacgct ggcccaatcg cgcccggaca gatgcgggag    4260
cctcgcggct ctgacattgc cggcaccacc tctacactgc aagagcaaat cggatggatg    4320
accaacaatc ctcccatccc agttggagaa atctataaac ggtggatcat cctgggcctg    4380
aacaagatcg tgcgcatgta ctctccgaca tccatccttg acattagaca gggacccaaa    4440
gagcctttta gggattacgt cgaccggttt tataagaccc tgcgagcaga gcaggcctct    4500
caggaggtca aaactggat gacggagaca ctcctggtac agaacgctaa ccccgactgc    4560
aaaacaatct tgaaggcact aggcccggct gccaccctgg aagagatgat gaccgcctgt    4620
cagggagtag gcggacccgg acacaaagcc agagtgttgt aa                       4662
```

<210> SEQ ID NO 85
<211> LENGTH: 1553
<212> TYPE: PRT
<213> ORGANISM: Artificial Sequence
<220> FEATURE:
<223> OTHER INFORMATION: HIV-1 ds-gp120c RT trNef p17/24 fusion

<400> SEQUENCE: 85

Met Ala Glu Gln Leu Trp Val Thr Val Tyr Tyr Gly Val Pro Val Trp
 1               5                  10                  15

Lys Glu Ala Thr Thr Thr Leu Phe Cys Ala Ser Asp Ala Lys Ala Tyr
             20                  25                  30

Asp Thr Glu Val His Asn Val Trp Ala Thr His Ala Cys Val Pro Thr
         35                  40                  45

```
Asp Pro Asn Pro Gln Glu Val Val Leu Gly Asn Val Thr Glu Tyr Phe
 50                  55                  60

Asn Met Trp Lys Asn Asn Met Val Asp Gln Met His Glu Asp Ile Ile
 65                  70                  75                  80

Ser Leu Trp Asp Gln Ser Leu Lys Pro Cys Val Lys Leu Thr Pro Leu
                 85                  90                  95

Cys Val Thr Leu Asp Cys Asp Val Asn Thr Thr Asn Ser Thr Thr
                100                 105                 110

Thr Thr Ser Asn Gly Trp Thr Gly Glu Ile Arg Lys Gly Glu Ile Lys
            115                 120                 125

Asn Cys Ser Phe Asn Ile Thr Thr Ser Ile Arg Asp Lys Val Gln Lys
130                 135                 140

Glu Tyr Ala Leu Phe Tyr Asn Leu Asp Val Val Pro Ile Asp Asp Asp
145                 150                 155                 160

Asn Ala Thr Thr Lys Asn Lys Thr Thr Arg Asn Phe Arg Leu Ile His
                165                 170                 175

Cys Asn Ser Ser Val Met Thr Gln Ala Cys Pro Lys Val Ser Phe Glu
            180                 185                 190

Pro Ile Pro Ile His Tyr Cys Ala Pro Ala Gly Phe Ala Ile Leu Lys
            195                 200                 205

Cys Asn Asn Lys Thr Phe Asp Gly Lys Gly Leu Cys Thr Asn Val Ser
210                 215                 220

Thr Val Gln Cys Thr His Gly Ile Arg Pro Val Val Ser Thr Gln Leu
225                 230                 235                 240

Leu Leu Asn Gly Ser Leu Ala Glu Glu Val Val Ile Arg Ser Asp
                245                 250                 255

Asn Phe Met Asp Asn Thr Lys Thr Ile Ile Val Gln Leu Asn Glu Ser
            260                 265                 270

Val Ala Ile Asn Cys Thr Arg Pro Asn Asn Asn Thr Arg Lys Gly Ile
            275                 280                 285

His Ile Gly Pro Gly Arg Ala Phe Tyr Ala Ala Arg Lys Ile Ile Gly
290                 295                 300

Asp Ile Arg Gln Ala His Cys Asn Leu Ser Arg Ala Gln Trp Asn Asn
305                 310                 315                 320

Thr Leu Lys Gln Ile Val Ile Lys Leu Arg Glu His Phe Gly Asn Lys
            325                 330                 335

Thr Ile Lys Phe Asn Gln Ser Ser Gly Gly Asp Pro Glu Ile Val Arg
            340                 345                 350

His Ser Phe Asn Cys Gly Gly Glu Phe Phe Tyr Cys Asp Thr Thr Gln
            355                 360                 365

Leu Phe Asn Ser Thr Trp Asn Gly Thr Glu Gly Asn Asn Thr Glu Gly
            370                 375                 380

Asn Ser Thr Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gly Gly Gln
                405                 410                 415

Ile Arg Cys Ser Ser Asn Ile Thr Gly Leu Leu Leu Thr Arg Asp Gly
            420                 425                 430

Gly Thr Glu Gly Asn Gly Thr Glu Asn Glu Thr Glu Ile Phe Arg Pro
            435                 440                 445

Gly Gly Gly Asp Met Arg Asp Asn Trp Arg Ser Glu Leu Tyr Lys Tyr
450                 455                 460
```

```
Lys Val Val Lys Val Glu Pro Leu Gly Val Ala Pro Thr Arg Ala Lys
465                 470                 475                 480

Arg Arg Val Val Gln Arg Met Gly Pro Ile Ser Pro Ile Glu Thr Val
                485                 490                 495

Pro Val Lys Leu Lys Pro Gly Met Asp Gly Pro Lys Val Lys Gln Trp
            500                 505                 510

Pro Leu Thr Glu Glu Lys Ile Lys Ala Leu Val Glu Ile Cys Thr Glu
            515                 520                 525

Met Glu Lys Glu Gly Lys Ile Ser Lys Ile Gly Pro Glu Asn Pro Tyr
            530                 535                 540

Asn Thr Pro Val Phe Ala Ile Lys Lys Lys Asp Ser Thr Lys Trp Arg
545                 550                 555                 560

Lys Leu Val Asp Phe Arg Glu Leu Asn Lys Arg Thr Gln Asp Phe Trp
                565                 570                 575

Glu Val Gln Leu Gly Ile Pro His Pro Ala Gly Leu Lys Lys Lys Lys
            580                 585                 590

Ser Val Thr Val Leu Asp Val Gly Asp Ala Tyr Phe Ser Val Pro Leu
            595                 600                 605

Asp Glu Asp Phe Arg Lys Tyr Thr Ala Phe Thr Ile Pro Ser Ile Asn
610                 615                 620

Asn Glu Thr Pro Gly Ile Arg Tyr Gln Tyr Asn Val Leu Pro Gln Gly
625                 630                 635                 640

Trp Lys Gly Ser Pro Ala Ile Phe Gln Ser Ser Met Thr Lys Ile Leu
                645                 650                 655

Glu Pro Phe Arg Lys Gln Asn Pro Asp Ile Val Ile Tyr Gln Tyr Met
            660                 665                 670

Asp Asp Leu Tyr Val Gly Ser Asp Leu Glu Ile Gly Gln His Arg Thr
            675                 680                 685

Lys Ile Glu Glu Leu Arg Gln His Leu Leu Arg Trp Gly Leu Thr Thr
690                 695                 700

Pro Asp Lys Lys His Gln Lys Glu Pro Pro Phe Leu Lys Met Gly Tyr
705                 710                 715                 720

Glu Leu His Pro Asp Lys Trp Thr Val Gln Pro Ile Val Leu Pro Glu
                725                 730                 735

Lys Asp Ser Trp Thr Val Asn Asp Ile Gln Lys Leu Val Gly Lys Leu
            740                 745                 750

Asn Trp Ala Ser Gln Ile Tyr Pro Gly Ile Lys Val Arg Gln Leu Cys
            755                 760                 765

Lys Leu Leu Arg Gly Thr Lys Ala Leu Thr Glu Val Ile Pro Leu Thr
            770                 775                 780

Glu Glu Ala Glu Leu Glu Leu Ala Glu Asn Arg Glu Ile Leu Lys Glu
785                 790                 795                 800

Pro Val His Gly Val Tyr Tyr Asp Pro Ser Lys Asp Leu Ile Ala Glu
                805                 810                 815

Ile Gln Lys Gln Gly Gln Gly Gln Trp Thr Tyr Gln Ile Tyr Gln Glu
            820                 825                 830

Pro Phe Lys Asn Leu Lys Thr Gly Lys Tyr Ala Arg Met Arg Gly Ala
            835                 840                 845

His Thr Asn Asp Val Lys Gln Leu Thr Glu Ala Val Gln Lys Ile Thr
850                 855                 860

Thr Glu Ser Ile Val Ile Trp Gly Lys Thr Pro Lys Phe Lys Leu Pro
865                 870                 875                 880

Ile Gln Lys Glu Thr Trp Glu Thr Trp Trp Thr Glu Tyr Trp Gln Ala
```

-continued

```
                885                 890                 895
Thr Trp Ile Pro Glu Trp Glu Phe Val Asn Thr Pro Leu Val Lys
            900                 905                 910
Leu Trp Tyr Gln Leu Glu Lys Glu Pro Ile Val Gly Ala Glu Thr Phe
            915                 920                 925
Tyr Val Asp Gly Ala Ala Asn Arg Glu Thr Lys Leu Gly Lys Ala Gly
            930                 935                 940
Tyr Val Thr Asn Arg Gly Arg Gln Lys Val Val Thr Leu Thr Asp Thr
945                 950                 955                 960
Thr Asn Gln Lys Thr Glu Leu Gln Ala Ile Tyr Leu Ala Leu Gln Asp
                965                 970                 975
Ser Gly Leu Glu Val Asn Ile Val Thr Asp Ser Gln Tyr Ala Leu Gly
            980                 985                 990
Ile Ile Gln Ala Gln Pro Asp Gln Ser Glu Ser Glu Leu Val Asn Gln
            995                 1000                1005
Ile Ile Glu Gln Leu Ile Lys Lys Glu Lys Val Tyr Leu Ala Trp Val
            1010                1015                1020
Pro Ala His Lys Gly Ile Gly Gly Asn Glu Gln Val Asp Lys Leu Val
1025                1030                1035                1040
Ser Ala Gly Ile Arg Lys Val Leu Met Val Gly Phe Pro Val Thr Pro
                1045                1050                1055
Gln Val Pro Leu Arg Pro Met Thr Tyr Lys Ala Ala Val Asp Leu Ser
            1060                1065                1070
His Phe Leu Lys Glu Lys Gly Gly Leu Glu Gly Leu Ile His Ser Gln
            1075                1080                1085
Arg Arg Gln Asp Ile Leu Asp Leu Trp Ile Tyr His Thr Gln Gly Tyr
            1090                1095                1100
Phe Pro Asp Trp Gln Asn Tyr Thr Pro Gly Pro Gly Val Arg Tyr Pro
1105                1110                1115                1120
Leu Thr Phe Gly Trp Cys Tyr Lys Leu Val Pro Val Glu Pro Asp Lys
                1125                1130                1135
Val Glu Glu Ala Asn Lys Gly Glu Asn Thr Ser Leu Leu His Pro Val
            1140                1145                1150
Ser Leu His Gly Met Asp Asp Pro Glu Arg Glu Val Leu Glu Trp Arg
            1155                1160                1165
Phe Asp Ser Arg Leu Ala Phe His His Val Ala Arg Glu Leu His Pro
            1170                1175                1180
Glu Tyr Phe Lys Asn Cys Met Gly Ala Arg Ala Ser Val Leu Ser Gly
1185                1190                1195                1200
Gly Glu Leu Asp Arg Trp Glu Lys Ile Arg Leu Arg Pro Gly Gly Lys
                1205                1210                1215
Lys Lys Tyr Lys Leu Lys His Ile Val Trp Ala Ser Arg Glu Leu Glu
            1220                1225                1230
Arg Phe Ala Val Asn Pro Gly Leu Leu Glu Thr Ser Glu Gly Cys Arg
            1235                1240                1245
Gln Ile Leu Gly Gln Leu Gln Pro Ser Leu Gln Thr Gly Ser Glu Glu
            1250                1255                1260
Leu Arg Ser Leu Tyr Asn Thr Val Ala Thr Leu Tyr Cys Val His Gln
1265                1270                1275                1280
Arg Ile Glu Ile Lys Asp Thr Lys Glu Ala Leu Asp Lys Ile Glu Glu
                1285                1290                1295
Glu Gln Asn Lys Ser Lys Lys Lys Ala Gln Gln Ala Ala Ala Asp Thr
            1300                1305                1310
```

```
Gly His Ser Asn Gln Val Ser Gln Asn Tyr Pro Ile Val Gln Asn Ile
        1315                1320                1325

Gln Gly Gln Met Val His Gln Ala Ile Ser Pro Arg Thr Leu Asn Ala
    1330                1335                1340

Trp Val Lys Val Val Glu Lys Ala Phe Ser Pro Glu Val Ile Pro
1345                1350                1355                1360

Met Phe Ser Ala Leu Ser Glu Gly Ala Thr Pro Gln Asp Leu Asn Thr
            1365                1370                1375

Met Leu Asn Thr Val Gly Gly His Gln Ala Ala Met Gln Met Leu Lys
        1380                1385                1390

Glu Thr Ile Asn Glu Glu Ala Ala Glu Trp Asp Arg Val His Pro Val
    1395                1400                1405

His Ala Gly Pro Ile Ala Pro Gly Gln Met Arg Glu Pro Arg Gly Ser
    1410                1415                1420

Asp Ile Ala Gly Thr Thr Ser Thr Leu Gln Glu Gln Ile Gly Trp Met
1425                1430                1435                1440

Thr Asn Asn Pro Pro Ile Pro Val Gly Glu Ile Tyr Lys Arg Trp Ile
            1445                1450                1455

Ile Leu Gly Leu Asn Lys Ile Val Arg Met Tyr Ser Pro Thr Ser Ile
        1460                1465                1470

Leu Asp Ile Arg Gln Gly Pro Lys Glu Pro Phe Arg Asp Tyr Val Asp
    1475                1480                1485

Arg Phe Tyr Lys Thr Leu Arg Ala Glu Gln Ala Ser Gln Glu Val Lys
    1490                1495                1500

Asn Trp Met Thr Glu Thr Leu Leu Val Gln Asn Ala Asn Pro Asp Cys
1505                1510                1515                1520

Lys Thr Ile Leu Lys Ala Leu Gly Pro Ala Ala Thr Leu Glu Glu Met
            1525                1530                1535

Met Thr Ala Cys Gln Gly Val Gly Gly Pro Gly His Lys Ala Arg Val
        1540                1545                1550

Leu

<210> SEQ ID NO 86
<211> LENGTH: 4662
<212> TYPE: DNA
<213> ORGANISM: Artificial Sequence
<220> FEATURE:
<223> OTHER INFORMATION: HIV-1 RT trNef p17/24 ds gp120c fusion

<400> SEQUENCE: 86
atgggcccca tcagtcccat cgagaccgtg ccggtgaagc tgaaacccgg gatggacggc        60
cccaaggtca agcagtggcc actcaccgag gagaagatca aggccctggt ggagatctgc       120
accgagatgg agaagagggg caagatcagc aagatcgggc cggagaaccc atacaacacc       180
cccgtgtttg ccatcaagaa gaaggacagc accaagtggc gcaagctggt ggatttccgg       240
gagctgaata gcggacccca ggatttctgg gaggtccagc tgggcatccc catccggcc        300 ggcctgaaga agaagaagag cgtgaccgtg ctggacgtgg cgacgctta cttcagcgtc       360 cctctggacg aggactttag aaagtacacc gcctttacca tcccatctat caacaacgag       420 accctggca tcagatatca gtacaacgtc tcccccagg gctggaaggg ctctcccgcc       480 atttttccaga gctccatgac caagatcctg agccgtttc ggaagcagaa cccgatatc       540 gtcatctacc agtacatgga cgacctgtac gtgggctctg acctggaaat cgggcagcat       600
cgcacgaaga ttgaggagct gaggcagcat ctgctgagat ggggcctgac cactccggac       660
```

-continued

```
aagaagcatc agaaggagcc gccattcctg aagatgggct acgagctcca tcccgacaag    720
tggaccgtgc agcctatcgt cctccccgag aaggacagct ggaccgtgaa cgacatccag    780
aagctggtgg gcaagctcaa ctgggctagc cagatctatc ccgggatcaa ggtgcgccag    840
ctctgcaagc tgctgcgcgg caccaaggcc ctgaccgagg tgattcccct cacggaggaa    900
gccgagctcg agctggctga gaaccgggag atcctgaagg agcccgtgca cggcgtgtac    960
tatgacccct ccaaggacct gatcgccgaa atccagaagc agggccaggg gcagtggaca   1020
taccagattt accaggagcc tttcaagaac ctcaagaccg gcaagtacgc ccgcatgagg   1080
ggcgcccaca ccaacgatgt caagcagctg accgaggccg tccagaagat cacgaccgag   1140
tccatcgtga tctgggggaa gacacccaag ttcaagctgc ctatccagaa ggagacctgg   1200
gagacgtggt ggaccgaata ttggcaggcc acctggattc ccgagtggga gttcgtgaat   1260
acacctcctc tggtgaagct gtggtaccag ctcgagaagg agccatcgt gggcgcggag    1320
acattctacg tggacggcgc ggccaaccgc gaaacaaagc tcgggaaggc cgggtacgtc   1380
accaaccggg gccgcagaa ggtcgtcacc ctgaccgaca ccaccaacca gaagacggag    1440
ctgcaggcca tctatctcgc tctccaggac tccggcctgg aggtgaacat cgtgacggac   1500
agccagtacg cgctgggcat tattcaggcc cagccggacc agtccgagag cgaactggtg   1560
aaccagatta tcgagcagct gatcaagaaa gagaaggtct acctcgcctg ggtcccggcc   1620
cataagggca ttggcggcaa cgagcaggtc gacaagctgg tgagtgcggg gattagaaag   1680
gtgctgatgg tgggtttcc agtcacacct caggtacctt taagaccaat gacttacaag    1740
gcagctgtag atcttagcca cttttaaaa gaaaagggg gactggaagg gctaattcac     1800
tcccaaagaa gacaagatat ccttgatctg tggatctacc acacacaagg ctacttccct   1860
gattggcaga actacacacc agggccaggg gtcagatatc cactgacctt tggatggtgc   1920
tacaagctag taccagttga gccagataag gtagaagagg ccaataaagg agagaacacc   1980
agcttgttac accctgtgag cctgcatggg atggatgacc cggagagaga agtgttagag   2040
tggaggtttg acagccgcct agcatttcat cacgtggccc gagagctgca tccggagtac   2100
ttcaagaact gcatgggtgc ccgagcttcg gtactgtctg gtggagagct ggacagatgg   2160
gagaaaatta ggctgcgccc gggaggcaaa aagaaataca agctcaagca tatcgtgtgg   2220
gcctcgaggg agcttgaacg gtttgccgtg aacccaggcc tgctggaaac atctgaggga   2280
tgtcgccaga tcctggggca attgcagcca tccctccaga ccgggagtga agagctgagg   2340
tccttgtata acacagtggc taccctctac tgcgtacacc agaggatcga gattaaggat   2400
accaaggagg ccttggacaa aattgaggag gagcaaaaca agagcaagaa gaaggcccag   2460
caggcagctg ctgacactgg gcatagcaac caggtatcac agaactatcc tattgtccaa   2520
aacattcagg gccagatggt tcatcaggcc atcagccccc ggacgctcaa tgcctgggtg   2580
aaggttgtcg aagagaaggc ctttctcct gaggttatcc ccatgttctc cgctttgagt   2640
gagggggcca ctcctcagga cctcaataca atgcttaata ccgtgggcgg ccatcaggcc   2700
gccatgcaaa tgttgaagga gactatcaac gaggaggcag ccgagtggga cagagtgcat   2760
cccgtccacg ctggcccaat cgcgcccgga cagatgcggg agcctcgcgg ctctgacatt   2820
gccggcacca cctctacact gcaagagcaa atcggatgga tgaccaacaa tcctccccatc   2880
ccagttggag aaatctataa acggtggatc atcctgggcc tgaacaagat cgtgcgcatg   2940
tactctccga catccatcct tgacattaga cagggaccca aagagccttt tagggattac   3000
```

-continued

```
gtcgaccggt tttataagac cctgcgagca gagcaggcct ctcaggaggt caaaaactgg   3060
atgacggaga cactcctggt acagaacgct aaccccgact gcaaaacaat cttgaaggca   3120
ctaggcccgg ctgccaccct ggaagagatg atgaccgcct gtcagggagt aggcggaccc   3180
ggacacaaag ccagagtgtt gatggccgag cagctgtggg tcaccgtcta ctacggcgtg   3240
cctgtgtgga aggaggccac gaccaccctc ttctgcgcga gcgacgccaa ggcctacgac   3300
acggaagtgc ataacgtgtg ggcgacgcat gcttgcgtgc ctacggaccc caacccccag   3360
gaggtggtgc tgggaaacgt gaccgagtac ttcaacatgt ggaagaataa catggtggat   3420
cagatgcacg aggacatcat ctctctgtgg gaccagtccc tgaagccctg cgtgaagctg   3480
acgcctctct gcgtgacact ggactgtgac gacgtcaaca ccaccaacag cactaccacc   3540
accagcaacg gctggaccgg agagattcgg aagggcgaga tcaagaactg ctccttcaat   3600
atcacgacct cgatcagaga caaggtgcag aaggaatacg cgctgtttta taatctcgat   3660
gtggtcccca tcgacgacga caatgccacc accaagaaca agacgacgcg taatttcaga   3720
ctcattcact gcaacagcag cgtcatgacg caggcctgcc ccaaggtgtc cttcgaacca   3780
atcccgatcc attactgtgc ccctgccgga ttcgcgatcc tcaagtgtaa caacaagacc   3840
ttcgacggga agggcctgtg caccaacgtc agcacggtgc agtgcaccca tggcatccgc   3900
cccgtcgtga gcacccagct gctgctgaac gggtccctgg ctgaggagga ggtggtgatc   3960
cggtcggaca acttcatgga caacaccaag acaatcatcg tccagctgaa cgagtctgtg   4020
gcgattaact gtacccggcc taacaacaac acccgtaagg gcatccacat cgggcctgga   4080
cgggccttct atgccgcccg caagatcatc ggcgacatcc ggcaggccca ttgcaacctc   4140
tcccgcgccc agtggaataa caccctgaag cagatcgtga tcaagctgag agagcacttt   4200
ggaaacaaga ccatcaagtt caatcagagt tctggcggag accccgagat cgtgcggcac   4260
tccttcaact gcgggggcga gttcttctac tgcgatacga cacagctctt caactccacc   4320
tggaacggca ccgagggcaa caacacagag ggaaactcca ctatcaccct cccttgccgc   4380
atcaagcaga tcatcaacat gtggcaggag gtgggaaagg ccatgtatgc ccccccccatc   4440 gggggccaga tccgctgctc ctccaacatc accggcctgc tgctcaccag agacgggggc   4500
accgagggca acggcacgga gaacgagacg gagatcttca ggcccggcgg cggcgacatg   4560
agggataact ggcggagcga gctgtacaag tacaaggtgg tgaaggtgga gccgctcggc   4620
gtggccccca cccgggccaa gcgccgcgtc gtgcagagat ga                      4662
```

<210> SEQ ID NO 87
<211> LENGTH: 1553
<212> TYPE: PRT
<213> ORGANISM: Artificial Sequence
<220> FEATURE:
<223> OTHER INFORMATION: HIV-1 RT trNef p17/24 ds gp120c fusion

<400> SEQUENCE: 87

```
Met Gly Pro Ile Ser Pro Ile Glu Thr Val Pro Val Lys Leu Lys Pro
 1               5                  10                  15

Gly Met Asp Gly Pro Lys Val Lys Gln Trp Pro Leu Thr Glu Glu Lys
            20                  25                  30

Ile Lys Ala Leu Val Glu Ile Cys Thr Glu Met Glu Lys Glu Gly Lys
        35                  40                  45

Ile Ser Lys Ile Gly Pro Glu Asn Pro Tyr Asn Thr Pro Val Phe Ala
    50                  55                  60

Ile Lys Lys Lys Asp Ser Thr Lys Trp Arg Lys Leu Val Asp Phe Arg
```

-continued

```
               65                  70                  75                  80
           Glu Leu Asn Lys Arg Thr Gln Asp Phe Trp Glu Val Gln Leu Gly Ile
                           85                  90                  95

Pro His Pro Ala Gly Leu Lys Lys Lys Ser Val Thr Val Leu Asp
                       100                 105                 110

Val Gly Asp Ala Tyr Phe Ser Val Pro Leu Asp Glu Asp Phe Arg Lys
                       115                 120                 125

Tyr Thr Ala Phe Thr Ile Pro Ser Ile Asn Asn Glu Thr Pro Gly Ile
                       130                 135                 140

Arg Tyr Gln Tyr Asn Val Leu Pro Gln Gly Trp Lys Gly Ser Pro Ala
           145                 150                 155                 160

Ile Phe Gln Ser Ser Met Thr Lys Ile Leu Glu Pro Phe Arg Lys Gln
                           165                 170                 175

Asn Pro Asp Ile Val Ile Tyr Gln Tyr Met Asp Asp Leu Tyr Val Gly
                       180                 185                 190

Ser Asp Leu Glu Ile Gly Gln His Arg Thr Lys Ile Glu Glu Leu Arg
                       195                 200                 205

Gln His Leu Leu Arg Trp Gly Leu Thr Thr Pro Asp Lys Lys His Gln
               210                 215                 220

Lys Glu Pro Pro Phe Leu Lys Met Gly Tyr Glu Leu His Pro Asp Lys
           225                 230                 235                 240

Trp Thr Val Gln Pro Ile Val Leu Pro Glu Lys Asp Ser Trp Thr Val
                           245                 250                 255

Asn Asp Ile Gln Lys Leu Val Gly Lys Leu Asn Trp Ala Ser Gln Ile
                       260                 265                 270

Tyr Pro Gly Ile Lys Val Arg Gln Leu Cys Lys Leu Leu Arg Gly Thr
                       275                 280                 285

Lys Ala Leu Thr Glu Val Ile Pro Leu Thr Glu Glu Ala Glu Leu Glu
               290                 295                 300

Leu Ala Glu Asn Arg Glu Ile Leu Lys Glu Pro Val His Gly Val Tyr
           305                 310                 315                 320

Tyr Asp Pro Ser Lys Asp Leu Ile Ala Glu Ile Gln Lys Gln Gly Gln
                       325                 330                 335

Gly Gln Trp Thr Tyr Gln Ile Tyr Gln Glu Pro Phe Lys Asn Leu Lys
                       340                 345                 350

Thr Gly Lys Tyr Ala Arg Met Arg Gly Ala His Thr Asn Asp Val Lys
                       355                 360                 365

Gln Leu Thr Glu Ala Val Gln Lys Ile Thr Thr Glu Ser Ile Val Ile
               370                 375                 380

Trp Gly Lys Thr Pro Lys Phe Lys Leu Pro Ile Gln Lys Glu Thr Trp
           385                 390                 395                 400

Glu Thr Trp Trp Thr Glu Tyr Trp Gln Ala Thr Trp Ile Pro Glu Trp
                           405                 410                 415

Glu Phe Val Asn Thr Pro Pro Leu Val Lys Leu Trp Tyr Gln Leu Glu
                       420                 425                 430

Lys Glu Pro Ile Val Gly Ala Glu Thr Phe Tyr Val Asp Gly Ala Ala
                       435                 440                 445

Asn Arg Glu Thr Lys Leu Gly Lys Ala Gly Tyr Val Thr Asn Arg Gly
                       450                 455                 460

Arg Gln Lys Val Val Thr Leu Thr Asp Thr Thr Asn Gln Lys Thr Glu
           465                 470                 475                 480

Leu Gln Ala Ile Tyr Leu Ala Leu Gln Asp Ser Gly Leu Glu Val Asn
                           485                 490                 495
```

```
Ile Val Thr Asp Ser Gln Tyr Ala Leu Gly Ile Ile Gln Ala Gln Pro
            500                 505                 510

Asp Gln Ser Glu Ser Glu Leu Val Asn Gln Ile Ile Glu Gln Leu Ile
            515                 520                 525

Lys Lys Glu Lys Val Tyr Leu Ala Trp Val Pro Ala His Lys Gly Ile
            530                 535                 540

Gly Gly Asn Glu Gln Val Asp Lys Leu Val Ser Ala Gly Ile Arg Lys
545                 550                 555                 560

Val Leu Met Val Gly Phe Pro Val Thr Pro Gln Val Pro Leu Arg Pro
                565                 570                 575

Met Thr Tyr Lys Ala Ala Val Asp Leu Ser His Phe Leu Lys Glu Lys
            580                 585                 590

Gly Gly Leu Glu Gly Leu Ile His Ser Gln Arg Arg Gln Asp Ile Leu
            595                 600                 605

Asp Leu Trp Ile Tyr His Thr Gln Gly Tyr Phe Pro Asp Trp Gln Asn
            610                 615                 620

Tyr Thr Pro Gly Pro Gly Val Arg Tyr Pro Leu Thr Phe Gly Trp Cys
625                 630                 635                 640

Tyr Lys Leu Val Pro Val Glu Pro Asp Lys Val Glu Glu Ala Asn Lys
                645                 650                 655

Gly Glu Asn Thr Ser Leu Leu His Pro Val Ser Leu His Gly Met Asp
            660                 665                 670

Asp Pro Glu Arg Glu Val Leu Glu Trp Arg Phe Asp Ser Arg Leu Ala
            675                 680                 685

Phe His His Val Ala Arg Glu Leu His Pro Glu Tyr Phe Lys Asn Cys
            690                 695                 700

Met Gly Ala Arg Ala Ser Val Leu Ser Gly Gly Glu Leu Asp Arg Trp
705                 710                 715                 720

Glu Lys Ile Arg Leu Arg Pro Gly Gly Lys Lys Lys Tyr Lys Leu Lys
                725                 730                 735

His Ile Val Trp Ala Ser Arg Glu Leu Glu Arg Phe Ala Val Asn Pro
            740                 745                 750

Gly Leu Leu Glu Thr Ser Glu Gly Cys Arg Gln Ile Leu Gly Gln Leu
            755                 760                 765

Gln Pro Ser Leu Gln Thr Gly Ser Glu Glu Leu Arg Ser Leu Tyr Asn
            770                 775                 780

Thr Val Ala Thr Leu Tyr Cys Val His Gln Arg Ile Glu Ile Lys Asp
785                 790                 795                 800

Thr Lys Glu Ala Leu Asp Lys Ile Glu Glu Glu Gln Asn Lys Ser Lys
                805                 810                 815

Lys Lys Ala Gln Gln Ala Ala Ala Asp Thr Gly His Ser Asn Gln Val
            820                 825                 830

Ser Gln Asn Tyr Pro Ile Val Gln Asn Ile Gln Gly Gln Met Val His
            835                 840                 845

Gln Ala Ile Ser Pro Arg Thr Leu Asn Ala Trp Val Lys Val Val Glu
            850                 855                 860

Glu Lys Ala Phe Ser Pro Glu Val Ile Pro Met Phe Ser Ala Leu Ser
865                 870                 875                 880

Glu Gly Ala Thr Pro Gln Asp Leu Asn Thr Met Leu Asn Thr Val Gly
                885                 890                 895

Gly His Gln Ala Ala Met Gln Met Leu Lys Glu Thr Ile Asn Glu Glu
            900                 905                 910
```

```
Ala Ala Glu Trp Asp Arg Val His Pro Val His Ala Gly Pro Ile Ala
        915                 920                 925
Pro Gly Gln Met Arg Glu Pro Arg Gly Ser Asp Ile Ala Gly Thr Thr
    930                 935                 940
Ser Thr Leu Gln Glu Gln Ile Gly Trp Met Thr Asn Asn Pro Pro Ile
945                 950                 955                 960
Pro Val Gly Glu Ile Tyr Lys Arg Trp Ile Ile Leu Gly Leu Asn Lys
                965                 970                 975
Ile Val Arg Met Tyr Ser Pro Thr Ser Ile Leu Asp Ile Arg Gln Gly
            980                 985                 990
Pro Lys Glu Pro Phe Arg Asp Tyr Val Asp Arg Phe Tyr Lys Thr Leu
        995                 1000                1005
Arg Ala Glu Gln Ala Ser Gln Glu Val Lys Asn Trp Met Thr Glu Thr
    1010                1015                1020
Leu Leu Val Gln Asn Ala Asn Pro Asp Cys Lys Thr Ile Leu Lys Ala
1025                1030                1035                1040
Leu Gly Pro Ala Ala Thr Leu Glu Glu Met Met Thr Ala Cys Gln Gly
                1045                1050                1055
Val Gly Gly Pro Gly His Lys Ala Arg Val Leu Met Ala Glu Gln Leu
            1060                1065                1070
Trp Val Thr Val Tyr Tyr Gly Val Pro Val Trp Lys Glu Ala Thr Thr
        1075                1080                1085
Thr Leu Phe Cys Ala Ser Asp Ala Lys Ala Tyr Asp Thr Glu Val His
    1090                1095                1100
Asn Val Trp Ala Thr His Ala Cys Val Pro Thr Asp Pro Asn Pro Gln
1105                1110                1115                1120
Glu Val Val Leu Gly Asn Val Thr Glu Tyr Phe Asn Met Trp Lys Asn
                1125                1130                1135
Asn Met Val Asp Gln Met His Glu Asp Ile Ile Ser Leu Trp Asp Gln
            1140                1145                1150
Ser Leu Lys Pro Cys Val Lys Leu Thr Pro Leu Cys Val Thr Leu Asp
        1155                1160                1165
Cys Asp Asp Val Asn Thr Thr Asn Ser Thr Thr Thr Ser Asn Gly
    1170                1175                1180
Trp Thr Gly Glu Ile Arg Lys Gly Glu Ile Lys Asn Cys Ser Phe Asn
1185                1190                1195                1200
Ile Thr Thr Ser Ile Arg Asp Lys Val Gln Lys Glu Tyr Ala Leu Phe
                1205                1210                1215
Tyr Asn Leu Asp Val Val Pro Ile Asp Asp Asn Ala Thr Thr Lys
            1220                1225                1230
Asn Lys Thr Thr Arg Asn Phe Arg Leu Ile His Cys Asn Ser Ser Val
        1235                1240                1245
Met Thr Gln Ala Cys Pro Lys Val Ser Phe Glu Pro Ile Pro Ile His
    1250                1255                1260
Tyr Cys Ala Pro Ala Gly Phe Ala Ile Leu Lys Cys Asn Asn Lys Thr
1265                1270                1275                1280
Phe Asp Gly Lys Gly Leu Cys Thr Asn Val Ser Thr Val Gln Cys Thr
                1285                1290                1295
His Gly Ile Arg Pro Val Val Ser Thr Gln Leu Leu Leu Asn Gly Ser
            1300                1305                1310
Leu Ala Glu Glu Glu Val Val Ile Arg Ser Asp Asn Phe Met Asp Asn
        1315                1320                1325
Thr Lys Thr Ile Ile Val Gln Leu Asn Glu Ser Val Ala Ile Asn Cys
```

-continued

```
                1330              1335              1340
Thr Arg Pro Asn Asn Thr Arg Lys Gly Ile His Ile Gly Pro Gly
1345              1350              1355              1360
Arg Ala Phe Tyr Ala Ala Arg Lys Ile Ile Gly Asp Ile Arg Gln Ala
                1365              1370              1375
His Cys Asn Leu Ser Arg Ala Gln Trp Asn Asn Thr Leu Lys Gln Ile
            1380              1385              1390
Val Ile Lys Leu Arg Glu His Phe Gly Asn Lys Thr Ile Lys Phe Asn
            1395              1400              1405
Gln Ser Ser Gly Gly Asp Pro Glu Ile Val Arg His Ser Phe Asn Cys
    1410              1415              1420
Gly Gly Glu Phe Phe Tyr Cys Asp Thr Thr Gln Leu Phe Asn Ser Thr
1425              1430              1435              1440
Trp Asn Gly Thr Glu Gly Asn Asn Thr Glu Gly Asn Ser Thr Ile Thr
                1445              1450              1455
Leu Pro Cys Arg Ile Lys Gln Ile Ile Asn Met Trp Gln Glu Val Gly
            1460              1465              1470
Lys Ala Met Tyr Ala Pro Pro Ile Gly Gly Gln Ile Arg Cys Ser Ser
    1475              1480              1485
Asn Ile Thr Gly Leu Leu Leu Thr Arg Asp Gly Gly Thr Glu Gly Asn
        1490              1495              1500
Gly Thr Glu Asn Glu Thr Glu Ile Phe Arg Pro Gly Gly Gly Asp Met
1505              1510              1515              1520
Arg Asp Asn Trp Arg Ser Glu Leu Tyr Lys Tyr Lys Val Val Lys Val
                1525              1530              1535
Glu Pro Leu Gly Val Ala Pro Thr Arg Ala Lys Arg Arg Val Val Gln
            1540              1545              1550
Arg
```

```
<210> SEQ ID NO 88
<211> LENGTH: 3204
<212> TYPE: DNA
<213> ORGANISM: Artificial Sequence
<220> FEATURE:
<223> OTHER INFORMATION: HIV-1 RT trNef p17/24 fusion

<400> SEQUENCE: 88
atgggcccca tcagtcccat cgagaccgtg ccggtgaagc tgaaacccgg gatggacggc      60
cccaaggtca gcagtggcc actcaccgag gagaagatca aggccctggt ggagatctgc     120
accgagatgg agaaagaggg caagatcagc aagatcgggc tgagaaccc atacaacacc     180 cccgtgtttg ccatcaagaa gaaggacagc accaagtggc gcaagctggt ggatttccgg     240
gagctgaata gcggaccca ggatttctgg gaggtccagc tgggcatccc catccggcc     300 ggcctgaaga agaagaagag cgtgaccgtg ctggacgtgg cgacgctta cttcagcgtc     360 cctctggacg aggactttag aaagtacacc gcctttacca tcccatctat caacaacgag     420 accctggca tcagatatca gtacaacgtc ctcccccagg ctggaaggg ctctcccgcc     480 attttccaga gctccatgac caagatcctg gagccgtttc ggaagcagaa ccccgatatc     540
gtcatctacc agtacatgga cgacctgtac gtgggctctg acctggaaat cgggcagcat     600
cgcacgaaga ttgaggagct gaggcagcat ctgctgagat ggggcctgac cactccggac     660
aagaagcatc agaaggagcc gccattcctg aagatgggct acgagctcca tcccgacaag     720
tggaccgtgc agcctatcgt cctccccgag aaggacagct ggaccgtgaa cgacatccag     780
```

```
aagctggtgg gcaagctcaa ctgggctagc cagatctatc ccgggatcaa ggtgcgccag    840
ctctgcaagc tgctgcgcgg caccaaggcc ctgaccgagg tgattcccct cacggaggaa    900
gccgagctcg agctggctga gaaccgggag atcctgaagg agcccgtgca cggcgtgtac    960
tatgacccct ccaaggacct gatcgccgaa atccagaagc agggccaggg gcagtggaca   1020
taccagattt accaggagcc tttcaagaac ctcaagaccg gcaagtacgc ccgcatgagg   1080
ggcgcccaca ccaacgatgt caagcagctg accgaggccg tccagaagat cacgaccgag   1140
tccatcgtga tctgggggaa gacacccaag ttcaagctgc ctatccagaa ggagacctgg   1200
gagacgtggt ggaccgaata ttggcaggcc acctggattc ccgagtggga gttcgtgaat   1260
acacctcctc tggtgaagct gtggtaccag ctcgagaagg agcccatcgt gggcgcggag   1320
acattctacg tggacggcgc ggccaaccgc gaaacaaagc tcgggaaggc cgggtacgtc   1380
accaaccggg gccgccagaa ggtcgtcacc ctgaccgaca ccaccaacca gaagacggag   1440
ctgcaggcca tctatctcgc tctccaggac tccggcctgg aggtgaacat cgtgacggac   1500
agccagtacg cgctgggcat tattcaggcc cagccggacc agtccgagag cgaactggtg   1560
aaccagatta tcgagcagct gatcaagaaa gagaaggtct acctcgcctg ggtcccggcc   1620
cataagggca ttggcggcaa cgagcaggtc gacaagctgg tgagtgcggg gattagaaag   1680
gtgctgatgg tgggttttcc agtcacacct caggtacctt taagaccaat gacttacaag   1740
gcagctgtag atcttagcca ctttttaaaa gaaaagggg gactggaagg gctaattcac     1800
tcccaaagaa gacaagatat ccttgatctg tggatctacc acacacaagg ctacttccct   1860
gattggcaga actacacacc agggccaggg gtcagatatc cactgacctt tggatggtgc   1920
tacaagctag taccagttga gccagataag gtagaagagg ccaataaagg agagaacacc   1980
agcttgttac accctgtgag cctgcatggg atggatgacc cggagagaga agtgttagag   2040
tggaggtttg acagccgcct agcatttcat cacgtggccc gagagctgca tccggagtac   2100
ttcaagaact gcatgggtgc ccgagcttcg gtactgtctg gtggagagct ggacagatgg   2160
gagaaaatta ggctgcgccc gggaggcaaa aagaaataca agctcaagca tatcgtgtgg   2220
gcctcgaggg agcttgaacg gtttgccgtg aacccaggcc tgctggaaac atctgaggga   2280
tgtcgccaga tcctgggca attgcagcca tccctccaga ccgggagtga agagctgagg   2340
tccttgtata acacagtggc taccctctac tgcgtacacc agaggatcga gattaaggat   2400
accaaggagg ccttggacaa aattgaggag gagcaaaaca agagcaagaa gaaggcccag   2460
caggcagctg ctgacactgg gcatagcaac caggtatcac agaactatcc tattgtccaa   2520
aacattcagg gccagatggt tcatcaggcc atcagccccc ggacgctcaa tgcctgggtg   2580
aaggttgtcg aagagaaggc ctttctcct gaggttatcc ccatgttctc cgctttgagt   2640
gagggggcca ctcctcagga cctcaataca atgcttaata ccgtgggcgg ccatcaggcc   2700
gccatgcaaa tgttgaagga gactatcaac gaggaggcag ccgagtggga cagagtgcat   2760
cccgtccacg ctggcccaat cgcgcccgga cagatgcggg agcctcgcgg ctctgacatt   2820
gccggcacca cctctacact gcaagagcaa atcggatgga tgaccaacaa tcctcccatc   2880
ccagttggag aaatctataa acggtggatc atcctgggcc tgaacaagat cgtgcgcatg   2940
tactctccga catccatcct tgacattaga cagggaccca agagcctt tagggattac     3000 gtcgaccggt tttataagac cctgcgagca gagcaggcct ctcaggaggt caaaaactgg   3060
atgacgagga cactcctggt acagaacgct aaccccgact gcaaaacaat cttgaaggca   3120
ctaggcccgg ctgccaccct ggaagagatg atgaccgcct gtcagggagt aggcggaccc   3180
```
ggacacaaag ccagagtgtt gtaa                                           3204

<210> SEQ ID NO 89
<211> LENGTH: 1067
<212> TYPE: PRT
<213> ORGANISM: Artificial Sequence
<220> FEATURE:
<223> OTHER INFORMATION: HIV-1 RT trNef p17/24 fusion

<400> SEQUENCE: 89

Met Gly Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
            20                  25                  30

Ile Lys Ala Leu Val Glu Ile Cys Thr Glu Met Glu Lys Glu Gly Lys
        35                  40                  45

Ile Ser Lys Ile Gly Pro Glu Asn Pro Tyr Asn Thr Pro Val Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Ser Val Thr Val Leu Asp
            100                 105                 110

Val Gly Asp Ala Tyr Phe Ser Val Pro Leu Asp Glu Asp Phe Arg Lys
        115                 120                 125

Tyr Thr Ala Phe Thr Ile Pro Ser Ile Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
                165                 170                 175

Asn Pro Asp Ile Val Ile Tyr Gln Tyr Met Asp Asp Leu Tyr Val Gly
            180                 185                 190

Ser Asp Leu Glu Ile Gly Gln His Arg Thr Lys Ile Glu Glu Leu Arg
        195                 200                 205

Gln His Leu Leu Arg Trp Gly Leu Thr Thr Pro Asp Lys Lys His Gln
    210                 215                 220

Lys Glu Pro Pro Phe Leu Lys Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Pro Gly Ile Lys Val Arg Gln Leu Cys Lys Leu Leu Arg Gly Thr
        275                 280                 285

Lys Ala Leu Thr Glu Val Ile Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
                325                 330                 335

Gly Gln Trp Thr Tyr Gln Ile Tyr Gln Glu Pro Phe Lys Asn Leu Lys
            340                 345                 350

```
Thr Gly Lys Tyr Ala Arg Met Arg Gly Ala His Thr Asn Asp Val Lys
        355                 360                 365

Gln Leu Thr Glu Ala Val Gln Lys Ile Thr Thr Glu Ser Ile Val Ile
        370                 375                 380

Trp Gly Lys Thr Pro Lys Phe Lys Leu Pro Ile Gln Lys Glu Thr Trp
385                 390                 395                 400

Glu Thr Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
                420                 425                 430

Lys Glu Pro Ile Val Gly Ala Glu Thr Phe Tyr Val Asp Gly Ala Ala
            435                 440                 445

Asn Arg Glu Thr Lys Leu Gly Lys Ala Gly Tyr Val Thr Asn Arg Gly
        450                 455                 460

Arg Gln Lys Val Val Thr Leu Thr Asp Thr Thr Asn Gln Lys Thr Glu
465                 470                 475                 480

Leu Gln Ala Ile Tyr Leu Ala Leu Gln Asp Ser Gly Leu Glu Val Asn
                485                 490                 495

Ile Val Thr Asp Ser Gln Tyr Ala Leu Gly Ile Ile Gln Ala Gln Pro
                500                 505                 510

Asp Gln Ser Glu Ser Glu Leu Val Asn Gln Ile Ile Glu Gln Leu Ile
            515                 520                 525

Lys Lys Glu Lys Val Tyr Leu Ala Trp Val Pro Ala His Lys Gly Ile
        530                 535                 540

Gly Gly Asn Glu Gln Val Asp Lys Leu Val Ser Ala Gly Ile Arg Lys
545                 550                 555                 560

Val Leu Met Val Gly Phe Pro Val Thr Pro Gln Val Pro Leu Arg Pro
                565                 570                 575

Met Thr Tyr Lys Ala Ala Val Asp Leu Ser His Phe Leu Lys Glu Lys
                580                 585                 590

Gly Gly Leu Glu Gly Leu Ile His Ser Gln Arg Arg Gln Asp Ile Leu
            595                 600                 605

Asp Leu Trp Ile Tyr His Thr Gln Gly Tyr Phe Pro Asp Trp Gln Asn
        610                 615                 620

Tyr Thr Pro Gly Pro Gly Val Arg Tyr Pro Leu Thr Phe Gly Trp Cys
625                 630                 635                 640

Tyr Lys Leu Val Pro Val Glu Pro Asp Lys Val Glu Glu Ala Asn Lys
                645                 650                 655

Gly Glu Asn Thr Ser Leu Leu His Pro Val Ser Leu His Gly Met Asp
            660                 665                 670

Asp Pro Glu Arg Glu Val Leu Glu Trp Arg Phe Asp Ser Arg Leu Ala
        675                 680                 685

Phe His His Val Ala Arg Glu Leu His Pro Glu Tyr Phe Lys Asn Cys
        690                 695                 700

Met Gly Ala Arg Ala Ser Val Leu Ser Gly Gly Glu Leu Asp Arg Trp
705                 710                 715                 720

Glu Lys Ile Arg Leu Arg Pro Gly Gly Lys Lys Tyr Lys Leu Lys
                725                 730                 735

His Ile Val Trp Ala Ser Arg Glu Leu Glu Arg Phe Ala Val Asn Pro
                740                 745                 750

Gly Leu Leu Glu Thr Ser Glu Gly Cys Arg Gln Ile Leu Gly Gln Leu
            755                 760                 765

Gln Pro Ser Leu Gln Thr Gly Ser Glu Glu Leu Arg Ser Leu Tyr Asn
```

-continued

```
                    770                 775                 780
Thr Val Ala Thr Leu Tyr Cys Val His Gln Arg Ile Glu Ile Lys Asp
785                 790                 795                 800

Thr Lys Glu Ala Leu Asp Lys Ile Glu Glu Gln Asn Lys Ser Lys
                805                 810                 815

Lys Lys Ala Gln Gln Ala Ala Ala Asp Thr Gly His Ser Asn Gln Val
                820                 825                 830

Ser Gln Asn Tyr Pro Ile Val Gln Asn Ile Gln Gly Gln Met Val His
                835                 840                 845

Gln Ala Ile Ser Pro Arg Thr Leu Asn Ala Trp Val Lys Val Val Glu
850                 855                 860

Glu Lys Ala Phe Ser Pro Glu Val Ile Pro Met Phe Ser Ala Leu Ser
865                 870                 875                 880

Glu Gly Ala Thr Pro Gln Asp Leu Asn Thr Met Leu Asn Thr Val Gly
                885                 890                 895

Gly His Gln Ala Ala Met Gln Met Leu Lys Glu Thr Ile Asn Glu Glu
                900                 905                 910

Ala Ala Glu Trp Asp Arg Val His Pro Val His Ala Gly Pro Ile Ala
                915                 920                 925

Pro Gly Gln Met Arg Glu Pro Arg Gly Ser Asp Ile Ala Gly Thr Thr
                930                 935                 940

Ser Thr Leu Gln Glu Gln Ile Gly Trp Met Thr Asn Asn Pro Pro Ile
945                 950                 955                 960

Pro Val Gly Glu Ile Tyr Lys Arg Trp Ile Ile Leu Gly Leu Asn Lys
                965                 970                 975

Ile Val Arg Met Tyr Ser Pro Thr Ser Ile Leu Asp Ile Arg Gln Gly
                980                 985                 990

Pro Lys Glu Pro Phe Arg Asp Tyr Val Asp Arg Phe Tyr Lys Thr Leu
                995                 1000                1005

Arg Ala Glu Gln Ala Ser Gln Glu Val Lys Asn Trp Met Thr Glu Thr
                1010                1015                1020

Leu Leu Val Gln Asn Ala Asn Pro Asp Cys Lys Thr Ile Leu Lys Ala
1025                1030                1035                1040

Leu Gly Pro Ala Ala Thr Leu Glu Glu Met Met Thr Ala Cys Gln Gly
                1045                1050                1055

Val Gly Gly Pro Gly His Lys Ala Arg Val Leu
                1060                1065
```